US00RE51067E

(19) United States
(12) Reissued Patent
Lu et al.

(10) Patent Number: US RE51,067 E
(45) **Date of Reissued Patent: *Oct. 13, 2026**

(54) BENZOFURAN DERIVATIVE, PREPARATION METHOD THEREOF AND USE THEREOF IN MEDICINE

(71) Applicant: JIANGSU HENGRUI MEDICINE CO., LTD., Lianyungang (CN)

(72) Inventors: Biao Lu, Shanghai (CN); Xiaodong Shen, Shanghai (CN); Mingxun He, Shanghai (CN); Dong Liu, Shanghai (CN); Minsheng Zhang, Shanghai (CN)

(73) Assignee: Jiangsu Hengrui Medicine Co., LTD., Lianyungang (CN)

( * ) Notice: This patent is subject to a terminal disclaimer.

(21) Appl. No.: 18/350,655

(22) Filed: Jul. 11, 2023

Related U.S. Patent Documents

Reissue of:
(64) Patent No.: 10,759,787
Issued: Sep. 1, 2020
Appl. No.: 15/775,958
PCT Filed: Nov. 2, 2016
PCT No.: PCT/CN2016/104318
§ 371 (c)(1),
(2) Date: May 14, 2018
PCT Pub. No.: WO2017/084494
PCT Pub. Date: May 26, 2017

(30) Foreign Application Priority Data

Nov. 19, 2015 (CN) ..... 201510800975.7

(51) Int. Cl.

| | |
|---|---|
| ***C07D 405/14*** | (2006.01) |
| ***A61K 31/4433*** | (2006.01) |
| ***A61K 31/4545*** | (2006.01) |
| ***A61K 31/496*** | (2006.01) |
| ***A61K 31/5377*** | (2006.01) |
| ***A61P 35/00*** | (2006.01) |
| ***C07D 405/12*** | (2006.01) |
| ***C07D 409/14*** | (2006.01) |

(52) U.S. Cl.
CPC ..... *C07D 405/14* (2013.01); *A61K 31/4433* (2013.01); *A61K 31/4545* (2013.01); *A61K 31/496* (2013.01); *A61K 31/5377* (2013.01); *A61P 35/00* (2018.01); *C07D 405/12* (2013.01); *C07D 409/14* (2013.01)

(58) Field of Classification Search
None
See application file for complete search history.

(56) References Cited

U.S. PATENT DOCUMENTS

| | | | |
|---|---|---|---|
| 3,236,625 | A | 2/1966 | Klein et al. |
| 5,344,968 | A | 9/1994 | Lilitkarntakul et al. |
| 6,211,203 | B1 | 4/2001 | Amschler |

(Continued)

FOREIGN PATENT DOCUMENTS

| | | | |
|---|---|---|---|
| CN | 1426388 | A | 6/2003 |
| CN | 101434582 | A | 5/2009 |

(Continued)

OTHER PUBLICATIONS

Anandan et al., "1-(1-Acetyl-peperidin-4-yl)-3-adamantan-1-yl-urea (AR9281) as a potent, selective, and orally available soluble epoxide hydrolase inhibitor with efficacy in rodent models of hypertension and dysglycemia," Bioorganic & Medicinal Chemistry Letters, vol. 21, pp. 983-988 (2011).

(Continued)

*Primary Examiner* — Joseph R Kosack
(74) *Attorney, Agent, or Firm* — Goodwin Procter LLP

(57) ABSTRACT

The present invention relates to a benzofuran derivative, a preparation method thereof and a use thereof in medicine. In particular, the present invention relates to the benzofuran derivative as shown by general formula (I), the preparation method thereof, a pharmaceutical composition containing the derivative, and uses thereof as an EZH2 inhibitor and in the prevention and/or treatment of diseases such as tumours and cancers, etc., and in particular, uses thereof in the prevention and/or treatment of non-Hodgkin's lymphoma, diffuse large B-cell lymphoma, follicular lymphoma and synovial sarcoma, wherein the definitions of the substituents in the general formula (I) are the same as those defined in the description.

(I)

90 Claims, No Drawings

(56) References Cited

U.S. PATENT DOCUMENTS

| | | | |
|---|---|---|---|
| 6,331,556 | B2 | 12/2001 | Dyke et al. |
| 7,057,067 | B2 | 6/2006 | Kodama et al. |
| 8,030,529 | B2 | 10/2011 | Wang et al. |
| 8,846,935 | B2 | 9/2014 | Duquenne et al. |
| 9,018,382 | B2 | 4/2015 | Duquenne et al. |
| 9,730,925 | B2 | 8/2017 | Creasy et al. |
| 10,017,500 | B2 | 7/2018 | Kanno et al. |
| 10,759,787 | B2 | 9/2020 | Lu et al. |
| 11,059,811 | B2 | 7/2021 | Lu et al. |
| 11,065,239 | B2 | 7/2021 | Ma et al. |
| 11,155,537 | B2 | 10/2021 | Creasy et al. |
| 11,390,614 | B2 | 7/2022 | Lu et al. |
| 2002/0128290 | A1 | 9/2002 | Ohshima et al. |
| 2003/0181759 | A1 | 9/2003 | Kodama et al. |
| 2004/0034047 | A1 | 2/2004 | Burri et al. |
| 2009/0131688 | A1 | 5/2009 | Burgos et al. |
| 2013/0053383 | A1 | 2/2013 | Duquenne et al. |
| 2014/0350013 | A1 | 11/2014 | Duquenne et al. |
| 2015/0065483 | A1 | 3/2015 | Kuntz et al. |
| 2016/0022684 | A1 | 1/2016 | Kuo et al. |
| 2018/0282313 | A1 | 10/2018 | Kanno et al. |
| 2018/0327394 | A1 | 11/2018 | Lu et al. |
| 2020/0262813 | A1 | 8/2020 | Zhou et al. |
| 2021/0309630 | A1 | 10/2021 | Mahajan et al. |
| 2022/0127568 | A1 | 4/2022 | Mclean et al. |
| 2022/0192984 | A1 | 6/2022 | Mclean et al. |
| 2022/0281872 | A1 | 9/2022 | Jin et al. |
| 2024/0325371 | A1 | 10/2024 | Zhang et al. |
| 2025/0092026 | A1 | 3/2025 | Chen et al. |

FOREIGN PATENT DOCUMENTS

| | | | |
|---|---|---|---|
| CN | 103987842 | A | 8/2014 |
| CN | 110179796 | A | 8/2019 |
| CN | 110590559 | A | 12/2019 |
| CN | 112007162 | A | 12/2020 |
| CN | 112870365 | A | 6/2021 |
| CN | 112870366 | A | 6/2021 |
| CN | 112870367 | A | 6/2021 |
| CN | 110563590 | B | 3/2022 |
| CN | 114456156 | A | 5/2022 |
| CN | 110483222 | B | 6/2022 |
| CN | 110498745 | B | 6/2022 |
| CN | 118084881 | A | 5/2024 |
| CN | 113649053 | B | 6/2024 |
| EP | 1848678 | B1 | 7/2015 |
| EP | 3378859 | B1 | 10/2019 |
| EP | 3626715 | A1 | 3/2020 |
| JP | 2011512341 | A | 4/2011 |
| JP | 6828229 | B2 | 2/2021 |
| WO | WO-2008/117241 | A2 | 10/2008 |
| WO | 2011140325 | A1 | 11/2011 |
| WO | 2012005805 | A1 | 1/2012 |
| WO | 2012050532 | A1 | 4/2012 |
| WO | 2012061602 | A1 | 5/2012 |
| WO | 2012118812 | A2 | 9/2012 |
| WO | 2012142504 | A1 | 10/2012 |
| WO | 2012142513 | A1 | 10/2012 |
| WO | 2013039988 | A1 | 3/2013 |
| WO | 2013049770 | A2 | 4/2013 |
| WO | 2013067300 | A1 | 5/2013 |
| WO | 2013173441 | A2 | 11/2013 |
| WO | WO-2014062732 | A1 | 4/2014 |
| WO | 2014097041 | A1 | 6/2014 |
| WO | WO-2014166820 | A1 | 10/2014 |
| WO | WO-2014168975 | A1 | 10/2014 |
| WO | 2014177982 | A1 | 11/2014 |
| WO | 2015141616 | A1 | 9/2015 |
| WO | WO-2015146159 | A1 | 10/2015 |
| WO | WO-2016007185 | A1 | 1/2016 |
| WO | WO-2016073903 | A1 | 5/2016 |
| WO | WO-2016201328 | A1 | 12/2016 |
| WO | WO-2017073335 | A1 | 5/2017 |
| WO | WO-2017084494 | A1 | 5/2017 |
| WO | WO-2018086589 | A1 | 5/2018 |
| WO | WO-2018133795 | A1 | 7/2018 |
| WO | WO-2018210296 | A1 | 11/2018 |
| WO | WO-2018210302 | A1 | 11/2018 |
| WO | WO-2019091450 | A1 | 5/2019 |
| WO | WO-2020063863 | A1 | 4/2020 |
| WO | WO-2020163813 | A1 | 8/2020 |
| WO | WO-2020163814 | A1 | 8/2020 |
| WO | WO-2020/190754 | A1 | 9/2020 |
| WO | WO-2020192652 | A1 | 10/2020 |
| WO | WO-2020210388 | A1 | 10/2020 |
| WO | WO-2020224607 | A1 | 11/2020 |
| WO | WO-2020228591 | A1 | 11/2020 |
| WO | WO-2021035194 | A1 | 2/2021 |
| WO | WO-2021063331 | A1 | 4/2021 |
| WO | WO-2021063332 | A1 | 4/2021 |
| WO | WO-2021063340 | A1 | 4/2021 |
| WO | WO-2021074620 | A1 | 4/2021 |
| WO | WO-2021142230 | A1 | 7/2021 |
| WO | WO-2021209520 | A1 | 10/2021 |
| WO | WO-2022058405 | A2 | 3/2022 |
| WO | WO-2022087230 | A1 | 4/2022 |
| WO | WO-2022179584 | A1 | 9/2022 |
| WO | WO-2022212746 | A1 | 10/2022 |
| WO | WO-2022212748 | A1 | 10/2022 |
| WO | WO-2022232435 | A1 | 11/2022 |
| WO | WO-2023011533 | A1 | 2/2023 |
| WO | WO-2023015164 | A1 | 2/2023 |
| WO | WO-2023025856 | A1 | 3/2023 |
| WO | WO-2023030299 | A1 | 3/2023 |
| WO | WO-2023055885 | A2 | 4/2023 |
| WO | WO-2023061446 | A1 | 4/2023 |
| WO | WO-2023061467 | A1 | 4/2023 |
| WO | WO-2023108563 | A1 | 6/2023 |
| WO | WO-2023114460 | A1 | 6/2023 |
| WO | WO-2023209591 | A1 | 11/2023 |
| WO | WO-2023212504 | A1 | 11/2023 |
| WO | WO-2023215449 | A1 | 11/2023 |
| WO | WO-2023215471 | A1 | 11/2023 |
| WO | WO-2023215482 | A1 | 11/2023 |
| WO | WO-2023240038 | A1 | 12/2023 |
| WO | WO-2023244917 | A1 | 12/2023 |
| WO | WO-2023244918 | A1 | 12/2023 |
| WO | WO-2023249714 | A1 | 12/2023 |
| WO | WO-2024015566 | A1 | 1/2024 |

OTHER PUBLICATIONS

Horig, H., Pullman, W. From bench to clinic and back: Perspective on the 1st IQPC Translational Research conference. Journal of Translational Medicine. Dec. 2004, 2, 44.

International Search Report issued Jan. 22, 2017 in International Application No. PCT/CN2016/104318.

Int'l Search Report issued Aug. 14, 2018 in Int'l Application No. PCT/CN2018/087272.

Morissette et al, Advanced Drug Delivery Reviews, vol. 56, pp. 275-300 (Year: 2004).

Abdel-Wahab, Omar, et al. "ASXL1 Mutations Promote Myeloid Transformation through Loss of PRC2-Mediated Gene Repression." Cancer Cell, vol. 22, No. 2, Aug. 2012, pp. 180-193. Crossref, https://doi.org/10.1016/j.ccr.2012.06.032.

Abdulla, Maysaa, et al. "Cell-of-origin Determined by Both Gene Expression Profiling and Immunohistochemistry Is the Strongest Predictor of Survival in Patients with Diffuse Large B-cell Lymphoma." American Journal of Hematology, vol. 95, No. 1, Nov. 2019, pp. 57-67. Portico, Crossref, https://doi.org/10.1002/ajh.25666.

Abrisqueta, Pau. "New Insights into First-Line Therapy in Diffuse Large B-Cell Lymphoma: Are We Improving Outcomes?" Journal of Clinical Medicine, vol. 13, No. 7, Mar. 2024, p. 1929. Crossref, https://doi.org/10.3390/jcm13071929.

Adams, Scott V., et al. "Racial Patterns of Peripheral T-Cell Lymphoma Incidence and Survival in the United States." Journal of Clinical Oncology, vol. 34, No. 9, Mar. 2016, pp. 963-971. Crossref, https://doi.org/10.1200/jco.2015.63.5540.

(56) References Cited

OTHER PUBLICATIONS

Al Khatib, MHD Ouis, et al. "Benefits and Challenges of Inhibiting EZH2 in Malignant Pleural Mesothelioma." Cancers, vol. 15, No. 5, Feb. 2023, p. 1537. Crossref, https://doi.org/10.3390/cancers15051537.

Alaggio, Rita, et al. "The 5th Edition of the World Health Organization Classification of Haematolymphoid Tumours: Lymphoid Neoplasms." Leukemia, vol. 36, No. 7, Jun. 2022, pp. 1720-1748. Crossref, https://doi.org/10.1038/s41375-022-01620-2.

Al-Hasani, Keith, et al. "EZH2 Inhibitors Promote ß-like Cell Regeneration in Young and Adult Type 1 Diabetes Donors." Signal Transduction and Targeted Therapy, vol. 9, No. 1, Jan. 2024. Crossref, https://doi.org/10.1038/s41392-023-01707-x.

Alldredge, Jill K., and Ramez N. Eskander. "EZH2 Inhibition in ARID1A Mutated Clear Cell and Endometrioid Ovarian and Endometrioid Endometrial Cancers." Gynecologic Oncology Research and Practice, vol. 4, No. 1, Oct. 2017. Crossref, https://doi.org/10.1186/s40661-017-0052-y.

Amengual, J. E., et al. "ETCTN P10500: Phase 1/Expansion Study of Tazemetostat Plus Belinostat for the Treatment of Relapsed or Refractory Lymphoma." Hematological Oncology, vol. 41, No. S2, Jun. 2023, pp. 833-834. Portico, Crossref, https://doi.org/10.1002/hon.3166_ot14.

An, Ran, et al. "EZH½ as Targets for Cancer Therapy." Cancer Gene Therapy, vol. 30, No. 2, Nov. 2022, pp. 221-235. Crossref, https://doi.org/10.1038/s41417-022-00555-1.

Archer, Clive B., et al. "Management of Cutaneous T-Cell Lymphoma." Clinical Medicine, vol. 12, No. 2, Apr. 2012, pp. 160-164. Crossref, https://doi.org/10.7861/clinmedicine. 12-2-160.

Argon, Evren Kocabas, et al. "Abstract CT170: Phase 1 Study to Characterize the Pharmacokinetics and Safety of Tazemetostat in b-Cell Lymphomas or Advanced Solid Tumors." Cancer Research, vol. 80, No. 16_Supplement, Aug. 2020, pp. CT170-CT170. Crossref, https://doi.org/10.1158/1538-7445.am2020-ct170.

Atallah-Yunes, Suheil Albert, et al. "Epigenetic Aberrations and Targets in Peripheral T-Cell Lymphoma." Clinical Lymphoma Myeloma and Leukemia, vol. 22, No. 9, Sep. 2022, pp. 659-665. Crossref, https://doi.org/10.1016/j.clml.2022.04.015.

Bagnato, Gianmarco, et al. "Successful Bridging to Allogeneic Transplantation With Valemetostat in Two Refractory/Relapsed Peripheral T-Cell Lymphoma Patients." Mediterranean Journal of Hematology and Infectious Diseases, vol. 16, No. 1, Jan. 2024, p. e2024004. Crossref, https://doi.org/10.4084/mjhid.2024.004.

Barghout, Samir H., et al. "Chemical Biology and Pharmacology of Histone Lysine Methylation Inhibitors." Biochimica et Biophysica Acta (BBA)—Gene Regulatory Mechanisms, vol. 1865, No. 6, Aug. 2022, p. 194840. Crossref, https://doi.org/10.1016/j.bbagrm.2022.194840.

Bashore, Frances M., et al. "Protac Linkerology Leads to an Optimized Bivalent Chemical Degrader of Polycomb Repressive Complex 2 (PRC2) Components." ACS Chemical Biology, vol. 18, No. 3, Mar. 2023, pp. 494-507. Crossref, https://doi.org/10.1021/acschembio.2c00804.

Batlevi, C. L., et al. "Characteristics of Patients Achieving Complete or Partial Response (CR/PR) With Tazemetostat (TAZ) in Wild-Type Relapsed/Refractory (R/R) Follicular Lymphoma (FL)." Hematological Oncology, vol. 39, No. S2, Jun. 2021. Portico, Crossref, https://doi.org/10.1002/hon.21_2880.

Batlevi, Connie Lee, et al. "Updated Interim Analysis of the Randomized Phase 1b/3 Study of Tazemetostat in Combination with Lenalidomide and Rituximab in Patients with Relapsed/Refractory Follicular Lymphoma." Journal of Clinical Oncology, vol. 40, No. 16_suppl, Jun. 2022, pp. 7572-7572. Crossref, https://doi.org/10.1200/jco.2022.40.16_suppl.7572.

Béguelin, Wendy, et al. "EZH2 and BCL6 Cooperate to Assemble CBX8-BCOR Complex to Repress Bivalent Promoters, Mediate Germinal Center Formation and Lymphomagenesis." Cancer Cell, vol. 30, No. 2, Aug. 2016, pp. 197-213. Crossref, https://doi.org/10.1016/j.ccell.2016.07.006.

Béguelin, Wendy, et al. "EZH2 Enables Germinal Centre Formation through Epigenetic Silencing of CDKN1A and an Rb-E2F1 Feedback Loop." Nature Communications, vol. 8, No. 1, Oct. 2017. Crossref, https://doi.org/10.1038/s41467-017-01029-x.

Béguelin, Wendy, et al. "EZH2 Is Required for Germinal Center Formation and Somatic EZH2 Mutations Promote Lymphoid Transformation." Cancer Cell, vol. 23, No. 5, May 2013, pp. 677-692. Crossref, https://doi.org/10.1016/j.ccr.2013.04.011.

Béguelin, Wendy, et al. "Mutant EZH2 Induces a Pre-Malignant Lymphoma Niche by Reprogramming the Immune Response." Cancer Cell, vol. 37, No. 5, May 2020, pp. 655-673.e11. Crossref, https://doi.org/10.1016/j.ccell.2020.04.004.

Bekric, Dino, et al. "Evaluation of Tazemetostat as a Therapeutically Relevant Substance in Biliary Tract Cancer." Cancers, vol. 15, No. 5, Mar. 2023, p. 1569. Crossref, https://doi.org/10.3390/cancers15051569.

Bellas, Carmen, et al. "Immunohistochemical and Molecular Characteristics with Prognostic Significance in Diffuse Large B-Cell Lymphoma." PLoS One, edited by Syed A. Aziz, vol. 9, No. 6, Jun. 2014, p. e98169. Crossref, https://doi.org/10.1371/journal.pone.0098169.

Bellei, Monica, et al. "The Outcome of Peripheral T-Cell Lymphoma Patients Failing First-Line Therapy: A Report from the Prospective, International T-Cell Project." Haematologica, vol. 103, No. 7, Mar. 2018, pp. 1191-1197. Crossref, https://doi.org/10.3324/haematol.2017.186577.

Benevolo Savelli, Corrado, et al. "Advances in Hodgkin Lymphoma Treatment: From Molecular Biology to Clinical Practice." Cancers, vol. 16, No. 10, May 2024, p. 1830. Crossref, https://doi.org/10.3390/cancers16101830.

Blakemore, S. J., et al. "Preliminary Evidence of a Molecular Predictor of Tazemetostat Response, Beyond EZH2 Mutation, in NHL Patients Via Characterization of Archive Tumor and Circulating Tumor DNA." Hematological Oncology, vol. 35, No. S2, Jun. 2017, pp. 159-160. Portico, Crossref, https://doi.org/10.1002/hon.2438_14.

Bosisio, Francesca M., and Lorenzo Cerroni. "Expression of T-Follicular Helper Markers in Sequential Biopsies of Progressive Mycosis Fungoides and Other Primary Cutaneous T-Cell Lymphomas." The American Journal of Dermatopathology, vol. 37, No. 2, Feb. 2015, pp. 115-121. Crossref, https://doi.org/10.1097/dad.0000000000000258.

Boss, Isaac W., and Ari M. Melnick. "VII. Are Lymphomas Driven by Epigenetic Lesions?" Hematological Oncology, vol. 33, No. S1, Jun. 2015, pp. 42-45. Portico, Crossref, https://doi.org/10.1002/hon.2215.

Broccoli, Alessandro, et al. "Peripheral T-Cell Lymphomas: Focusing on Novel Agents in Relapsed and Refractory Disease." Cancer Treatment Reviews, vol. 60, Nov. 2017, pp. 120-129. Crossref, https://doi.org/10.1016/j.ctrv.2017.09.002.

Buteyn, Nathaniel J., et al. EZH2-Driven Immune Evasion Defines High-Risk Pediatric AML with t(16;21) FUS::ERG Gene Fusion. May 2024. Crossref, https://doi.org/10.1101/2024.05.14.594150.

Caganova, Marieta, et al. "Germinal Center Dysregulation by Histone Methyltransferase EZH2 Promotes Lymphomagenesis." Journal of Clinical Investigation, vol. 123, No. 12, Nov. 2013, pp. 5009-5022. Crossref, https://doi.org/10.1172/jci70626.

Cai, Jin, et al. "Design, Synthesis and Activity Evaluation of Quinolinone Derivatives as EZH2 Inhibitors." Bioorganic & Medicinal Chemistry Letters, vol. 105, Jun. 2024, p. 129726. Crossref, https://doi.org/10.1016/j.bmcl.2024.129726.

Cai, Zhuo Ran, et al. "Incidence Trends of Primary Cutaneous T-Cell Lymphoma in the US From 2000 to 2018." JAMA Oncology, vol. 8, No. 11, Nov. 2022, p. 1690. Crossref, https://doi.org/10.1001/jamaoncol.2022.3236.

Campo, Elias, et al. "The International Consensus Classification of Mature Lymphoid Neoplasms: A Report from the Clinical Advisory Committee." Blood, vol. 140, No. 11, Sep. 2022, pp. 1229-1253. Crossref, https://doi.org/10.1182/blood.2022015851.

Campolo, Michela, et al. "EZH2 Inhibition to Counteract Oral Cancer Progression through Wnt/ß-Catenin Pathway Modulation." Pharmaceuticals, vol. 17, No. 8, Aug. 2024, p. 1102. Crossref, https://doi.org/10.3390/ph17081102.

(56) References Cited

OTHER PUBLICATIONS

Cao, Ruolin, et al. "Recent Advances in Enhancer of Zeste Homolog 2 Inhibitors: Structural Insights and Therapeutic Applications." Bioorganic Chemistry, vol. 154, Jan. 2025, p. 108070. Crossref, https://doi.org/10.1016/j.bioorg.2024.108070.
Chang, Esther Wei Yin, et al. "Novel Clinical Risk Stratification and Treatment Strategies in Relapsed/Refractory Peripheral T-Cell Lymphoma." Journal of Hematology & Oncology, vol. 17, No. 1, Jun. 2024. Crossref, https://doi.org/10.1186/s13045-024-01560-7.
Chatterjee, Shankha S., et al. "Increased Translation Driven by Non-Canonical EZH2 Creates a Synthetic Vulnerability in Enzalutamide-Resistant Prostate Cancer." Nature Communications, vol. 15, No. 1, Nov. 2024. Crossref, https://doi.org/10.1038/s41467-024-53874-2.
Chebly, Alain, et al. "Diagnosis and Treatment of Lymphomas in the Era of Epigenetics." Blood Reviews, vol. 48, Jul. 2021, p. 100782. Crossref, https://doi.org/10.1016/j.blre.2020.100782.
Chen, Lingli, et al. "Compound AC1Q3QWB Upregulates CDKN1A and SOX17 by Interrupting the Hotair-EZH2 Interaction and Enhances the Efficacy of Tazemetostat in Endometrial Cancer." Cancer Letters, vol. 578, Dec. 2023, p. 216445. Crossref, https://doi.org/10.1016/j.canlet.2023.216445.
Chen, Yue, et al. "Five Trends of China's Pharmaceutical Industry in 2022." Acta Pharmaceutica Sinica B, vol. 13, No. 6, Jun. 2023, pp. 2812-2814. Crossref, https://doi.org/10.1016/j.apsb.2023.04.004.
Cheng, Yuxi, et al. "Polycomb Repressive Complex 2 and Its Core Component EZH2: Potential Targeted Therapeutic Strategies for Head and Neck Squamous Cell Carcinoma." Clinical Epigenetics, vol. 16, No. 1, Apr. 2024. Crossref, https://doi.org/10.1186/s13148-024-01666-2.
Cheson, Bruce D., et al. "Recommendations for Initial Evaluation, Staging, and Response Assessment of Hodgkin and Non-Hodgkin Lymphoma: The Lugano Classification." Journal of Clinical Oncology, vol. 32, No. 27, Sep. 2014, pp. 3059-3067. Crossref, https://doi.org/10.1200/jco.2013.54.8800.
Chi, Susan N., et al. "Phase I Study of Tazemetostat, an Enhancer of Zeste Homolog-2 Inhibitor, in Pediatric Pts with Relapsed/Refractory Integrase Interactor 1-Negative Tumors." Journal of Clinical Oncology, vol. 38, No. 15_suppl, May 2020, pp. 10525-10525. Crossref, https://doi.org/10.1200/jco.2020.38.15_suppl.10525.
Chi, Susan N., et al. "Tazemetostat in Patients with Tumors with Alterations in EZH2 or the SWI/SNF Complex: Results from NCI-COG Pediatric Match Trial Arm C (APEC1621C)." Journal of Clinical Oncology, vol. 40, No. 16_suppl, Jun. 2022, pp. 10009-10009. Crossref, https://doi.org/10.1200/jco.2022.40.16_suppl.10009.
Chibaya, Loretah, et al. "EZH2 Inhibition Remodels the Inflammatory Senescence-Associated Secretory Phenotype to Potentiate Pancreatic Cancer Immune Surveillance." Nature Cancer, vol. 4, No. 6, May 2023, pp. 872-892. Crossref, https://doi.org/10.1038/s43018-023-00553-8.
Chu, Liping, et al. "EZH2 W113C Is a Gain-of-Function Mutation in B-Cell Lymphoma Enabling Both PRC2 Methyltransferase Activation and Tazemetostat Resistance." Journal of Biological Chemistry, vol. 299, No. 4, Apr. 2023, p. 103073. Crossref, https://doi.org/10.1016/j.jbc.2023.103073.
Collinson, Adam, et al. "Deletion of the Polycomb-Group Protein EZH2 Leads to Compromised Self-Renewal and Differentiation Defects in Human Embryonic Stem Cells." Cell Reports, vol. 17, No. 10, Dec. 2016, pp. 2700-2714. Crossref, https://doi.org/10.1016/j.celrep.2016.11.032.
Crotty, Shane. "Follicular Helper CD4 T Cells (TFH)." Annual Review of Immunology, vol. 29, No. 1, Apr. 2011, pp. 621-663. Crossref, https://doi.org/10.1146/annurev-immunol-031210-101400.
D'Amore, F., et al. "Peripheral T-Cell Lymphomas: ESMO Clinical Practice Guidelines for Diagnosis, Treatment and Follow-Up." Annals of Oncology, vol. 26, Sep. 2015, pp. v108-15. Crossref, https://doi.org/10.1093/annonc/mdv201.
De Leval, Laurence, et al. "A Practical Approach to the Modern Diagnosis and Classification of T- and NK-Cell Lymphomas." Blood, vol. 144, No. 18, Oct. 2024, pp. 1855-1872. Crossref, https://doi.org/10.1182/blood.2023021786.
Dockerill, Milly, et al. "Targeting PRC2 for the Treatment of Cancer: An Updated Patent Review (2016-2020)." Expert Opinion on Therapeutic Patents, vol. 31, No. 2, Jan. 2021, pp. 119-135. Crossref, https://doi.org/10.1080/13543776.2021.1841167.
Drescher, Charles, et al. "EZH2/EZH1 Inhibitor Tulmimetostat (CPI-0209) in Patients with Advanced Solid Tumors or Hematologic Malignancies: Preliminary Phase II Results." Journal of Clinical Oncology, vol. 41, No. 16_suppl, Jun. 2023, pp. 3094-3094. Crossref, https://doi.org/10.1200/jco.2023.41.16_suppl.3094.
Du, Jun, et al. "Comparison of Allogeneic Stem Cell Transplant and Autologous Stem Cell Transplant in Refractory or Relapsed Peripheral T-Cell Lymphoma." JAMA Network Open, vol. 4, No. 5, May 2021, p. e219807. Crossref, https://doi.org/10.1001/jamanetworkopen.2021.9807.
Duan, Ran, et al. "EZH2: A Novel Target for Cancer Treatment." Journal of Hematology & Oncology, vol. 13, No. 1, Jul. 2020. Crossref, https://doi.org/10.1186/s13045-020-00937-8.
DuCote, Tanner J., et al. "EZH2 Inhibition Promotes Tumor Immunogenicity in Lung Squamous Cell Carcinomas." Cancer Research Communications, Jan. 2024. Crossref, https://doi.org/10.1158/2767-9764.crc-23-0399.
DuCote, Tanner J., et al. EZH2 Inhibition Promotes Tumor Immunogenicity in Lung Squamous Cell Carcinomas. Jun. 2023. Crossref, https://doi.org/10.1101/2023.06.06.543919.
Dummer, Reinhard, et al. "Prospective International Multicenter Phase II Trial of Intravenous Pegylated Liposomal Doxorubicin Monochemotherapy in Patients With Stage IIB, IVA, or IVB Advanced Mycosis Fungoides: Final Results From EORTC 21012." Journal of Clinical Oncology, vol. 30, No. 33, Nov. 2012, pp. 4091-4097. Crossref, https://doi.org/10.1200/jco.2011.39.8065.
Dumont, Maëlle, et al. "Allogeneic Hematopoietic Stem Cell Transplantation in Cutaneous T-Cell Lymphomas." Cancers, vol. 12, No. 10, Oct. 2020, p. 2856. Crossref, https://doi.org/10.3390/cancers12102856.
Durand, Marie-Alice, et al. "Distinct Regulation of EZH2 and Its Repressive H3K27me3 Mark in Polyomavirus-Positive and -Negative Merkel Cell Carcinoma." Journal of Investigative Dermatology, vol. 143, No. 10, Oct. 2023, pp. 1937-1946.e7. Crossref, https://doi.org/10.1016/j.jid.2023.02.038.
Eich, Marie-Lisa, et al. "EZH2-Targeted Therapies in Cancer: Hype or a Reality." Cancer Research, vol. 80, No. 24, Dec. 2020, pp. 5449-5458. Crossref, https://doi.org/10.1158/0008-5472.can-20-2147.
Ennishi, Daisuke, et al. "Molecular and Genetic Characterization of MHC Deficiency Identifies EZH2 as Therapeutic Target for Enhancing Immune Recognition." Cancer Discovery, vol. 9, No. 4, Apr. 2019, pp. 546-563. Crossref, https://doi.org/10.1158/2159-8290.cd-18-1090.
Entezari, Maliheh, et al. "The Pharmacological and Biological Importance of EZH2 Signaling in Lung Cancer." Biomedicine & Pharmacotherapy, vol. 160, Apr. 2023, p. 114313. Crossref, https://doi.org/10.1016/j.biopha.2023.114313.
Epstein-Peterson, Zachary D., and Steven M. Horwitz. "Molecularly Targeted Therapies for Relapsed and Refractory Peripheral T-Cell Lymphomas." Seminars in Hematology, vol. 58, No. 2, Apr. 2021, pp. 78-84. Crossref, https://doi.org/10.1053/j.seminhematol.2021.02.004.
Extended European Search Report issued Feb. 4, 2021 in European Application No. 18802340.2.
Fang, Jinyong, et al. "The Epigenetic Role of EZH2 in Acute Myeloid Leukemia." PeerJ, vol. 12, Dec. 2024, p. e18656. Portico, Crossref, https://doi.org/10.7717/peerj.18656.
Fang, Minggang, et al. "EZH2 Inhibition Reactivates Epigenetically Silenced FMR1 and Normalizes Molecular and Electrophysiological Abnormalities in Fragile X Syndrome Neurons." Frontiers in Neuroscience, vol. 18, Feb. 2024. Crossref, https://doi.org/10.3389/fnins.2024.1348478.

(56) References Cited

OTHER PUBLICATIONS

Feldman, Andrew L., et al. "Classification and Diagnostic Evaluation of Nodal T- and NK-Cell Lymphomas." Virchows Archiv, vol. 482, No. 1, Oct. 2022, pp. 265-279. Crossref, https://doi.org/10.1007/s00428-022-03412-6.

Feng, Kaichao, et al. "Phase I Study of the Bifunctional Anti-PD-L1/TGF-BRII Agent SHR-1701 Combined with SHR2554, an EZH2 Inhibitor, in Patients with Previously Treated Advanced Lymphoma and Solid Tumors." Journal of Clinical Oncology, vol. 41, No. 16_suppl, Jun. 2023, pp. 2507-2507. Crossref, https://doi.org/10.1200/jco.2023.41.16_suppl.2507.

Fenu, Elena M., et al. "Primary Cutaneous T-follicular Helper Lymphoma." EJHaem, vol. 4, No. 4, Jul. 2023, pp. 1176-1178. Portico, Crossref, https://doi.org/10.1002/jha2.737.

Fernández-Serrano, Miranda, et al. "Histone Modifications and Their Targeting in Lymphoid Malignancies." International Journal of Molecular Sciences, vol. 23, No. 1, Dec. 2021, p. 253. Crossref, https://doi.org/10.3390/ijms23010253.

Fischetti, Irene, et al. "Combined Therapy Targeting AR and EZH2 Curbs Castration-Resistant Prostate Cancer Enhancing Anti-Tumor T-Cell Response." Epigenomics, vol. 16, No. 9, Mar. 2024, pp. 653-670. Crossref, https://doi.org/10.2217/epi-2023-0374.

Foss, Francine M., and Michael Girardi. "Mycosis Fungoides and Sezary Syndrome." Hematology/Oncology Clinics of North America, vol. 31, No. 2, Apr. 2017, pp. 297-315. Crossref, https://doi.org/10.1016/j.hoc.2016.11.008.

Francine M. Foss, et al., "A Global Phase 2 Study of Valemetostat Tosylate (Valemetostat) in Patients with Relapsed or Refractory (R/R) Peripheral T-Cell Lymphoma (PTCL), Including R/R Adult T-Cell Leukemia/Lymphoma (ATL)—Valentine-PTCL01", Blood, 138:2533-2535, (2021).

Fukae, Masato, et al. "Bayesian Sparse Regression for Exposure—Response Analyses of Efficacy and Safety Endpoints to Justify the Clinical Dose of Valemetostat for Adult T-cell Leukemia/Lymphoma." CPT: Pharmacometrics & Systems Pharmacology, vol. 13, No. 10, Aug. 2024, pp. 1655-1669. Portico, Crossref, https://doi.org/10.1002/psp4.13203.

Fukae, Masato, et al. "Population Pharmacokinetics of Total and Unbound Valemetostat and Platelet Dynamics in Healthy Volunteers and Patients with Non-Hodgkin Lymphoma." CPT: Pharmacometrics & Systems Pharmacology, vol. 13, No. 10, Jul. 2024, pp. 1641-1654. Portico, Crossref, https://doi.org/10.1002/psp4.13201.

Gallardo, Amador, et al. "EZH2 Represses Mesenchymal Genes and Upholds the Epithelial State of Breast Carcinoma Cells." Cell Death & Disease, vol. 15, No. 8, Aug. 2024. Crossref, https://doi.org/10.1038/s41419-024-07011-y.

Gallardo, Amador, et al. EZH2 Represses Mesenchymal Genes and Upholds the Epithelial State of Breast Carcinoma Cells. Mar. 2023. Crossref, https://doi.org/10.1101/2023.03.13.532335.

Gan, Lu, et al. "Epigenetic Regulation of Cancer Progression by EZH2: From Biological Insights to Therapeutic Potential." Biomarker Research, vol. 6, No. 1, Mar. 2018. Crossref, https://doi.org/10.1186/s40364-018-0122-2.

Garber, Ken. "Histone-Writer Cancer Drugs Enter Center Stage." Nature Biotechnology, vol. 38, No. 8, Aug. 2020, pp. 909-912. Crossref, https://doi.org/10.1038/s41587-020-0621-1.

Gardner, Eric E., et al. "Chemosensitive Relapse in Small Cell Lung Cancer Proceeds through an EZH2-SLFN11 Axis." Cancer Cell, vol. 31, No. 2, Feb. 2017, pp. 286-299. Crossref, https://doi.org/10.1016/j.ccell.2017.01.006.

Gaut, Daria, et al. "B-Cell Acute Lymphoblastic Leukemia as a Secondary Malignancy Following Diffuse Large B-Cell Lymphoma." Hematology Reports, vol. 11, No. 2, Jun. 2019, p. 8100. Crossref, https://doi.org/10.4081/hr.2019.8100.

Ghione, Paola, et al. "T Follicular Helper Phenotype Predicts Response to Histone Deacetylase Inhibitors in Relapsed/Refractory Peripheral T-Cell Lymphoma." Blood Advances, vol. 4, No. 19, Sep. 2020, pp. 4640-4647. Crossref, https://doi.org/10.1182/bloodadvances.2020002396.

Gilson, D., et al. "British Association of Dermatologists and U.K. Cutaneous Lymphoma Group Guidelines for the Management of Primary Cutaneous Lymphomas 2018." British Journal of Dermatology, vol. 180, No. 3, Dec. 2018, pp. 496-526. Portico, Crossref, https://doi.org/10.1111/bjd.17240.

Giri, Smith, et al. "Risk of Second Primary Malignancies in Patients With Follicular Lymphoma: A United States Population-Based Study." Clinical Lymphoma Myeloma and Leukemia, vol. 17, No. 9, Sep. 2017, pp. 569-574. Crossref, https://doi.org/10.1016/j.clml.2017.06.028.

Göbel, Camiel, et al. Targeting DOT1L and EZH2 Synergizes in Breaking the Germinal Center Identity of Diffuse Large B Cell Lymphoma. Jun. 2024. Crossref, https://doi.org/10.1101/2024.06.05.597556.

Gold, Sarah, and Ali Shilatifard. "Epigenetic therapies targeting histone lysine methylation: complex mechanisms and clinical challenges." The Journal of Clinical Investigation 134.20 (2024).

Gounder, Mrinal, et al. "Tazemetostat in Advanced Epithelioid Sarcoma with Loss of INI1/SMARCB1: An International, Open-Label, Phase 2 Basket Study." The Lancet Oncology, vol. 21, No. 11, Nov. 2020, pp. 1423-1432. Crossref, https://doi.org/10.1016/s1470-2045(20)30451-4.

Groß, Elisabeth, et al. "SAM-Competitive EZH2-Inhibitors Induce Platinum Resistance by EZH2-Independent Induction of ABC-Transporters." Cancers, vol. 15, No. 11, Jun. 2023, p. 3043. Crossref, https://doi.org/10.3390/cancers 15113043.

Grover, Natalie S., et al. "The Optimal Management of Relapsed and Refractory Hodgkin Lymphoma: Post—Brentuximab and Checkpoint Inhibitor Failure." Hematology, vol. 2023, No. 1, Dec. 2023, pp. 510-518. Crossref, https://doi.org/10.1182/hematology.2023000450.

Guo, Chunming, et al. "Targeting the PRC2-Dependent Epigenetic Program Alleviates Urinary Tract Infections." IScience, vol. 26, No. 6, Jun. 2023, p. 106925. Crossref, https://doi.org/10.1016/j.isci.2023.106925.

Guo, Shuangping, et al. "Clinicopathological Features of Primary Diffuse Large B-cell Lymphoma of the Central Nervous System—Strong EZH2 Expression Implying Diagnostic and Therapeutic Implication." APMIS, vol. 124, No. 12, Nov. 2016, pp. 1054-1062. Portico, Crossref, https://doi.org/10.1111/apm.12623.

Guo, Yunyun, et al. "Regulation of EZH2 Protein Stability: New Mechanisms, Roles in Tumorigenesis, and Roads to the Clinic." EBioMedicine, vol. 100, Feb. 2024, p. 104972. Crossref, https://doi.org/10.1016/j.ebiom.2024.104972.

Guo, Zhirong, et al. "Design and Synthesis of Dual EZH2/BRD4 Inhibitors to Target Solid Tumors." Journal of Medicinal Chemistry, vol. 65, No. 9, May 2022, pp. 6573-6592. Crossref, https://doi.org/10.1021/acs.jmedchem.1c01876.

Hanaki, Shunsuke, and Midori Shimada. "Targeting EZH2 as Cancer Therapy." The Journal of Biochemistry, vol. 170, No. 1, Feb. 2021, pp. 1-4. Crossref, https://doi.org/10.1093/jb/mvab007.

Hara, Natsumi, and Yu Sawada. "Epigenetics of Cutaneous T-Cell Lymphomas." International Journal of Molecular Sciences, vol. 23, No. 7, Mar. 2022, p. 3538. Crossref, https://doi.org/10.3390/ijms23073538.

Hashemi, Mehrdad, et al. "EZH2 as a Potential Therapeutic Target for Gastrointestinal Cancers." Pathology—Research and Practice, vol. 253, Jan. 2024, p. 154988. Crossref, https://doi.org/10.1016/j.prp.2023.154988.

Hathuc, Vivian, and Friederike Kreisel. "Genetic Landscape of Peripheral T-Cell Lymphoma." Life, vol. 12, No. 3, Mar. 2022, p. 410. Crossref, https://doi.org/10.3390/life12030410.

Hein, Kyaw Z., et al. "Therapeutic Role of Synthetic Lethality in ARID1A-Deficient Malignancies." Journal of Immunotherapy and Precision Oncology, vol. 7, No. 1, Feb. 2024, pp. 41-52. Crossref, https://doi.org/10.36401/jipo-22-37.

Hong, Huangming, et al. "A Multicenter, Open-Label, Single-Arm, Phase lb Clinical Trial of HH2853 in the Treatment of Patients with Relapsed and/or Refractory Peripheral T-Cell Lymphoma." Blood, vol. 142, No. Supplement 1, Nov. 2023, pp. 304-304. Crossref, https://doi.org/10.1182/blood-2023-180372.

(56) References Cited

OTHER PUBLICATIONS

Hong, Seong Hwi, et al. "Inhibition of EZH2 Exerts Antitumorigenic Effects in Renal Cell Carcinoma via LATS1." FEBS Open Bio, vol. 13, No. 4, Mar. 2023, pp. 724-735. Portico, Crossref, https://doi.org/10.1002/2211-5463.13579.
Honma, Daisuke, et al. "DS-3201, a Potent EZH1/2 Dual Inhibitor, Demonstrates Antitumor Activity Against Non-Hodgkin Lymphoma (NHL) Regardless of EZH2 Mutation." Blood, vol. 132, No. Supplement 1, Nov. 2018, pp. 2217-2217. Crossref, https://doi.org/10.1182/blood-2018-99-113379.
Honma, Daisuke, et al. "Novel Orally Bioavailable EZH½ Dual Inhibitors with Greater Antitumor Efficacy than an EZH2 Selective Inhibitor." Cancer Science, vol. 108, No. 10, Aug. 2017, pp. 2069-2078. Portico, Crossref, https://doi.org/10.1111/cas.13326.
Horwitz, Steven M., et al. "Efficacy and Safety of Valemetostat Monotherapy in Patients with Relapsed or Refractory Peripheral T-Cell Lymphomas: Primary Results of the Phase 2 Valentine-PTCL01 Study." Blood, vol. 142, No. Supplement 1, Nov. 2023, pp. 302-302. Crossref, https://doi.org/10.1182/blood-2023-179304.
Horwitz, Steven M., et al. "T-Cell Lymphomas, Version 2.2022, NCCN Clinical Practice Guidelines in Oncology." Journal of the National Comprehensive Cancer Network, vol. 20, No. 3, Mar. 2022, pp. 285-308. Crossref, https://doi.org/10.6004/jnccn.2022.0015.
Horwitz, Steven, et al. "Brentuximab Vedotin with Chemotherapy for CD30-Positive Peripheral T-Cell Lymphoma (ECHELON-2): A Global, Double-Blind, Randomised, Phase 3 Trial." The Lancet, vol. 393, No. 10168, Jan. 2019, pp. 229-240. Crossref, https://doi.org/10.1016/s0140-6736(18)32984-2.
Horwitz, Steven, et al. "TCL-394 Valemetostat for Patients With R/R Peripheral T-Cell Lymphomas (PTCLs): A Phase 2 Valentine-PTCL01 Trial." Clinical Lymphoma Myeloma and Leukemia, vol. 24, Sep. 2024, pp. S524-S525. Crossref, https://doi.org/10.1016/s2152-2650(24)01618-5.
Hou, Yingqin, and Peng Wu. "Abstract LB339: Transient EZH2 Suppression by Tazemetostat during in Vitro Expansion Maintains T Cell Stemness and Improves Adoptive T Cell Therapy." Cancer Research, vol. 84, No. 7_Supplement, Apr. 2024, pp. LB339-LB339. Crossref, https://doi.org/10.1158/1538-7445.am2024-lb339.
Hou, Yingqin, et al. Transient EZH2 Suppression by Tazemetostat duringin VitroExpansion Maintains T Cell Stemness and Improves Adoptive T Cell Therapy. Feb. 2023. Crossref, https://doi.org/10.1101/2023.02.07.527459.
Hristov, Alexandra C., et al. "Cutaneous T-cell Lymphomas: 2023 Update on Diagnosis, Risk-stratification, and Management." American Journal of Hematology, vol. 98, No. 1, Oct. 2022, pp. 193-209. Portico, Crossref, https://doi.org/10.1002/ajh.26760.
https://clinicaltrials.gov/study/NCT06093945.
https://clinicaltrials.gov/study/NCT06122389?term=NCT06122389&rank=1.
https://clinicaltrials.gov/study/NCT06519526?term=NCT06519526&rank=1.
https://seekingalpha.com/article/4598609-daiichi-sankyo-company-limited-dskyf-q4-2022-earnings-call-transcript.
https://www.onclive.com/view/tazemetostat-nda-receives-priority-review-in-china-for-r-r-follicular-lymphoma.
https://www.oncologypipeline.com/apexonco/ipsen-casts-doubt-pfizers-prostate-plan Jacob Plieth, Ipsen casts doubt on Pfizer's prostate plan, ApexOnco.
https://www.pharmaceutical-technology.com/news/eisai-national-cancer-center-tazemetostat/.
Hu, H., et al. "1941P Preliminary Efficacy and Safety of SHR-2554 in Advanced Epithelioid Sarcoma: A Phase II Trial." Annals of Oncology, vol. 34, Oct. 2023, p. S1042. Crossref, https://doi.org/10.1016/j.annonc.2023.09.1170.
Huang, Jiaqi, et al. "Easy or Not—The Advances of EZH2 in Regulating T Cell Development, Differentiation, and Activation in Antitumor Immunity." Frontiers in Immunology, vol. 12, Oct. 2021. Crossref, https://doi.org/10.3389/fimmu.2021.741302.
Huang, Xun, et al. "Targeting Epigenetic Crosstalk as a Therapeutic Strategy for EZH2-Aberrant Solid Tumors." Cell, vol. 175, No. 1, Sep. 2018, pp. 186-199.e19. Crossref, https://doi.org/10.1016/j.cell.2018.08.058.
Huang, Yeying, et al. EZH2 Synergizes with BRD4-NUT to Drive NUT Carcinoma Growth through Silencing of Key Tumor Suppressor Genes. Aug. 2023. Crossref, https://doi.org/10.1101/2023.08.15.553204.
International Search Report (and English translation thereof) dated Dec. 15, 2022 issued in International Application No. PCT/CN2022/125302.
International Search Report (and English translation thereof) dated Nov. 28, 2022 issued in International Application No. PCT/CN2022/115763.
Ishitsuka, K., et al. "First-in-Human Study of the EZH1 and EZH2 Dual Inhibitor Valemetostat Tosylate (DS-3201B) in Patients With Relapsed or Refractory Non-Hodgkin Lymphomas." Hematological Oncology, vol. 39, No. S2, Jun. 2021. Portico, Crossref, https://doi.org/10.1002/hon.14_2879.
Isshiki, Yusuke, and Ari Melnick. "Epigenetic Mechanisms of Therapy Resistance in Diffuse Large B Cell Lymphoma (DLBCL)." Current Cancer Drug Targets, vol. 21, No. 4, Apr. 2021, pp. 274-282. Crossref, https://doi.org/10.2174/1568009620666210106122750.
Isshiki, Yusuke, et al. "EZH2 Inhibition Enhances T Cell Immunotherapies by Inducing Lymphoma Immunogenicity and Improving T Cell Function." Cancer Cell, vol. 43, No. 1, Jan. 2025, pp. 49-68.e9. Crossref, https://doi.org/10.1016/j.ccell.2024.11.006.
Italiano, Antoine, et al. "Tazemetostat, an EZH2 Inhibitor, in Relapsed or Refractory B-Cell Non-Hodgkin Lymphoma and Advanced Solid Tumours: A First-in-Human, Open-Label, Phase 1 Study." The Lancet Oncology, vol. 19, No. 5, May 2018, pp. 649-659. Crossref, https://doi.org/10.1016/s1470-2045(18)30145-1.
Izutsu, Koji, et al. "An Open-Label, Single-Arm Phase 2 Trial of Valemetostat for Relapsed or Refractory Adult T-Cell Leukemia/Lymphoma." Blood, vol. 141, No. 10, Mar. 2023, pp. 1159-1168. Crossref, https://doi.org/10.1182/blood.2022016862.
Izutsu, Koji, et al. "Phase II Study of Tazemetostat for Relapsed or Refractory B-cell Non-Hodgkin Lymphoma with EZH2 Mutation in Japan." Cancer Science, vol. 112, No. 9, Jul. 2021, pp. 3627-3635. Portico, Crossref, https://doi.org/10.1111/cas.15040.
Izutsu, Koji, et al. "Tazemetostat for Relapsed/Refractory B-Cell Non-Hodgkin Lymphoma with EZH2 Mutation in Japan: 3-Year Follow-up for a Phase II Study." International Journal of Hematology, vol. 120, No. 5, Aug. 2024, pp. 621-630. Crossref, https://doi.org/10.1007/s12185-024-03834-9.
Izutsu, Koji, et al. "Valemetostat for Relapsed or Refractory B-Cell Lymphomas: Primary Results from a Phase 1 Trial." Blood, vol. 142, No. Supplement 1, Nov. 2023, pp. 1731-1731. Crossref, https://doi.org/10.1182/blood-2023-179301.
Jacobsen, Eric, et al. "Valemetostat for Relapsed or Refractory Peripheral T-Cell Lymphomas: Primary Results from a Phase 1 Trial." Blood, vol. 142, No. Supplement 1, Nov. 2023, pp. 303-303. Crossref, https://doi.org/10.1182/blood-2023-172512.
Jawed, Sarah I., et al. "Primary Cutaneous T-Cell Lymphoma (Mycosis Fungoides and Sézary Syndrome)." Journal of the American Academy of Dermatology, vol. 70, No. 2, Feb. 2014, pp. 205.e1-205.e16. Crossref, https://doi.org/10.1016/j.jaad.2013.07.049.
Jeon, Eun Young, et al. Inhibiting EZH2 Complements Steroid Effects in Duchenne Muscular Dystrophy. Aug. 2024. Crossref, https://doi.org/10.1101/2024.08.22.609220.
Jiang, Yanwen, et al. "The Many Layers of Epigenetic Dysfunction in B-Cell Lymphomas." Current Opinion in Hematology, vol. 23, No. 4, Jul. 2016, pp. 377-384. Crossref, https://doi.org/10.1097/moh.0000000000000249.
Jin, Cheng, et al. "EZH2 Deletion Promotes Spermatogonial Differentiation and Apoptosis." Reproduction, vol. 154, No. 5, Nov. 2017, pp. 615-625. Crossref, https://doi.org/10.1530/rep-17-0302.
Kaniskan, H. Ümit, et al. "Selective Inhibitors of Protein Methyltransferases." Journal of Medicinal Chemistry, vol. 58, No. 4, Dec. 2014, pp. 1596-1629. Crossref, https://doi.org/10.1021/jm501234a.

(56) References Cited

OTHER PUBLICATIONS

Kaur, Parminder, et al. "EZH2-Mediated Development of Therapeutic Resistance in Cancer." Cancer Letters, vol. 586, Apr. 2024, p. 216706. Crossref, https://doi.org/10.1016/j.canlet.2024.216706.
Kazansky, Yaniv, et al. "Overcoming Clinical Resistance to EZH2 Inhibition Using Rational Epigenetic Combination Therapy." Cancer Discovery, vol. 14, No. 6, Jun. 2024, pp. 965-981. Crossref, https://doi.org/10.1158/2159-8290.cd-23-0110.
Keam, Susan J. "Valemetostat Tosilate: First Approval." Drugs, vol. 82, No. 16, Nov. 2022, pp. 1621-1627. Crossref, https://doi.org/10.1007/s40265-022-01800-5.
Kenkre, Vaishalee P., et al. "A Phase I/II Study of Tazemetostat Combined with Abbreviated Rituximab/Bendamustine Therapy for High Tumor Burden Follicular Lymphoma in Frontline Treatment: A Big Ten Cancer Research Consortium Study." Blood, vol. 144, No. Supplement 1, Nov. 2024, pp. 4415-4415. Crossref, https://doi.org/10.1182/blood-2024-202639.
Khanna, Avinash, et al. "Design, Synthesis, and Pharmacological Evaluation of Second Generation EZH2 Inhibitors with Long Residence Time." ACS Medicinal Chemistry Letters, vol. 11, No. 6, Mar. 2020, pp. 1205-1212. Crossref, https://doi.org/10.1021/acsmedchemlett.0c00045.
Kim, Youn H., et al. "Mogamulizumab versus Vorinostat in Previously Treated Cutaneous T-Cell Lymphoma (MAVORIC): An International, Open-Label, Randomised, Controlled Phase 3 Trial." The Lancet Oncology, vol. 19, No. 9, Sep. 2018, pp. 1192-1204. Crossref, https://doi.org/10.1016/s1470-2045(18)30379-6.
Knutson, Sarah K., et al. "A Selective Inhibitor of EZH2 Blocks H3K27 Methylation and Kills Mutant Lymphoma Cells." Nature Chemical Biology, vol. 8, No. 11, Sep. 2012, pp. 890-896. Crossref, https://doi.org/10.1038/nchembio.1084.
Konze, Kyle D., et al. "An Orally Bioavailable Chemical Probe of the Lysine Methyltransferases EZH2 and EZH1." ACS Chemical Biology, vol. 8, No. 6, Apr. 2013, pp. 1324-1334. Crossref, https://doi.org/10.1021/cb400133j.
Kung, Pei-Pei, et al. "Optimization of Orally Bioavailable Enhancer of Zeste Homolog 2 (EZH2) Inhibitors Using Ligand and Property-Based Design Strategies: Identification of Development Candidate (R)-5,8-Dichloro-7-(Methoxy(Oxetan-3-Yl)Methyl)-2-((4-Methoxy-6-Methyl-2-Oxo-1,2-Dihydropyridin-3-Yl)Methyl)-3,4-Dihydroisoquinolin-1(2H)-One (PF-06821497)." Journal of Medicinal Chemistry, vol. 61, No. 3, Dec. 2017, pp. 650-665. Crossref, https://doi.org/10.1021/acs.jmedchem.7b01375.
Kunhong Deng, et al., "Study on pharmacokinetic interactions between SHR2554 and itraconazole in healthy subjects: A single-center, open-label phase I trial", Cancer Medicine, 12:1431-1440, (2023).
Kwok, Hui Si, et al. "Drug Addiction Unveils a Repressive Methylation Ceiling in EZH2-Mutant Lymphoma." Nature Chemical Biology, vol. 19, No. 9, Mar. 2023, pp. 1105-1115. Crossref, https://doi.org/10.1038/s41589-023-01299-1.
LaFave, Lindsay M., et al. "Loss of BAP1 Function Leads to EZH2-Dependent Transformation." Nature Medicine, vol. 21, No. 11, Oct. 2015, pp. 1344-1349. Crossref, https://doi.org/10.1038/nm.3947.
Lakhani, Nehal J., et al. "Phase ½ First-in-Human (FIH) Study of CPI-0209, a Novel Small Molecule Inhibitor of Enhancer of Zeste Homolog 2 (EZH2) in Patients with Advanced Tumors." Journal of Clinical Oncology, vol. 39, No. 15_suppl, May 2021, pp. 3104-3104. Crossref, https://doi.org/10.1200/jco.2021.39.15_suppl.3104.
Landman, Nick, et al. "Combination of EZH2 and ATM Inhibition in BAP1-Deficient Mesothelioma." British Journal of Cancer, vol. 130, No. 11, Mar. 2024, pp. 1855-1865. Crossref, https://doi.org/10.1038/s41416-024-02661-3.
Lanzi, Cinzia, et al. "Targeting EZH2 in SMARCB1-Deficient Sarcomas: Advances and Opportunities to Potentiate the Efficacy of EZH2 Inhibitors." Biochemical Pharmacology, vol. 215, Sep. 2023, p. 115727. Crossref, https://doi.org/10.1016/j.bcp.2023.115727.
Laribi, Kamel, et al. "Recent Advances in the Treatment of Peripheral T-Cell Lymphoma." The Oncologist, vol. 23, No. 9, Apr. 2018, pp. 1039-1053. Crossref, https://doi.org/10.1634/theoncologist.2017-0524.
Le, Meiling, et al. "Design, Synthesis, and Biological Evaluation of Potent EZH2/LSD1 Dual Inhibitors for Prostate Cancer." Journal of Medicinal Chemistry, vol. 67, No. 17, Aug. 2024, pp. 15586-15605. Crossref, https://doi.org/10.1021/acs.jmedchem.4c01250.
Li, Chen, et al. "Finding an Easy Way to Harmonize: A Review of Advances in Clinical Research and Combination Strategies of EZH2 Inhibitors." Clinical Epigenetics, vol. 13, No. 1, Mar. 2021. Crossref, https://doi.org/10.1186/s13148-021-01045-1.
Li, Fengyin, et al. "Ezh2 Programs TFH Differentiation by Integrating Phosphorylation-Dependent Activation of Bcl6 and Polycomb-Dependent Repression of P19Arf." Nature Communications, vol. 9, No. 1, Dec. 2018. Crossref, https://doi.org/10.1038/s41467-018-07853-z.
Li, Meng, and Ari M. Melnick. "An 'EZ' Epigenetic Road to Leukemia Stem Cell Metabolic Reprogramming?" Cancer Discovery, vol. 9, No. 9, Sep. 2019, pp. 1158-1160. Crossref, https://doi.org/10.1158/2159-8290.cd-19-0737.
Li, Mengjia, et al. "Stage-Specific Dual Function: EZH2 Regulates Human Erythropoiesis by Eliciting Histone and Non-Histone Methylation." Haematologica, Apr. 2023. Crossref, https://doi.org/10.3324/haematol.2022.282016.
Li, Ruoyan, et al. Cutaneous T Cell Lymphoma Atlas Reveals Malignant Th2 Cells Supported by a B Cell-Rich Microenvironment. Nov. 2023. Crossref, https://doi.org/10.1101/2023.11.06.565474.
Liao, Qili, et al. "Novel Insights into Histone Lysine Methyltransferases in Cancer Therapy: From Epigenetic Regulation to Selective Drugs." Journal of Pharmaceutical Analysis, vol. 13, No. 2, Feb. 2023, pp. 127-141. Crossref, https://doi.org/10.1016/j.jpha.2022.11.009.
Lin, Jiunn-Miin, et al. "BCL-6 Promotes the Methylation of miR-34a by Recruiting EZH2 and Upregulating CTRP9 to Protect Ischemic Myocardial Injury." BioFactors, vol. 47, No. 3, Jan. 2021, pp. 386-402. Portico, Crossref, https://doi.org/10.1002/biof.1704.
Lin, Xiao-Hu, et al. "The Heightened Importance of EZH2 in Cancer Immunotherapy." Cancer Screening and Prevention, vol. 000, No. 000, Jun. 2023, pp. 000-000. Crossref, https://doi.org/10.14218/csp.2023.00006.
Link, Brian K., et al. "Rates and Outcomes of Follicular Lymphoma Transformation in the Immunochemotherapy Era: A Report From the University of Iowa/Mayo Clinic Specialized Program of Research Excellence Molecular Epidemiology Resource." Journal of Clinical Oncology, vol. 31, No. 26, Sep. 2013, pp. 3272-3278. Crossref, https://doi.org/10.1200/jco.2012.48.3990.
Liu, Dongdong, et al. "BMP-ACVR1 Axis Is Critical for Efficacy of PRC2 Inhibitors in B-Cell Lymphoma." Advanced Science, vol. 11, No. 12, Jan. 2024. Portico, Crossref, https://doi.org/10.1002/advs.202306499.
Liu, Jiaxin, et al. "The Status and Prospects of Epigenetics in the Treatment of Lymphoma." Frontiers in Oncology, vol. 12, Apr. 2022. Crossref, https://doi.org/10.3389/fonc.2022.874645.
Liu, Linshan, et al. "Ezh2 Promotes Mammary Tumor Initiation through Epigenetic Regulation of the Wnt and MTORC1 Signaling Pathways." Proceedings of the National Academy of Sciences, vol. 120, No. 33, Aug. 2023. Crossref, https://doi.org/10.1073/pnas.2303010120.
Liu, Shuo, et al. "Epidemiological Characteristics of Peripheral T-Cell Lymphoma: A Population-Based Study." Frontiers in Oncology, vol. 12, Jul. 2022. Crossref, https://doi.org/10.3389/fonc.2022.863269.
Liu, Yuankai, and Qiong Yang. "The Roles of EZH2 in Cancer and Its Inhibitors." Medical Oncology, vol. 40, No. 6, May 2023. Crossref, https://doi.org/10.1007/s12032-023-02025-6.
Loi, Patrick, et al. "Epigenetic and Oncogenic Inhibitors Cooperatively Drive Differentiation and Kill KRAS-Mutant Colorectal Cancers." Cancer Discovery, vol. 14, No. 12, Aug. 2024, pp. 2430-2449. Crossref, https://doi.org/10.1158/2159-8290.cd-23-0866.
Lu, Biao, et al. "Discovery of EBI-2511: A Highly Potent and Orally Active EZH2 Inhibitor for the Treatment of Non-Hodgkin's Lym-

(56) References Cited

OTHER PUBLICATIONS phoma." ACS Medicinal Chemistry Letters, vol. 9, No. 2, Feb. 2018, pp. 98-102. Crossref, https://doi.org/10.1021/acsmedchemlett.7b00437.
Luan, Yunpeng, et al. "Therapeutic Challenges in Peripheral T-Cell Lymphoma." Molecular Cancer, vol. 23, No. 1, Jan. 2024. Crossref, https://doi.org/10.1186/s12943-023-01904-w.
Lund, K., et al. "EZH2 in Normal and Malignant Hematopoiesis." Leukemia, vol. 28, No. 1, Oct. 2013, pp. 44-49. Crossref, https://doi.org/10.1038/leu.2013.288.
Ma, Anqi, et al. "Discovery of a First-in-Class EZH2 Selective Degrader." Nature Chemical Biology, vol. 16, No. 2, Dec. 2019, pp. 214-222. Crossref, https://doi.org/10.1038/s41589-019-0421-4.
Ma, Helen, et al. "The Peripheral T-Cell Lymphomas: An Unusual Path to Cure." The Lancet Haematology, vol. 7, No. 10, Oct. 2020, pp. e765-71. Crossref, https://doi.org/10.1016/s2352-3026(20)30207-6.
Ma, Zetao, et al. "Novel Insights of EZH2-Mediated Epigenetic Modifications in Degenerative Musculoskeletal Diseases." Ageing Research Reviews, vol. 90, Sep. 2023, p. 102034. Crossref, https://doi.org/10.1016/j.arr.2023.102034.
Marchi, Enrica, and Owen A. O'Connor. "The Rapidly Changing Landscape in Mature T-cell Lymphoma (MTCL) Biology and Management." CA: A Cancer Journal for Clinicians, vol. 70, No. 1, Dec. 2019, pp. 47-70. Portico, Crossref, https://doi.org/10.3322/caac.21589.
Martin, M. Cynthia, et al. "Small Molecule Approaches for Targeting the Polycomb Repressive Complex 2 (PRC2) in Cancer." Journal of Medicinal Chemistry, vol. 63, No. 24, Dec. 2020, pp. 15344-15370. Crossref, https://doi.org/10.1021/acs.jmedchem.0c01344.
Maruyama, Dai, et al. "TCL-391 Valemetostat Monotherapy in Patients With Relapsed/Refractory Non-Hodgkin Lymphomas: Primary Results From a Phase 1 Trial." Clinical Lymphoma Myeloma and Leukemia, vol. 24, Sep. 2024, pp. S523-S524. Crossref, https://doi.org/10.1016/s2152-2650(24)01617-3.
Maruyama, Dai, et al. "Valemetostat Monotherapy in Patients with Relapsed or Refractory Non-Hodgkin Lymphoma: A First-in-Human, Multicentre, Open-Label, Single-Arm, Phase 1 Study." The Lancet Oncology, vol. 25, No. 12, Dec. 2024, pp. 1589-1601. Crossref, https://doi.org/10.1016/s1470-2045(24)00502-3.
Marzochi, Ludimila Leite, et al. "Use of Histone Methyltransferase Inhibitors in Cancer Treatment: A Systematic Review." European Journal of Pharmacology, vol. 944, Apr. 2023, p. 175590. Crossref, https://doi.org/10.1016/j.ejphar.2023.175590.
Maurer, Matthew J., et al. "International Assessment of Event-Free Survival at 24 Months and Subsequent Survival in Peripheral T-Cell Lymphoma." Journal of Clinical Oncology, vol. 35, No. 36, Dec. 2017, pp. 4019-4026. Crossref, https://doi.org/10.1200/jco.2017.73.8195.
McCabe, Michael T., et al. "EZH2 Inhibition as a Therapeutic Strategy for Lymphoma with EZH2-Activating Mutations." Nature, vol. 492, No. 7427, Oct. 2012, pp. 108-112. Crossref, https://doi.org/10.1038/nature11606.
Mehta-Shah, Neha, and Steven M. Horwitz. "Failing Forward in Peripheral T-Cell Lymphoma." Journal of Clinical Oncology, vol. 42, No. 14, May 2024, pp. 1599-1602. Crossref, https://doi.org/10.1200/jco.23.02658.
Mehta-Shah, Neha, et al. "Prediction of Clinical Response By Phased Variants in Circulating Tumor DNA (CtDNA) in the Valentine-PTCL01 Trial of Patients with Relapsed or Refractory (R/R) Peripheral T-Cell Lymphoma (PTCL)." Blood, vol. 144, No. Supplement 1, Nov. 2024, pp. 4342-4342. Crossref, https://doi.org/10.1182/blood-2024-207594.
Mei, Husheng, et al. "Discovery of IHMT-337 as a Potent Irreversible EZH2 Inhibitor Targeting CDK4 Transcription for Malignancies." Signal Transduction and Targeted Therapy, vol. 8, No. 1, Jan. 2023. Crossref, https://doi.org/10.1038/s41392-022-01240-3.
Melnick, Ari. "Epigenetic Therapy Leaps Ahead with Specific Targeting of EZH2." Cancer Cell, vol. 22, No. 5, Nov. 2012, pp. 569-570. Crossref, https://doi.org/10.1016/j.ccr.2012.10.016.
Meng, Qingshu, et al. "EZH2 Directly Methylates PARP1 and Regulates Its Activity in Cancer." Science Advances, vol. 10, No. 48, Nov. 2024. Crossref, https://doi.org/10.1126/sciadv.adl2804.
Meyerson, Howard J., et al. "Follicular Center Helper T-Cell (TFH) Marker Positive Mycosis Fungoides/Sezary Syndrome." Modern Pathology, vol. 26, No. 1, Jan. 2013, pp. 32-43. Crossref, https://doi.org/10.1038/modpathol.2012.124.
Mhaidly, Rana, et al. "New Preclinical Models for Angioimmunoblastic T-Cell Lymphoma: Filling the Gap." Oncogenesis, vol. 9, No. 8, Aug. 2020. Crossref, https://doi.org/10.1038/s41389-020-00259-x.
Minson, Adrian, et al. "Targeted Agents in the Treatment of Indolent B-Cell Non-Hodgkin Lymphomas." Cancers, vol. 14, No. 5, Mar. 2022, p. 1276. Crossref, https://doi.org/10.3390/cancers14051276.
Miyashiro, Denis, and José Antonio Sanches. "Mycosis Fungoides and Sézary Syndrome: Clinical Presentation, Diagnosis, Staging, and Therapeutic Management." Frontiers in Oncology, vol. 13, Apr. 2023. Crossref, https://doi.org/10.3389/fonc.2023.1141108.
Mondejar, Rufino, et al. "Molecular Basis of Targeted Therapy in T/NK-Cell Lymphoma/Leukemia: A Comprehensive Genomic and Immunohistochemical Analysis of a Panel of 33 Cell Lines." Plos One, edited by Renato Franco, vol. 12, No. 5, May 2017, p. e0177524. Crossref, https://doi.org/10.1371/journal.pone.0177524.
Montoto, Silvia, and Jude Fitzgibbon. "Transformation of Indolent B-Cell Lymphomas." Journal of Clinical Oncology, vol. 29, No. 14, May 2011, pp. 1827-1834. Crossref, https://doi.org/10.1200/jco.2010.32.7577.
Morris, Stephan W., et al. "Fusion of a Kinase Gene, ALK, to a Nucleolar Protein Gene, NPM, in Non-Hodgkin's Lymphoma." Science, vol. 263, No. 5151, Mar. 1994, pp. 1281-1284. Crossref, https://doi.org/10.1126/science.8122112.
Morschhauser, F., et al. "Interim Report From a Phase 2 Multicenter Study of Tazemetostat, an EZH2 Inhibitor, in Patients With Relapsed or Refractory B-Cell Non-Hodgkin Lymphomas." Hematological Oncology, vol. 35, No. S2, Jun. 2017, pp. 24-25. Portico, Crossref, https://doi.org/10.1002/hon.2437_3.
Morschhauser, Franck, et al. "Taking the EZ Way: Targeting Enhancer of Zeste Homolog 2 in B-Cell Lymphomas." Blood Reviews, vol. 56, Nov. 2022, p. 100988. Crossref, https://doi.org/10.1016/j.blre.2022.100988.
Morschhauser, Franck, et al. "Tazemetostat for Patients with Relapsed or Refractory Follicular Lymphoma: An Open-Label, Single-Arm, Multicentre, Phase 2 Trial." The Lancet Oncology, vol. 21, No. 11, Nov. 2020, pp. 1433-1442. Crossref, https://doi.org/10.1016/s1470-2045(20)30441-1.
Moskowitz, Alison J., et al. "Current and Upcoming Treatment Approaches to Common Subtypes of PTCL (PTCL, NOS; ALCL; and TFHs)." Blood, vol. 144, No. 18, Oct. 2024, pp. 1887-1897. Crossref, https://doi.org/10.1182/blood.2023021789.
Munakata, Wataru, et al. "Phase 1 Study of Tazemetostat in Japanese Patients with Relapsed or Refractory B-cell Lymphoma." Cancer Science, vol. 112, No. 3, Feb. 2021, pp. 1123-1131. Portico, Crossref, https://doi.org/10.1111/cas.14822.
Naina Marikar, Safiya, et al. "Pharmacological Inhibition of Human EZH2 Can Influence a Regenerative ß-like Cell Capacity with in Vitro Insulin Release in Pancreatic Ductal Cells." Clinical Epigenetics, vol. 15, No. 1, Jun. 2023. Crossref, https://doi.org/10.1186/s13148-023-01491-z.
Nakayama, Hirotaka, et al. "Validation of EZH2 Inhibitor Efficiency in Anaplastic Thyroid Carcinoma Cell Lines." Anticancer Research, vol. 43, No. 3, Feb. 2023, pp. 1073-1077. Crossref, https://doi.org/10.21873/anticanres.16252.
Nanjappa, Manjunatha K., et al. "The Histone Methyltransferase EZH2 Is Required for Normal Uterine Development and Function in Mice†." Biology of Reproduction, vol. 101, No. 2, Jun. 2019, pp. 306-317. Crossref, https://doi.org/10.1093/biolre/ioz097.
Naso, Julia R., et al. "EZH2 and POU2F3 Can Aid in the Distinction of Thymic Carcinoma from Thymoma." Cancers, vol. 15, No. 8, Apr. 2023, p. 2274. Crossref, https://doi.org/10.3390/cancers15082274.

(56) References Cited

OTHER PUBLICATIONS

Nastoupil, Loretta J., et al. "An Externally Controlled Trial to Indirectly Compare Tazemetostat Plus Lenalidomide and Rituximab Versus Lenalidomide and Rituximab after at Least One Prior Systemic Therapy in Patients with Refractory and Relapsed Follicular Lymphoma." Blood, vol. 142, No. Supplement 1, Nov. 2023, pp. 4410-4410. Crossref, https://doi.org/10.1182/blood-2023-181807.
Neves Filho, Eduardo Henrique, et al. "EZH2 Expression Is Dependent on MYC and TP53 Regulation in Diffuse Large B-cell Lymphoma." APMIS, vol. 128, No. 4, Feb. 2020, pp. 308-315. Portico, Crossref, https://doi.org/10.1111/apm.13029.
Ngu, Henry S., and Kerry J. Savage. "Frontline Management of Nodal Peripheral T-Cell Lymphomas." American Society of Clinical Oncology Educational Book, No. 43, May 2023. Crossref, https://doi.org/10.1200/edbk_390334.
Nizamuddin, Imran A., and Neha Mehta-Shah. "BV and beyond: How to Incorporate Novel Agents into PTCL Management." Hematology, vol. 2024, No. 1, Dec. 2024, pp. 54-61. Crossref, https://doi.org/10.1182/hematology.2024000530.
O'Brien, Eleanor, et al. "Pharmacological EZH2 Inhibition Combined with Retinoic Acid Treatment Promotes Differentiation and Apoptosis in Rhabdomyosarcoma Cells." Clinical Epigenetics, vol. 15, No. 1, Oct. 2023. Crossref, https://doi.org/10.1186/s13148-023-01583-w.
O'Donnell, Edmond, et al. Genetic and Epigenetic Characterization of Sarcoma Stem Cells Across Subtypes Identifies EZH2 as a Therapeutic Target. May 2024. Crossref, https://doi.org/10.1101/2024.05.14.594060.
Oaknin, Ana, et al. "Phase II Dose Optimization with EZH2/EZH1 Inhibitor Tulmimetostat in Patients (Pts) with Advanced Solid Tumors or Hematologic Malignancies." Journal of Clinical Oncology, vol. 42, No. 16_suppl, Jun. 2024, pp. 3097-3097. Crossref, https://doi.org/10.1200/jco.2024.42.16_suppl.3097.
Office action for Taiwan application No. 107139895 issued on Feb. 5, 2020 as well as its English Translation.
Office action for Taiwan application No. 107139895 issued on Jun. 3, 2020 as well as its English Translation.
Office action for Taiwan application No. 107139895 issued on Sep. 4, 2019 as well as its English Translation.
Olsen, Elise A., et al. "Primary Cutaneous Lymphoma: Recommendations for Clinical Trial Design and Staging Update from the ISCL, USCLC, and EORTC." Blood, vol. 140, No. 5, Aug. 2022, pp. 419-437. Crossref, https://doi.org/10.1182/blood.2021012057.
Ondrejka, Sarah L., et al. "Follicular Helper T-Cell Lymphomas: Disease Spectrum, Relationship with Clonal Hematopoiesis, and Mimics. A Report of the 2022 EA4HP/SH Lymphoma Workshop." Virchows Archiv, vol. 483, No. 3, Jul. 2023, pp. 349-365. Crossref, https://doi.org/10.1007/s00428-023-03607-5.
Oricchio, Elisa, et al. "Genetic and Epigenetic Inactivation of SESTRIN1 Controls MTORC1 and Response to EZH2 Inhibition in Follicular Lymphoma." Science Translational Medicine, vol. 9, No. 396, Jun. 2017. Crossref, https://doi.org/10.1126/scitranslmed.aak9969.
Ozgun, Gizem, et al. "Retinoids and EZH2 Inhibitors Cooperate to Orchestrate Anti-Oncogenic Effects on Bladder Cancer Cells." Cancer Gene Therapy, vol. 31, No. 4, Jan. 2024, pp. 537-551. Crossref, https://doi.org/10.1038/s41417-024-00725-3.
Ozgun, Gizem, et al. Retinoids and EZH2 Inhibitors Cooperate to Orchestrate Cytotoxic Effects on Bladder Cancer Cells. Apr. 2023. Crossref, https://doi.org/10.1101/2023.04.19.537500.
Palomba, M. L., et al. "Safety and Clinical Activity of Atezolizumab in Combination With Tazemetostat in Relapsed or Refractory Diffuse Large B-Cell Lymphoma: Primary Analysis of a Phase 1B Study." Hematological Oncology, vol. 37, No. S2, Jun. 2019, pp. 517-519. Portico, Crossref, https://doi.org/10.1002/hon.203_2631.
Palomba, Maria Lia, et al. "Combination of Atezolizumab and Tazemetostat in Patients With Relapsed/Refractory Diffuse Large B-Cell Lymphoma: Results From a Phase lb Study." Clinical Lymphoma Myeloma and Leukemia, vol. 22, No. 7, Jul. 2022, pp. 504-512. Crossref, https://doi.org/10.1016/j.clml.2021.12.014.
Park, Steven I., et al. "The Role of Autologous Stem Cell Transplantation in Patients with Nodal Peripheral T-cell Lymphomas in First Complete Remission: Report from Complete, a Prospective, Multicenter Cohort Study." Cancer, vol. 125, No. 9, Jan. 2019, pp. 1507-1517. Portico, Crossref, https://doi.org/10.1002/cncr.31861.
Peng, Yu, et al. "The Role of EZH2 in Ocular Diseases: A Narrative Review." Epigenomics, vol. 15, No. 9, May 2023, pp. 557-570. Crossref, https://doi.org/10.2217/epi-2023-0147.
Prince, H. Miles, et al. "Brentuximab Vedotin or Physician's Choice in CD30-Positive Cutaneous T-Cell Lymphoma (Alcanza): An International, Open-Label, Randomised, Phase 3, Multicentre Trial." The Lancet, vol. 390, No. 10094, Aug. 2017, pp. 555-566. Crossref, https://doi.org/10.1016/s0140-6736(17)31266-7.
Prorok, Paulina, et al. "Loss of Ezh2 Function Remodels the DNA Replication Initiation Landscape." Cell Reports, vol. 42, No. 4, Apr. 2023, p. 112280. Crossref, https://doi.org/10.1016/j.celrep.2023.112280.
Proudman, David, et al. "Tazemetostat (TAZ) in Relapsed/Refractory (R/R) Follicular Lymphoma (FL): Propensity-Score Matched Analysis of E7438-G000-101 Trial Outcomes." Journal of Clinical Oncology, vol. 39, No. 15_suppl, May 2021, pp. e18627-e18627. Crossref, https://doi.org/10.1200/jco.2021.39.15_suppl.e18627.
Qiang, Na, et al. "Alteration of the Tumor Microenvironment by Pharmacological Inhibition of EZH2 in Hepatocellular Carcinoma." International Immunopharmacology, vol. 118, May 2023, p. 110068. Crossref, https://doi.org/10.1016/j.intimp.2023.110068.
Quereux, Gaëlle, et al. "Prospective Multicenter Study of Pegylated Liposomal Doxorubicin Treatment in Patients With Advanced or Refractory Mycosis Fungoides or Sézary Syndrome." Archives of Dermatology, vol. 144, No. 6, Jun. 2008. Crossref, https://doi.org/10.1001/archderm.144.6.727.
Rai, Shinya, et al. "Abstract CT176: Phase 2 Study of Tazemetostat in Japanese Patients with Relapsed or Refractory EZH2 Mutation-Positive B-Cell Non-Hodgkin's Lymphoma." Cancer Research, vol. 81, No. 13_Supplement, Jul. 2021, pp. CT176-CT176. Crossref, https://doi.org/10.1158/1538-7445.am2021-ct176.
Richart, Laia, and Raphaël Margueron. "Drugging Histone Methyltransferases in Cancer." Current Opinion in Chemical Biology, vol. 56, Jun. 2020, pp. 51-62. Crossref, https://doi.org/10.1016/j.cbpa.2019.11.009.
Ridwansyah, Hastono, et al. "The Role of Chidamide in the Treatment of B-Cell Non-Hodgkin Lymphoma: An Updated Systematic Review." Biomolecules and Biomedicine, Mar. 2023. Crossref, https://doi.org/10.17305/bb.2023.8791.
Romero, Pierre, et al. "EZH2 Mutations in Follicular Lymphoma Distort H3K27me3 Profiles and Alter Transcriptional Responses to PRC2 Inhibition." Nature Communications, vol. 15, No. 1, Apr. 2024. Crossref, https://doi.org/10.1038/s41467-024-47701-x.
Rondeaux, Julie, et al. "Ezh2 Emerges as an Epigenetic Checkpoint Regulator during Monocyte Differentiation Limiting Cardiac Dysfunction Post-MI." Nature Communications, vol. 14, No. 1, Jul. 2023. Crossref, https://doi.org/10.1038/s41467-023-40186-0.
Sabour-Takanlou, Maryam, et al. "EZH2-associated Tumor Malignancy: A Prominent Target for Cancer Treatment." Clinical Genetics, vol. 106, No. 4, Jun. 2024, pp. 377-385. Portico, Crossref, https://doi.org/10.1111/cge.14576.
Sadaf, Hummaira, et al. "New Molecular Targets in Hodgkin and Reed-Sternberg Cells." Frontiers in Immunology, vol. 14, May 2023. Crossref, https://doi.org/10.3389/fimmu.2023.1155468.
Saleh, Khalil, et al. "Updates in the Treatment of Peripheral T-Cell Lymphomas." Journal of Experimental Pharmacology, vol. vol. 13, Jun. 2021, pp. 577-591. Crossref, https://doi.org/10.2147/jep.s262344.
Salles, Gilles, et al. "IBCL-485 A Phase III, Randomized, Double-Blind, Study of Tazemetostat or Placebo Plus Lenalidomide and Rituximab in Patients With Relapsed/Refractory Follicular Lymphoma." Clinical Lymphoma Myeloma and Leukemia, vol. 23, Sep. 2023, pp. S454-S455. Crossref, https://doi.org/10.1016/s2152-2650(23)01363-0.
Sarkozy, Clémentine, et al. "A Lysa Phase lb Study of Tazemetostat (EPZ-6438) plus R-CHOP in Patients with Newly Diagnosed Dif-

(56) References Cited

OTHER PUBLICATIONS fuse Large B-Cell Lymphoma (DLBCL) with Poor Prognosis Features." Clinical Cancer Research, vol. 26, No. 13, Jul. 2020, pp. 3145-3153. Crossref, https://doi.org/10.1158/1078-0432.ccr-19-3741.
Satoko Morishima, et al., "First-in-Human Study of the EZH½ Dual Inhibitor Valemetostat in Relapsed or Refractory Non-Hodgkin Lymphoma (NHL)—Updated Results Focusing on Adult T-Cell Leukemia-Lymphoma (ATL)", Blood, Nov. 13, 2019.
Sawalha, Amr H. "BCL-6 and EZH2 Cooperate to Epigenetically Repress Anti-Inflammatory MiR-142-3p/5p in Lupus CD4+T Cells." Cellular & Molecular Immunology, vol. 18, No. 2, Sep. 2019, pp. 504-505. Crossref, https://doi.org/10.1038/s41423-019-0288-z.
Scarisbrick, Julia J., et al. "Cutaneous Lymphoma International Consortium Study of Outcome in Advanced Stages of Mycosis Fungoides and Sézary Syndrome: Effect of Specific Prognostic Markers on Survival and Development of a Prognostic Model." Journal of Clinical Oncology, vol. 33, No. 32, Nov. 2015, pp. 3766-3773. Crossref, https://doi.org/10.1200/jco.2015.61.7142.
Schade, Amy E., et al. "AKT and EZH2 Inhibitors Kill TNBCs by Hijacking Mechanisms of Involution." Nature, vol. 635, No. 8039, Oct. 2024, pp. 755-763. Crossref, https://doi.org/10.1038/s41586-024-08031-6.
Schade, Amy E., et al. "Combating Castration-Resistant Prostate Cancer by Co-Targeting the Epigenetic Regulators EZH2 and HDAC." PLOS Biology, edited by Albana Gattelli, vol. 21, No. 4, Apr. 2023, p. e3002038. Crossref, https://doi.org/10.1371/journal.pbio.3002038.
Scholze, Hanna, et al. "Combined EZH2 and Bcl-2 Inhibitors as Precision Therapy for Genetically Defined DLBCL Subtypes." Blood Advances, vol. 4, No. 20, Oct. 2020, pp. 5226-5231. Crossref, https://doi.org/10.1182/bloodadvances.2020002580.
Schümann, Franziska Lea, et al. "Divergent Effects of EZH1 and EZH2 Protein Expression on the Prognosis of Patients with T-Cell Lymphomas." Biomedicines, vol. 9, No. 12, Dec. 2021, p. 1842. Crossref, https://doi.org/10.3390/biomedicines9121842.
Schweizer, M., et al. "488P Phase I Trial of PF-06821497, a Potent and Selective Inhibitor of Enhancer of Zeste Homolog 2 (EZH2), in Follicular Lymphoma (FL), Small Cell Lung Cancer (SCLC) and Castration-Resistant Prostate Cancer (CRPC)." Annals of Oncology, vol. 33, Sep. 2022, pp. S763-S764. Crossref, https://doi.org/10.1016/j.annonc.2022.07.616.
Schweizer, Michael Thomas, et al. "Phase 1 Trial of Mevrometostat (PF-06821497), a Potent and Selective Inhibitor of Enhancer of Zeste Homolog 2 (EZH2), in Castration-Resistant Prostate Cancer (CRPC)." Journal of Clinical Oncology, vol. 42, No. 16_suppl, Jun. 2024, pp. 5061-5061. Crossref, https://doi.org/10.1200/jco.2024.42.16_suppl.5061.
Serganova, Inna, et al. "Epigenetic, Metabolic, and Immune Crosstalk in Germinal-Center-Derived B-Cell Lymphomas: Unveiling New Vulnerabilities for Rational Combination Therapies." Frontiers in Cell and Developmental Biology, vol. 9, Jan. 2022. Crossref, https://doi.org/10.3389/fcell.2021.805195.
Sermer, David, et al. "Emerging Epigenetic-Modulating Therapies in Lymphoma." Nature Reviews Clinical Oncology, vol. 16, No. 8, Mar. 2019, pp. 494-507. Crossref, https://doi.org/10.1038/s41571-019-0190-8.
Shen, Yue, et al. "Differences between Lung Adenocarcinoma and Lung Squamous Cell Carcinoma: Driver Genes, Therapeutic Targets, and Clinical Efficacy." Genes & Diseases, Jul. 2024, p. 101374. Crossref, https://doi.org/10.1016/j.gendis.2024.101374.
Shi, Lihong, et al. "Pharmacological Inhibition of EZH2 Using a Covalent Inhibitor Suppresses Human Ovarian Cancer Cell Migration and Invasion." Molecular and Cellular Biochemistry, vol. 479, No. 4, May 2023, pp. 831-841. Crossref, https://doi.org/10.1007/s11010-023-04767-3.
Shin, Daniel Sanghoon, et al. "Targeting EZH2 to Overcome the Resistance to Immunotherapy in Lung Cancer." Seminars in Oncology, vol. 49, No. 3-4, Jun. 2022, pp. 306-318. Crossref, https://doi.org/10.1053/j.seminoncol.2022.06.005.
Shishido, Katherine, et al. "Targeting B7-H3 through EZH2 Inhibition in MYC-positive Group 3 Medulloblastoma." Oncology Reports, vol. 49, No. 6, Apr. 2023. Crossref, https://doi.org/10.3892/or.2023.8556.
Sibon, David. "Peripheral T-Cell Lymphomas: Therapeutic Approaches." Cancers, vol. 14, No. 9, May 2022, p. 2332. Crossref, https://doi.org/10.3390/cancers14092332.
Simon, R et al. "Randomized phase II clinical trials." Cancer treatment reports vol. 69, 12 (1985):1375-81.
Singh, Pankaj Kumar. "Histone Methyl Transferases: A Class of Epigenetic Opportunities to Counter Uncontrolled Cell Proliferation." European Journal of Medicinal Chemistry, vol. 166, Mar. 2019, pp. 351-368. Crossref, https://doi.org/10.1016/j.ejmech.2019.01.069.
Song, Y., et al. "Enhancer of Zeste Homolog 2 (EZH2) Inhibitor SHR2554 in Relapsed or Refractory (R/R) Peripheral T-Cell Lymphoma (PTCL): Updated Outcomes From the First-in-Human Phase 1 Study." Hematological Oncology, vol. 41, No. S2, Jun. 2023, pp. 132-134. Portico, Crossref, https://doi.org/10.1002/hon.3163_89.
Song, Yuqin, et al. "SHR2554, an Enhancer of Zeste Homolog 2 (EZH2) Inhibitor, in Relapsed or Refractory (r/r) Mature Lymphoid Neoplasms: A First-in-Human Phase 1 Study." Journal of Clinical Oncology, vol. 40, No. 16_suppl, Jun. 2022, pp. 7525-7525. Crossref, https://doi.org/10.1200/jco.2022.40.16_suppl.7525.
Sprinzen Houghton, Lisa, et al. EZH2 Inhibition Sensitizes IDH1R132H Mutant Gliomas to Histone Deacetylase Inhibitor. Aug. 2023. Crossref, https://doi.org/10.1101/2023.07.31.551045.
Sprinzen, Lisa, et al. "EZH2 Inhibition Sensitizes IDH1R132H-Mutant Gliomas to Histone Deacetylase Inhibitor." Cells, vol. 13, No. 3, Jan. 2024, p. 219. Crossref, https://doi.org/10.3390/cells13030219.
Stein, H., et al. "The Expression of the Hodgkin's Disease Associated Antigen Ki-1 in Reactive and Neoplastic Lymphoid Tissue: Evidence That Reed-Sternberg Cells and Histiocytic Malignancies Are Derived from Activated Lymphoid Cells." Blood, vol. 66, No. 4, Oct. 1985, pp. 848-858. Crossref, https://doi.org/10.1182/blood.v66.4.848.848.
Straining, PharmD, Rachael, and William Eighmy, PharmD. "Tazemetostat: EZH2 Inhibitor." Journal of the Advanced Practitioner in Oncology, vol. 13, No. 2, Mar. 2022, pp. 158-163. Crossref, https://doi.org/10.6004/jadpro.2022.13.2.7.
Stuckey, Jacob I., et al. "Identification and Characterization of Second-Generation EZH2 Inhibitors with Extended Residence Times and Improved Biological Activity." Journal of Biological Chemistry, vol. 296, Jan. 2021, p. 100349. Crossref, https://doi.org/10.1016/j.jbc.2021.100349.
Stuver, Robert, and Shamir Geller. "Advances in the Treatment of Mycoses Fungoides and Sézary Syndrome: A Narrative Update in Skin-Directed Therapies and Immune-Based Treatments." Frontiers in Immunology, vol. 14, Oct. 2023. Crossref, https://doi.org/10.3389/fimmu.2023.1284045.
Stuver, Robert, et al. "Cumulative Incidence of Myeloid Neoplasms in Patients with Nodal T-Follicular Helper Cell Lymphoma." Blood, vol. 142, No. Supplement 1, Nov. 2023, pp. 4438-4438. Crossref, https://doi.org/10.1182/blood-2023-182272.
Sun, Shanshan, et al. "EZH2, a Prominent Orchestrator of Genetic and Epigenetic Regulation of Solid Tumor Microenvironment and Immunotherapy." Biochimica et Biophysica Acta (BBA)—Reviews on Cancer, vol. 1877, No. 2, Mar. 2022, p. 188700. Crossref, https://doi.org/10.1016/j.bbcan.2022.188700.
Sun, Yichen, et al. "Therapeutic Potential of Tucidinostat, a Subtype-Selective HDAC Inhibitor, in Cancer Treatment." Frontiers in Pharmacology, vol. 13, Sep. 2022. Crossref, https://doi.org/10.3389/fphar.2022.932914.
Susanibar-Adaniya, Sandra, and Stefan K. Barta. "2021 Update on Diffuse Large B Cell Lymphoma: A Review of Current Data and Potential Applications on Risk Stratification and Management." American Journal of Hematology, vol. 96, No. 5, Mar. 2021, pp. 617-629. Portico, Crossref, https://doi.org/10.1002/ajh.26151.
Tabata Hidetsugu et al: ""A Complete Gear System in N -Benzoyl-Carbazole Derivatives"", Organic Letters., [Online] vol. 16, No. 5, Feb. 24, 2014 (Feb. 24, 2014 ), pp. 1514-1517, XP055808348, us ISSN: 1523-7060, DOI: 10.1021/ol500417t Retrieved from the

(56) References Cited

OTHER PUBLICATIONS

Internet: URL:https://pubs.acs.org/doi/pdf/10.1021 lo 1500417t> [retrieved on May 27, 2021] * Scheme 1; Citation 4 *.
Tabata Hidetsugu et al: ""Supporting Information A Complete Gear System in N-Benzoyl-Carbazole Derivatives"", Organic Letters, Feb. 14, 2014 (Feb. 14, 2014), pp. S0-S45, XP055808305, Retrieved from the Internet: URL:https://pubs.acs.org/doi/full/10.1021 /ol500417t [retrieved on May 27, 2021] * p. SI, paragraph 2., compound SI *.
Takata, Katsuyoshi, et al. "Tumor-Associated Antigen Prame Exhibits Dualistic Functions That Are Targetable in Diffuse Large B Cell Lymphoma." Journal of Clinical Investigation, vol. 132, No. 10, May 2022. Crossref, https://doi.org/10.1172/jci145343.
Teras, Lauren R., et al. "2016 US Lymphoid Malignancy Statistics by World Health Organization Subtypes." CA: A Cancer Journal for Clinicians, vol. 66, No. 6, Sep. 2016, pp. 443-459. Portico, Crossref, https://doi.org/10.3322/caac.21357.
Thandra, Krishna C., et al. "Epidemiology of Non-Hodgkin's Lymphoma." Medical Sciences, vol. 9, No. 1, Jan. 2021, p. 5. Crossref, https://doi.org/10.3390/medsci9010005.
Twiss and Heinzelmann, "The Oxidation of Iodinated Phthalic and Benzoic Acids", The Journal of Organic Chemistry, 1950, pp. 496-510.
Vaswani, Rishi G., et al. "Identification of (R)-N-((4-Methoxy-6-Methyl-2-Oxo-1,2-Dihydropyridin-3-Yl)Methyl)-2-Methyl-1-(1-(1-(2,2,2-Trifluoroethyl)Piperidin-4-Yl)Ethyl)-1H-Indole-3-Carboxamide (CPI-1205), a Potent and Selective Inhibitor of Histone Methyltransferase EZH2, Suitable for Phase I Clinical Trials for B-Cell Lymphomas." Journal of Medicinal Chemistry, vol. 59, No. 21, Oct. 2016, pp. 9928-9941. Crossref, https://doi.org/10.1021/acs.jmedchem.6b01315.
Velez, Julia, et al. "Discovery of a Novel, Highly Potent EZH2 Protac Degrader for Targeting Non-Canonical Oncogenic Functions of EZH2." European Journal of Medicinal Chemistry, vol. 267, Mar. 2024, p. 116154. Crossref, https://doi.org/10.1016/j.ejmech.2024.116154.
Velichutina, Irina, et al. "EZH2-Mediated Epigenetic Silencing in Germinal Center B Cells Contributes to Proliferation and Lymphomagenesis." Blood, vol. 116, No. 24, Dec. 2010, pp. 5247-5255. Crossref, https://doi.org/10.1182/blood-2010-04-280149.
Verma, Ayushi, et al. "Emerging Role of EZH2 in Solid Tumor Metastasis." Biochimica et Biophysica Acta (BBA)—Reviews on Cancer, vol. 1880, No. 1, Feb. 2025, p. 189253. Crossref, https://doi.org/10.1016/j.bbcan.2024.189253.
Von Keudell, Gottfried, and Gilles Salles. "The Role of Tazemetostat in Relapsed/Refractory Follicular Lymphoma." Therapeutic Advances in Hematology, vol. 12, Jan. 2021. Crossref, https://doi.org/10.1177/20406207211015882.
Vose, Julie et al. "International Peripheral T-Cell and Natural Killer/T-Cell Lymphoma Study: Pathology Findings and Clinical Outcomes." Journal of Clinical Oncology, vol. 26, No. 25, Sep. 2008, pp. 4124-4130. Crossref, https://doi.org/10.1200/jco.2008.16.4558.
Wan, Guoquan, et al. "A Patent Review of EZH2 Inhibitors from 2017 and Beyond." Expert Opinion on Therapeutic Patents, vol. 33, No. 4, Apr. 2023, pp. 293-308. Crossref, https://doi.org/10.1080/13543776.2023.2206018.
Wang, Bohan, et al. "EZH2 in Hepatocellular Carcinoma: Progression, Immunity, and Potential Targeting Therapies." Experimental Hematology & Oncology, vol. 12, No. 1, Jun. 2023. Crossref, https://doi.org/10.1186/s40164-023-00405-2.
Wang, Jun, et al. "EZH2 Noncanonically Binds CMyc and P300 through a Cryptic Transactivation Domain to Mediate Gene Activation and Promote Oncogenesis." Nature Cell Biology, vol. 24, No. 3, Feb. 2022, pp. 384-399. Crossref, https://doi.org/10.1038/s41556-022-00850-x.
Wei, Lai, et al. "Dual-Target EZH2 Inhibitor: Latest Advances in Medicinal Chemistry." Future Medicinal Chemistry, vol. 16, No. 15, Jul. 2024, pp. 1561-1582. Crossref, https://doi.org/10.1080/17568919.2024.2380243.
Whittaker, Sean, et al. "How I Treat Mycosis Fungoides and Sézary Syndrome." Blood, vol. 127, No. 25, Jun. 2016, pp. 3142-3153. Crossref, https://doi.org/10.1182/blood-2015-12-611830.
Wilhelm, M., et al. "First-Line Therapy of Peripheral T-Cell Lymphoma: Extension and Long-Term Follow-up of a Study Investigating the Role of Autologous Stem Cell Transplantation." Blood Cancer Journal, vol. 6, No. 7, Jul. 2016, pp. e452-e452. Crossref, https://doi.org/10.1038/bcj.2016.63.
Wozniak, Michal, and Malgorzata Czyz. "Exploring Oncogenic Roles and Clinical Significance of EZH2: Focus on Non-Canonical Activities." Therapeutic Advances in Medical Oncology, vol. 17, Jan. 2025. Crossref, https://doi.org/10.1177/17588359241306026.
Written Opinion of the International Search Authority (and English translation thereof) dated Dec. 15, 2022 issued in International Application No. PCT/CN2022/125302.
Written Opinion of the International Search Authority (and English translation thereof) dated Nov. 28, 2022 issued in International Application PCT/CN2022/115763.
Wu, Di, et al. "Discovery of Novel Pyridone-Benzamide Derivatives Possessing a 1-Methyl-2-Benzimidazolinone Moiety as Potent EZH2 Inhibitors for the Treatment of B-Cell Lymphomas." Bioorganic & Medicinal Chemistry, vol. 105, May 2024, p. 117725. Crossref, https://doi.org/10.1016/j.bmc.2024.117725.
Wu, Gongwei, et al. "TP63 Fusions Drive Multicomplex Enhancer Rewiring, Lymphomagenesis, and EZH2 Dependence." Science Translational Medicine, vol. 15, No. 714, Sep. 2023. Crossref, https://doi.org/10.1126/scitranslmed.adi7244.
Xiao, Boren, et al. "Design, Synthesis, and Evaluation of VHL-Based EZH2 Degraders for Breast Cancer." Bioorganic Chemistry, vol. 143, Feb. 2024, p. 107078. Crossref, https://doi.org/10.1016/j.bioorg.2023.107078.
Xie, Caiqin, et al. "Molecular Insights into Pathogenesis and Targeted Therapy of Peripheral T Cell Lymphoma." Experimental Hematology & Oncology, vol. 9, No. 1, Nov. 2020. Crossref, https://doi.org/10.1186/s40164-020-00188-w.
Xie, Huiru, et al. "Design, Synthesis and Evaluation of EZH2-Based PROTACs Targeting PRC2 Complex in Lymphoma." Bioorganic Chemistry, vol. 140, Nov. 2023, p. 106762. Crossref, https://doi.org/10.1016/j.bioorg.2023.106762.
Xing Wang, et al., "The Synergistic Anti-Tumor Activity of EZH2 Inhibitor SHR2554 and HDAC Inhibitor Chidamide through ORC1 Reduction of DNA Replication Process in Diffuse Large B Cell Lymphoma", Cancers, 13:4249-4249, (2021).
Xu, Mengfei, et al. "Treating Human Cancer by Targeting EZH2." Genes & Diseases, Apr. 2024, p. 101313. Crossref, https://doi.org/10.1016/j.gendis.2024.101313.
Xu, Pingsheng, et al. Effect of a Strong CYP3A4 Inducer Rifampin on the Pharmacokinetics of SHR2554 in Healthy Chinese Volunteers: A Drug-Drug Interaction Study. May 2023. Crossref, https://doi.org/10.22541/au.168322865.51461018/v1.
Xu, Xin, et al. "Conformationally Constrained Potent Inhibitors for Enhancer of Zeste Homolog 2 (EZH2)." Bioorganic & Medicinal Chemistry Letters, vol. 97, Jan. 2024, p. 129558. Crossref, https://doi.org/10.1016/j.bmcl.2023.129558.
Yamagishi, Makoto, et al. "Mechanisms of action and resistance in histone methylation-targeted therapy." Nature 627.8002 (2024): 221-228.
Yang, Xiaobao, et al. "Structure—Activity Relationship Studies for Enhancer of Zeste Homologue 2 (EZH2) and Enhancer of Zeste Homologue 1 (EZH1) Inhibitors." Journal of Medicinal Chemistry, vol. 59, No. 16, Aug. 2016, pp. 7617-7633. Crossref, https://doi.org/10.1021/acs.jmedchem.6b00855.
Yang, Xiaojuan, et al. "Recent Advances in EZH2-Based Dual Inhibitors in the Treatment of Cancers." European Journal of Medicinal Chemistry, vol. 256, Aug. 2023, p. 115461. Crossref, https://doi.org/10.1016/j.ejmech.2023.115461.
Yang, Yiqi, et al. "FGFR4 and EZH2 Inhibitors Synergistically Induce Hepatocellular Carcinoma Apoptosis via Repressing YAP Signaling." Journal of Experimental & Clinical Cancer Research, vol. 42, No. 1, Apr. 2023. Crossref, https://doi.org/10.1186/s13046-023-02659-4.
Yang, Yiying, et al. "EZH2 Inhibition Dampens Autoantibody Production in Lupus by Restoring B Cell Immune Tolerance."

(56) References Cited

OTHER PUBLICATIONS

International Immunopharmacology, vol. 119, Jun. 2023, p. 110155. Crossref, https://doi.org/10.1016/j.intimp.2023.110155.
Yomtoubian, Shira, et al. "Inhibition of EZH2 Catalytic Activity Selectively Targets a Metastatic Subpopulation in Triple-Negative Breast Cancer." Cell Reports, vol. 30, No. 3, Jan. 2020, pp. 755-770.e6. Crossref, https://doi.org/10.1016/j.celrep.2019.12.056.
Yoshimitsu, Makoto, et al. "Pivotal Phase 2 Study of the EZH1 and EZH2 Inhibitor Valemetostat Tosylate (DS-3201b) in Patients with Relapsed or Refractory Adult T-Cell Leukemia/Lymphoma." Blood, vol. 138, No. Supplement 1, Nov. 2021, pp. 303-303. Crossref, https://doi.org/10.1182/blood-2021-146657.
Ysebaert, Loic, et al. "Tazemetostat in Combination with R-CHOP in Patients with High-Risk, Frontline Follicular Lymphoma (Epi-RCHOP): A Phase II Study from the Lysa." Blood, vol. 142, No. Supplement 1, Nov. 2023, pp. 297-297. Crossref, https://doi.org/10.1182/blood-2023-185057.
Yu, Lei, et al. "Dysregulation of Iron Homeostasis by TfR-1 Renders EZH2 Wild Type Diffuse Large B-Cell Lymphoma Resistance to EZH2 Inhibition." Acta Pharmacologica Sinica, vol. 44, No. 10, May 2023, pp. 2113-2124. Crossref, https://doi.org/10.1038/s41401-023-01097-4.
Yu, Xufen, et al. "Dissecting and Targeting Noncanonical Functions of EZH2 in Multiple Myeloma via an EZH2 Degrader." Oncogene, vol. 42, No. 13, Feb. 2023, pp. 994-1009. Crossref, https://doi.org/10.1038/s41388-023-02618-5.
Yuan, Hongchao, et al. "Epigenetic Inhibitors for Cancer Treatment." Epigenetic Regulation of Cancer—Part B, 2024, pp. 89-144. Crossref, https://doi.org/10.1016/bs.ircmb.2023.06.003.
Yun Kyoung Ryu, et al., "Easy does it! New EZH2 inhibitor SHR2554 is safe and active in relapsed or refractory lymphoma", The Lancet Haematology, 9:e463-e465, Jul. 2022.
Yuqin Song, et al., "Enhancer of zeste homolog 2 inhibitor SHR2554 in relapsed or refractory peripheral T-cell lymphoma: data from the first-in-human phase 1 study", Clinical Cancer Research, Jan. 9, 2024.
Yuqin Song, et al., "SHR2554, an EZH2 inhibitor, in relapsed or refractory mature lymphoid neoplasms: a first-in-human, dose-escalation, dose-expansion, and clinical expansion phase 1 trial", The Lancet Haematology, 9:e493-e503, Jul. 2022.
Zain, Jasmine, and Avyakta Kallam. "Challenges in Nodal Peripheral T-Cell Lymphomas: From Biological Advances to Clinical Applicability." Frontiers in Oncology, vol. 13, Apr. 2023. Crossref, https://doi.org/10.3389/fonc.2023.1150715.
Zauderer, Marjorie G., et al. "EZH2 Inhibitor Tazemetostat in Patients with Relapsed or Refractory, BAP1-Inactivated Malignant Pleural Mesothelioma: A Multicentre, Open-Label, Phase 2 Study." The Lancet Oncology, vol. 23, No. 6, Jun. 2022, pp. 758-767. Crossref, https://doi.org/10.1016/s1470-2045(22)00277-7.
Zauderer, Marjorie Glass, et al. "Safety and Efficacy of Tazemetostat, an Enhancer of Zeste-Homolog 2 Inhibitor, in Patients with Relapsed or Refractory Malignant Mesothelioma." Journal of Clinical Oncology, vol. 38, No. 15_suppl, May 2020, pp. 9058-9058. Crossref, https://doi.org/10.1200/jco.2020.38.15_suppl.9058.
Zeng, Jia, et al. "Targeting EZH2 for Cancer Therapy: From Current Progress to Novel Strategies." European Journal of Medicinal Chemistry, vol. 238, Aug. 2022, p. 114419. Crossref, https://doi.org/10.1016/j.ejmech.2022.114419.
Zhang, Huilai, et al. "Clinical Significance of Enhancer of Zeste Homolog 2 and Histone Deacetylases 1 and 2 Expression in Peripheral T-cell Lymphoma." Oncology Letters, May 2019. Crossref, https://doi.org/10.3892/ol.2019.10410.
Zhang, Jinwei, et al. Discovery of Epigenetic Modulators Targeting Hdacs and Ezh2 Simultaneously for the Treatment of Hematological Malignancies. 2024. Crossref, https://doi.org/10.2139/ssrn.4987105.
Zhang, Ping, and Mingzhi Zhang. "Epigenetic Alterations and Advancement of Treatment in Peripheral T-Cell Lymphoma." Clinical Epigenetics, vol. 12, No. 1, Nov. 2020. Crossref, https://doi.org/10.1186/s13148-020-00962-x.
Zhang, Qian, et al. "EZH2 Serves as a Promising Therapeutic Target for Fibrosis." Bioorganic Chemistry, vol. 137, Aug. 2023, p. 106578. Crossref, https://doi.org/10.1016/j.bioorg.2023.106578.
Zhang, Shengzhe, et al. CRACD Loss Promotes Small Cell Lung Cancer Tumorigenesis via EZH2-Mediated Immune Evasion. Feb. 2023. Crossref, https://doi.org/10.1101/2023.02.15.528365.
Zhang, Xi, et al. "Combined Inhibition of PARP and EZH2 for Cancer Treatment: Current Status, Opportunities, and Challenges." Frontiers in Pharmacology, vol. 13, Oct. 2022. Crossref, https://doi.org/10.3389/fphar.2022.965244.
Zhang, Yaping, et al. "Therapeutic Options in Peripheral T Cell Lymphoma." Journal of Hematology & Oncology, vol. 9, No. 1, Apr. 2016. Crossref, https://doi.org/10.1186/s13045-016-0267-0.
Zhang, Yi, et al. "Discovery of a New-Generation S-Adenosylmethionine-Noncompetitive Covalent Inhibitor Targeting the Lysine Methyltransferase Enhancer of Zeste Homologue 2." Journal of Medicinal Chemistry, vol. 66, No. 11, May 2023, pp. 7629-7644. Crossref, https://doi.org/10.1021/acs.jmedchem.3c00504.
Zhang, Zhuangzhuang, et al. "Downregulation of EZH2 Inhibits Epithelial—Mesenchymal Transition in Enzalutamide-resistant Prostate Cancer." The Prostate, vol. 83, No. 15, Jul. 2023, pp. 1458-1469. Portico, Crossref, https://doi.org/10.1002/pros.24602.
Zhao, Zhou, et al. "Safety Profile of EZH2 Inhibitors for Cancer: A Systematic Review and Meta-Analysis." PeerJ, vol. 13, Jan. 2025, p. e18871. Portico, Crossref, https://doi.org/10.7717/peerj.18871.
Zheng, Xiaoqing, et al. "Ezh2 Knockout in B Cells Impairs Plasmablast Differentiation and Ameliorates Lupus-like Disease in MRL/Lpr Mice." Arthritis & Rheumatology, vol. 75, No. 8, May 2023, pp. 1395-1406. Portico, Crossref, https://doi.org/10.1002/art.42492.
Zhou, Bin, et al. "Discovery of Dihydropyridinone Derivative as a Covalent EZH2 Degrader." European Journal of Medicinal Chemistry, vol. 261, Dec. 2023, p. 115825. Crossref, https://doi.org/10.1016/j.ejmech.2023.115825.
Zhou, Yan, et al. "Efficacy and Safety of SHR-2554 in Advanced Epithelioid Sarcoma: A Phase 2 Trial." Journal of Clinical Oncology, vol. 42, No. 16_suppl, Jun. 2024, pp. 11549-11549. Crossref, https://doi.org/10.1200/jco.2024.42.16_suppl.11549.
Zhu, Yongxia, et al. "Pharmacological Inhibition of EZH2 by ZLD1039 Suppresses Tumor Growth and Pulmonary Metastasis in Melanoma Cells in Vitro and in Vivo." Biochemical Pharmacology, vol. 210, Apr. 2023, p. 115493. Crossref, https://doi.org/10.1016/j.bcp.2023.115493.
Zinzani, Pier Luigi, et al. "Valemetostat for Patients with Relapsed or Refractory Peripheral T-Cell Lymphoma (Valentine-PTCL01): A Multicentre, Open-Label, Single-Arm, Phase 2 Study." The Lancet Oncology, vol. 25, No. 12, Dec. 2024, pp. 1602-1613. Crossref, https://doi.org/10.1016/s1470-2045(24)00503-5.
Zlocowski, N., et al. "The Epigenetic EZH2/H3K27me3 Axis Modulates Lactotroph Tumor Cell Proliferation." Journal of Endocrinology, vol. 257, No. 2, Feb. 2023. Crossref, https://doi.org/10.1530/joe-22-0195.
Maruyama, Dai, et al. "Valemetostat Monotherapy in Patients With Relapsed/Refractory Non-Hodgkin Lymphomas: Primary Results From a Phase 1 Trial." Clinical Lymphoma Myeloma and Leukemia, vol. 24, Sep. 2024, p. S229. Crossref, https://doi.org/10.1016/s2152-2650(24)00908-x.
Chemical Abstracts Registry No. 1804457-76-8, indexed in the Registry file on Sep. 10, 2015. (Year:2015).
Chemical Abstracts Registry No. 1895361-02-0, indexed in the Registry file on Apr. 22, 2016. (Year:2016).
Chemical Abstracts Registry No. 1896401-67-4, indexed in the Registry file on Apr. 24, 2016. (Year:2016).
Chemical Abstracts Registry No. 2110161-86-7, indexed in the Registry file on Aug. 8, 2017. (Year:2017).
International Search Report and Written Opinion for International Patent Application No. PCT/CN2018/087246, mailed Aug. 1, 2018.
International Search Report and Written Opinion for International Patent Application No. PCT/CN2018/114798, mailed Feb. 15, 2019.
Knutson, Sarah K., et al. "Selective Inhibition of EZH2 by EPZ-6438 Leads to Potent Antitumor Activity in EZH2-Mutant Non-

(56) References Cited

OTHER PUBLICATIONS

Hodgkin Lymphoma." Molecular Cancer Therapeutics, vol. 13, No. 4, Apr. 2014, pp. 842-854. Crossref, https://doi.org/10.1158/1535-7163.mct-13-0773.

Schafer, S., Kolkhof, P. Failure is an option: learning from unsuccessful proof-of-concept trials. Drug Discovery Today. Nov. 2008, 13, 913-916.*

Honig, H., Pullman, W. From bench to clinic and back: Perspective on the 1st IQPC Translational Research conference. Journal of Translational Medicine. Dec. 2004, 2, 44.*

Lue et al., Emerging EZH2 inhibitors and Their Application in Lymphoma. Current Hematologic Malignancy Reports, 2018, 13, 369-382.*

Anandan et al., "1-(1-Acetyl-piperidin-4-yl)-3-adamantan-1-yl-urea (AR9281) as a potent, selective, and orally available soluble epoxide hydrolase inhibitor with efficacy in rodent models of hypertension and dysglycemia," Bioorganic & Medicinal Chemistry Letters, vol. 21, pp. 983-988 (2011).

Arbuckle et al., "Optimisation of Pharmacokinetic Properties to Afford an Orally Bioavailable and Selective V1A Receptor Antagonist," Bioorganic & Medicinal Chemistry Letters, vol. 21, pp. 4622-4628 (2011).

Hewings et al., "Optimization of 3,5-Dimethylisoxazole Derivatives as Potent Bromodomain Ligands," Journal of Medicinal Chemistry, vol. 56, pp. 3217-3227 (2013).

International Search Report dated Jan. 22, 2017 in International Application No. PCT/CN2016/104318.

Schultz et al., "Asymmetric Syntheses of 1,6-Dialkyl-1,4-cyclohexadiene Derivatives," Journal of American Chemical Society, vol. 113, No. 13, pp. 4931-4936 (1991).

Chang et al., "The Role of EZH2 in Tumour Progression," British Journal of Cancer, vol. 106, No. 2, pp. 243-247 (2012).

Lund et al., "EZH2 in Normal and Malignant Hematopoiesis," Leukemia, vol. 28, No. 1, pp. 44-49 (2014).

Shen et al., "Update of Research on the Role of EZH2 in Cancer Progression," OncoTargets and Therapy, vol. 6, pp. 321-324 (2013).

Yan et al., "EZH2 Overexpression in Natural Killer/T-cell Lymphoma Confers Growth Advantage Independently of Histone Methyltransferase Activity," Blood, vol. 121, pp. 4512-4520 (2013).

* cited by examiner

BENZOFURAN DERIVATIVE, PREPARATION METHOD THEREOF AND USE THEREOF IN MEDICINE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application is a *reissue application of U.S. application Ser. No. 15/775,958, filed May 14, 2018, which issued as U.S. Pat. No. 10,759,787 on Sep. 1, 2020, and which is a* Section 371 of International Application No. PCT/CN2016/104318, filed Nov. 2, 2016, which was published in the Chinese language on May 26, 2017, under International Publication No. WO 2017/084494 A1, which claims priority under 35 U.S.C. § 119(b) to Chinese Application No. 201510800975.7, filed Nov. 19, 2015.

FIELD OF THE INVENTION

The present invention belongs to the filed of medicine and relates to a benzofuran derivative, a preparation method thereof and a use thereof in the medical research. The present invention discloses the use of the devivative as an EZH2 inhibitor in the prevention and/or treatment of diseases such as tumours and cancers, etc., in particular, in the prevention and/or treatment of non-Hodgkin's lymphoma, diffuse large B-cell lymphoma, follicular lymphoma and synovial sarcoma, etc.

BACKGROUND OF THE INVENTION

The occurrence of tumor is an evolution process of multi-factors and multi-stages, involving mutation and epigenetic changes of multiple genes such as oncogene, anti-oncogene and DNA damage repair gene. Strictly speaking, epigenetics is defined as a combination of genetic mechanisms capable of altering genome function in addition to the direct alteration of the DNA sequence. Herein, "epigenetics" refers broadly to elements of chromatin structure that control genome function, regardless of whether the control is heritable. Epigenetic or chromatin-based regulation plays an important role in gene expression in normal physiological function or in cancer evolution Polycomb group protein (PcG) is an important protein factor involved in the negative regulation of chromatin gene epigenetics. In mammals, PcG is mainly divided into two types with different structures and functions: polycomb repressive complex 2 (PRC2) and polycomb repressive complex 1 (PRC1). The histone methyltransferase encoded by the EZH2 gene is the catalytic component of polycomb repressive complex 2 (PRC2) and exerts the trimethyltransferase activity on the lysine 27 (H3K27) of histone H3 to generate H3K27me3 by means of the SET domain of the EZH2 subunit. It promotes transcriptional repression by means of various mechanisms including the urgent recruitment of DNA methyltransferases (DNMT) and PRC1 that ubiquitinates H2AK119. The codon mutation at codon 641 of EZH2, the most common mutation hotspot, is a gain-of-function mutation leading to an enhanced trimethylation of histone H3K27, and plays an important role in the tumorigenesis of GCB-type diffuse large B-cell lymphoma (DLBCL) and follicular lymphoma (FL). Recurrent somatic mutations in the SET domain of EZH2 are common in patients with diffused large B cell lymphomas (DLBCL). In addition, EZH2 overexpression is common in a variety of tumor types with poor prognosis, including cancers, lymphomas and soft tissue sarcomas etc. EZH2 expression in synovial sarcoma is associated with high H3K27 trimethylation. EZH2 levels are abnormally elevated in cancer tissues compared to normal tissues, and EZH2 is most highly expressed in advanced cancers or poor prognosis. In some types of cancers, EZH2 overexpression occurs simultaneously with amplification of the EZH2 gene. A large number of si/shRNA experimental studies show that reduction of EZH2 expression in tumor cell lines can inhibit tumor cell proliferation, migration, and invasion, or angiogenesis, and lead to apoptosis.

Patent applications disclosing EZH2 selective inhibitors include WO2012005805, WO2012050532, WO2012118812, WO2012142513, WO2012142504, WO2013049770, WO2013039988, WO2013067300, WO2015141616, and WO2011140325, etc.

EZH2 inhibitors as drugs have promising application prospects in the medical industry. However, there is still a need to develop new EZH2 inhibitors for achieving better therapeutic effects in tumors and cancers, and which better meets the maket demand.

SUMMARY OF THE INVENTION

The present invention is directed to a compound of formula (I) or a tautomer, mesomer, racemate, enantiomer, diastereomer, or mixture thereof, or a pharmaceutically acceptable salt thereof, wherein the structure of the compound of formula (I) is as follows:

(I)

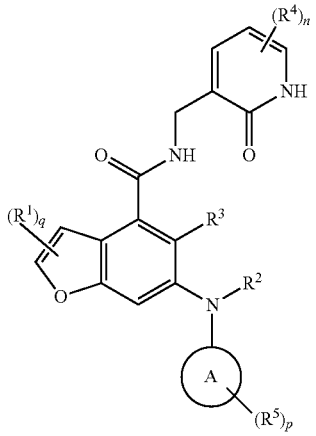

wherein:

ring A is selected from the group consisting of heterocyclyl and cycloalkyl;

each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$(CH_2)_xR^a$, wherein the alkyl, haloalkyl, heterocyclyl, aryl and heteroaryl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, and heteroaryl;

$R^2$ is hydrogen or alkyl, wherein the alkyl is optionally substituted by one or more groups selected from the group consisting of halogen, hydroxy, cyano, cycloalkyl and heterocyclyl;

$R^3$ is selected from the group consisting of hydrogen, alkyl, halogen, cyano, alkoxy and haloalkyl;

each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;

each $R^5$ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;

$R^6$ is selected from the group consisting of hydrogen, alkyl, haloalkyl, alkoxy, hydroxyalkyl, hydroxy, amino, cycloalkyl, heterocyclyl, aryl and heteroaryl;

$R^7$ and $R^8$ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

m is 0, 1 or 2;

n is 0, 1, 2 or 3;

p is 0, 1, 2, 3, 4 or 5;

q is 0, 1 or 2; and x is 0, 1, 2 or 3.

In a preferred embodiment of the present invention, in a compound of formula (I) or a tautomer, mesomer, racemate, enantiomer, diastereomer, or mixture thereof, or a pharmaceutically acceptable salt thereof, n is 2.

In a preferred embodiment of the present invention, in a compound of formula (I) or a tautomer, mesomer, racemate, enantiomer, diastereomer, or mixture thereof, or a pharmaceutically acceptable salt thereof, q is 0 or 1.

In a preferred embodiment of the present invention, in a compound of formula (I) or a tautomer, mesomer, racemate, enantiomer, diastereomer, or mixture thereof, or a pharmaceutically acceptable salt thereof, p is 0 or 1.

In a preferred embodiment of the present invention, in a compound of formula (I) or a tautomer, mesomer, racemate, enantiomer, diastereomer, or mixture thereof, or a pharmaceutically acceptable salt thereof, each $R^1$ is identical or different and each is independently selected from the group consisting of hydrogen, halogen, alkyl, haloalkyl, cyano, cycloalkyl, heterocyclyl and —$(CH_2)_xR^a$, wherein the alkyl and heterocyclyl are each independently and optionally substituted by one or more groups selected from the group consisting of alkyl, hydroxyalkyl and halogen; and $R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of hydroxyalkyl, alkyl and halogen; and $R^7$, $R^8$ and x are as defined in formula (I).

In a preferred embodiment of the present invention, in a compound of formula (I) or a tautomer, mesomer, racemate, enantiomer, diastereomer, or mixture thereof, or a pharmaceutically acceptable salt thereof, each $R^1$ is identical or different and each is independently selected from the group consisting of hydrogen, alkyl, haloalkyl, cyano and —$(CH_2)_xR^a$, wherein x is 0, and $R^a$ is halogen or cycloalkyl.

In a preferred embodiment of the present invention, in a compound of formula (I) or a tautomer, mesomer, racemate, enantiomer, diastereomer, or mixture thereof, or a pharmaceutically acceptable salt thereof, $R^2$ is alkyl optionally substituted by cycloalkyl.

In a preferred embodiment of the present invention, in a compound of formula (I) or a tautomer, mesomer, racemate, enantiomer, diastereomer, or mixture thereof, or a pharmaceutically acceptable salt thereof, $R^3$ is selected from the group consisting of alkyl, halogen and haloalkyl.

In a preferred embodiment of the present invention, in a compound of formula (I) or a tautomer, mesomer, racemate, enantiomer, diastereomer, or mixture thereof, or a pharmaceutically acceptable salt thereof, each $R^4$ is identical or different and each is independently selected from the group consisting of hydrogen, alkyl and alkoxy.

In a preferred embodiment of the present invention, in a compound of formula (I), or a tautomer, mesomer, racemate, enantiomer, diastereomer, or mixture thereof, or a pharmaceutically acceptable salt thereof, each $R^5$ is identical or different and each is independently selected from the group consisting of hydrogen, halogen, oxo, haloalkyl, —$C(O)R^6$, —$S(O)_mR^6$ and —$NR^7R^8$, wherein $R^6$ to $R^8$ and m are as defined in formula (I), preferably hydrogen.

In a preferred embodiment of the present invention, a compound of formula (I) or a tautomer, mesomer, racemate, enantiomer, diastereomer, or mixture thereof, or a pharmaceutically acceptable salt thereof, is a compound of formula (II) or a tautomer, mesomer, racemate, enantiomer, diastereomer, or mixture thereof, or a pharmaceutically acceptable salt thereof:

(II)

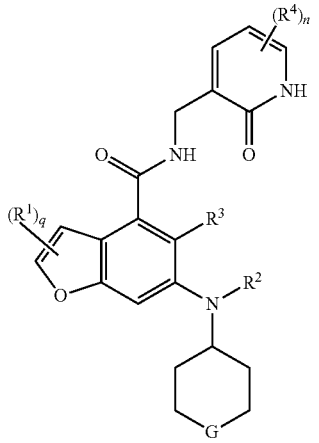

wherein:

G is selected from the group consisting of $CR^bR^c$, C═O, $S(O)_m$, $NR^d$ and oxygen; $R^b$ and $R^c$ are each independently selected from the group consisting of hydrogen, alkyl, alkoxy, halogen, amino, nitro, hydroxy, cyano, cycloalkyl, heterocyclyl, aryl, heteroaryl, —$OR^6$, —$C(O)R^6$, —$C(O)OR^6$, —$S(O)_mR^6$ and —$NR^7R^8$;

$R^d$ is selected from the group consisting of hydrogen, alkyl, cycloalkyl, haloalkyl, hydroxyalkyl, heterocyclyl, aryl, heteroaryl, —$C(O)R^6$, —$C(O)OR^6$ and —$S(O)_mR^6$; and $R^1$ to $R^4$, $R^6$ to $R^8$, n, m and q are as defined in formula (I).

In a preferred embodiment of the present invention, a compound of formula (II) or a tautomer, mesomer, racemate, enantiomer, diastereomer, or mixture thereof, or a pharmaceutically acceptable salt thereof, is a compound of formula (III), or a tautomer, mesomer, racemate, enantiomer, diastereomer, or mixture thereof, or a pharmaceutically acceptable salt thereof:

(III)

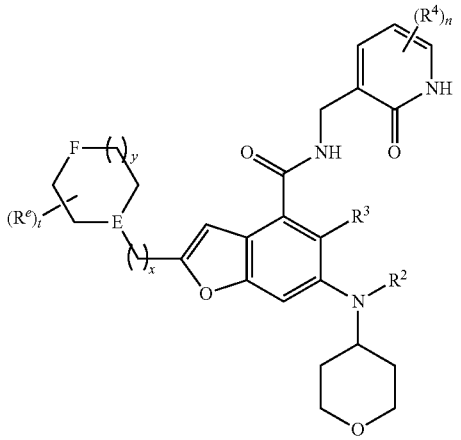

wherein:

E is CH or nitrogen;

F is selected from the group consisting of $CR^bR^c$, C═O, $NR^d$ and oxygen;

$R^b$ and $R^c$ are each independently selected from the group consisting of hydrogen, alkyl, alkoxy, halogen, amino, nitro, hydroxy, cyano, cycloalkyl, heterocyclyl, aryl, heteroaryl, —$OR^6$, —$C(O)R^6$, —$C(O)OR^6$, —$S(O)_mR^6$ and —$NR^7R^8$;

$R^d$ is selected from the group consisting of hydrogen, alkyl, cycloalkyl, haloalkyl, hydroxyalkyl, heterocyclyl, aryl, heteroaryl, —$C(O)R^6$, —$C(O)OR^6$ and —$S(O)_mR^6$;

each $R^e$ is identical or different and each is independently selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl;

t is 0, 1, 2, 3, 4 or 5;

x is 0, 1, 2 or 3;

y is 0, 1, 2 or 3; and $R^1$ to $R^4$, $R^6$ to $R^8$, m and n are as defined in formula (I).

In a preferred embodiment of the present invention, a compound of formula (III) or a tautomer, mesomer, racemate, enantiomer, diastereomer, or mixture thereof, or a pharmaceutically acceptable salt thereof, is a compound of formula (IV), or a tautomer, mesomer, racemate, enantiomer, diastereomer, or mixture thereof, or a pharmaceutically acceptable salt thereof:

(IV)

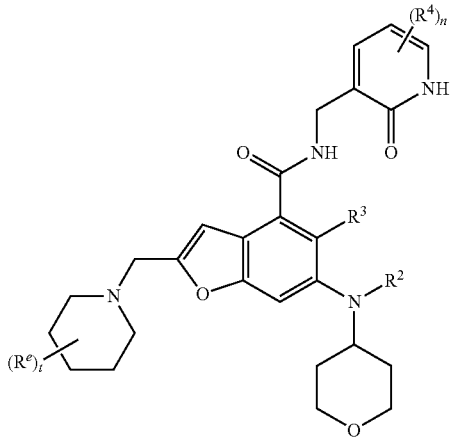

wherein:

each $R^e$ is identical or different and is independently selected from the group consisting of hydrogen, alkyl and halogen;

t is 0, 1, 2, 3, 4 or 5; and $R^2$ to $R^4$ and n are as defined in formula (I).

In a preferred embodiment of the present invention, a compound of formula (III) or a tautomer, mesomer, racemate, enantiomer, diastereomer, or mixture thereof, or a pharmaceutically acceptable salt thereof, is a compound of formula (V), or a tautomer, mesomer, racemate, enantiomer, diastereomer, or mixture thereof, or a pharmaceutically acceptable salt thereof:

(V)

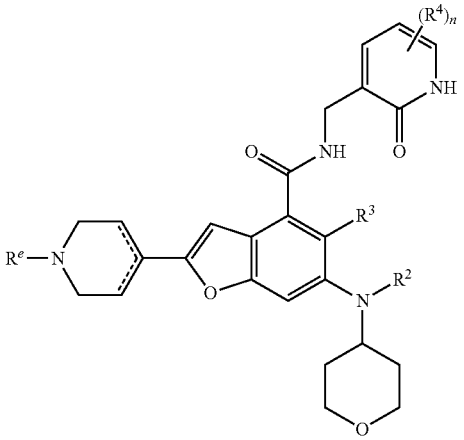

wherein:

$R^e$ is selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl; and $R^2$ to $R^4$ and n are as defined in formula (I).

Typical compounds of formula (I) or a tautomer, mesomer, racemate, enantiomer, diastereomer, or mixture thereof, or a pharmaceutically acceptable salt thereof, include, but are not limited to:

| Example No. | Structure and Name |
|---|---|
| 1 | 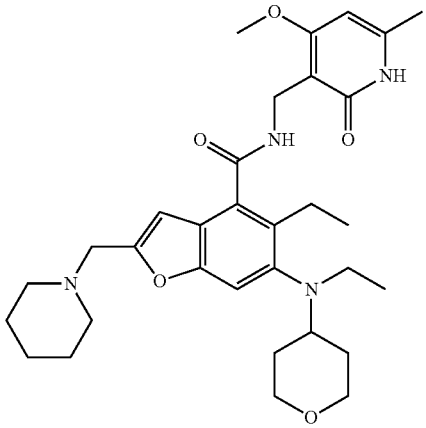 1 5-ethyl-6-(ethyl(tetrahydro-2H-pyran-4-yl)amino)-N-((4-methoxy-6-methyl-2-oxo-1,2-dihydropyridin-3-yl)methyl)-2-(piperidin-1-ylmethyl)benzofuran-4-carboxamide |
| 2 | 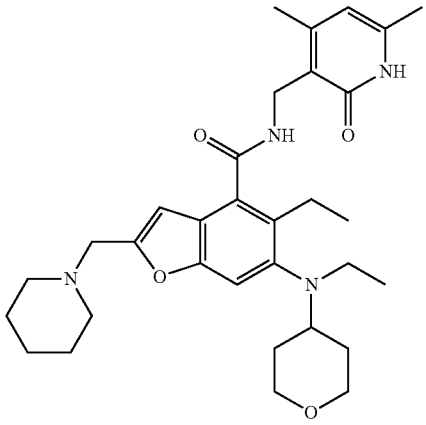 2 N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide |
| 3 | 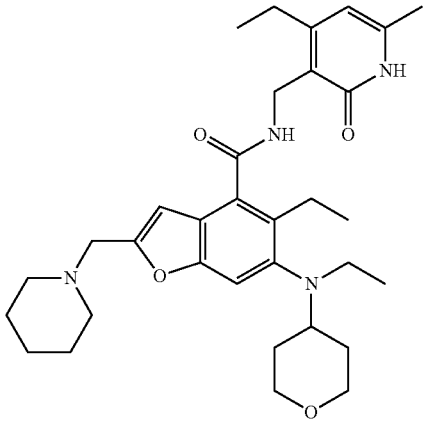 3 5-ethyl-6-(ethyl(tetrahydro-2H-pyran-4-yl)amino)-N-((4-ethyl-6-methyl-2-oxo-1 ,2-dihydropyridin-3-yl)methyl)-2-(piperidin-1-ylmethyl)benzofuran-4-carboxamide |

-continued

| Example No. | Structure and Name |
|---|---|
| 4 | 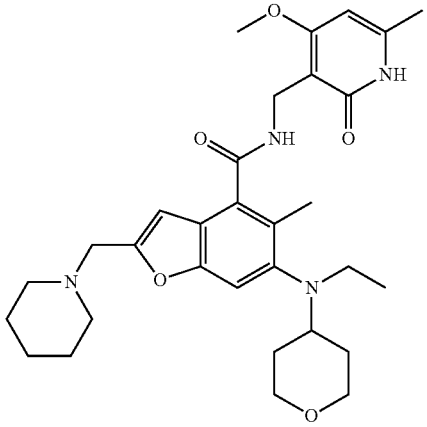 4 6-(ethyl(tetrahydro-2H-pyran-4-yl)amino)-N-((4-methoxy-6-methyl-2-oxo-1,2-dihydropyridin-3-yl)methyl)-5-methyl-2-(piperidin-1-ylmethyl)benzofuran-4-carboxamide |
| 5 | 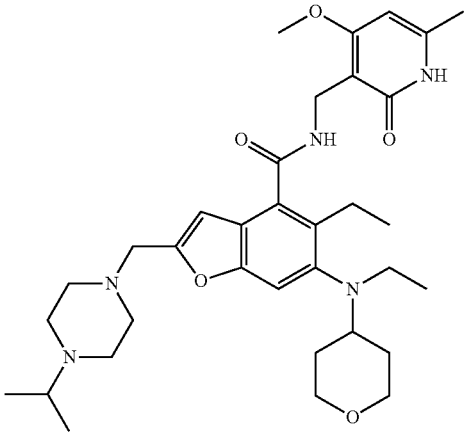 5 5-ethyl-6-(ethyl(tetrahydro-2H-pyran-4-yl)amino)-2-((4-isopropylpiperazin-1-yl)methyl)-N-((4-methoxy-6-methyl-2-oxo-1,2-dihydropyridin-3-yl)methyl)benzofuran-4-carboxamide |
| 6 | 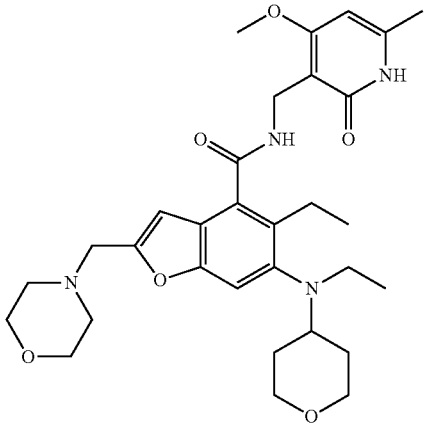 6 5-ethyl-6-(ethyl(tetrahydro-2H-pyran-4-yl)amino)-N-((4-methoxy-6-methyl-2-oxo-1,2-dihydropyridin-3-yl)methyl)-2-(morpholinomethyl)benzofuran-4-carboxamide |

-continued

| Example No. | Structure and Name |
|---|---|
| 7 | 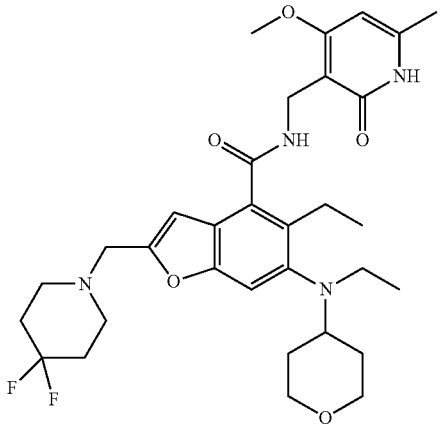 7 2-((4,4-difluoropiperidin-1-yl)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide |
| 8 | 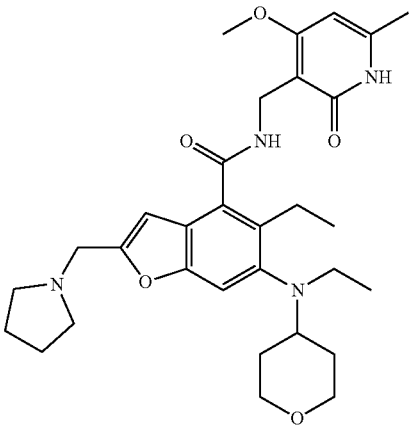 8 5-ethyl-6-(ethyl(tetrahydro-2H-pyran-4-yl)amino)-N-((4-methoxy-6-methyl-2-oxo-1,2-dihydropyridin-3-yl)methyl)-2-(pyrrolidin-1-ylmethyl)benzofuran-4-carboxamide |
| 9 | 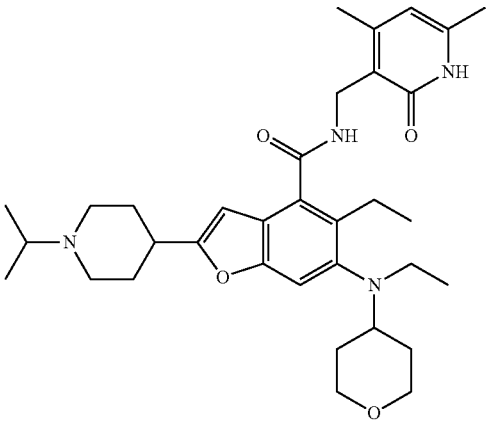 9 N-((4,6-dimethyl-2-oxo-1,2-dihydropyridin-3-yl)methyl)-5-ethyl-6-(ethyl(tetrahydro-2H-pyran-4-yl)amino)-2-(1-isopropyl-piperidin-4-yl)benzofuran-4-carboxamide |

-continued

| Example No. | Structure and Name |
|---|---|
| 10 | 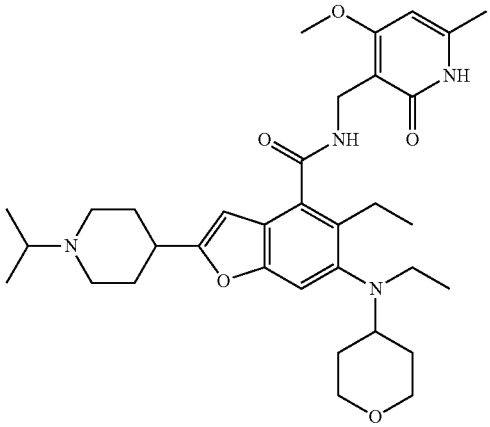 10 5-ethyl-6-(ethyl(tetrahydro-2H-pyran-4-yl)amino)-2-(1-isopropylpiperidin-4-yl)-N-((4-methoxy-6-methyl-2-oxo-1,2-dihydropyridin-3-yl)methyl)benzofuran-4-carboxamide |
| 11 | 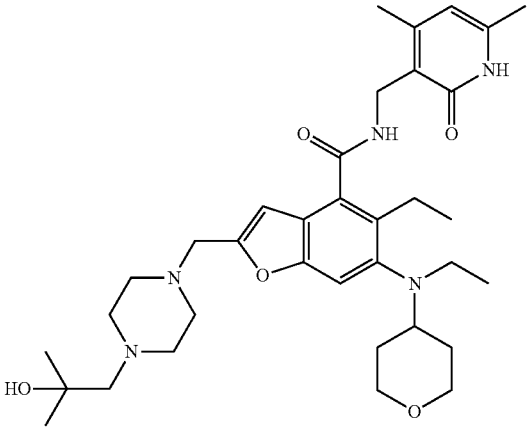 11 N-((4,6-dimethyl-2-oxo-1,2-dihydropyridin-3-yl)methyl)-5-ethyl-6-(ethyl(tetrahydro-2H-pyran-4-yl)amino)-2-((4-(2-hydroxy-2-methylpropyl) piperazin-1-yl)methyl)benzofuran-4-carboxmide |
| 12 | 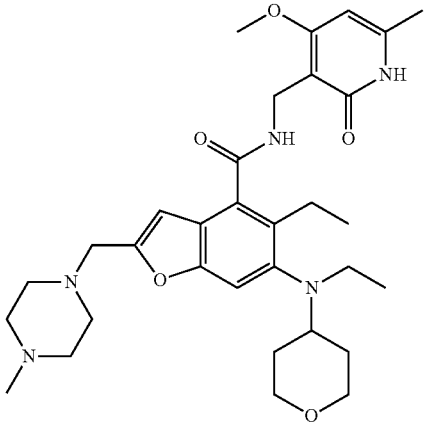 |

-continued

| Example No. | Structure and Name |
|---|---|
| 12 | 5-ethyl-6-(ethyl(tetrahydro-2H-pyran-4-yl)amino)-N-((4-methoxy-6-methyl-2-oxo-1,2-dihydropyridin-3-yl)methyl)-2-((4-methylpiperazin-1-yl)methyl)benzofuran-4-carboxamide |
| 13 | 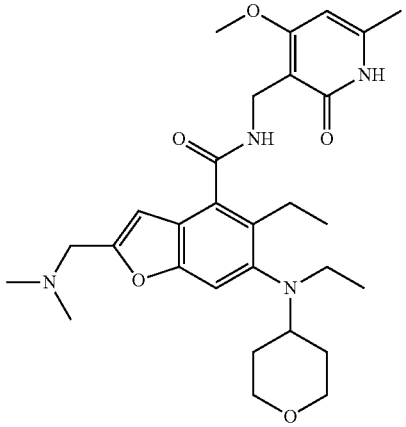 13 2-((dimethylamino)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxmide |
| 14 | 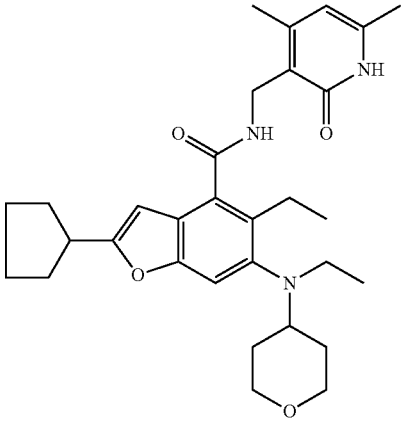 14 2-cyclopentyl-N-((4,6-dimethyl-2-oxo-1,2-dihydropyridin-3-yl)methyl)-5-ethyl-6-(ethyl(tetrahydro-2H-pyran-4-yl)amino)benzofuran-4-carboxamide |
| 15 | 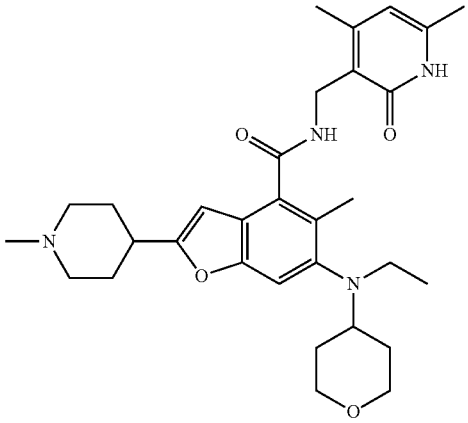 15 N-((4,6-dimethyl-2-oxo-1,2-dihydropyridin-3-yl)methyl)-6-(ethyl(tetrahydro-2H-pyran-4-yl)amino)-5-methyl-2-(1-methylpiperdin-4-yl)benzofuran-4-carboxmide |
| 16 | 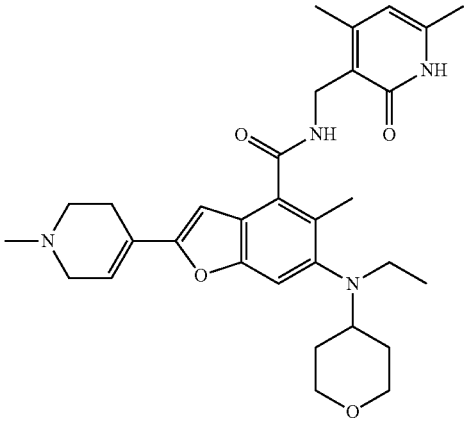 16 N-((4,6-dimethyl-2-oxo-1,2-dihydropyridin-3-yl)methyl)-6-(ethyl(tetrahydro-2H-pyran-4-yl)amino)-5-methyl-2-(1-methyl-1,2,3,6-tetrahydropyridin-4-yl)benzofuran-4-carboxamide |
| 17 | 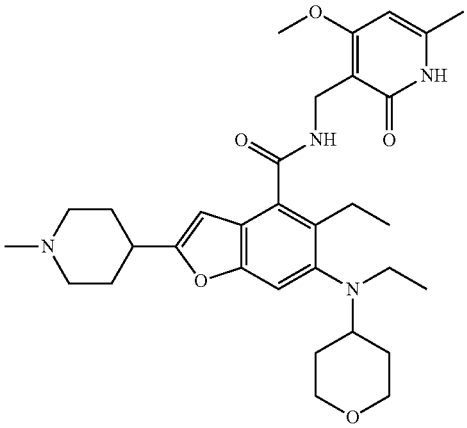 17 5-ethyl-6-(ethyl(tetrahydro-2H-pyran-4-yl)amino)-N-((4-methoxy-6-methyl-2-oxo-1,2-dihydropyridin-3-yl)methyl)-2-(1-methylpiperidin-4-yl)benzofuran-4-carboxamide |

-continued

| Example No. | Structure and Name |
|---|---|
| 18 | 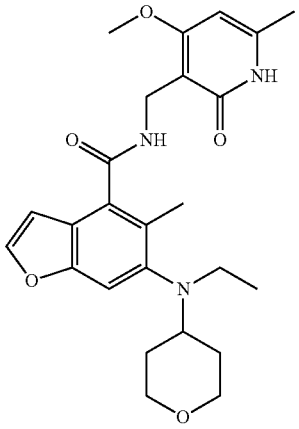 18 6-(ethyl(tetrahydro-2H-pyran-4-yl)amino)-N-((4-methoxy-6-methyl-2-oxo-1,2-dihydropyridin-3-yl)methyl)-5-methylbenzofuran-4-carboxamide |
| 19 | 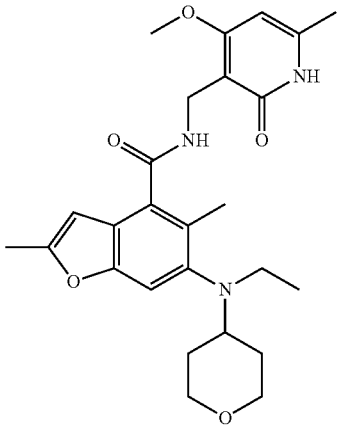 19 6-(ethyl(tetrahydro-2H-pyran-4-yl)amino)-N-((4-methoxy-6-methyl-2-oxo-1,2-dihydropyridin-3-yl)methyl)-2,5-dimethylbenzofuran-4-carboxamide |
| 20 | 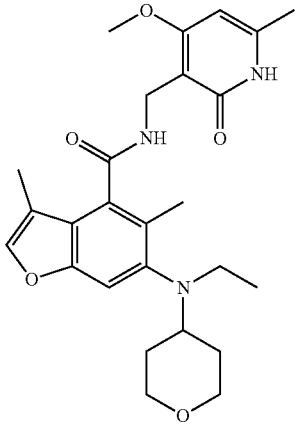 20 6-(ethyl(tetrahydro-2H-pyran-4-yl)amino)-N-((4-methoxy-6-methyl-2-oxo-1,2-dihydropyridin-3-yl)methyl)-3,5-dimethylbenzofuran-4-carboxamide |

-continued

| Example No. | Structure and Name |
|---|---|
| 21 | 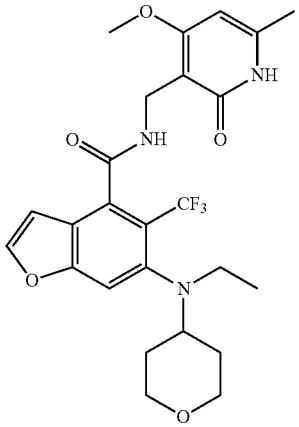 21 6-(ethyl(tetrahydro-2H-pyran-4-yl)amino)-N-((4-methoxy-6-methyl-2-oxo-1,2-dihydropyridin-3-yl)methyl)-5-(trifluoromethy)benzofuran-4-carboxamide |
| 22 | 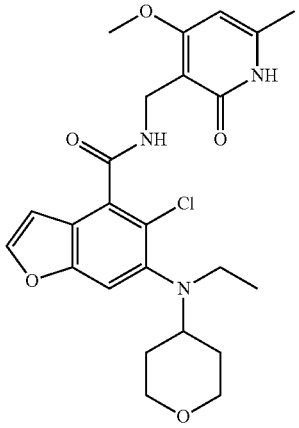 22 5-chloro-6-(ethyl(tetrahydro-2H-pyran-4-yl)amino)-N-((4-methoxy-6-methyl-2-oxo-1,2-dihydropyridin-3-yl)methyl)benzofuran-4-carboxamide |
| 23 | 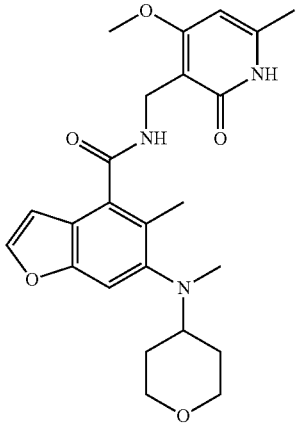 |

-continued

| Example No. | Structure and Name |
|---|---|
| 23 | N-((4-methoxy-6-methyl-2-oxo-1,2-dihydropyridin-3-yl)methyl)-5-methyl-6-(methyl(tetrahydro-2H-pyran-4-yl)amino)benzofuran-4-carboxamide |
| 24 | 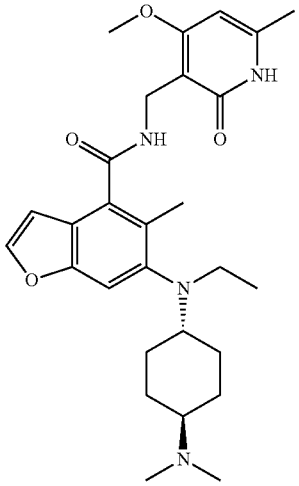 24 6-(((1r,4r)-4-(dimethylamino)cyclohexyl)(ethyl)amino)-N-((4-methoxy-6-methyl-2-oxo-1,2-dihydropyridin-3-yl)methyl)-5-methylbenzofuran-4-carboxamide |
| 25 | 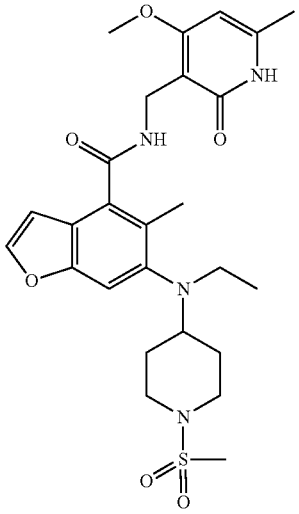 25 6-(ethyl(1-(methylsulfonyl)piperidin-4-yl)amino)-N-((4-methoxy-6-methyl-2-oxo-1,2-dihydropyridin-3-yl)methyl)-5-methyl-benzofuran-4-carboxamide |

-continued

| Example No. | Structure and Name |
|---|---|
| 26 | 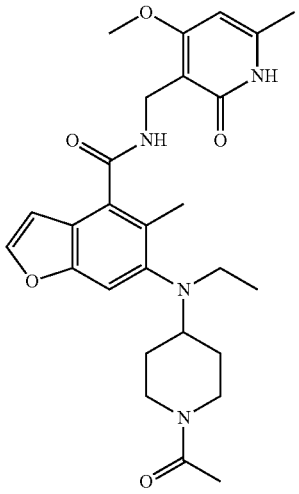 26 6-((1-acetylpiperidin-4-yl)(ethyl)amino)-N-((4-methoxy-6-methyl-2-oxo-1,2-dihydropyridin-3-yl)methyl)-5-methylbenzofuran-4-carboxamide |
| 27 | 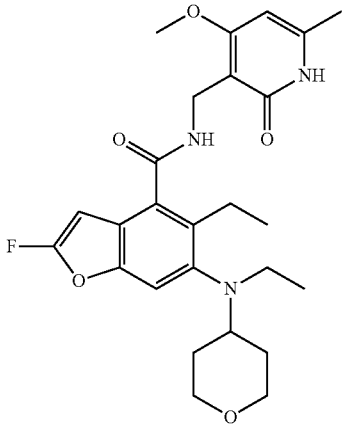 27 5-ethyl-6-(ethyl(tetrahydro-2H-pyran-4-yl)amino)-2-fluoro-N-((4-methoxy-6-methyl-2-oxo-1,2-dihydropyridin-3-yl)methyl)benzofuran-4-carboxamide |
| 28 | 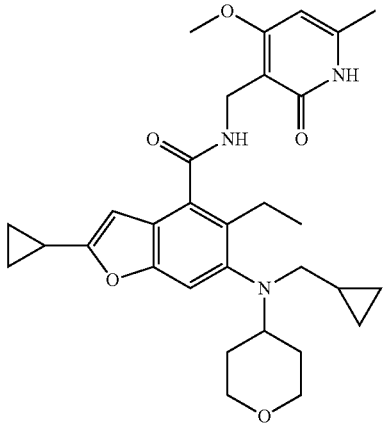 |

-continued

| Example No. | Structure and Name |
|---|---|
| 28 | 2-cyclopropyl-6-((cyclopropylmethyl)(tetrahydro-2H-pyran-4-yl)amino)-5-ethyl-N-((4-methoxy-6-methyl-2-oxo-1,2-dihydropyridin-3-yl)methyl)benzofuran-4-carboxamide |
| 29 | 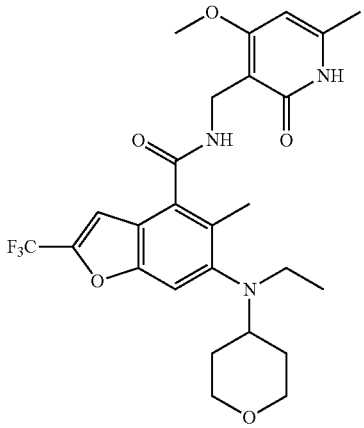 |
| 29 | 6-(ethyl(tetrahydro-2H-pyran-4-yl)amino)-N-((4-methoxy-6-methyl-2-oxo-1,2-dihydropyridin-3-yl)methyl)-5-methyl-2-(trifluoromethyl)benzofuran-4-carboxamide |
| 30 | 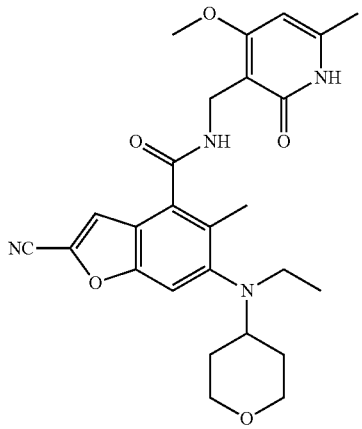 |
| 30 | 2-cyano-6-(ethyl(tetrahydro-2H-pyran-4-yl)amino)-N-((4-methoxy-6-methyl-2-oxo-1,2-dihydropyridin-3-yl)methyl)-5-methylbenzofuran-4-carboxamide |

-continued

| Example No. | Structure and Name |
|---|---|
| 31 | 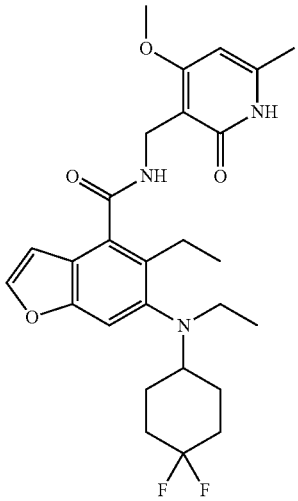 |
| 31 | 6-((4,4-difluorocyclohexyl)(ethyl)amino)-5-ethyl-N-((4-methoxy-6-methyl-2-oxo-1,2-dihydropyridin-3-yl)methyl)benzofuran-4-carboxamide |
| 32 | 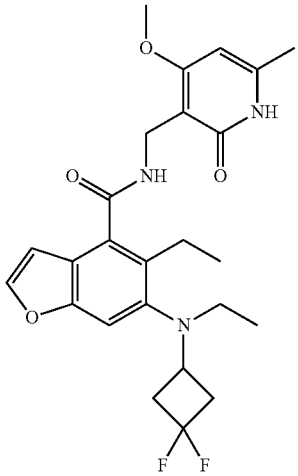 |
| 32 | 6-((3,3-difluorocyclobutyl)(ethyl)amino)-5-ethyl-N-((4-methoxy-6-methyl-2-oxo-1,2-dihydropyridin-3-yl)methyl)benzofuran-4-carboxamide |

-continued

| Example No. | Structure and Name |
|---|---|
| 33 | 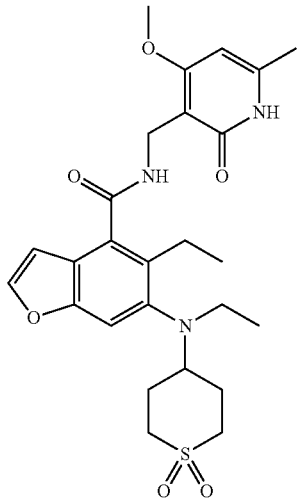 33 6-((1,1-dioxidotetrahydro-2H-thiopyran-4-yl)(ethyl)amino)-5-ethyl-N-((4-methoxy-6-methyl-2-oxo-1,2-dihydropyridin-3-yl)methyl)benzofuran-4-carboxamide |
| 34 | 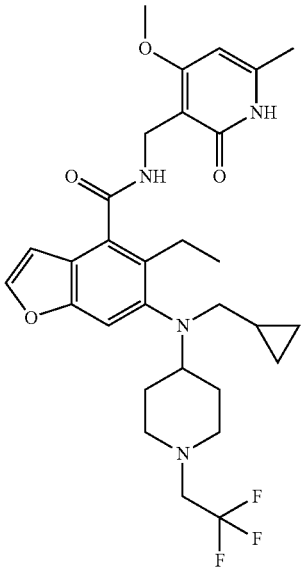 34 6-((cyclopropylmethyl)(1-(2,2,2-trifluorocethyl)piperidin-4-yl)amino)-5-ethyl-N-((4-methoxy-6-methyl-2-oxo-1,2-dihydropyridin-3-yl)methyl)benzofuran-4-carboxamide |

or a tautomer, mesomer, racemate, enantiomer, diastereomer, or mixture thereof, or a pharmaceutically acceptable salt thereof.

The present invention further provides an intermediate for preparing the compound of formula (I) or a tautomer, mesomer, racemate, enantiomer, diastereomer, or mixture thereof, or a pharmaceutically acceptable salt thereof, i.e., a compound of formula (VI):

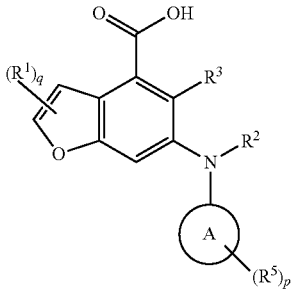

(VI)

or a tautomer, mesomer, racemate, enantiomer, diastereomer, or mixture thereof, or a pharmaceutically acceptable salt thereof, wherein:

ring A, $R^1$ to $R^3$, $R^5$, p and q are as defined in formula (I).

In another aspect, the present invention is also directed to a process for preparing a compound of formula (I) or a tautomer, mesomer, racemate, enantiomer, diastereomer, or mixture thereof, or a pharmaceutically acceptable salt thereof, comprising:

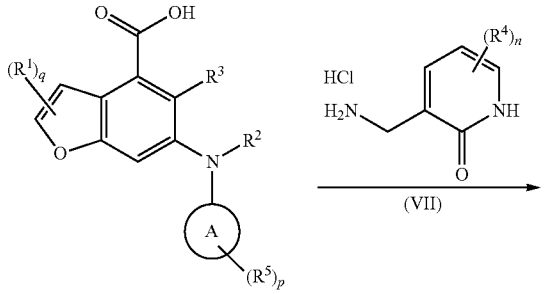

(VI) (VII)

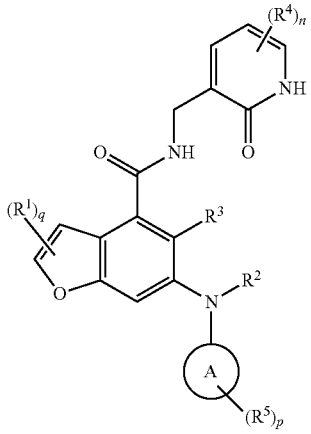

(I)

condensing a compound of formula (VI) with a compound of formula (VII) at room temperature to obtain the compound of formula (I);

wherein:

$R^1$ to $R^5$, ring A, p, q and n are as defined in (I).

In another aspect, the present invention is directed to a pharmaceutical composition comprising a therapeutically effective amount of a compound of formula (I), (II), (III), (IV) or (V), or a tautomer, mesomer, racemate, enantiomer, diastereomer, or mixture thereof, or a pharmaceutically acceptable salt thereof, and one or more pharmaceutically acceptable carriers, diluents or excipients. The present invention is also directed to a process for the preparation of the aforementioned composition comprising mixing a compound of formula (I), (II), (III), (IV) or (V) or a tautomer, mesomer, racemate, enantiomer, diastereomer, or mixture thereof, or a pharmaceutically acceptable salt thereof, with one or more pharmaceutically acceptable carriers, diluents or excipients.

The present invention is further directed to use of a compound of formula (I) or a tautomer, mesomer, racemate, enantiomer, diastereomer, or mixture thereof, or a pharmaceutically acceptable salt thereof, or a pharmaceutical composition comprising the same, in the preparation of a medicament for preventing and/or treating tumor and cancer, wherein the cancer is selected from the group consisting of lymphoma, leukemia, breast cancer, lung cancer, prostate cancer, ovarian cancer, liver cancer, melanoma, rhabdomyosarcoma, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck cancer, and myeloma; preferably lymphoma, leukemia, breast cancer, lung cancer, prostate cancer, ovarian cancer, liver cancer, melanoma, rhabdomyosarcoma, synovial sarcoma and mesothelioma; wherein the lung cancer is selected from the group consisting of small cell lung cancer and non-small cell lung cancer; wherein the leukemia is selected from the group consisting of chronic myeloid leukemia, acute myeloid leukemia and mixed lineage leukemia; wherein the lymphoma is selected from non-Hodgkin's lymphoma, diffuse large B-cell lymphoma and follicular lymphoma.

The present invention is further directed to a compound of formula (I) or a tautomer, mesomer, racemate, enantiomer, diastereomer, or mixture thereof, or a pharmaceutically acceptable salt thereof, or a pharmaceutical composition comprising the same for use as a medicament for preventing and/or treating tumor and cancer, wherein the tumor and cancer are as defined above.

The present invention is also directed to a method for the preventing and/or treating tumor and cancer, comprising administering to a patient in need thereof a therapeutically effective amount of a compound of formula (I) or a tautomer, mesomer, racemate, enantiomer, diastereomer, or mixture thereof, or a pharmaceutically acceptable salt thereof, or a pharmaceutical composition comprising the same, wherein the tumor and cancer are as defined above.

The present invention is further directed to use of a compound of formula (I) or a tautomer, mesomer, racemate, enantiomer, diastereomer, or mixture thereof, or a pharmaceutically acceptable salt thereof, or a pharmaceutical composition comprising the same, as an EZH2 inhibitor in the preparation of a medicament for preventing and/or treating tumor and cancer, wherein the tumor and cancer are as defined above.

The present invention is further directed to use of a compound of formula (I) or a tautomer, mesomer, racemate, enantiomer, diastereomer, or mixture thereof, or a pharmaceutically acceptable salt thereof, or a pharmaceutical composition comprising the same, in the preparation of a medicament for inhibiting EZH2.

The present invention is further directed to a compound of formula (I) or a tautomer, mesomer, racemate, enantiomer, diastereomer, or mixture thereof, or a pharmaceutically acceptable salt thereof, or a pharmaceutical composition comprising the same for use as a medicament for inhibiting EZH2.

The present invention also directed to a method for inhibiting EZH2, comprising administering to a patient in need thereof a therapeutically effective amount of the compound of formula (I) or a tautomer, mesomer, racemate, enantiomer, diastereomer, or mixture thereof, or a pharmaceutically acceptable salt thereof, or a pharmaceutical composition comprising the same.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any method known in the art for the preparation of pharmaceutical compositions. Such compositions can contain one or more agents selected from the group consisting of sweetening agents, flavoring agents, coloring agents and preservatives, in order to provide a pleasing and palatable pharmaceutical formulation. The tablet contains the active ingredient in admixture with non-toxic pharmaceutically acceptable excipients suitable for the manufacture of a tablet.

An aqueous suspension contains the active ingredient in admixture with excipients suitable for the manufacture of an aqueous suspension. The aqueous suspension can also contain one or more preservatives, such as ethylparaben or n-propylparaben, one or more coloring agents, one or more flavoring agents, and one or more sweetening agents, such as sucrose, saccharin or aspartame.

An oil suspension can be formulated by suspending the active ingredient in a vegetable oil. The oil suspension can contain a thickener. The aforementioned sweetening agents and flavoring agents can be added to provide a palatable preparation.

The active ingredient in admixture with the dispersing or wetting agents, suspending agents or one or more preservatives can be prepared as a dispersible powder or granule suitable for the preparation of an aqueous suspension by adding water. Suitable dispersant or wetting agents and suspending agents are exemplified by those already mentioned above. Additional excipients, such as sweetening, flavoring, and coloring agents, can also be added. These compositions can be preserved by adding an antioxidant such as ascorbic acid.

The present pharmaceutical composition can also be in the form of an oil-in-water emulsion.

The pharmaceutical composition can be in the form of sterile injectable aqueous solution. The acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. For example, the active ingredient can be firstly dissolved in a mixture of soybean oil and lecithin, the oil solution is then introduced into a mixture of water and glycerol and processed to form a microemulsion. The injectable solution or microemulsion can be introduced into an individual's bloodstream by local bolus injection. Alternatively, it can be advantageous to administer the solution or microemulsion in such a way as to maintain a constant circulating concentration of the present compound. In order to maintain such a constant concentration, a continuous intravenous delivery device can be utilized. An example of such a device is Deltec CADD-PLUS.™5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable preparation can also be a sterile injectable solution or suspension prepared in a nontoxic parenterally acceptable diluent or solvent. Moreover, a sterile fixed oil can easily be used as a solvent or suspending medium.

The present compound can be administrated in the form of a suppository for rectal administration. These pharmaceutical compositions can be prepared by mixing drug with a suitable non-irritating excipient that is solid at ordinary temperatures, but liquid in the rectum, thereby melting in the rectum to release the drug. Such materials include cocoa butter, glycerin gelatin, hydrogenated vegetable oils, mixtures of polyethylene glycols with various molecular weights and fatty acid esters of polyethylene glycols.

It is well known to those skilled in the art that the dosage of a drug depends on a variety of factors including, but not limited to, the following factors: activity of a specific compound, age of the patient, weight of the patient, general health of the patient, behavior of the patient, diet of the patient, administration time, administration route, excretion rate, drug combination and the like. In addition, the best treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

"Alkyl" refers to a saturated aliphatic hydrocarbon group including $C_1$ to $C_{20}$ straight chain and branched chain groups, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy, and alkoxycarbonyl.

"Alkylene" refers to an alkyl of which a hydrogen atom is further substituted, for example, "methylene" refers to —$CH_2$—, "ethylene" refers to —$(CH_2)_2$—, "propylene" refers to —$(CH_2)_3$—, "butylene" refers to —$(CH_2)_4$— and the like.

"Alkenyl" refers to an alkyl as defined above that has at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio and heterocyclic alkylthio.

"Cycloalkyl" refers to a saturated and/or partially unsaturated monocyclic or polycyclic hydrocarbon group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more rings can contain one or more double bonds, but none of the rings has a completely conjugated pi-electron system, preferably 6 to 14 membered spiro cycloalkyl, and more preferably 7 to 10 membered spiro cycloalkyl. According to the number of the spiro atoms shared between the rings, spiro cycloalkyl can be divided into mono-spiro cycloalkyl, di-spiro cycloalkyl, or poly-spiro cycloalkyl, preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyls include:

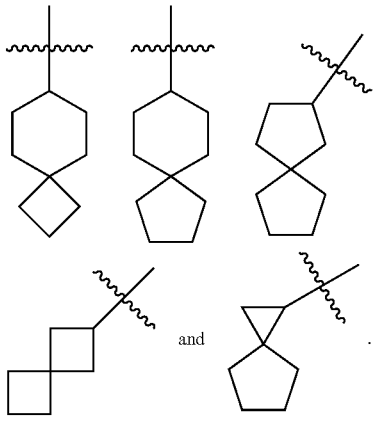

"Fused cycloalkyl" refers to a 5 to 20 membered full-carbon polycyclic group, wherein each ring in the system shares an adjacent pair of carbon atoms with another ring, wherein one or more rings can contain one or more double bonds, but none of the rings has a completely conjugated pi-electron system, preferably 6 to 14 membered fused cycloalkyl, more preferably 7 to 10 membered fused cycloalkyl. According to the number of membered rings, fused cycloalkyl can be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Non-limiting examples of fused cycloalkyls include:

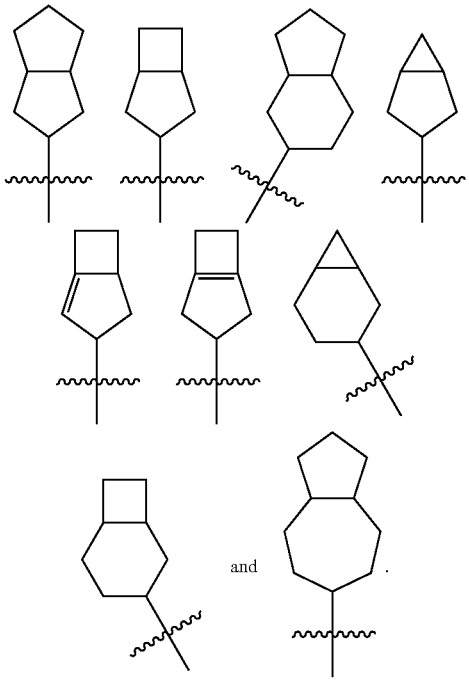

"Bridged cycloalkyl" refers to a 5 to 20 membered full-carbon polycyclic group, wherein every two rings in the system share two disconnected atoms, wherein the rings can have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl can be divided into bicyclic, tricyclic, tetracyclic or polycyclic bridged cycloalkyl, preferably bicyclic, tricyclic or tetracyclic bridged cycloalkyl, and more preferably bicyclic or tricyclic bridged cycloalkyl. Non-limiting examples of bridged cycloalkyls include:

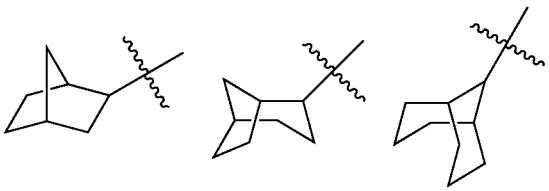

-continued

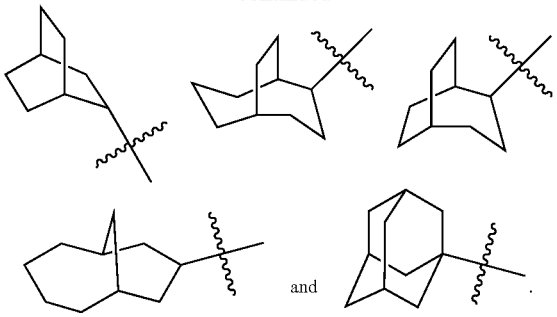

The aforementioned cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy and alkoxycarbonyl.

"Heterocyclyl" refers to a 3 to 20 membered saturated and/or partially unsaturated monocyclic or polycyclic hydrocarbon group having one or more heteroatoms selected from the group consisting of N, O, and S(O)m (wherein m is an integer of 0 to 2) as ring atoms, but excluding —O—O—, —O—S— or —S—S— in the ring, with the remaining ring atoms being carbon atoms. Preferably, heterocyclyl has 3 to 12 atoms wherein 1 to 4 atoms are heteroatoms, more preferably 3 to 8 atoms wherein 1 to 3 atoms are heteroatoms, and most preferably 3 to 6 atoms wherein 1 to 2 atoms are heteroatoms. Non-limiting examples of monocyclic heterocyclyl include pyrrolidinyl, imidazolidinyl, tetrahydrofuranyl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl, pyranyl and the like, preferably piperidinyl, pyrrolidinyl, pyranyl, morpholinyl or

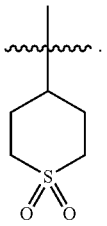

Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called a spiro atom), wherein the rings have one or more heteroatoms selected from the group consisting of N, O, and S(O)m (wherein m is an integer of 0 to 2) as ring atoms, with the remaining ring atoms being carbon atoms, wherein one or more rings can contain one or more double bonds, but none of the rings has a completely conjugated pi-electron system, preferably 6 to 14 membered spiro heterocyclyl, and more preferably 7 to 10 membered spiro heterocyclyl. According to the number of the spiro atoms shared between the rings, spiro heterocyclyl can be divided into mono-spiro heterocyclyl, di-spiro heterocyclyl, or poly-spiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

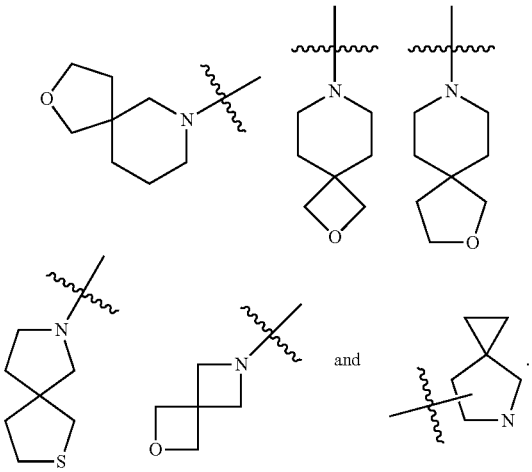

"Fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated pi-electron system, and wherein the rings have one or more heteroatoms selected from the group consisting of N, O, and S(O)m (wherein m is an integer of 0 to 2) as ring atoms, with the remaining ring atoms being carbon atoms, preferably 6 to 14 membered fused heterocyclyl, and more preferably 7 to 10 membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Non-limiting examples of fused heterocyclyls include:

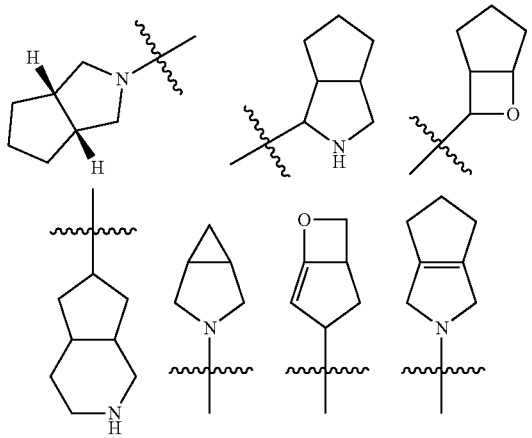

-continued

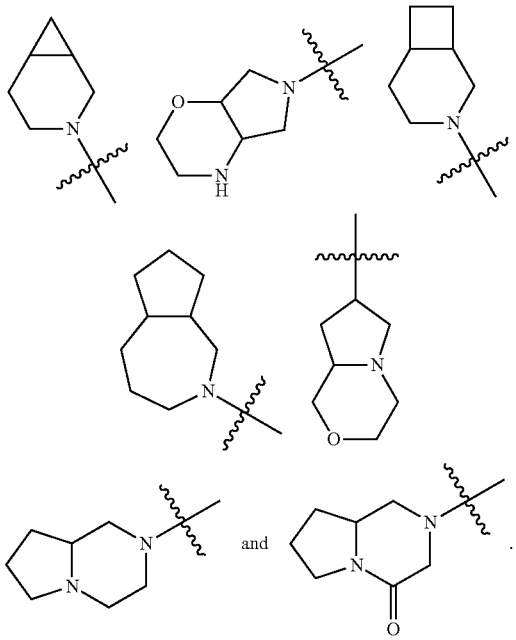

"Bridged heterocyclyl" refers to a 5 to 14 membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and S (O)m (wherein m is an integer of 0 to 2) as ring atoms, with the remaining ring atoms being carbon atoms, preferably 6 to 14 membered bridged heterocyclyl, and more preferably 7 to 10 membered bridged heterocyclyl. According to the number of membered rings, bridged heterocyclyl can be divided into bicyclic, tricyclic, tetracyclic or polycyclic bridged heterocyclyl, preferably bicyclic, tricyclic or tetracyclic bridged heterocyclyl, and more preferably bicyclic or tricyclic bridged heterocyclyl. Non-limiting examples of bridged heterocyclyls include:

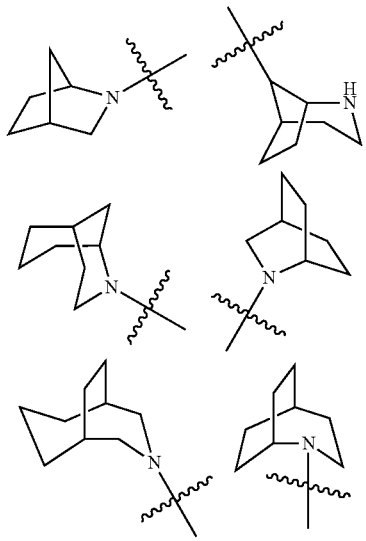

-continued

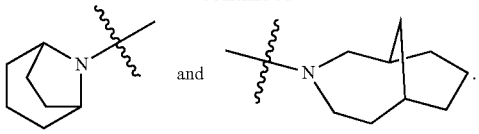

The heterocyclyl ring can be fused to the ring of aryl, heteroaryl or cycloalkyl, wherein the ring bound to the parent structure is heterocyclyl. Non-limiting examples include:

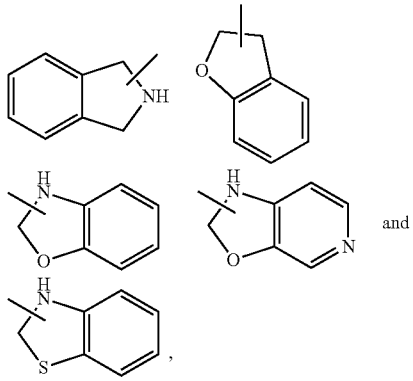

etc.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy and alkoxycarbonyl.

"Aryl" refers to a 6 to 14 membered full-carbon monocyclic ring or polycyclic fused ring (i.e. each ring in the system shares an adjacent pair of carbon atoms with another ring in the system) having a completely conjugated pi-electron system, preferably 6 to 10 membered aryl, for example, phenyl and naphthyl, and more preferably phenyl. The aryl ring can be fused to the ring of heteroaryl, heterocyclyl or cycloalkyl, wherein the ring bound to the parent structure is aryl ring. Non-limiting examples include:

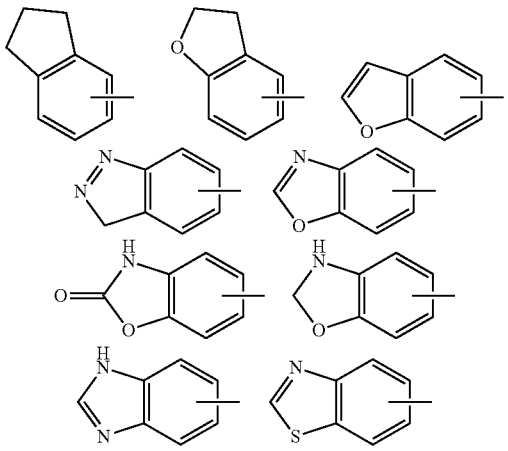

-continued

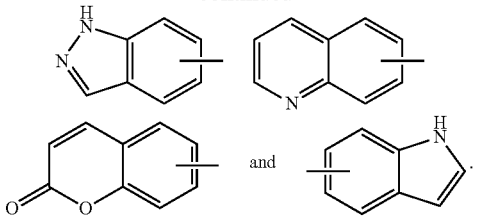

The aryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Heteroaryl" refers to a 5 to 14 membered heteroaromatic system having 1 to 4 heteroatoms selected from the group consisting of O, S and N as ring atoms, preferably 5 to 10 membered heteroaryl with 1 to 3 heteroatoms, more preferably 5 or 6 membered heteroaryl with 1 to 2 heteroatoms, for example, imidazolyl, furyl, thienyl, thiazolyl, pyrazolyl, oxazolyl, pyrrolyl, tetrazolyl, pyridinyl, pyrimidinyl, thiadiazole, pyrazinyl and the like, preferably imidazolyl, tetrazolyl, thienyl, pyrazolyl, pyrimidinyl or thiazolyl, and more preferably pyrazolyl or thiazolyl. The heteroaryl ring can be fused to the ring of aryl, heterocyclyl or cycloalkyl, wherein the ring bound to the parent structure is heteroaryl ring. Non-limiting examples include:

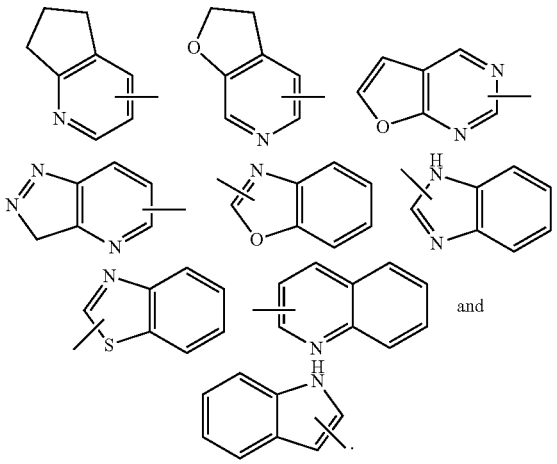

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Alkoxy" refers to an —O-(alkyl) or an —O-(unsubstituted cycloalkyl) group, wherein the alkyl is as defined above. Non-limiting examples include methoxy, ethoxy, propoxy, butoxy, cyclopropyloxy, cyclobutyloxy, cyclopentyloxy, cyclohexyloxy, and the like. The alkoxy can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Haloalkyl" refers to an alkyl group substituted by one or more halogens, wherein the alkyl is as defined above.

"Haloalkoxy" refers to an alkoxy group substituted by one or more halogens, wherein the alkoxy is as defined above.

"Hydroxyalkyl" refers to an alkyl substituted by hydroxy(s), wherein the alkyl is as defined above.

"Hydroxy" refers to an —OH group.

"Halogen" refers to fluorine, chlorine, bromine or iodine.

"Amino" refers to a —$NH_2$ group.

"Cyano" refers to a —CN group.

"Nitro" refers to a —$NO_2$ group.

"Oxo" refers to a =O group.

"Carbonyl" refers to a C=O group.

"Carboxy" refers to a —C(O)OH group.

"Isocyanato" refers to a —NCO group.

"Hydroxyimino" refers to a =N—OH group.

"Alkoxycarbonyl" refers to a —C(O)O(alkyl) or —C(O)O(cycloalkyl) group, wherein the alkyl and cycloalkyl are as defined above.

"Acyl halide" refers to a compound comprising a —C(O)-halogen group.

"Optional" or "optionally" means that the event or circumstance described subsequently can, but need not, occur, and such a description includes the situation in which the event or circumstance does or does not occur. For example, "the heterocyclyl group optionally substituted by an alkyl" means that an alkyl group can be, but need not be, present, and such a description includes the situation of the heterocyclyl group being substituted by an alkyl and the heterocyclyl group being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) can be unstable.

A "pharmaceutical composition" refers to a mixture of one or more of the compounds according to the present invention or physiologically/pharmaceutically acceptable salts or prodrugs thereof and other chemical components, and other components such as physiologically/pharmaceutically acceptable carriers and excipients. The purpose of a pharmaceutical composition is to facilitate administration of a compound to an organism, which is conducive to the absorption of the active ingredient, thus displaying biological activity.

"Pharmaceutically acceptable salt" refers to a salt of the compound of the present invention, which is safe and effective in mammals and has the desired biological activity.

Synthesis Method of the Compound of the Present Invention

In order to achieve the object of the present invention, the present invention applies the following synthesis technical solutions.

A process for preparing a compound of formula (I) of the present invention or a tautomer, mesomer, racemate, enantiomer, diastereomer, or mixture thereof, or a pharmaceutically acceptable salt thereof, comprises the following steps:

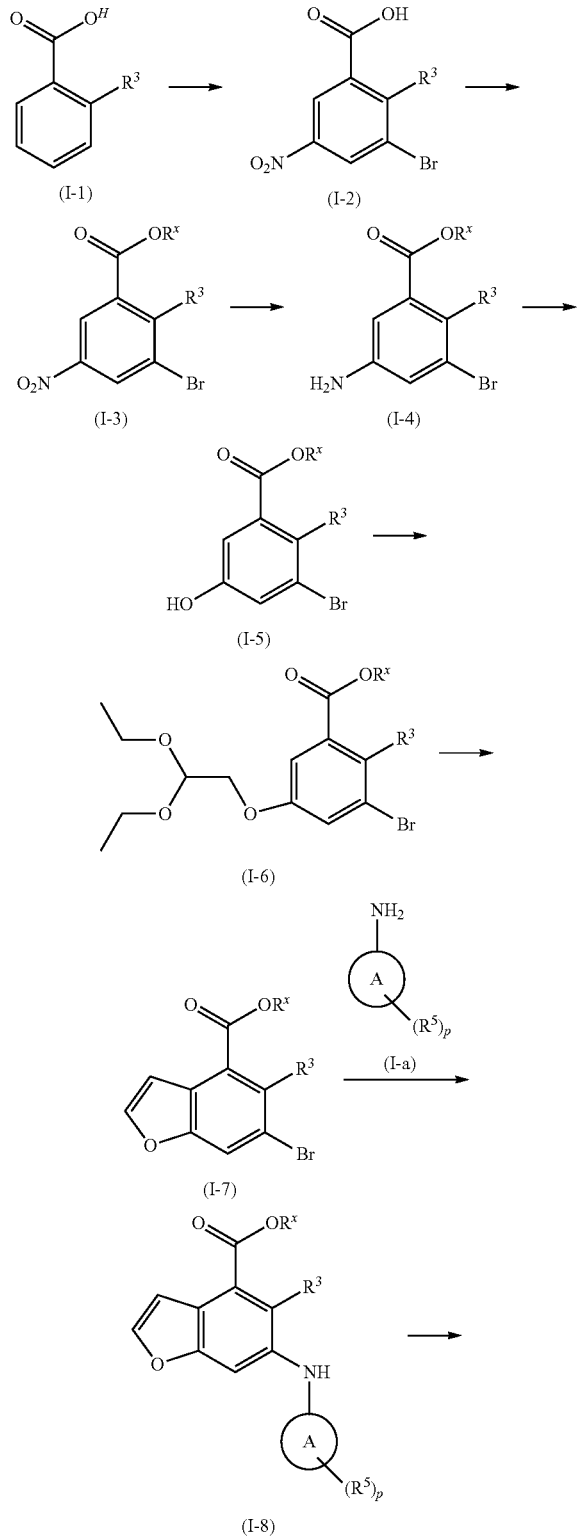

-continued

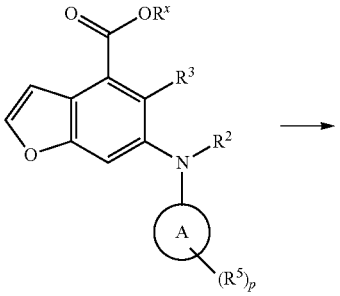

(I-9)

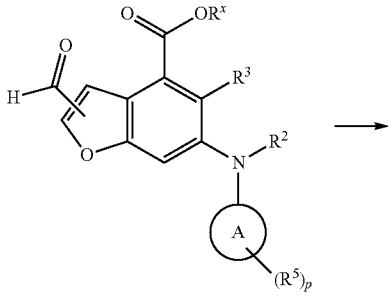

(I-10)

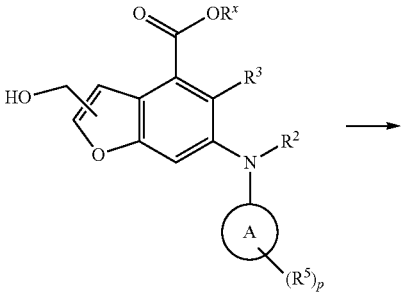

(I-11)

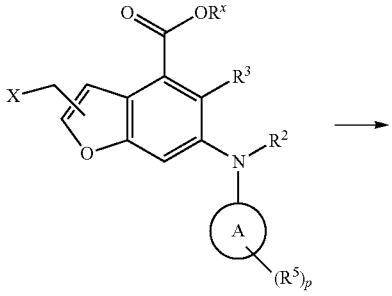

(I-12)

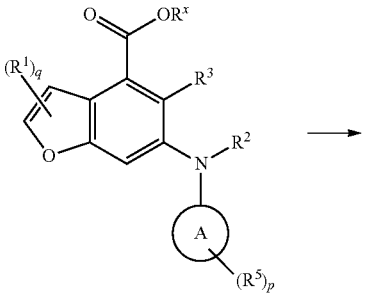

(I-13)

-continued

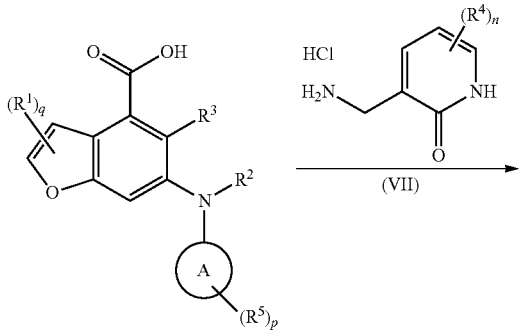

(VI)

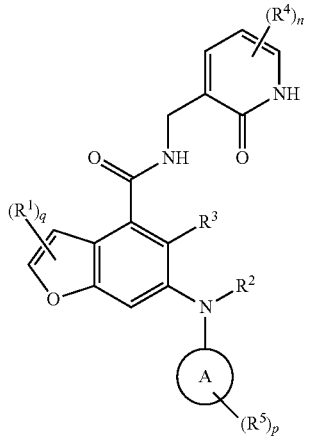

(I)

A compound of formula (I-1) is added to sulfuric acid, then sodium nitrate and N-bromosuccinimide are added in batches in an ice bath. The mixture is heated to obtain a compound of formula (I-2). The compound of formula (I-2) is subjected to an esterification reaction with a chloride under an alkaline condition to obtain a compound of formula (I-3), wherein the alkaline reagent that provides the alkaline condition is preferably potassium carbonate. The compound of formula (I-3) is reduced to obtain a compound of formula (I-4). A compound of (I-5) is obtained in the presence of sulfuric acid and sodium nitrite from the compound of formula (I-4). The compound of formula (I-5) reacts with 2-bromo-1,1-diethoxyethane under an alkaline condition to obtain a compound of formula (I-6). The compound of formula (I-6) is subjected to a cyclization reaction with 3-bromo-5-(2,2-diethoxyethoxy)-2-ethylbenzoate under heating and in an acidic condition to obtain a compound of formula (I-7). The compound of formula (I-7) is reacted with a compound of formula (Ia) in the presence of a catalyst under heating and in an alkaline condition to obtain a compound of of formula (I-8), wherein the alkaline reagent that provides the alkaline condition for this reaction is preferably potassium carbonate, and the catalyst is preferably tris(dibenzylideneacetone)dipalladium, or (±)-2,2'-bis (diphenylphosphino)-1,1'-binaphthalene. The compound of formula (I-8) is reacted with an alkyl halide under an alkaline condition to obtain a compound of formula (I-9). The compound of formula (I-9) is reacted with N,N-dimethylformamide under an alkaline condition to obtain a compound of formula (I-10), wherein the alkaline reagent that provides the alkaline condition for this reaction is preferably lithium diisopropylamide. The compound of formula (I-10) is reduced to a compound of formula (I-11) in the presence of a reducing agent, wherein the reducing agent under this condition is preferably sodium borohydride. The compound of formula (I-11) is reacted with phosphorus tribromide to obtain a compound of formula (I-12). The compound of formula (I-12) is reacted with $R^1H$ to obtain a compound of formula (I-13). The compound of formula (I-13) is hydrolyzed under an alkaline condition to obtain a compound of formula (VI), wherein the alkaline reagent that provides the alkaline condition for this reaction is preferably sodium hydroxide. The compound of formula (VI) is subjected to an acylation reaction with a compound of formula (VII) to obtain a compound of formula (I).

The reagent that provides an alkaline condition includes organic bases and inorganic bases, wherein the organic bases include, but are not limited to, triethylamine, N,N-diisopropylethylamine, n-butyllithium, lithium diisopropylamide, potassium acetate, sodium tert-butoxide and potassium tert-butoxide, and wherein the inorganic bases include, but are not limited to, sodium hydride, potassium phosphate, sodium carbonate, potassium carbonate and cesium carbonate.

The catalyst involved includes, but is not limited to, 2-dicyclohexylphosphino-2',4',6'-triisopropylbiphenyl, (±)-2,2'-bis(diphenylphosphino)-1,1'-binaphthalene, tris(dibenzylideneacetone)dipalladium, palladium acetate, [1,1'-bis(diphenylphosphino)ferrocene]dichloropalladium, triphenylphosphine, and tetrakistriphenylphosphine palladium.

Wherein:

$R^x$ is selected from the group consisting of hydrogen, alkyl, haloalkyl, hydroxyalkyl, cycloalkyl, heterocyclyl, aryl and heteroaryl, wherein the alkyl, cycloalkyl, heterocyclyl, aryl and heteroaryl are each independently and optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

X is halogen; and $R^1$ to $R^5$, ring A, p, q and n are as defined in formula (I).

Preferred Embodiments

The present invention will be further described with reference to the following examples, but the examples should not be considered as limiting the scope of the invention.

EXAMPLES

The structures of the compounds are identified by nuclear magnetic resonance (NMR) and/or mass spectrometry (MS). NMR is determined by a Bruker AVANCE-400 machine. The solvents for determination are deuterated-dimethyl sulfoxide (DMSO-$d_6$), deuterated-chloroform ($CDCl_3$) and deuterated-methanol ($CD_3OD$), the internal standard is tetramethylsilane (TMS), and NMR chemical shifts (δ) are given in $10^{-6}$ (ppm).

MS is determined by a FINNIGAN LCQAd (ESI) mass spectrometer (manufacturer: Thermo, type: Finnigan LCQ advantage MAX).

High performance liquid chromatography (HPLC) is determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average kinase inhibition rates and $IC_{50}$ values are determined by a NovoStar ELISA (BMG Co., Germany).

Yantai Huanghai HSGF254 or Qingdao GF254 silica gel plate is used for thin-layer silica gel chromatography (TLC). The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is used as a carrier for column chromatography.

The known starting materials of the present invention can be prepared by the conventional synthesis methods in the art, or can be purchased from ABCR GmbH & Co. KG, Acros Organnics, Aldrich Chemical Company, Accela ChemBio Inc., or Dari chemical Company, etc.

Unless otherwise stated, the reactions are carried out under an argon atmosphere or nitrogen atmosphere.

The term "argon atmosphere" or "nitrogen atmosphere" means that a reaction flask is equipped with a 1 L argon or nitrogen balloon.

The term "hydrogen atmosphere" means that a reaction flask is equipped with a 1 L hydrogen balloon.

Pressurized hydrogenation reactions are performed with a Parr 3916EKX hydrogenation instrument and a QL-500 hydrogen generator or HC2-SS hydrogenation instrument.

In hydrogenation reactions, the reaction system is generally vacuumed and filled with hydrogen, with the above operation repeated three times.

CEM Discover-S 908860 type microwave reactor is used in microwave reaction.

Unless otherwise stated, the solution used in the reactions refers to an aqueous solution.

Unless otherwise stated, the reaction temperature in the reactions refers to room temperature.

Room temperature is the most appropriate reaction temperature, and ranges from 20° C. to 30° C.

The reaction process is monitored by thin layer chromatography (TLC), and the developing solvent system includes: A: dichloromethane and methanol system, B: n-hexane and ethyl acetate system, C: petroleum ether and ethyl acetate system, D: acetone. The ratio of the volume of the solvent can be adjusted according to the polarity of the compounds.

The elution system for purification of the compounds by column chromatography and thin layer chromatography includes: A: dichloromethane and methanol system, B: n-hexane and ethyl acetate system, C: n-hexane, ethyl acetate and dichloromethane system, D: petroleum ether and ethyl acetate system, E: ethyl acetate. The ratio of the volume of the solvent can be adjusted according to the polarity of the compounds, and sometimes a little alkaline reagent such as triethylamine or acidic reagent can be added.

Example 1
5-Ethyl-6-(ethyl(tetrahydro-2H-pyran-4-yl)amino)-N-((4-methoxy-6-methyl-2-oxo-1,2-dihydropyridin-3-yl)methyl)-2-(piperidin-1-ylmethyl)benzofuran-4-carboxamide
1
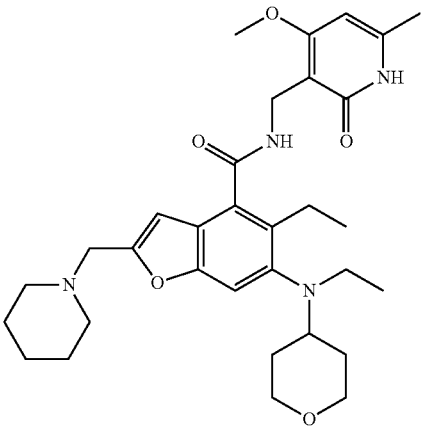
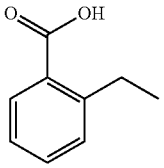
step 1
1a
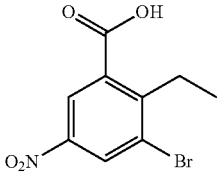
step 2
1b
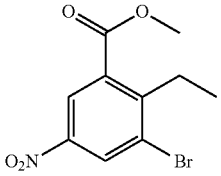
step 3
1c
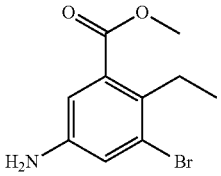
step 4
1d
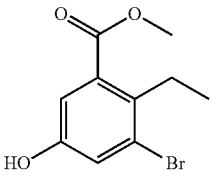
step 5
1e
-continued
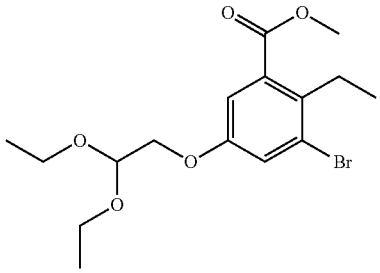
step 6
1f
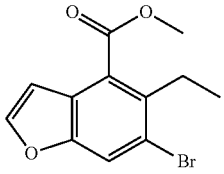
step 7
1g
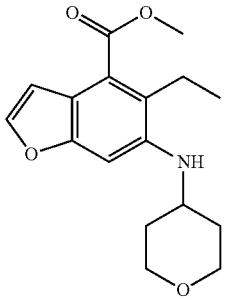
step 8
1h
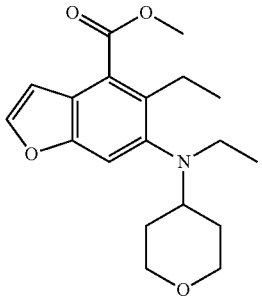
step 9
1i
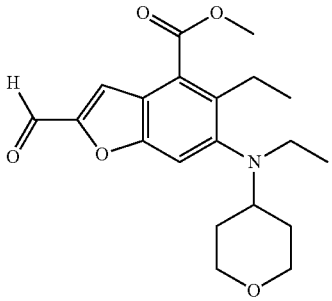
step 10
1j -continued

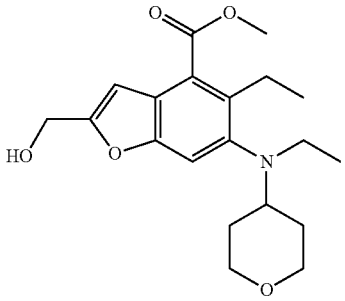

1k

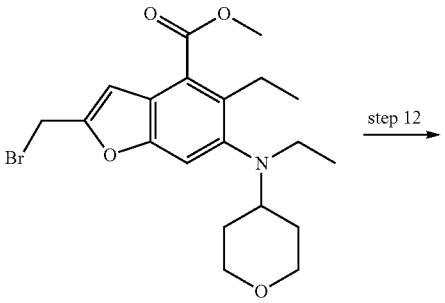

1l

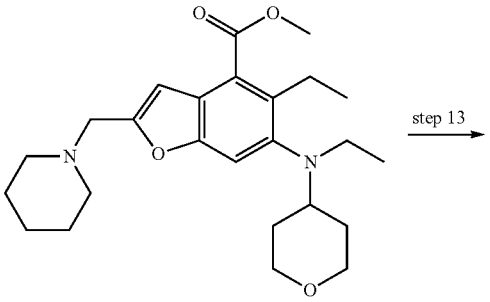

1m

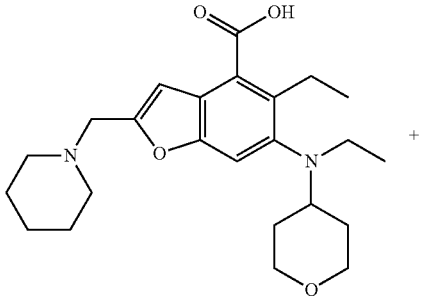

1n

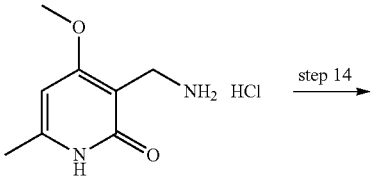

1o

-continued

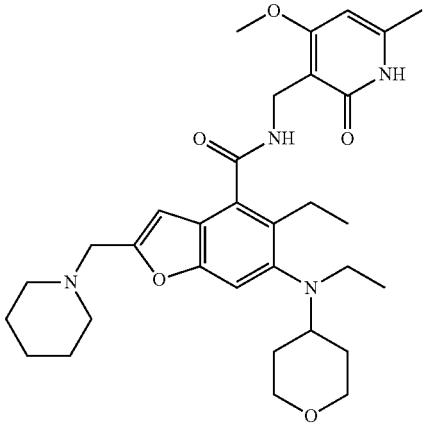

1

Step 1

3-Bromo-2-ethyl-5-nitrobenzoic Acid

2-Ethylbenzoic acid 1a (20.0 g, 133 mmol, prepared by a method disclosed in "Journal of the American Chemical Society, 1991, 113(13), 4931-6") was added to 150 mL of sulfuric acid, then sodium nitrate (11.3 g, 133 mmol) was added in batches in an ice bath. The mixture was stirred for 3 hours, then N-bromosuccinimide (2.6 g, 14.5 mmol) was added in batches. The reaction system was stirred for 1 hour at 60° C. After the reaction was completed, the reaction solution was poured to ice water, stirred well and filtered. The filtrate was washed with water, and concentrated under reduced pressure to obtain the crude title compound 3-bromo-2-ethyl-5-nitrobenzoic acid 1b (35 g) as a white solid, which was directly used in the next step without further purification.

Step 2

Methyl 3-bromo-2-ethyl-5-nitrobenzoate

The crude 3-bromo-2-ethyl-5-nitrobenzoic acid 1b (35 g, 128 mmol) was dissolved in 200 mL of N,N-dimethylformamide, then iodomethane (21.8 g, 153 mmol) and potassium carbonate (35.3 g, 255 mmol) were added. The reaction system was stirred for 2 hours at room temperature. After the reaction was completed, the reaction solution was concentrated under reduced pressure. Excess water was added, and the mixture was extracted with ethyl acetate. The organic phases were combined, washed with water and saturated sodium chloride solution, dried over anhydrous sodium sulfate, and filtered. The filtrate was concentrated under reduced pressure to obtain the crude title compound methyl 3-bromo-2-ethyl-5-nitrobenzoate 1c (36 g) as a yellow oil, which was directly used in the next step without further purification.

Step 3

Methyl 5-amino-3-bromo-2-ethylbenzoate

The crude methyl 3-bromo-2-ethyl-5-nitrobenzoate 1c (35.0 g, 121 mmol) was added to 250 mL of ethanol and 150 mL of water. The mixture was heated to 70° C., then ammonium chloride (52.8 g, 969 mmol) was added, then iron powder (34 g, 606 mmol) was added in batches. The reaction system was stirred for 2 hours at 70° C. After the reaction was completed, the mixture was filtered through celite while hot. The filter cake was washed with hot ethanol, then the filtrate was combined and concentrated under reduced pressure. Ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 5-amino-3-bromo-2-ethylbenzoate 1d (22.0 g, yield 70%) as a yellow solid.

Step 4

Methyl 3-bromo-2-ethyl-5-hydroxybenzoate

Methyl 5-amino-3-bromo-2-ethylbenzoate 1d (15.0 g, 58 mmol) was dissolved in 10 mL of acetonitrile, then 200 mL of 10% sulfuric acid was added. The mixture was stirred well and cooled down to 3° C. in an ice-salt bath, then 10 mL of a pre-prepared solution of sodium nitrite (4.4 g, 64 mmol) was added. The mixture was stirred for 4 hours at the above temperature, added dropwise with 200 mL of 50% sulfuric acid, then stirred for 1 hour at 90° C. After the reaction was completed, the reaction solution was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 3-bromo-2-ethyl-5-hydroxybenzoate 1e (5.5 g, yield 37%) as a brown solid.

Step 5

Methyl 3-bromo-5-(2,2-diethoxyethoxy)-2-ethylbenzoate

Methyl 3-bromo-2-ethyl-5-hydroxybenzoate 1e (35 g, 135 mmol) was dissolved in 200 mL of N,N-dimethylformamide, then 2-bromo-1,1-diethoxyethane (40 g, 202 mmol) and potassium carbonate (37 g, 269 mmol) were added. The reaction system was stirred at 120° C. for 12 hours. After the reaction was completed, the reaction solution was concentrated under reduced pressure to remove N,N-dimethylformamide. Water was added, and the mixture was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 3-bromo-5-(2,2-diethoxyethoxy)-2-ethylbenzoate 1f (40 g, yield 80%) as a light yellow oil.

Step 6

Methyl 6-bromo-5-ethylbenzofuran-4-carboxylate

Polyphosphoric acid (30 g) was added to 400 mL of toluene. The mixture was heated to 100° C., 50 mL of a pre-prepared solution of methyl 3-bromo-5-(2,2-diethoxyethoxy)-2-ethylbenzoate 1f (40 g, 107 mmol) in toluene was added with stirring. The mixture was stirred for 16 hours at 100° C. After the reaction was completed, the supernatant was decanted. Water and ethyl acetate were added to the residue. Two phases were separated, and the aqueous phase was extracted with ethyl acetate. The organic phases were combined, washed with saturated sodium carbonate solution and saturated sodium chloride solution, dried over anhydrous sodium sulfate, and filtered. The filtrate was concentrated under reduced pressure, and the resulting residue was purified by silica gel column chromatography with elution system B to obtain the title compound methyl 6-bromo-5-ethylbenzofuran-4-carboxylate 1g (11.8 g, yield 39%) as a yellow solid.

Step 7

Methyl 5-ethyl-6-((tetrahydro-2H-pyran-4-yl)amino) benzofuran-4-carboxylate

Methyl 6-bromo-5-ethylbenzofuran-4-carboxylate 1g (11.0 g, 39 mmol), tetrahydro-2H-pyran-4-amine (5.89 g, 58 mmol), tris(dibenzylideneacetone)dipalladium (3.6 g, 3.9 mmol), (±)-2,2'-bis(diphenylphosphino)-1,1'-binaphthalene (4.86 g, 7.8 mmol) and cesium carbonate (38 g, 117 mmol) were dissolved in 100 mL of toluene. The mixture was stirred for 12 hours at 100° C. After the reaction was completed, the mixture was filtered through a pad of celite, and the filter cake was washed with ethyl acetate. The organic phases were combined, dried over anhydrous sodium sulfate, and filtered. The filtrate was concentrated under reduced pressure, and the resulting residue was purified by silica gel column chromatography with elution system B to obtain the title compound methyl 5-ethyl-6-((tetrahydro-2H-pyran-4-yl)amino)benzofuran-4-carboxylate 1h (10.0 g, yield 85%) as a yellow solid.

Step 8

Methyl 5-ethyl-6-(ethyl(tetrahydro-2H-pyran-4-yl) amino)benzofuran-4-carboxylate Methyl 5-ethyl-6-((tetrahydro-2H-pyran-4-yl)amino)benzofuran-4-carboxylate 1h (10.0 g, 0.033 mmol) was dissolved in 150 mL of 1,2-dichloroethane, then acetaldehyde (7.2 g, 0.165 mmol) and acetic acid (9.9 g, 0.165 mmol) were added. The mixture was stirred for 1 hour, then sodium triacetoxyborohydride (20.8 g, 0.1 mmol) was added. The mixture was stirred for 12 hours at room temperature. After the reaction was completed, the reaction solution was concentrated under reduced pressure, neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 5-ethyl-6-(ethyl(tetrahydro-2H-pyran-4-yl)amino)benzofuran-4-carboxylate 1i (7.8 g, yield 71%) as a white solid.

MS m/z (LC-MS): 332.4 [M+1]

Step 9

Methyl 5-ethyl-6-(ethyl(tetrahydro-2H-pyran-4-yl) amino)-2-formylbenzofuran-4-carboxylate Methyl 5-ethyl-6-(ethyl(tetrahydro-2H-pyran-4-yl) amino)benzofuran-4-carboxylate 1i (1.6 g, 4.8 mmol) was dissolved in 25 mL of tetrahydrofuran. The mixture was cooled down to −70° C., then 2.0 M lithium diisopropylamide (3.6 mL, 7.3 mmol) was added dropwise under an argon atmosphere. At −70° C., the mixture was stirred for 90 minutes, then N,N-dimethylformamide (536 mg, 7.3 mmol) was added. The mixture was stirred for 2 hours, then slowly warmed up to room temperature. Excess ammonium chloride was added. The mixture was stirred well and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 5-ethyl-6-(ethyl(tetrahydro-2H-pyran-4-yl)amino)-2-formylbenzofuran-4-carboxylate 1j (1.3 g, yield 75%) as a yellow oil.

MS m/z (ESI):360.2 [M+1]

Step 10

Methyl 5-ethyl-6-(ethyl(tetrahydro-2H-pyran-4-yl) amino)-2-(hydroxymethyl)benzofuran-4-carboxylate Methyl 5-ethyl-6-(ethyl(tetrahydro-2H-pyran-4-yl) amino)-2-formylbenzofuran-4-carboxylate 1j (1.4 g, 3.9 mmol) was dissolved in 5 mL of tetrahydrofuran and 10 mL of methanol, then sodium borohydride (222 mg, 5.8 mmol) was added. The mixture was stirred for 30 minutes at room temperature. After the reaction was completed, the reaction solution was concentrated under reduced pressure, water and saturated sodium bicarbonate solution were added, and the mixture was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 5-ethyl-6-(ethyl(tetrahydro-2H-pyran-4-yl)amino)-2-(hydroxymethyl)benzofuran-4-carboxylate 1k (1.4 g, yield 99%) as a yellow oil.

Step 11

Methyl 2-(bromomethyl)-5-ethyl-6-(ethyl(tetrahydro-2H-pyran-4-yl)amino)benzofuran-4-carboxylate Methyl 5-ethyl-6-(ethyl(tetrahydro-2H-pyran-4-yl) amino)-2-(hydroxymethyl) benzofuran-4-carboxylate 1k (1.0 g, 2.8 mmol) was dissolved in 30 mL of tetrahydrofuran, then phosphorus tribromide (1.12 g, 4.2 mmol) was added dropwise. The mixture was stirred for 12 hours at room temperature. After the reaction was completed, the mixture was neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure to obtain the crude title compound methyl 2-(bromomethyl)-5-ethyl-6-(ethyl(tetrahydro-2H-pyran-4-yl)amino) benzofuran-4-carboxylate 11 (1.15 g) as a yellow oil, which was directly used in the next step without further purification.

Step 12

Methyl 5-ethyl-6-(ethyl(tetrahydro-2H-pyran-4-yl) amino)-2-(piperidin-1-ylmethyl)benzofuran-4-carboxylate The crude methyl 2-(bromomethyl)-5-ethyl-6-(ethyl(tetrahydro-2H-pyran-4-yl)amino)benzofuran-4-carboxylate 11 (1.15 g, 2.7 mmol) was dissolved in 15 mL of acetonitrile, then 10 mL of a pre-prepared solution of piperidine (362 mg, 4.3 mmol) in acetonitrile were added dropwise. The mixture was stirred for 30 minutes at room temperature. After the reaction was completed, the reaction solution was concentrated under reduced pressure. Ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system A to obtain the title compound methyl 5-ethyl-6-(ethyl(tetrahydro-2H-pyran-4-yl)amino)-2-(piperidin-1-ylmethyl)benzofuran-4-carboxylate 1m (1.2 g, yield 99%) as a yellow oil.

MS m/z (LC-MS): 429.2[M+1]

Step 13

5-Ethyl-6-(ethyl(tetrahydro-2H-pyran-4-yl)amino)-2-(piperidin-1-ylmethyl)benzofuran-4-carboxylic acid Methyl 5-ethyl-6-(ethyl(tetrahydro-2H-pyran-4-yl) amino)-2-(piperidin-1-ylmethyl) benzofuran-4-carboxylate 1m (1.2 g, 2.7 mmol) was dissolved in 5 mL of tetrahydrofuran and 20 mL of methanol, then 5 mL of 4M sodium hydroxide solution were added. The mixture was stirred for 12 hours at 60° C. After the reaction was completed, concentrated hydrochloric acid was added to adjust the pH of the reaction solution to 4. The mixture was concentrated under reduced pressure, and the residue was dissolved in a mixture of dichloromethane and methanol (V:V=5:1) and filtered. The filter cake was washed with a mixture of dichoromethane and methanol (V:V=5:1). The filtrate was combined, and concentrated under reduced pressure to obtain the crude title compound 5-ethyl-6-(ethyl(tetrahydro-2H-pyran-4-yl)amino)-2-(piperidin-1-ylmethyl)benzofuran-4-carboxylic acid 1n (1.1 g) as a yellow solid, which was directly used in the next step without further purification.

MS m/z (LC-MS): 415.2[M+1]

Step 14

5-Ethyl-6-(ethyl(tetrahydro-2H-pyran-4-yl)amino)-N-((4-methoxy-6-methyl-2-oxo-1,2-dihydropyridin-3-yl)methyl)-2-(piperidin-1-ylmethyl)benzofuran-4-carboxamide The crude 5-ethyl-6-(ethyl(tetrahydro-2H-pyran-4-yl) amino)-2-(piperidin-1-ylmethyl)benzofuran-4-carboxylic acid in (150 mg, 0.36 mmol) was dissolved in 5 mL of N,N-dimethylformamide, then 1-ethyl-3-(3-dimethylaminopropyl)carbodiimide (104 mg, 0.54 mmol), 1-hydroxybenzotriazole (73 mg, 0.54 mmol) and N,N-diisopropylethylamine (232 mg, 1.8 mmol) were added. The mixture was stirred 1 hour, then 3-(aminomethyl)-4-methoxy-6-methylpyridin-2(1H)-one hydrochloride 1o (96 mg, 0.47 mmol, prepared by a method disclosed in the patent application "WO2014177982") was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-N-((4-methoxy-6-methyl-2-oxo-1,2-dihydropyridin-3-yl)methyl)-2-(piperidin-1-ylmethyl)benzofuran-4-carboxamide 1 (155 mg, yield 76%) as a white solid.

MS m/z (ESI): 565.3 [M+1]

$^1$H NMR (400 MHz, DMSO-$d_6$): δ 11.44 (s, 1H), 8.00 (s, 1H), 7.40 (s, 1H), 6.53 (brs, 1H), 6.10 (s, 1H), 4.29 (d, 2H), 3.85 (brs, 2H), 3.83 (s, 3H), 3.56 (brs, 2H), 3.22 (t, 2H), 3.03-3.08 (m, 2H), 2.93-2.98 (m, 1H), 2.78-2.84 (m, 2H), 2.42 (brs, 4H), 2.18 (s, 3H), 1.64-1.67 (brd, 2H), 1.47-1.56 (m, 6H), 1.38 (brs, 2H), 1.06 (t, 3H), 0.83 (t, 3H).

Example 2

N-((4,6-Dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide

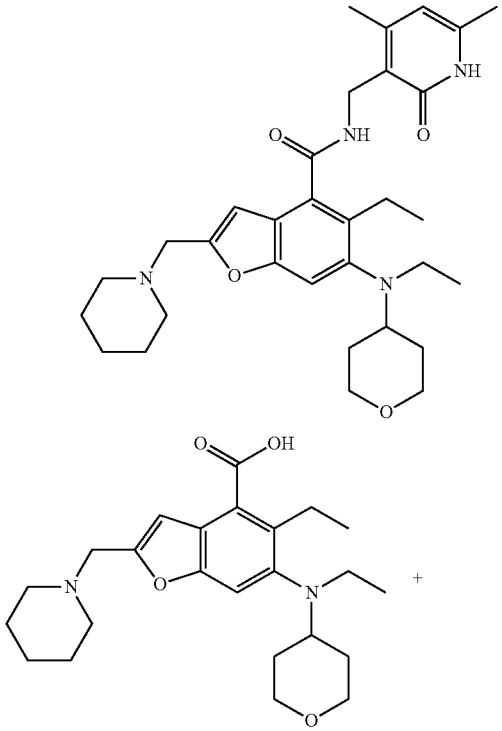

1n

-continued

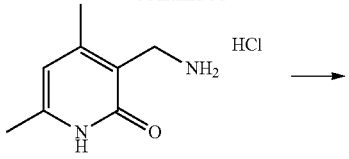

2a

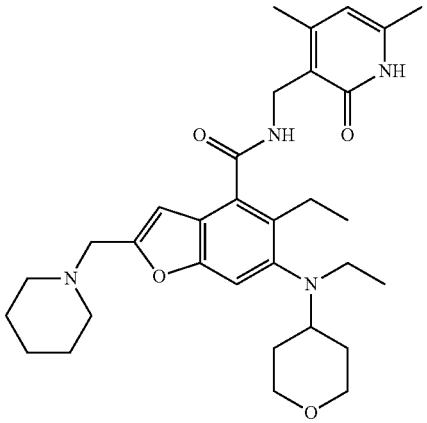

2

5-Ethyl-6-(ethyl(tetrahydro-2H-pyran-4-yl)amino)-2-(piperidin-1-ylmethyl)benzofuran-4-carboxylic acid in (1.0 g, 2.4 mmol) was dissolved in 30 mL of N,N-dimethylformamide, then 1-ethyl-3-(3-dimethylaminopropyl)carbodiimide (696 mg, 3.6 mmol), 1-hydroxybenzotriazole (490 mg, 3.6 mmol) and N,N-diisopropylethylamine (1.56 g, 12.1 mmol) were added. The mixture was stirred for 1 hour, then 3-(aminomethyl)-4,6-dimethylpyridin-2(1H)-one hydrochloride 2a (593 mg, 3.0 mmol, prepared by a method disclosed in the patent application "WO2014097041") was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by silica gel column chromatography with elution system A to obtain the title compound N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide 2 (750 mg, yield 57%) as a white solid.

MS m/z (ESI): 549.7 [M+1]

$^1$H NMR (400 MHz, DMSO-$d_6$): δ 11.48 (s, 1H), 8.15 (t, 1H), 7.39 (s, 1H), 6.46 (s, 1H), 5.86 (s, 1H), 4.32 (d, 2H), 3.83 (d, 2H), 3.54 (s, 2H), 3.21 (t, 2H), 3.01-3.07 (m, 2H), 2.92-2.97 (m, 1H), 2.77-2.82 (m, 2H), 2.39 (brs, 4H), 2.23 (s, 3H), 2.11 (s, 3H), 1.64-1.67 (brd, 2H), 1.47-1.55 (m, 6H), 1.36-1.37 (brd, 2H), 1.02 (t, 3H), 0.82 (t, 3H).

Example 3

5-Ethyl-6-(ethyl(tetrahydro-2H-pyran-4-yl)amino)-N-((4-ethyl-6-methyl-2-oxo-1,2-dihydropyridin-3-yl)methyl)-2-(piperidin-1-ylmethyl)benzofuran-4-carboxamide

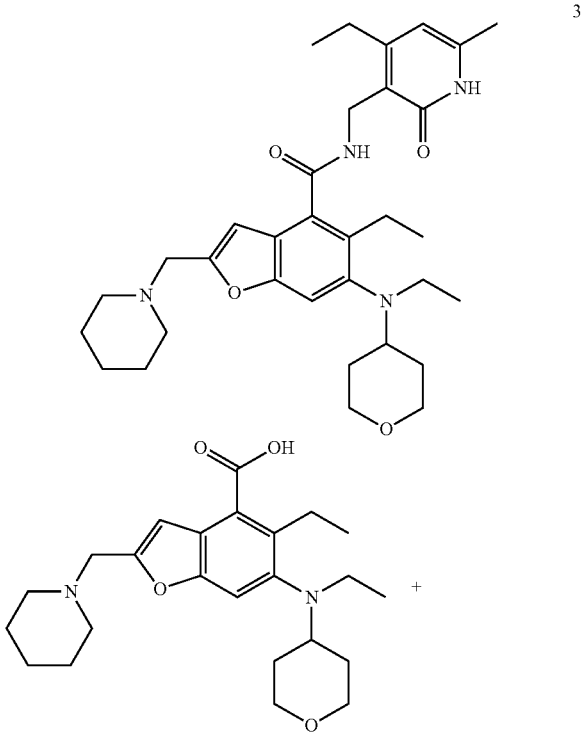

1n

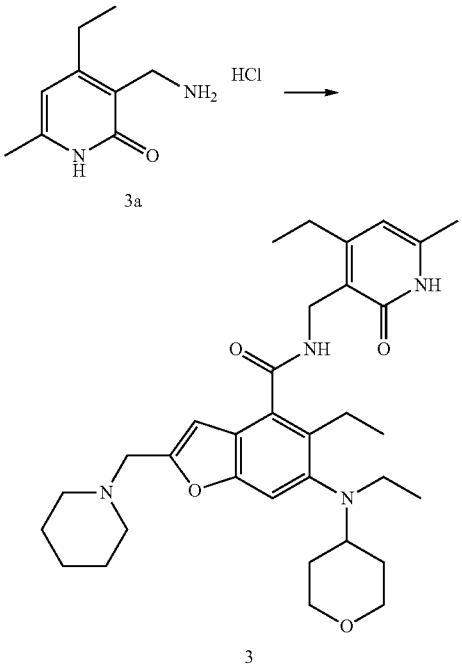

3a

3

5-Ethyl-6-(ethyl(tetrahydro-2H-pyran-4-yl)amino)-2-(piperidin-1-ylmethyl)benzofuran-4-carboxylic acid in (50 mg, 0.12 mmol) was dissolved in 3 mL of N,N-dimethylformamide, then 1-ethyl-3-(3-dimethylaminopropyl)carbodiimide (35 mg, 0.18 mmol), 1-hydroxybenzotriazole (24 mg, 0.18 mmol) and N,N-diisopropylethylamine (78 mg, 0.60 mmol) were added. The mixture was stirred for 1 hour, then 3-(aminomethyl)-4-ethyl-6-methylpyridin-2(1H)-one hydrochloride 3a (36 mg, 0.18 mmol, prepared by a method disclosed in the patent application "WO2013173441") was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-N-((4-ethyl-6-methyl-2-oxo-1,2-dihydropyridin-3-yl)methyl)-2-(piperidin-1-ylmethyl)benzofuran-4-carboxamide 3 (58 mg, yield 85%) as a white solid.

MS m/z (ESI): 563.7 [M+1]

$^1$H NMR (400 MHz, DMSO-$d_6$): δ 11.51 (s, 1H), 8.12 (t, 1H), 7.39 (s, 1H), 6.47 (s, 1H), 5.91 (s, 1H), 4.33 (d, 2H), 3.81-3.83 (brd, 2H), 3.54 (brs, 2H), 3.20 (t, 2H), 3.01-3.06 (m, 2H), 2.91-2.97 (m, 1H), 2.76-2.82 (m, 2H), 2.59 (q, 2H), 2.39 (brs, 4H), 2.13 (s, 3H), 1.63-1.66 (brd, 2H), 1.48-1.50 (m, 6H), 1.36 (brs, 2H), 1.37 (t, 3H), 1.01 (t, 3H), 0.81 (t, 3H).

Example 4

6-(Ethyl(tetrahydro-2H-pyran-4-yl)amino)-N-((4-methoxy-6-methyl-2-oxo-1,2-dihydro pyridin-3-yl) methyl)-5-methyl-2-(piperidin-1-ylmethyl)benzofuran-4-carboxamide

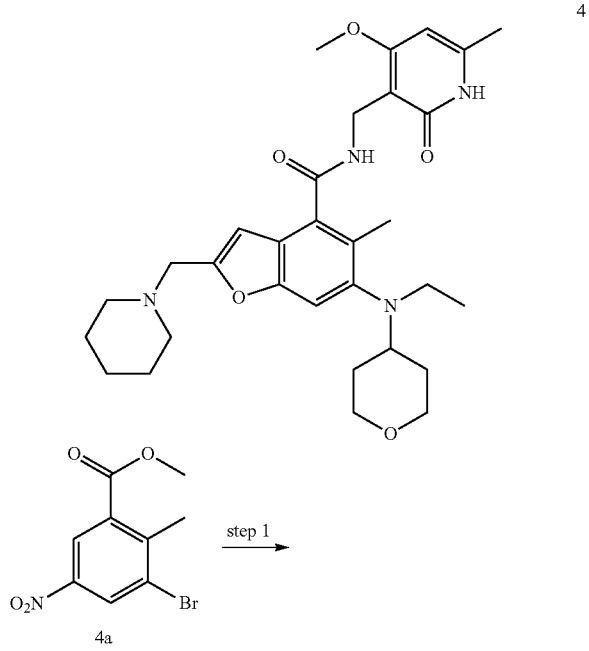

4a

4

-continued
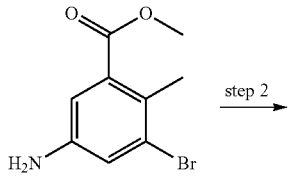
4b
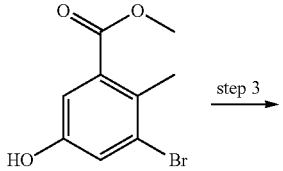
4c
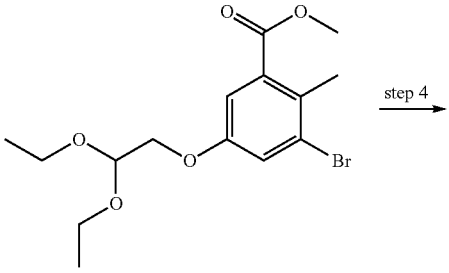
4d
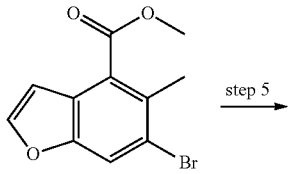
4e
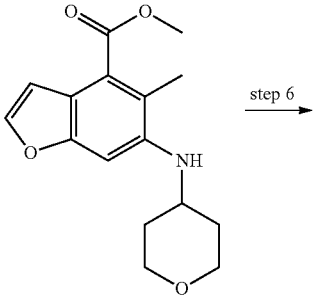
4f
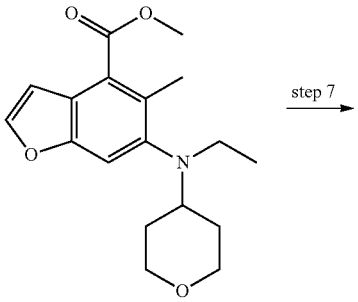
4g
-continued
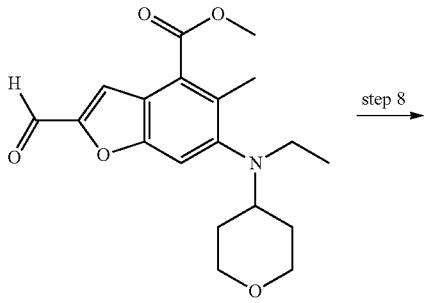
4h
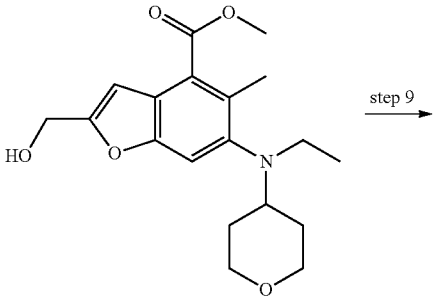
4i
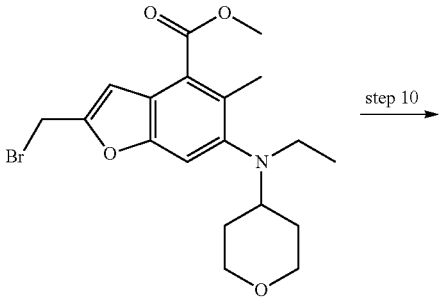
4j
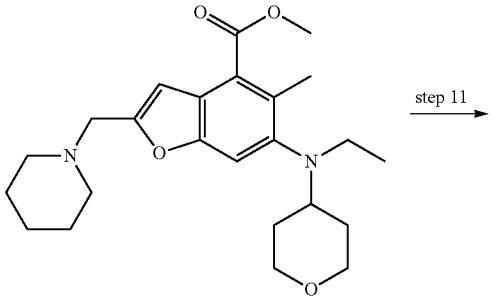
4k
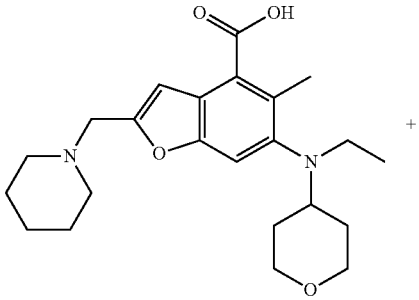
4l -continued

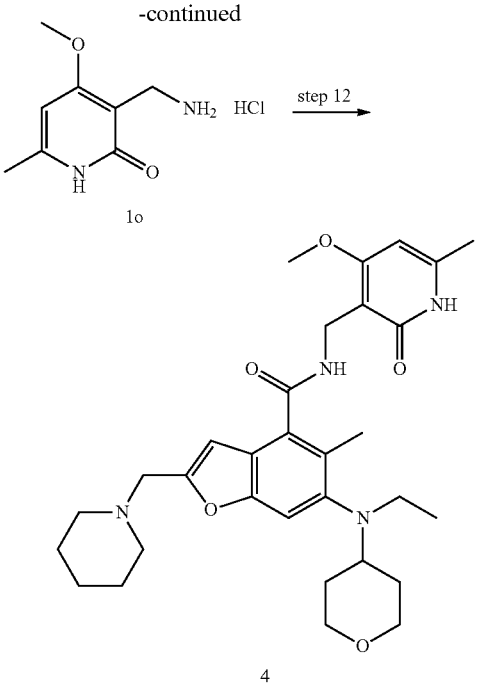

Step 1

Methyl 5-amino-3-bromo-2-methylbenzoate

Methyl 3-bromo-2-methyl-5-nitrobenzoate 4a (13 g, 47.3 mmol, prepared by a method disclosed in the patent application "WO2012061602") was added to 200 mL of ethanol and 50 mL of water. The mixture was heated to 70° C., then ammonium chloride (20.6 g, 378 mmol) was added, and iron powder (13.3 g, 236 mmol) was added in batches. The reaction system was stirred for 2 hours at 70° C. After the reaction was completed, the mixture was filtered through a pad of celite while hot. The filter cake was washed with hot ethanol, then the filtrate was combined and concentrated under reduced pressure. The residue was neutralized with saturated sodium bicarbonate solution, and extracted three times with ethyl acetate. The organic phases were combined, dried over anhydrous sodium sulfate, and filtered. The filtrate was concentrated under reduced pressure, and the resulting residue was purified by silica gel column chromatography with elution system B to obtain the title compound methyl 5-amino-3-bromo-2-methylbenzoate 4b (11.0 g, yield 95%) as a yellow solid.

Step 2

Methyl 3-bromo-5-hydroxy-2-methylbenzoate

Methyl 5-amino-3-bromo-2-methylbenzoate 4b (3.0 g, 0.012 mmol) was suspended in 20 mL of 10% sulfuric acid. The mixture was cooled down to 0° C., then 5 mL of a pre-prepared solution of sodium nitrite (1.0 g, 14.7 mmol) were added dropwise. After stirring for 3 hours at the above temperature, the reaction solution was poured into 30 mL of pre-prepared 10% sulfuric acid at 80° C., then stirred for 1 hour at 80° C. After the reaction was completed, the reaction solution was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 3-bromo-5-hydroxy-2-methylbenzoate 4c (1.1 g, yield 32%) as a yellow solid.

Step 3

Methyl 3-bromo-5-(2,2-diethoxyethoxy)-2-methylbenzoate

Methyl 3-bromo-5-hydroxy-2-methylbenzoate 4c (800 mg, 3.3 mmol) was dissolved in 15 mL of N,N-dimethylformamide, then 2-bromo-1,1-diethoxyethane (965 mg, 4.9 mmol) and potassium carbonate (900 mg, 6.5 mmol) were added. The reaction system was stirred for 12 hours at 120° C. After the reaction was completed, excess water was added, and the mixture was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 3-bromo-5-(2,2-diethoxyethoxy)-2-methylbenzoate 4d (820 mg, yield 69%) as a light yellow oil.

Step 4

Methyl 6-bromo-5-methylbenzofuran-4-carboxylate

Methyl 3-bromo-5-(2,2-diethoxyethoxy)-2-methylbenzoate 4d (650 mg, 1.8 mmol) was dissolved in 10 mL of toluene, then 10 mL of a pre-prepared solution of polyphosphoric acid (10 g) in toluene was added. The mixture was stirred for 5 hours at 100° C. After the reaction was completed, the upper organic phase was decanted. The residue was added with water, and extracted with ethyl acetate. The organic phases were combined, washed with saturated sodium carbonate solution and saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-bromo-5-methylbenzofuran-4-carboxylate 4e (220 mg, yield 45%) as a yellow solid.

Step 5

Methyl 5-methyl-6-((tetrahydro-2H-pyran-4-yl)amino)benzofuran-4-carboxylate

Methyl 6-bromo-5-methylbenzofuran-4-carboxylate 4e (250 mg, 0.93 mmol), tetrahydro-2H-pyran-4-amine (141 mg, 1.4 mmol), tris(dibenzylideneacetone)dipalladium (85 mg, 0.09 mmol), (±)-2,2'-bis(diphenylphosphino)-1,1'-binaphthalene (116 mg, 0.19 mmol) and cesium carbonate (909 mg, 2.79 mmol) were dissolved in 10 mL of toluene. The mixture was stirred for 12 hours at 100° C. After the reaction was completed, the mixture was filtered through a pad of celite, and the filter cake was washed with ethyl acetate. The organic phases were combined, dried over anhydrous sodium sulfate, and filtered. The filtrate was concentrated under reduced pressure, and the resulting residue was purified by thin-layer chromatography with elution system B to obtain the title compound methyl 5-methyl-6-

((tetrahydro-2H-pyran-4-yl)amino)benzofuran-4-carboxylate 4f (250 mg, yield 90%) as a yellow solid.

Step 6

Methyl 6-(ethyl(tetrahydro-2H-pyran-4-yl)amino)-5-methylbenzofuran-4-carboxylate Methyl 5-methyl-6-((tetrahydro-2H-pyran-4-yl)amino) benzofuran-4-carboxylate 4f (250 mg, 0.87 mmol) was dissolved in 10 mL of 1,2-dichloroethane, then acetaldehyde (190 mg, 4.3 mmol) and acetic acid (260 mg, 4.3 mmol) were added. The mixture was stirred for 1 hour, then sodium triacetoxyborohydride (545 mg, 2.6 mmol) was added. The mixture was stirred for 12 hours at room temperature. After the reaction was completed, the reaction solution was concentrated under reduced pressure. Ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-(ethyl(tetrahydro-2H-pyran-4-yl)amino)-5-methylbenzofuran-4-carboxylate 4g (180 mg, yield 56%) as a yellow oil.

MS m/z (LC-MS): 318.2[M+1]

Step 7

Methyl 6-(ethyl(tetrahydro-2H-pyran-4-yl)amino)-2-formyl-5-methylbenzofuran-4-carboxylate Methyl 6-(ethyl(tetrahydro-2H-pyran-4-yl)amino)-5-methylbenzofuran-4-carboxylate 4g (180 mg, 0.57 mmol) was dissolved in 5 mL of tetrahydrofuran. The mixture was cooled down to −70° C., and 2.0 M lithium diisopropylamide (0.57 mL, 1.14 mmol) was added dropwise under an argon atmosphere. At −70° C., the mixture was stirred for 1 hour, then 4-formylmorpholine (98 mg, 0.85 mmol) was added. The mixture was stirred for 1 hour, then slowly warmed up to room temperature, and ammonium chloride solution was added. The mixture was stirred for 20 minutes, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-(ethyl(tetrahydro-2H-pyran-4-yl) amino)-2-formyl-5-methylbenzofuran-4-carboxylate 4h (130 mg, yield 66%) as a yellow oil.

Step 8

Methyl 6-(ethyl(tetrahydro-2H-pyran-4-yl)amino)-2-(hydroxymethyl)-5-methylbenzofuran-4-carboxylate Methyl 6-(ethyl(tetrahydro-2H-pyran-4-yl)amino)-2-formyl-5-methylbenzofuran-4-carboxylate 4h (130 mg, 0.38 mmol) was dissolved in 1 mL of tetrahydrofuran and 5 mL of methanol, then sodium borohydride (22 mg, 0.57 mmol) was added in batches. The reaction mixture was stirred for 1 hour at room temperature. After the reaction was completed, the reaction solution was concentrated under reduced pressure. Saturated sodium bicarbonate solution was added, and the mixture was extracted three times with ethyl acetate. The organic phases were combined, washed with saturated sodium chloride solution, dried over anhydrous sodium sulfate, and filtered. The filtrate was concentrated under reduced pressure to obtain the crude title compound methyl 6-(ethyl(tetrahydro-2H-pyran-4-yl)amino)-2-(hydroxymethyl)-5-methylbenzofuran-4-carboxylate 4i (120 mg) as a yellow oil, which was directly used in the next step without further purification.

MS m/z (LC-MS): 348.0 [M+1]

Step 9

Methyl 2-(bromomethyl)-6-(ethyl(tetrahydro-2H-pyran-4-yl)amino)-5-methylbenzofuran-4-carboxylate The crude methyl 6-(ethyl(tetrahydro-2H-pyran-4-yl) amino)-2-(hydroxymethyl)-5-methylbenzofuran-4-carboxylate 4i (130 mg, 0.36 mmol) was dissolved in 5 mL of tetrahydrofuran, then phosphorus tribromide (146 mg, 0.54 mmol) was added dropwise. The mixture was stirred for 12 hours at room temperature. After the reaction was completed, water was added, and the mixture was extracted three times with ethyl acetate. The organic phases were combined, washed with saturated sodium bicarbonate solution and saturated sodium chloride solution, dried over anhydrous sodium sulfate, and filtered. The filtrate was concentrated under reduced pressure to obtain the crude title compound methyl 2-(bromomethyl)-6-(ethyl(tetrahydro-2H-pyran-4-yl)amino)-5-methylbenzofuran-4-carboxylate 4j (152 mg) as a yellow oil, which was directly used in the next step without further purification.

Step 10

Methyl 6-(ethyl(tetrahydro-2H-pyran-4-yl)amino)-5-methyl-2-(piperidin-1-ylmethyl)benzofuran-4-carboxylate The crude methyl 2-(bromomethyl)-6-(ethyl(tetrahydro-2H-pyran-4-yl)amino)-5-methylbenzofuran-4-carboxylate 4j (140 mg, 0.33 mmol) was dissolved in 5 mL of acetonitrile, then 5 mL of a pre-prepared solution of piperidine (56 mg, 0.66 mmol) in acetonitrile was added dropwise. The mixture was stirred for 1 hour at room temperature. After the reaction was completed, the reaction solution was concentrated under reduced pressure, then ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 6-(ethyl(tetrahydro-2H-pyran-4-yl)amino)-5-methyl-2-(piperidin-1-ylmethyl)benzofuran-4-carboxylate 4k (120 mg, yield 86%) as a colorless oil.

Step 11

6-(Ethyl(tetrahydro-2H-pyran-4-yl)amino)-5-methyl-2-(piperidin-1-ylmethyl)benzofuran-4-carboxylic acid Methyl 6-(ethyl(tetrahydro-2H-pyran-4-yl)amino)-5-methyl-2-(piperidin-1-ylmethyl)benzofuran-4-carboxylate 4k (120 mg, 0.29 mmol) was dissolved in 10 mL of methanol, then 3 mL of 4M sodium hydroxide solution was added. The mixture was stirred for 12 hours at 60° C. After the reaction was completed, concentrated hydrochloric acid was added to adjust the pH of the reaction solution to 4. The mixture was concentrated under reduced pressure, and the residue was dissolved in a mixture of dichloromethane and methanol (V:V=5:1) and filtered. The filter cake was washed with a mixture of dichoromethane and methanol (V:V=5:1). The filtrate was combined, and concentrated under reduced pressure to obtain the crude title compound 6-(ethyl(tetrahydro-2H-pyran-4-yl)amino)-5-methyl-2-(piperidin-1-ylmethyl)benzofuran-4-carboxylic acid 4i (120 mg) as a yellow solid, which was used directly in the next step without further purification.

MS m/z (LC-MS): 399.0[M+1]

Step 12

6-(Ethyl(tetrahydro-2H-pyran-4-yl)amino)-N-((4-methoxy-6-methyl-2-oxo-1,2-dihydro pyridin-3-yl) methyl)-5-methyl-2-(piperidin-1-ylmethyl)benzofuran-4-carboxamide The crude 6-(ethyl(tetrahydro-2H-pyran-4-yl)amino)-5-methyl-2-(piperidin-1-ylmethyl)benzofuran-4-carboxylic acid 4i (40 mg, 0.1 mmol) was dissolved in 3 mL of N,N-dimethylformamide, then 1-ethyl-3-(3-dimethylaminopropyl)carbodiimide (29 mg, 0.15 mmol), 1-hydroxybenzotriazole (20 mg, 0.15 mmol) and N,N-diisopropylethylamine (63 mg, 0.48 mmol) were added. The mixture was stirred for 16 hours, then 3-(aminomethyl)-4-methoxy-6-methylpyridin-2(1H)-one hydrochloride 1o (26 mg, 0.13 mmol) was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 6-(ethyl(tetrahydro-2H-pyran-4-yl)amino)-N-((4-methoxy-6-methyl-2-oxo-1,2-dihydropyridin-3-yl)methyl)-5-methyl-2-(piperidin-1-ylmethyl)benzofuran-4-carboxamide 4 (35 mg, yield 64%) as a white solid.

MS m/z (ESI): 551.7 [M+1]

$^1$H NMR (400 MHz, DMSO-$d_6$) δ 11.45 (s, 1H), 8.01 (s, 1H), 7.40 (s, 1H), 6.91 (brs, 1H), 6.12 (s, 1H), 4.30 (d, 2H), 3.84 (brs, 5H), 3.23 (t, 2H), 3.04-3.09 (m, 2H), 2.95-3.01 (m, 1H), 2.62 (s, 3H), 2.19 (s, 3H), 1.64-1.81 (brd, 6H), 1.50-1.55 (m, 4H), 1.38 (brs, 2H), 0.81 (t, 3H).

Example 5

5-Ethyl-6-(ethyl(tetrahydro-2H-pyran-4-yl)amino)-2-((4-isopropylpiperazin-1-yl)methyl)-N-((4-methoxy-6-methyl-2-oxo-1,2-dihydropyridin-3-yl) methyl)benzofuran-4-carboxamide

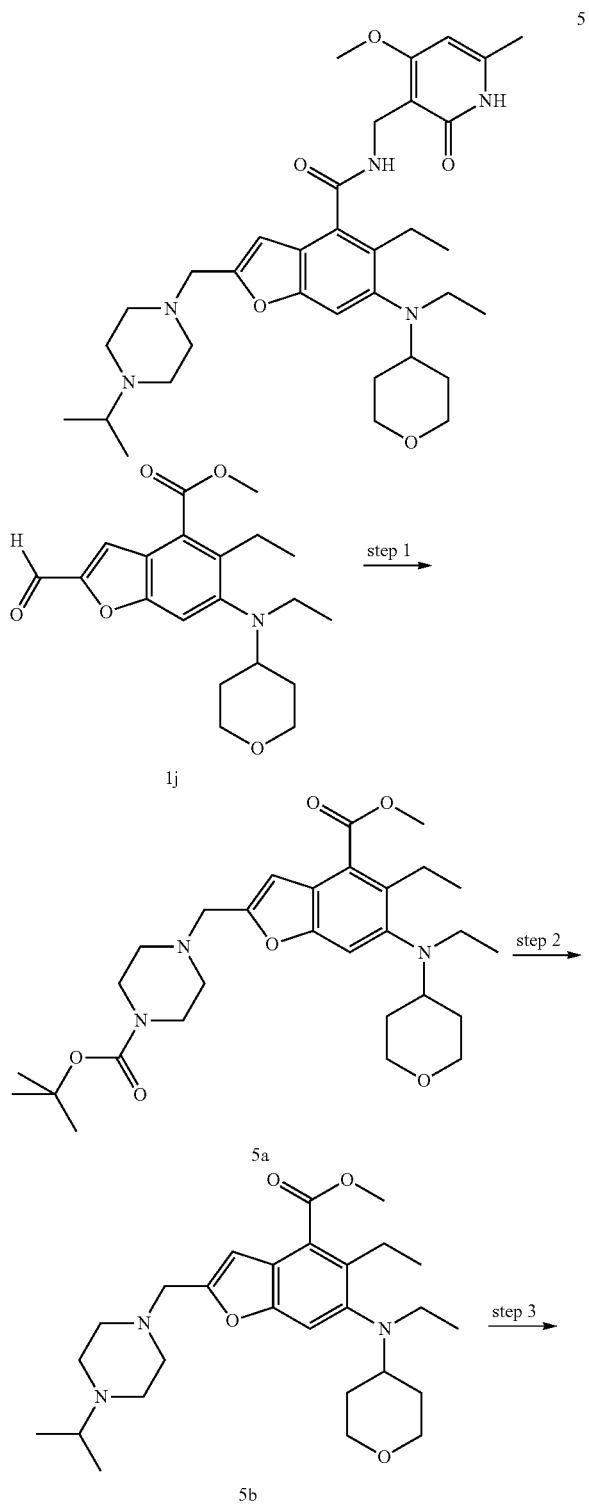

-continued

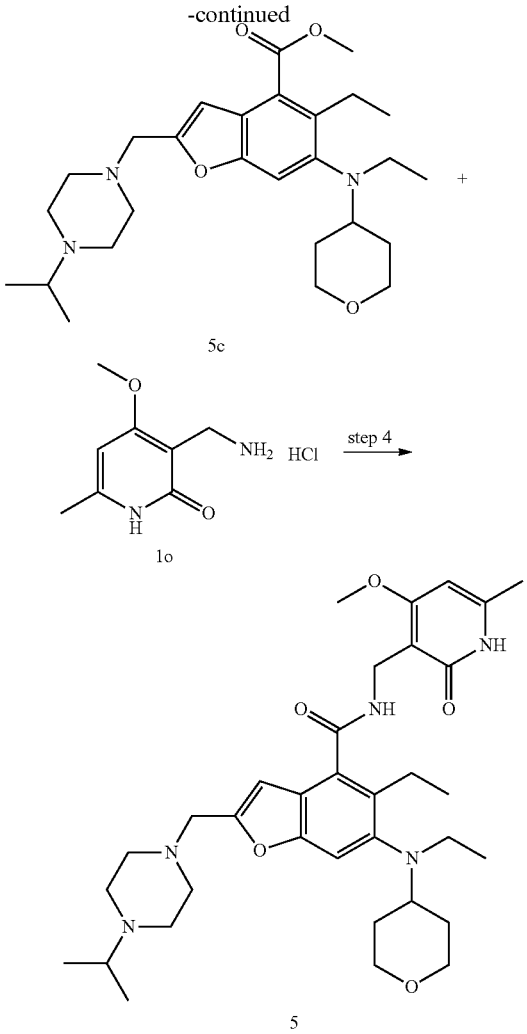

Step 1 tert-Butyl 4-((5-ethyl-6-(ethyl(tetrahydro-2H-pyran-4-yl)amino)-4-(methoxycarbonyl)benzofuran-2-yl)methyl)piperazine-1-carboxylate Methyl 5-ethyl-6-(ethyl(tetrahydro-2H-pyran-4-yl)amino)-2-formylbenzofuran-4-carboxylate 1j (30 mg, 0.083 mmol), 1-(tert-butoxycarbonyl)piperazine (24 mg, 0.13 mmol) and acetic acid (25 mg, 0.42 mmol) were added to 5 mL of methanol. The mixture was stirred for 1 hour, then sodium triacetoxyborohydride (53 mg, 0.25 mmol) was added. The mixture was stirred for 12 hours. After the reaction was completed, the reaction solution was concentrated under reduced pressure, neutralized with saturated sodium bicarbonate solution, extracted three times with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound tert-butyl 4-((5-ethyl-6-(ethyl(tetrahydro-2H-pyran-4-yl)amino)-4-(methoxycarbonyl)benzofuran-2-yl)methyl)piperazine-1-carboxylate 5a (40 mg, yield 90%) as a yellow oil.

MS m/z (LC-MS): 530.3 [M+1]

Step 2

Methyl 5-ethyl-6-(ethyl(tetrahydro-2H-pyran-4-yl)amino)-2-((4-isopropylpiperazin-1-yl)methyl)benzofuran-4-carboxylate tert-Butyl 4-((5-ethyl-6-(ethyl(tetrahydro-2H-pyran-4-yl)amino)-4-(methoxycarbonyl)benzofuran-2-yl)methyl)piperazine-1-carboxylate 5a (40 mg, 0.075 mmol) was added to 10 mL of trifluoroacetic acid. The mixture was stirred for 1 hour at room temperature, then concentrated under reduced pressure. Then, 5 mL of N,N-dimethylformamide and potassium carbonate (21 mg, 0.15 mmol) were added to the residue, and the mixture was stirred for 30 minutes. Then, 1-iodopropane (20 mg, 0.11 mmol) was added, and the reaction system was stirred for 1 hour at 70° C. After the reaction was completed, the reaction solution was poured into excess water, and extracted three times with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound methyl 5-ethyl-6-(ethyl(tetrahydro-2H-pyran-4-yl)amino)-2-((4-isopropylpiperazin-1-yl)methyl)benzofuran-4-carboxylate 5b (25 mg, yield 70%) as a colorless oil.

MS m/z (LC-MS): 472.3 [M+1]

Step 3

5-Ethyl-6-(ethyl(tetrahydro-2H-pyran-4-yl)amino)-2-((4-isopropylpiperazin-1-yl)methyl)benzofuran-4-carboxylic acid Methyl 5-ethyl-6-(ethyl(tetrahydro-2H-pyran-4-yl)amino)-2-((4-isopropylpiperazin-1-yl)methyl)benzofuran-4-carboxylate 5b (10 mg, 0.021 mmol) was dissolved in 3 mL of methanol and 1 mL of tetrahydrofuran, then 13 mL of 2M sodium hydroxide solution was added. The reaction system was stirred for 12 hours at 60° C. After the reaction was completed, the reaction solution was neutralized with concentrated sulfuric acid, then concentrated under reduced pressure. The residue was dissolved in a mixture of dichloromethane and methanol (V:V=5:1) and filtered. The filter cake was washed with a mixture of dichoromethane and methanol (V:V=5:1). The filtrate was combined, and concentrated under reduced pressure to obtain the crude title compound 5-ethyl-6-(ethyl(tetrahydro-2H-pyran-4-yl)amino)-2-((4-isopropylpiperazin-1-yl)methyl)benzofuran-4-carboxylic acid 5c (9 mg) as a white solid, which was used directly in the next step without further purification.

MS m/z (LC-MS): 458.4 [M+1]

Step 4

5-Ethyl-6-(ethyl(tetrahydro-2H-pyran-4-yl)amino)-2-((4-isopropylpiperazin-1-yl)methyl)-N-((4-methoxy-6-methyl-2-oxo-1,2-dihydropyridin-3-yl)methyl)benzofuran-4-carboxamide The crude 5-ethyl-6-(ethyl(tetrahydro-2H-pyran-4-yl)amino)-2-((4-isopropylpiperazin-1-yl)methyl)benzofuran-4-carboxylic acid 5c (10 mg, 0.022 mmol) was dissolved in 3 mL of N,N-dimethylformamide, then 1-ethyl-3-(3-dimethylaminopropyl)carbodiimide (7 mg, 0.033 mmol), 1-hydroxybenzotriazole (5 mg, 0.033 mmol) and N,N-diisopropylethylamine (6 mg, 0.044 mmol) were added. The mixture was stirred for 30 minutes, then 3-(aminomethyl)-4-methoxy-6-methylpyridin-2(1H)-one hydrochloride 1o (5.8 mg, 0.028) was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-2-((4-isopropylpiperazin-1-yl)methyl)-N-((4-methoxy-6-methyl-2-oxo-1,2-dihydropyridin-3-yl)methyl)benzofuran-4-carboxamide 5 (9 mg, yield 69%) as a white solid.

MS m/z (ESI): 608.6 [M+1]

$^1$H NMR (400 MHz, DMSO-$d_6$) δ 11.45 (s, 1H), 8.01 (s, 1H), 7.39 (s, 1H), 6.56 (brs, 1H), 6.11 (s, 1H), 4.29 (d, 2H), 3.85 (brs, 2H), 3.83 (s, 3H), 3.63 (brs, 3H), 3.22 (t, 2H), 3.03-3.07 (m, 2H), 2.93-2.99 (m, 2H), 2.79-2.82 (m, 2H), 2.34-2.68 (brs, 8H), 2.19 (s, 3H), 1.64-1.67 (brd, 2H), 1.50-1.52 (m, 2H), 1.24-1.26 (brd, 2H), 1.06 (t, 3H), 0.98 (brs, 6H), 0.83 (t, 3H).

Example 6

5-Ethyl-6-(ethyl(tetrahydro-2H-pyran-4-yl)amino)-N-((4-methoxy-6-methyl-2-oxo-1,2-dihydropyridin-3-yl)methyl)-2-(morpholinomethyl)benzofuran-4-carboxamide

6

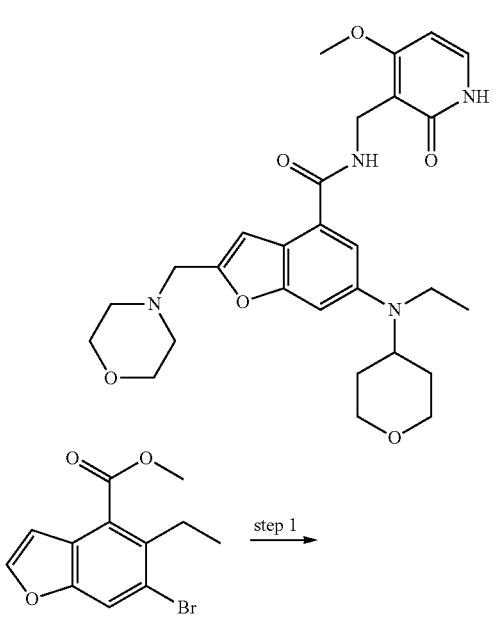

-continued

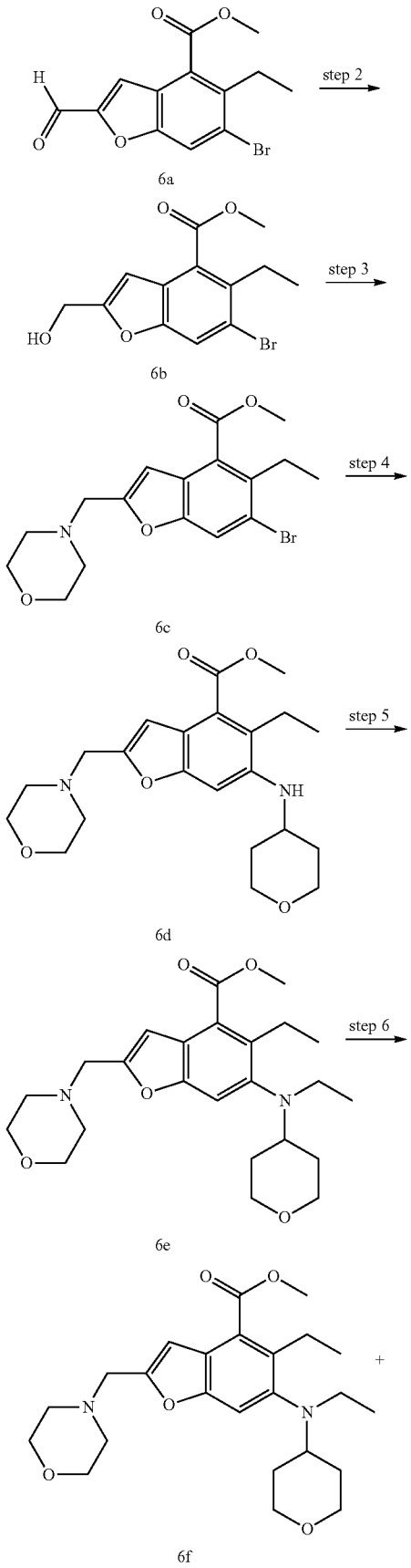

-continued

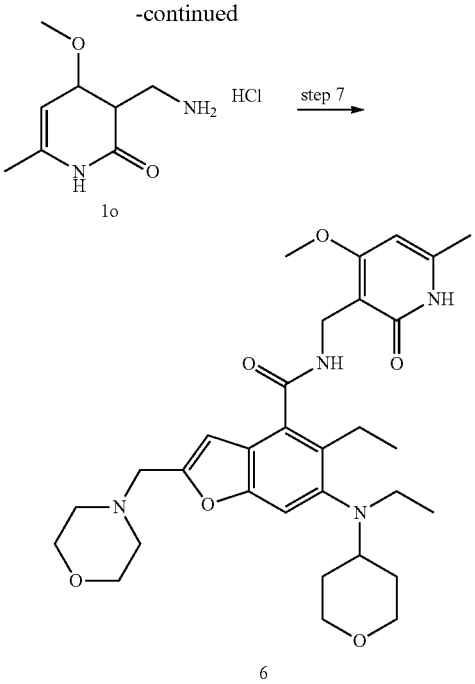

Step 1

Methyl 6-bromo-5-ethyl-2-formylbenzofuran-4-carboxylate

Methyl 6-bromo-5-ethylbenzofuran-4-carboxylate g (260 mg, 0.92 mmol) was dissolved in 8 mL of tetrahydrofuran. The mixture was cooled down to −70° C., then 2.0 M lithium diisopropylamide (0.92 mL, 1.84 mmol) was added dropwise under an argon atmosphere. At −70° C., the mixture was stirred for 1 hour, then 4-formylmorpholine (158 mg, 1.38 mmol) was added. The reaction was slowly warmed up to room temperature, and excess ammonium chloride was added. The mixture was stirred well, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-bromo-5-ethyl-2-formylbenzofuran-4-carboxylate 6a (80 mg, yield 48%) as a yellow and white solid.

Step 2

Methyl 6-bromo-5-ethyl-2-(hydroxymethyl)benzofuran-4-carboxylate

Methyl 6-bromo-5-ethyl-2-formylbenzofuran-4-carboxylate 6a (80 mg, 0.26 mmol)) was dissolved in 4 mL of methanol and 0.5 mL of tetrahydrofuran, then sodium borohydride (20 mg, 0.51 mmol) was added in batches at room temperature. The mixture was stirred for 3 minutes. After the reaction was completed, ethyl acetate and saturated sodium bicarbonate solution were added. Two phases was separated, and the mixture was extracted three times with ethyl acetate. The organic phases were combined, washed with saturated sodium chloride solution, dried over anhydrous sodium sulfate, and filtered. The filtrate was concentrated under reduced pressure to obtain the crude title compound methyl 6-bromo-5-ethyl-2-(hydroxymethyl)benzofuran-4-carboxylate 6b (80 mg) as a white solid, which was directly used in the next step without further purification.

Step 3

Methyl 6-bromo-5-ethyl-2-(morpholinomethyl)benzofuran-4-carboxylate

The crude methyl 6-bromo-5-ethyl-2-(hydroxymethyl) benzofuran-4-carboxylate 6b (80 mg, 0.26 mmol) was dissolved in 5 mL of dichloromethane, then methanesulfonyl chloride (45 mg, 0.38 mmol) and trifluoroacetic acid (130 mg, 1.29 mmol) were added. The mixture was stirred for 12 hours. The mixture was concentrated under reduced pressure, then 5 mL of N,N-dimethylformamide, potassium carbonate (71 mg, 0.51 mmol) and morpholine (40 mg, 0.51 mmol) were added. The reaction system was stirred for 1 hour at 80° C. After the reaction was completed, water was added, and the mixture was extracted three times with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-bromo-5-ethyl-2-(morpholinomethyl)benzofuran-4-carboxylate 6c (65 mg, yield 64%) as a white solid.

MS m/z (ESI): 382.0 [M+1]

Step 4

Methyl 5-ethyl-2-(morpholinomethyl)-6-((tetrahydro-2H-pyran-4-yl)amino)benzofuran-4-carboxylate Methyl 6-bromo-5-ethyl-2-(morpholinomethyl)benzofuran-4-carboxylate 6c (90 mg, 0.24 mmol), tetrahydro-2H-pyran-4-amine (36 mg, 0.35 mmol), tris(dibenzylideneacetone)dipalladium (22 mg, 0.02 mmol), (±)-2,2'-bis (diphenylphosphino)-1,1'-binaphthalene (30 mg, 0.05 mmol) and cesium carbonate (230 mg, 0.71 mmol) were dissolved in 5 mL of toluene. The mixture was stirred for 12 hours at 100° C. After the reaction was completed, the mixture was filtered through a pad of celite. The filtrate was concentrated under reduced pressure, and the resulting residue was purified by thin-layer chromatography with elution system A to obtain the title compound methyl 5-ethyl-2-(morpholinomethyl)-6-((tetrahydro-2H-pyran-4-yl)amino) benzofuran-4-carboxylate 6d (85 mg, yield 89%) as a white solid.

MS m/z (LC-MS): 401.2 [M+1]

Step 5

Methyl 5-ethyl-6-(ethyl(tetrahydro-2H-pyran-4-yl) amino)-2-(morpholinomethyl)benzofuran-4-carboxylate Methyl 5-ethyl-2-(morpholinomethyl)-6-((tetrahydro-2H-pyran-4-yl)amino) benzofuran-4-carboxylate 6d (85 mg, 0.21 mmol) was dissolved in 5 mL of 1,2-dichloroethane, then acetaldehyde (93 mg, 2.1 mmol) and acetic acid (63 mg, 1.06 mmo) were added. The mixture was stirred for 2 hours, then sodium triacetoxyborohydride (133 mg, 0.63 mmol) was added. The mixture was stirred for 12 hours at room temperature. After the reaction was completed, the reaction solution was concentrated under reduced pressure, neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 5-ethyl-6-(ethyl(tetrahydro-2H-pyran-4-yl)amino)-2-(morpholinomethyl)benzofuran-4-carboxylate 6e (75 mg, yield 82%) as a white solid.

MS m/z (LC-MS): 344.1 [M−86]

Step 6

5-Ethyl-6-(ethyl(tetrahydro-2H-pyran-4-yl)amino)-2-(morpholinomethyl)benzofuran-4-carboxylic acid Methyl 5-ethyl-6-(ethyl(tetrahydro-2H-pyran-4-yl)amino)-2-(morpholinomethyl) benzofuran-4-carboxylate 6e (75 mg, 0.17 mmol) was dissolved in 1 mL of tetrahydrofuran and 3 mL of methanol, then 3 mL of 4M sodium hydroxide solution was added. The mixture was stirred for 12 hours at 60° C. After the reaction was completed, concentrated hydrochloric acid was added to adjust the pH of the reaction solution to 4. The mixture was concentrated under reduced pressure. The residue was washed with methanol and filtered to remove a white solid. The filtrate was concentrated under reduced pressure to obtain the crude title compound 5-ethyl-6-(ethyl(tetrahydro-2H-pyran-4-yl)amino)-2-(morpholinomethyl)benzofuran-4-carboxylic acid 6f (71 mg) as a white solid, which was directly used in the next step without further purification.

Step 7

5-Ethyl-6-(ethyl(tetrahydro-2H-pyran-4-yl)amino)-N-((4-methoxy-6-methyl-2-oxo-1,2-dihydropyridin-3-yl)methyl)-2-(morpholinomethyl)benzofuran-4-carboxamide The crude 5-ethyl-6-(ethyl(tetrahydro-2H-pyran-4-yl)amino)-2-(morpholinomethyl)benzofuran-4-carboxylic acid 6f (45 mg, 0.11 mmol) was dissolved in 5 mL of N,N-dimethylformamide, then 1-ethyl-3-(3-dimethylaminopropyl)carbodiimide (31 mg, 0.16 mmol), 1-hydroxybenzotriazole (22 mg, 0.16 mmol) and N,N-diisopropylethylamine (70 mg, 0.54 mmol) were added. The mixture was stirred for 1 hour, then 3-(aminomethyl)-4-methoxy-6-methylpyridin-2(1H)-one hydrochloride 1o (33 mg, 0.16 mmol) was added. The mixture was stirred for 36 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-N-((4-methoxy-6-methyl-2-oxo-1,2-dihydropyridin-3-yl)methyl)-2-(morpholinomethyl)benzofuran-4-carboxamide 6 (35 mg, yield 57%) as a white solid.

MS m/z (ESI): 567.4 [M+1]

$^1$H NMR (400 MHz, DMSO-$d_6$) δ 11.43 (s, 1H), 7.99 (t, 1H), 7.39 (s, 1H), 6.54 (s, 1H), 6.10 (s, 1H), 4.28 (d, 2H), 3.84 (brs, 2H), 3.82 (s, 3H), 3.59 (s, 2H), 3.55-3.57 (m, 4H), 3.21 (t, 2H), 3.02-3.07 (m, 2H), 2.92-2.97 (m, 1H), 2.78-2.83 (m, 2H), 2.43 (brs, 4H), 2.18 (s, 3H), 1.64-1.67 (brd, 2H), 1.45-1.55 (m, 2H), 1.05 (t, 3H), 0.82 (t, 3H).

Example 7

2-((4,4-Difluoropiperidin-1-yl)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide

7

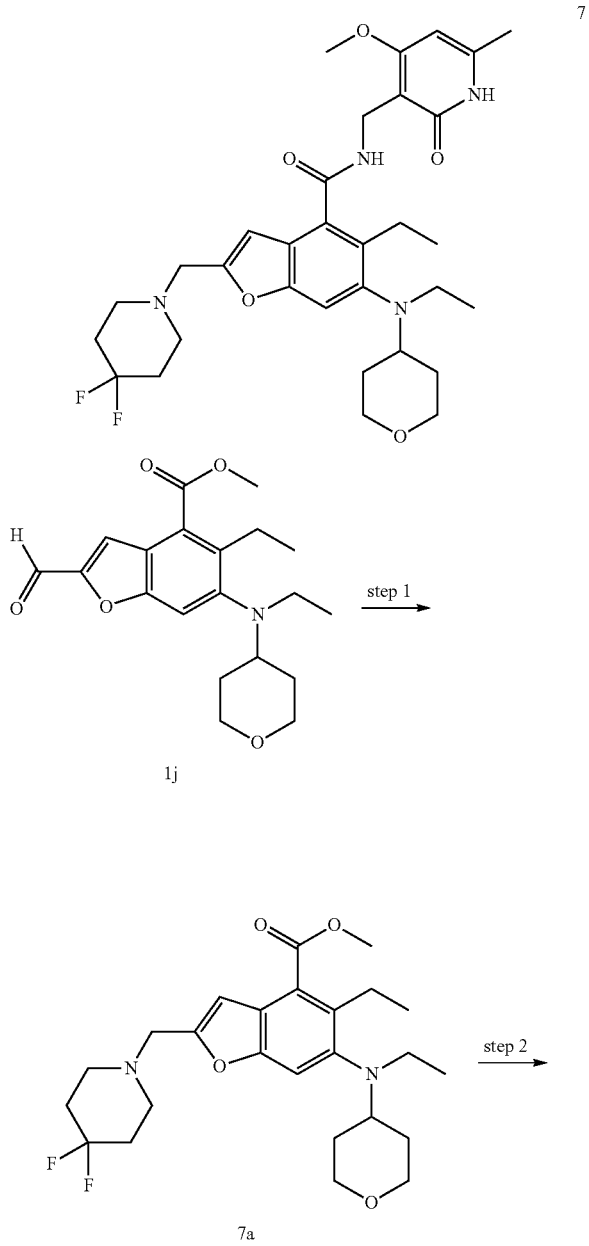

1j

7a

-continued
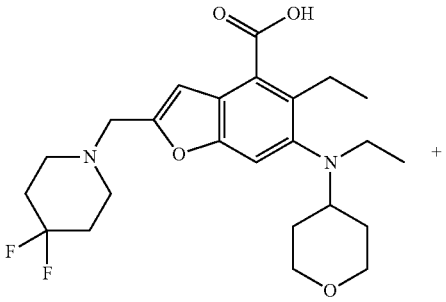
7b
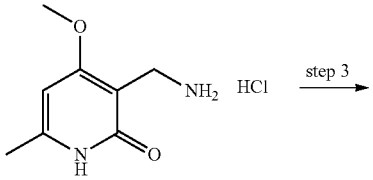
1o
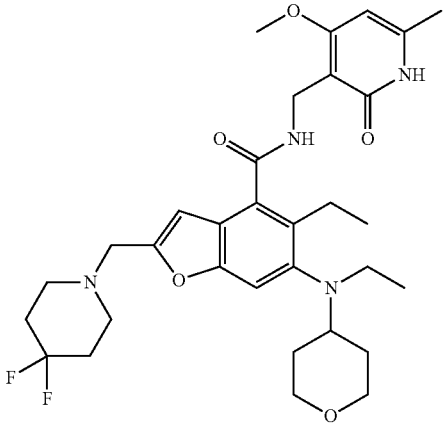
7
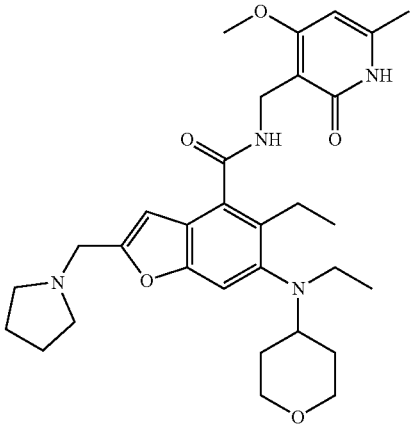
-continued
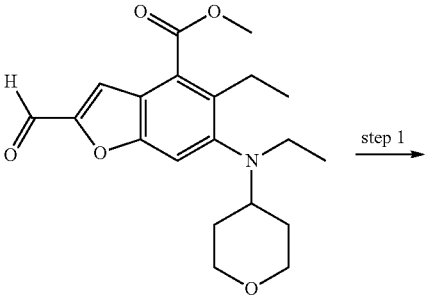
1j
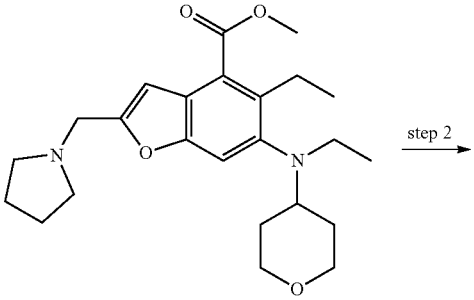
8a
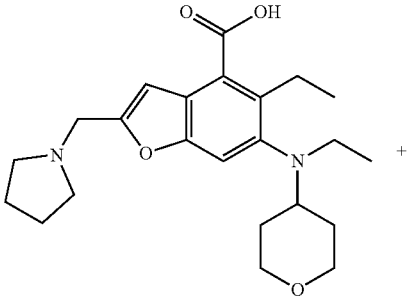
8b
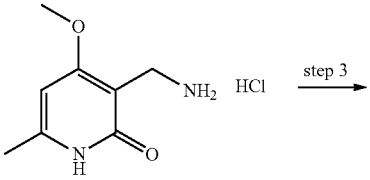
1o
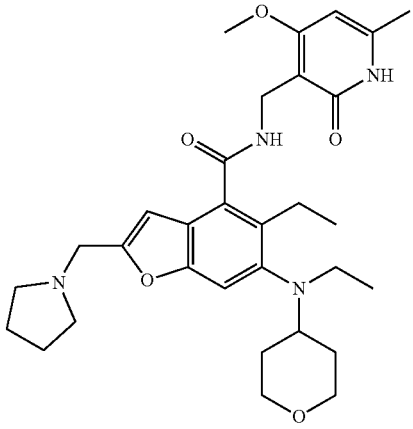
8

Step 1

Methyl 2-((4,4-difluoropiperidin-1-yl)methyl)-5-ethyl-6-(ethyl(tetrahydro-2H-pyran-4-yl)amino)benzofuran-4-carboxylate Methyl 5-ethyl-6-(ethyl(tetrahydro-2H-pyran-4-yl)amino)-2-formylbenzofuran-4-carboxylate 1j (50 mg, 0.14 mmol), 4,4-difluoropiperidine hydrochloride (33 mg, 0.21 mmol) and acetic acid (42 mg, 0.49 mmol) were added to 5 mL of methanol. The mixture was stirred 1 hour, then molecular sieves and sodium triacetoxyborohydride (88 mg, 0.42 mmol) were added. The mixture was stirred for 12 hours at room temperature. After the reaction was completed, the mixture was neutralized with saturated sodium bicarbonate solution, and extracted with a mixture of dichloromethane and methanol (V:V=5:1). The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 2-((4,4-difluoropiperidin-1-yl)methyl)-5-ethyl-6-(ethyl(tetrahydro-2H-pyran-4-yl)amino)benzofuran-4-carboxylate 7a (25 mg, yield 45%) as a colorless oil.

MS m/z (ESI): 465.1[M+1]

Step 2

2-((4,4-Difluoropiperidin-1-yl)methyl)-5-ethyl-6-(ethyl(tetrahydro-2H-pyran-4-yl)amino)benzofuran-4-carboxylic acid Methyl 2-((4,4-difluoropiperidin-1-yl)methyl)-5-ethyl-6-(ethyl(tetrahydro-2H-pyran-4-yl)amino)benzofuran-4-carboxylate 7a (20 mg, 0.043 mmol) was dissolved in 1 mL of tetrahydrofuran and 3 mL of methanol, then 3 mL of 4M sodium hydroxide solution was added. The mixture was stirred for 12 hours at 60° C. After the reaction was completed, the reaction solution was neutralized with concentrated hydrochloric acid, then concentrated under reduced pressure. The residue was dissolved in a mixture of dichloromethane and methanol (V:V=5:1) and filtered. The filter cake was washed with a mixture of dichoromethane and methanol (V:V=5:1). The filtrate was combined, and concentrated under reduced pressure to obtain the crude title compound 2-((4,4-difluoropiperidin-1-yl)methyl)-5-ethyl-6-(ethyl(tetrahydro-2H-pyran-4-yl)amino)benzofuran-4-carboxylic acid 7b (20 mg) as a white solid, which was directly used in the next step without further purification.

Step 3

2-((4,4-Difluoropiperidin-1-yl)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide The crude 2-((4,4-difluoropiperidin-1-yl)methyl)-5-ethyl-6-(ethyl(tetrahydro-2H-pyran-4-yl)amino)benzofuran-4-carboxylic acid 7b (20 mg, 0.044 mmol) was dissolved in 5 mL of N,N-dimethylformamide, then 1-ethyl-3-(3-dimethylaminopropyl)carbodiimide (13 mg, 0.066), 1-hydroxybenzotriazole (9 mg, 0.066 mmol) and N,N-diisopropylethylamine (29 mg, 0.22 mmol) were added. The mixture was stirred 1 hour, then 3-(aminomethyl)-4-methoxy-6-methylpyridin-2(1H)-one hydrochloride 1o (12 mg, 0.058 mmol) was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 2-((4,4-difluoropiperidin-1-yl)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide 7 (21 mg, yield 78%) as a white solid.

MS m/z (ESI): 601.5 [M+1]

$^1$H NMR (400 MHz, DMSO-$d_6$) δ 11.43 (s, 1H), 8.00 (t, 1H), 7.39 (s, 1H), 6.55 (s, 1H), 6.10 (s, 1H), 4.28 (d, 2H), 3.84 (brs, 2H), 3.82 (s, 3H), 3.69 (s, 2H), 3.21 (t, 2H), 3.02-3.07 (m, 2H), 2.92-2.98 (m, 1H), 2.78-2.83 (m, 2H), 2.57 (brs, 4H), 2.17 (s, 3H), 1.95-1.98 (m, 4H), 1.64-1.66 (brd, 2H), 1.46-1.55 (m, 2H), 1.05 (t, 3H), 0.82 (t, 3H).

Example 8

5-Ethyl-6-(ethyl(tetrahydro-2H-pyran-4-yl)amino)-N-((4-methoxy-6-methyl-2-oxo-1,2-dihydropyridin-3-yl)methyl)-2-(pyrrolidin-1-ylmethyl)benzofuran-4-carboxamide

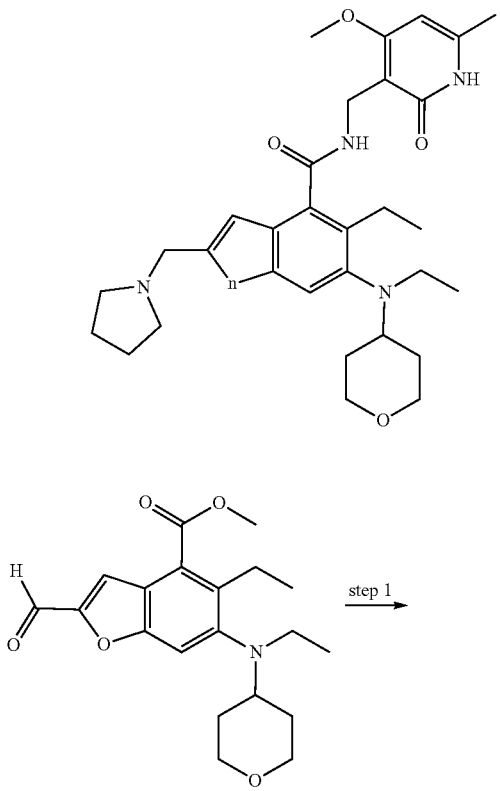

1j

-continued

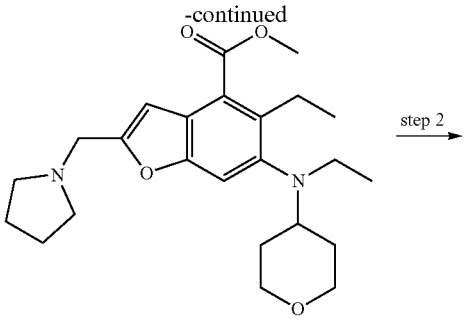

8a

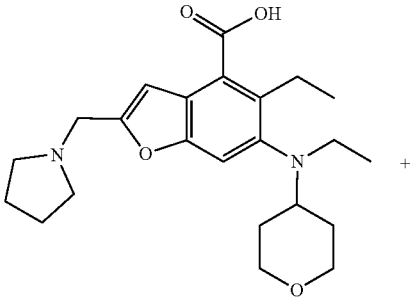

8b

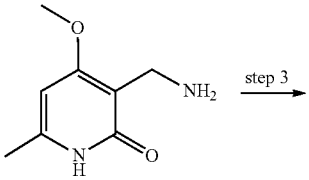

1o

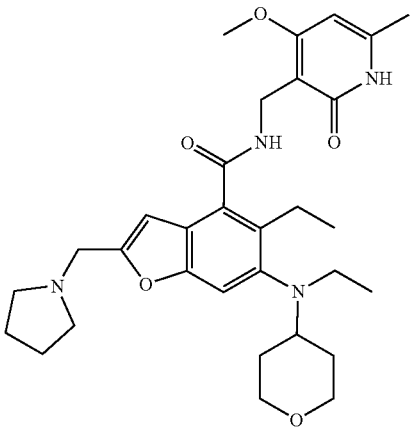

8

Step 1

Methyl 5-ethyl-6-(ethyl(tetrahydro-2H-pyran-4-yl)amino)-2-(pyrrolidin-1-ylmethyl)benzofuran-4-carboxylate Methyl 5-ethyl-6-(ethyl(tetrahydro-2H-pyran-4-yl)amino)-2-formylbenzofuran-4-carboxylate 1j (40 mg, 0.11 mmol), pyrrolidine (15 mg, 0.22 mmol) and acetic acid (30 mg, 0.55 mmol) were dissolved in 5 mL of methanol. The mixture was stirred 1 hour, then sodium triacetoxyborohydride (70 mg, 0.33 mmol) was added. The mixture was stirred for 12 hours at room temperature. After the reaction was completed, the mixture was neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 5-ethyl-6-(ethyl(tetrahydro-2H-pyran-4-yl)amino)-2-(pyrrolidin-1-ylmethyl)benzofuran-4-carboxylate 8a (44 mg, yield 95%) as a colorless oil.

Step 2

5-Ethyl-6-(ethyl(tetrahydro-2H-pyran-4-yl)amino)-2-(pyrrolidin-1-ylmethyl)benzofuran-4-carboxylic acid Methyl 5-ethyl-6-(ethyl(tetrahydro-2H-pyran-4-yl)amino)-2-(pyrrolidin-1-ylmethyl)benzofuran-4-carboxylate 8a (56 mg, 0.13 mmol) was dissolved in 1 mL of tetrahydrofuran and 5 mL of methanol, then 2 mL of 4M sodium hydroxide solution were added. The mixture was stirred for 12 hours at 60° C. After the reaction was completed, concentrated hydrochloric acid was added to adjust the pH to 4, then the mixture was concentrated under reduced pressure. The residue was dissolved in a mixture of dichloromethane and methanol (V:V=5:1) and filtered. The filter cake was washed with a mixture of dichoromethane and methanol (V:V=5:1). The filtrate was combined, and concentrated under reduced pressure to obtain the crude title compound 5-ethyl-6-(ethyl(tetrahydro-2H-pyran-4-yl)amino)-2-(pyrrolidin-1-ylmethyl)benzofuran-4-carboxylic acid 8b (50 mg) as a white solid, which was directly used in the next step without further purification.

MS m/z (ESI): 399.0 [M−1]

Step 3

5-Ethyl-6-(ethyl(tetrahydro-2H-pyran-4-yl)amino)-N-((4-methoxy-6-methyl-2-oxo-1,2-dihydropyridin-3-yl)methyl)-2-(pyrrolidin-1-ylmethyl)benzofuran-4-carboxamide The crude 5-ethyl-6-(ethyl(tetrahydro-2H-pyran-4-yl)amino)-2-(pyrrolidin-1-ylmethyl)benzofuran-4-carboxylic acid 8b (25 mg, 0.60 mmol) was dissolved in 3 mL of N,N-dimethylformamide, then 1-ethyl-3-(3-dimethylaminopropyl)carbodiimide (15 mg, 0.09 mmol), 1-hydroxybenzotriazole (12 mg, 0.09 mmol) and N,N-diisopropylethylamine (387 mg, 3.0 mmol) were added. The mixture was stirred 1 hour, then 3-(aminomethyl)-4-methoxy-6-methylpyridin-2(1H)-one hydrochloride 1o (16 mg, 0.078 mmol) was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-N-((4-methoxy-6-methyl-2-oxo-1,2-dihydropyridin-3-yl)methyl)-2-(pyrrolidin-1-ylmethyl)benzofuran-4-carboxamide 8 (12 mg, yield 36%) as a white solid.

MS m/z (ESI): 551.6 [M+1]

$^1$H NMR (400 MHz, DMSO-$d_6$) δ 11.43 (s, 1H), 7.99 (t, 1H), 7.37 (s, 1H), 6.50 (s, 1H), 6.10 (s, 1H), 4.28 (d, 2H), 3.84 (brs, 2H), 3.82 (s, 3H), 3.71 (brs, 2H), 3.18-3.26 (m, 4H), 3.03-3.07 (m, 2H), 2.92-2.97 (m, 1H), 2.78-2.81 (m, 2H), 2.17 (s, 3H), 1.70 (brs, 4H), 1.64 (brs, 2H), 1.46-1.54 (m, 2H), 1.23 (brs, 2H), 1.05 (t, 3H), 0.82 (t, 3H).
Example 9
N-((4,6-Dimethyl-2-oxo-1,2-dihydropyridin-3-yl)methyl)-5-ethyl-6-(ethyl(tetrahydro-2H-pyran-4-yl)amino)-2-(1-isopropylpiperidin-4-yl)benzofuran-4-carboxamide
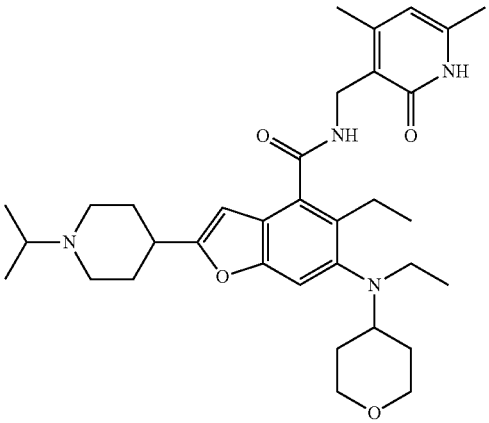
9
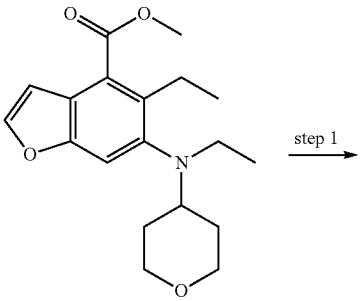
1i
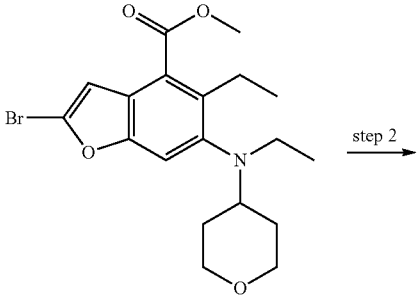
9a
-continued
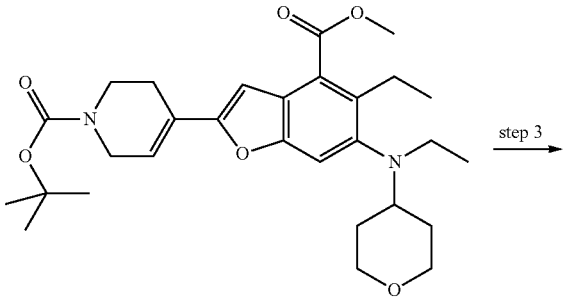
9b
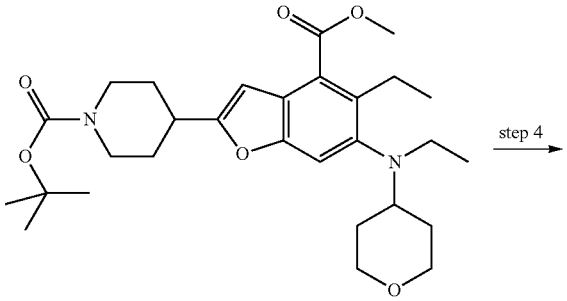
9c
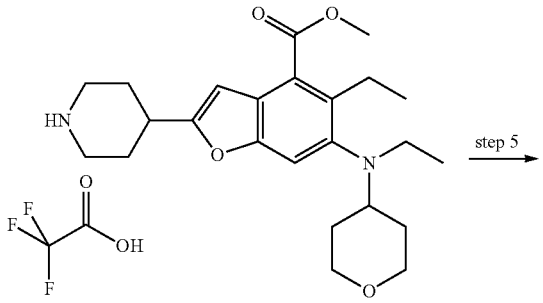
9c
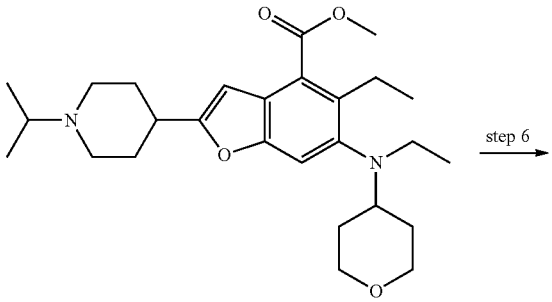
9e
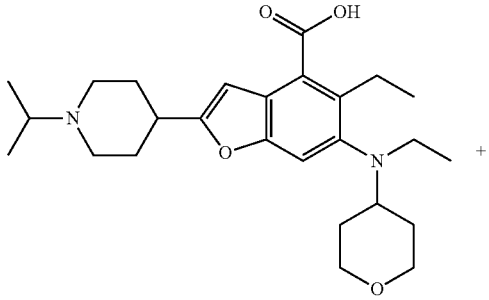
9f -continued

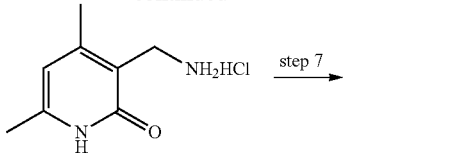

2a

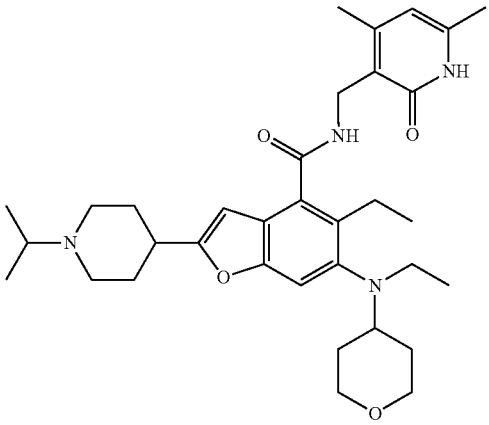

9

Step 1

Methyl 2-bromo-5-ethyl-6-(ethyl(tetrahydro-2H-pyran-4-yl)amino)benzofuran-4-carboxylate Methyl 5-ethyl-6-(ethyl(tetrahydro-2H-pyran-4-yl)amino)benzofuran-4-carboxylate 1i (1 g, 3.0 mmol) was dissolved in 15 mL of tetrahydrofuran, then 1.8 mL of 2M lithium diisopropylamide was added dropwise at −70° C. At −70° C., the mixture was stirred for 90 minutes before 1,2-dibromotetrachloroethane (978 mg, 3 mmol) was added. The reaction solution was stirred for 1 hour at −70° C., and warmed up to room temperature. Ammonium chloride solution was added, and the mixture was extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 2-bromo-5-ethyl-6-(ethyl(tetrahydro-2H-pyran-4-yl)amino)benzofuran-4-carboxylate 9a (320 mg, yield 40%) as a yellow oil.

Step 2 tert-Butyl 4-(5-ethyl-6-(ethyl(tetrahydro-2H-pyran-4-yl)amino)-4-(methoxycarbonyl) benzofuran-2-yl)-5,6-dihydropyridine-1(2H)-carboxylate Methyl 2-bromo-5-ethyl-6-(ethyl(tetrahydro-2H-pyran-4-yl)amino)benzofuran-4-carboxylate 9a (1.4 g, 3.4 mmol), tert-butyl 4-(4,4,5,5-tetramethyl-1,3,2-dioxaborolan-2-yl)-5,6-dihydropyridine-1(2H)-carboxylate (1.6 g, 5.1 mmol), tris(dibenzylideneacetone)dipalladium (312 mg, 0.34 mmol), 2-dicyclohexylphosphino-2',4',6'-triisopropylbiphenyl (325 mg, 0.68 mmol) and cesium carbonate (3.4 g, 10.2 mmol) were mixed in 50 mL of a mixture of 1,4-dioxane and water (V:V=4:1). The mixture was warmed up to 80° C. and stirred for 16 hours. The reaction solution was filtered through a pad of celite, and washed with ethyl acetate. Water was added to the filtrate, two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound tert-butyl 4-(5-ethyl-6-(ethyl(tetrahydro-2H-pyran-4-yl)amino)-4-(methoxycarbonyl) benzofuran-2-yl)-5,6-dihydropyridine-1(2H)-carboxylate 9b (1.67 g, yield 95%) as a purple oil.

Step 3 tert-Butyl 4-(5-ethyl-6-(ethyl(tetrahydro-2H-pyran-4-yl)amino)-4-(methoxycarbonyl)benzofuran-2-yl) piperidine-1-carboxylate tert-Butyl 4-(5-ethyl-6-(ethyl(tetrahydro-2H-pyran-4-yl) amino)-4-(methoxycarbonyl)benzofuran-2-yl)-5,6-dihydropyridine-1(2H)-carboxylate 9b (1.7 g, 3.3 mmol) was dissolved in 23 mL of a mixture of methanol and tetrahydrofuran (V:V=20:3), then Pd/C (200 mg, 10%) was added. The reaction system was purged three times with hydrogen and stirred for 1 hour. The reaction solution was filtered through a pad of celite. The filtrate was concentrated under reduced pressure, and the resulting residue was purified by silica gel column chromatography with elution system B to obtain the title compound tert-butyl 4-(5-ethyl-6-(ethyl(tetrahydro-2H-pyran-4-yl)amino)-4-(methoxycarbonyl)benzofuran-2-yl)piperidine-1-carboxylate 9c (1.6 g, yield 94%) as a light yellow oil. MS m/z (ESI): 515.0 [M+1]

Step 4

Methyl 5-ethyl-6-(ethyl(tetrahydro-2H-pyran-4-yl) amino)-2-(piperidin-4-yl)benzofuran-4-carboxylate 2,2,2-trifluoroacetate tert-Butyl 4-(5-ethyl-6-(ethyl(tetrahydro-2H-pyran-4-yl) amino)-4-(methoxycarbonyl)benzofuran-2-yl)piperidine-1-carboxylate 9c (1.6 g, 3.3 mmol) was dissolved in 20 mL of dichloromethane, then 4 mL of trifluoroacetic acid was added. The mixture was stirred for 2 hours, then concentrated under reduced pressure to obtain the crude title compound methyl 5-ethyl-6-(ethyl(tetrahydro-2H-pyran-4-yl)amino)-2-(piperidin-4-yl)benzofuran-4-carboxylate 2,2,2-trifluoroacetate 9d (1.3 g) as a light yellow oil, which was directly used in the next step without further purification.

MS m/z (ESI): 415.3 [M+1]

Step 5

Methyl 5-ethyl-6-(ethyl(tetrahydro-2H-pyran-4-yl) amino)-2-(1-isopropylpiperidin-4-yl)benzofuran-4-carboxylate The crude methyl 5-ethyl-6-(ethyl(tetrahydro-2H-pyran-4-yl)amino)-2-(piperidin-4-yl)benzofuran-4-carboxylate 2,2,2-trifluoroacetate 9d (1.3 g, 3.1 mmol) was dissolved in 30 mL of N,N-dimethylformamide, then potassium carbonate (1.3 g, 8.4 mmol) was added. The mixture was stirred for 10 minutes, then 2-bromopropane (575 mg, 4.7 mmol) and potassium iodide (261 mg, 1.5 mmol) were added. The mixture was stirred for 2 hours at 70° C., then water was added, and the reaction solution was extracted with a mixture of dichloromethane and methanol (V:V=5:1). The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 5-ethyl-6-(ethyl(tetrahydro-2H-pyran-4-yl)amino)-2-(1-isopropylpiperidin-4-yl)benzofuran-4-carboxylate 9e (1.4 g, yield 90%) as a colorless oil.

MS m/z (ESI): 457.0 [M+1]

Step 6

5-Ethyl-6-(ethyl(tetrahydro-2H-pyran-4-yl)amino)-2-(1-isopropylpiperidin-4-yl)benzofuran-4-carboxylic acid Methyl 5-ethyl-6-(ethyl(tetrahydro-2H-pyran-4-yl)amino)-2-(1-isopropylpiperidin-4-yl)benzofuran-4-carboxylate 9e (1.1 g, 2.4 mmol) was dissolved in 30 mL of methanol, then 5 mL of 4M sodium hydroxide solution was added. The mixture was stirred for 16 hours at 60° C., then concentrated hydrochloric acid was added to adjust the pH of the reaction solution to 4. The mixture was concentrated under reduced pressure, and the residue was dissolved in a mixture of dichloromethane and methanol (V:V=5:1) and filtered. The filter cake was washed with a mixture of dichloromethane and methanol (V:V=5:1). The filtrate was combined, and concentrated under reduced pressure to obtain the crude title compound 5-ethyl-6-(ethyl(tetrahydro-2H-pyran-4-yl)amino)-2-(1-isopropylpiperidin-4-yl)benzofuran-4-carboxylic acid 9f (1.4 g) as a white solid, which was used directly in the next step without further purification.

MS m/z (ESI): 443.3 [M+1]

Step 7

N-((4,6-Dimethyl-2-oxo-1,2-dihydropyridin-3-yl)methyl)-5-ethyl-6-(ethyl(tetrahydro-2H-pyran-4-yl)amino)-2-(1-isopropylpiperidin-4-yl)benzofuran-4-carboxamide The crude 5-ethyl-6-(ethyl(tetrahydro-2H-pyran-4-yl)amino)-2-(1-isopropylpiperidin-4-yl)benzofuran-4-carboxylic acid 9f (1.1 g, 2.5 mmol) was dissolved in 20 mL of N,N-dimethylformamide, then 1-ethyl-3-(3-dimethylaminopropyl)carbodiimide (715 mg, 3.7 mmol), 1-hydroxybenzotriazole (510 mg, 3.7 mmol) and N,N-diisopropylethylamine (1.6 g, 12.5 mmol) were added. The mixture was stirred for 1 hour, then 3-(aminomethyl)-4,6-dimethylpyridin-2(1H)-one hydrochloride 2a (470 mg, 2.5 mmol) was added. The mixture was stirred for 16 hours. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound N-((4,6-dimethyl-2-oxo-1,2-dihydropyridin-3-yl)methyl)-5-ethyl-6-(ethyl(tetrahydro-2H-pyran-4-yl)amino)-2-(1-isopropylpiperidin-4-yl)benzofuran-4-carboxamide 9 (850 mg, yield 59%) as a white solid.

MS m/z (ESI): 577.7 [M+1]

$^1$H NMR (400 MHz, DMSO-$d_6$) δ 11.50 (s, 1H), 8.16 (t, 1H), 7.38 (s, 1H), 6.37 (brs, 1H), 5.87 (s, 1H), 4.31 (d, 2H), 3.82 (d, 2H), 3.21 (t, 2H), 3.01-3.07 (m, 4H), 2.91-2.96 (m, 1H), 2.79-2.81 (m, 2H), 2.24 (s, 3H), 2.17 (brs, 2H), 2.12 (s, 3H), 2.02 (brs, 2H), 1.63-1.66 (brd, 2H), 1.45-1.54 (m, 2H), 1.25 (brs, 6H), 1.01 (t, 3H), 0.81 (t, 3H).

Example 10

5-Ethyl-6-(ethyl(tetrahydro-2H-pyran-4-yl)amino)-2-(1-isopropylpiperidin-4-yl)-N-((4-methoxy-6-methyl-2-oxo-1,2-dihydropyridin-3-yl)methyl)benzofuran-4-carboxamide

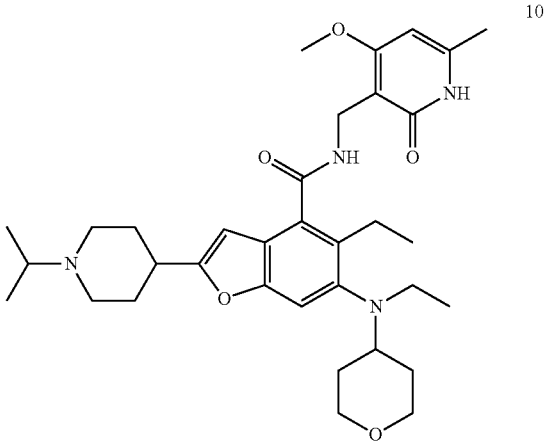

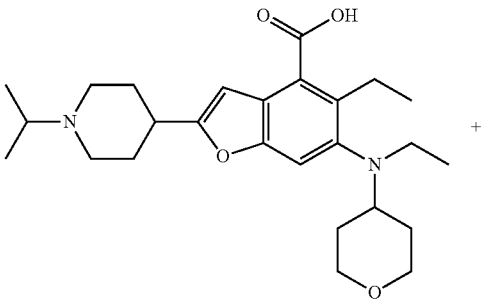

9f

-continued

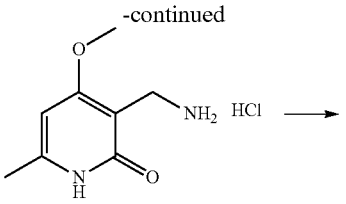

1o

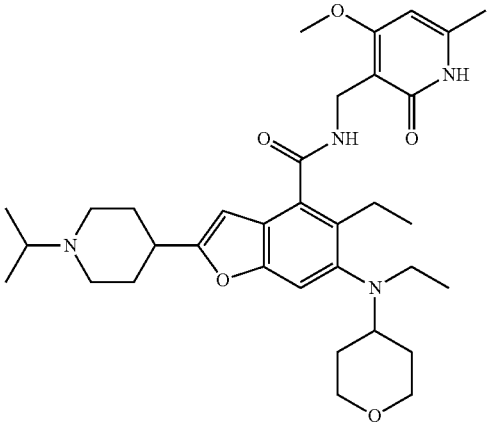

10

The crude 5-ethyl-6-(ethyl(tetrahydro-2H-pyran-4-yl)amino)-2-(1-isopropylpiperidin-4-yl)benzofuran-4-carboxylic acid 9f (30 mg, 0.07 mmol) was dissolved in 5 mL of N,N-dimethylformamide, then 1-ethyl-3-(3-dimethylaminopropyl)carbodiimide (20 mg, 0.1 mmol), 1-hydroxybenzotriazole (15 mg, 0.1 mmol) and N,N-diisopropylethylamine (45 mg, 0.34 mmol) were added. The mixture was stirred for 1 hour, then 3-(aminomethyl)-4-methoxy-6-methylpyridin-2(1H)-one hydrochloride 1o (21 mg, 0.1 mmol) was added. The mixture was stirred for 16 hours. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-2-(1-isopropylpiperidin-4-yl)-N-((4-methoxy-6-methyl-2-oxo-1,2-dihydropyridin-3-yl)methyl)benzofuran-4-carboxamide 10 (31 mg, yield 77%) as a white solid.

MS m/z (ESI): 593.3 [M+1]

$^1$H NMR (400 MHz, DMSO-$d_6$) δ 11.44 (s, 1H), 7.95 (brs, 1H), 7.36 (s, 1H), 6.37 (brs, 1H), 6.11 (s, 1H), 4.28 (d, 2H), 3.84 (brs, 2H), 3.82 (s, 3H), 3.21 (t, 3H), 3.01-3.06 (m, 3H), 2.90-2.96 (m, 2H), 2.77-2.83 (m, 3H), 2.19 (s, 3H), 2.01 (brs, 4H), 1.63-1.67 (brd, 2H), 1.45-1.53 (m, 2H), 1.22 (brs, 6H), 1.04 (t, 3H), 0.81 (t, 3H).

Example 11

N-((4,6-Dimethyl-2-oxo-1,2-dihydropyridin-3-yl)methyl)-5-ethyl-6-(ethyl(tetrahydro-2H-pyran-4-yl)amino)-2-((4-(2-hydroxy-2-methylpropyl)piperazin-1-yl)methyl)benzofuran-4-carboxamide 11

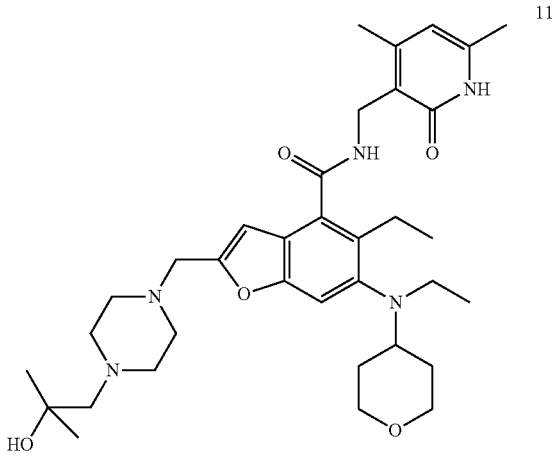

11

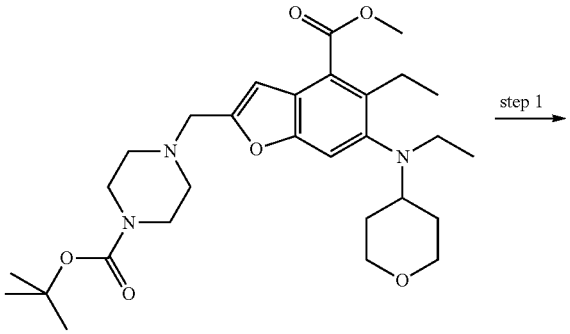

5a

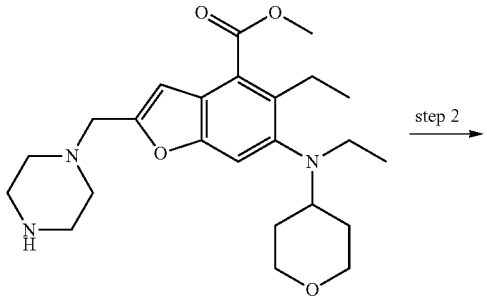

11a

-continued

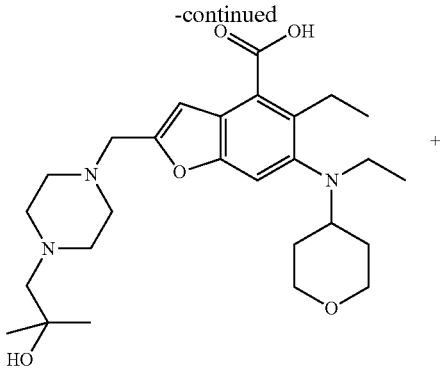

11b

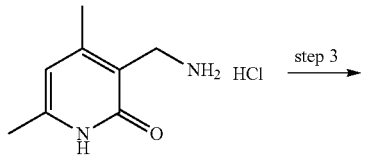

2a

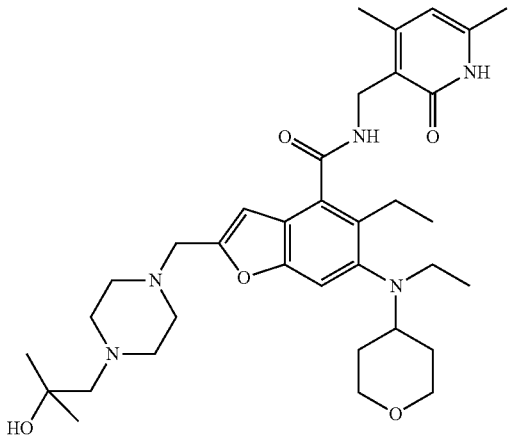

11

Step 1

Methyl 5-Ethyl-6-(ethyl(tetrahydro-2H-pyran-4-yl)amino)-2-(piperazin-1-ylmethyl)benzofuran-4-carboxylate 1a Compound 5a (60 mg, 0.12 mmol) was dissolved in 5 mL of dichloromethane, then 0.5 mL of trifluoroacetic acid was added. After stirring for 2 hours, the mixture was concentrated under reduced pressure, neutralized with saturated sodium carbonate solution, and extracted with a mixture of dichloromethane and methanol. The organic phases were combined, washed with saturated sodium chloride solution, dried over anhydrous sodium sulfate, and filtered. The filtrate was concentrated under reduced pressure to obtain the crude title compound 11a (45 mg) as a yellow solid, which was directly used in the next step without further purification.

Step 2

5-Ethyl-6-(ethyl(tetrahydro-2H-pyran-4-yl)amino)-2-((4-(2-hydroxy-2-methylpropyl)piperazin-1-yl)methyl)benzofuran-4-carboxylic acid 11b The crude 11a (25 mg, 0.06 mmol) was dissolved in 5 mL of ethanol, then 2,2-dimethyloxirane (6.5 mg, 0.09 mmol) and potassium carbonate (17 mg, 0.12 mmol) were added. The mixture was stirred at 60° C. for 12 hours. After the reaction was completed, the mixture was filtered, and 12M hydrochloric acid was added to adjust the pH to 4. The mixture was concentrated under reduced pressure, and the resulting residue was purified by high performance liquid chromatography to obtain the title compound 11b (15 mg, yield 52%) as a white solid.

Step 3

N-((4,6-Dimethyl-2-oxo-1,2-dihydropyridin-3-yl)methyl)-5-ethyl-6-(ethyl(tetrahydro-2H-pyran-4-yl)amino)-2-((4-(2-hydroxy-2-methylpropyl)piperazin-1-yl)methyl)benzofuran-4-carboxamide 11

Compound 11b (15 mg, 0.031 mmol) was dissolved in 4 mL of N,N-dimethylformamide, then 1-ethyl-3-(3-dimethylaminopropyl)carbodiimide (9 mg, 0.046 mmol), 1-hydroxybenzotriazole (7 mg, 0.046 mmol) and N,N-diisopropylethylamine (20 mg, 0.155 mmol) were added to the above reaction solution. The mixture was stirred for 1 hour, then compound 2a (9 mg, 0.046 mmol) was added to the above reaction solution. The mixture was stirred for 12 hours. After the reaction was completed, excess water was added, and the reaction solution was extracted with a mixture of dichloromethane and methanol (V:V=10:1) (10 mL). The organic phases were combined, washed with water (20 mL) and saturated sodium chloride solution (20 mL), dried over anhydrous sodium sulfate, and filtered. The filtrate was concentrated under reduced pressure, and the resulting residue was purified by thin-layer chromatography with elution system A to obtain the title compound 11 (13 mg, yield 70%) as a white solid.

MS m/z (ESI): 622.7 [M+1]

$_1$H NMR (400 MHz, DMSO-$d_6$) δ 11.48 (brs, 1H), 8.17 (t, 1H), 7.39 (s, 1H), 6.48 (s, 1H), 5.86 (s, 1H), 4.32 (d, 2H), 4.04 (brs, 1H), 3.83 (brd, 2H), 3.58 (s, 2H), 3.21 (t, 2H), 3.04 (q, 2H), 2.91-2.97 (m, 1H), 2.79 (q, 2H), 2.56 (brs, 4H), 2.45 (brs, 4H), 2.23 (s, 3H), 2.16 (brs, 2H), 2.11 (s, 3H), 1.63-1.66 (m, 2H), 1.48-1.52 (m, 2H), 1.00-1.06 (m, 9H), 0.82 (t, 3H).

Example 12

5-Ethyl-6-(ethyl(tetrahydro-2H-pyran-4-yl)amino)-N-((4-methoxy-6-methyl-2-oxo-1,2-dihydropyridin-3-yl)methyl)-2-((4-methylpiperazin-1-yl)methyl) benzofuran-4-carboxamide 12

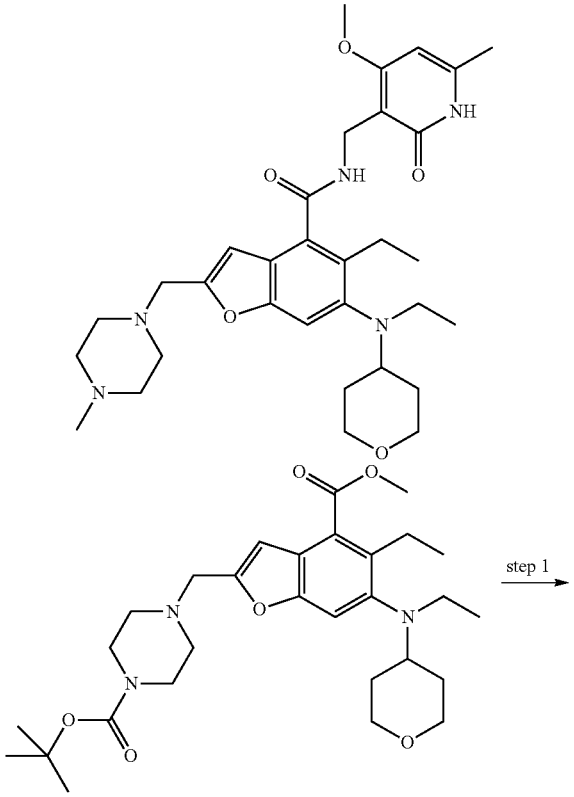

5a

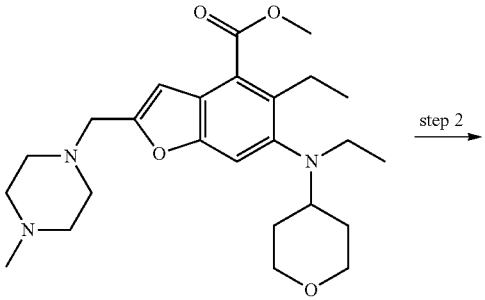

12a

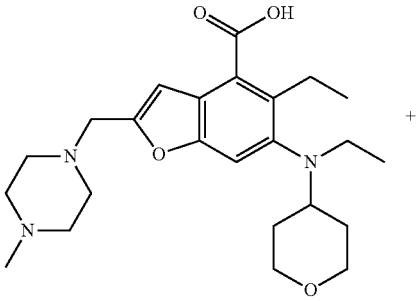

12b

-continued

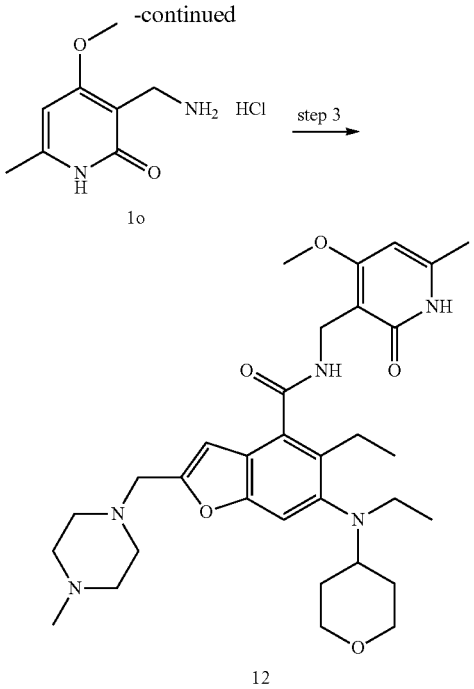

1o

12

Step 1

Methyl 5-ethyl-6-(ethyl(tetrahydro-2H-pyran-4-yl) amino)-2-((4-methylpiperazin-1-yl)methyl)benzo-furan-4-carboxylate 12a Compound 5a (74 mg, 0.14 mmol) was dissolved in 10 mL of 1,2-dichloroethane, then 1.0 mL of trifluoroacetic acid was added. After stirring for 1 hour, the mixture was concentrated under reduced pressure. Then, 5 mL of methanol, formaldehyde (61 mg, 1.4 mmol) and sodium triacetoxyborohydride (88 mg, 0.42 mmol) were added to the residue, successively. The mixture was stirred for 3 hours. After the reaction was completed, the mixture was concentrated under reduced pressure, neutralized with 20 mL of saturated sodium bicarbonate solution, and extracted with a mixture of dichloromethane and methanol (V:V=8:1) (10 mL). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system A to obtain the title compound 12a (60 mg, yield 97%) as a yellow oil.

Step 2

5-Ethyl-6-(ethyl(tetrahydro-2H-pyran-4-yl)amino)-2-((4-methylpiperazin-1-yl)methyl)benzofuran-4-carboxylic acid 12b Compound 12a (60 mg, 0.13 mmol) was dissolved in 4 mL of methanol, then 4 mL of 20% sodium hydroxide solution were added. The mixture was stirred for 12 hours at 60° C. After the reaction was completed, 12 M hydrochloric acid was added to adjust the pH to 4. The mixture was concentrated under reduced pressure, then the residue was dissolved in 10 mL of methanol and filtered. The filtrate was concentrated under reduced pressure to obtain the crude title compound 12b (55 mg) as a yellow solid, which was used directly in the next step without further purification.

Step 3

5-Ethyl-6-(ethyl(tetrahydro-2H-pyran-4-yl)amino)-N-((4-methoxy-6-methyl-2-oxo-1,2-dihydropyridin-3-yl)methyl)-2-((4-methylpiperazin-1-yl)methyl)benzofuran-4-carboxamide 12

The crude 12b (25 mg, 0.058 mmol) was dissolved in 3 mL of N,N-dimethylformamide, then 1-ethyl-3-(3-dimethylaminopropyl)carbodiimide (17 mg, 0.087 mmol), 1-hydroxybenzotriazole (12 mg, 0.087 mmol) and N,N-diisopropylethylamine (38 mg, 0.29 mmol) were added. The mixture was stirred 2 hours, then compound 1o (18 mg, 0.087 mmol) was added to the reaction solution. The mixture was stirred for 12 hours. After the reaction was completed, 20 mL of water was added, the reaction solution was extracted with a mixture of dichloromethane and methanol (V:V=8:1) (10 mL×3). The organic phases were combined, washed with water (10 mL) and saturated sodium chloride solution (10 mL), dried over anhydrous sodium sulfate, and filtered. The filtrate was concentrated under reduced pressure, and the resulting residue was purified by thin-layer chromatography with elution system A to obtain the title compound 12 (22 mg, yield 65%) as a white solid.

MS m/z (ESI): 580.3 [M+1]

$^1$H NMR (400 MHz, DMSO-$d_6$) δ 11.43 (brs, 1H), 7.99 (s, 1H), 7.38 (s, 1H), 6.56 (s, 1H), 6.10 (s, 1H), 4.28 (d, 2H), 3.85 (brs, 2H), 3.82 (s, 3H), 3.63 (s, 2H), 3.21 (t, 2H), 3.02-3.07 (m, 2H), 2.92-2.97 (m, 1H), 2.79-2.81 (m, 2H), 2.58 (brs, 4H), 2.40 (brs, 4H), 2.18 (s, 3H), 1.64-1.66 (m, 2H), 1.46-1.55 (m, 2H), 1.05 (t, 3H), 0.82 (t, 3H).

Example 13

2-((Dimethylamino)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide 13

13

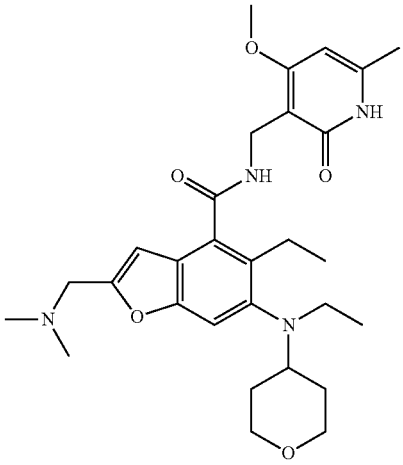

-continued

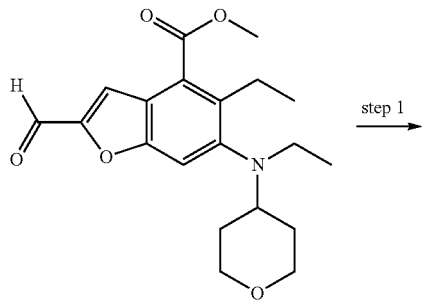

1j

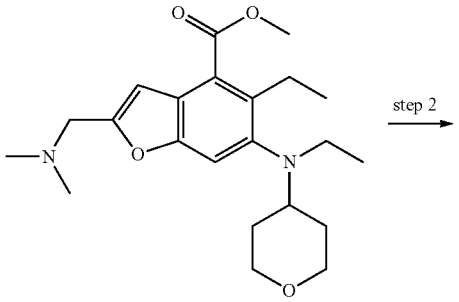

13a

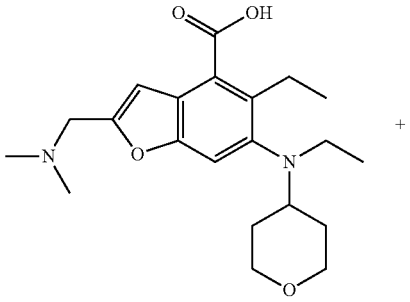

13b

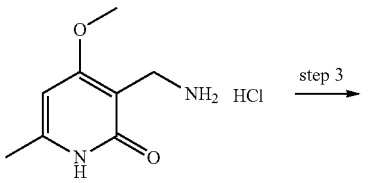

1o

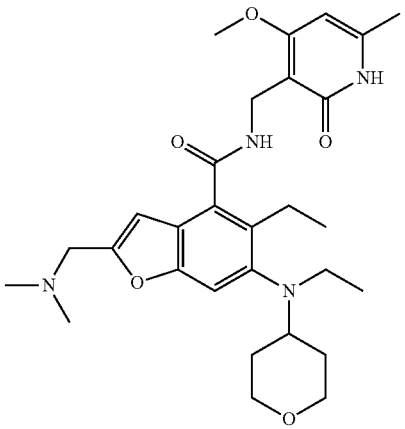

13

Step 1

Methyl 2-((dimethylamino)methyl)-5-ethyl-6-(ethyl(tetrahydro-2H-pyran-4-yl)amino)benzofuran-4-carboxylate 13a Compound 1j (30 mg, 0.084 mmol) was dissolved in 5 mL of methanol, then dimethylamine hydrochloride (14 mg, 0.17 mmol) was added. The mixture was stirred for 1 hour, then sodium triacetoxyborohydride (53 mg, 0.25 mmol) was added. The mixture was stirred for 12 hours. After the reaction was completed, the reaction solution was concentrated under reduced pressure, neutralized with saturated sodium bicarbonate solution, and extracted with a mixture of dichloromethane and methanol. The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound 13a (30 mg, yield 90%) as a yellow oil.

Step 2

2-((Dimethylamino)methyl)-5-ethyl-6-(ethyl(tetrahydro-2H-pyran-4-yl)amino)benzofuran-4-carboxylic acid 13b Compound 13a (30 mg, 0.077 mmol) was dissolved in 3 mL of ethanol and 1 mL of tetrahydrofuran, then 5 mL of 2N sodium hydroxide solution were added. The mixture was stirred for 12 hours at 60° C. After the reaction was completed, the reaction solution was adjusted to weak acidity with concentrated hydrochloric acid. The mixture was concentrated under reduced pressure, and the residue was dissolved in a mixture of dichloromethane and methanol (V:V=1:1) and filtered to remove inorganic salts. The filtrate was concentrated under reduced pressure to obtain the crude title compound 13b (25 mg) as a yellow oil, which was directly used in the next step without further purification.

Step 3

2-((Dimethylamino)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide 13

The crude 13b (15 mg, 0.040 mmol) was dissolved in 3 mL of N,N-dimethylformamide, then 1-ethyl-3-(3-dimethylaminopropyl)carbodiimide (7.7 mg, 0.04 mmol), 1-hydroxybenzotriazole (8 mg, 0.060 mmol) and N,N-diisopropylethylamine (26 mg, 0.20 mmol) were added. The mixture was stirred for 0.5 hour, then compound 1o (11 mg, 0.052 mmol) was added. The mixture was stirred for 12 hours. After the reaction was completed, excess water was added, and the reaction solution was extracted with a mixture of dichloromethane and methanol (V:V=8:1) (10 mL). The organic phases were combined, washed with water (10 mL) and saturated sodium chloride solution (10 mL), dried over anhydrous sodium sulfate, and filtered. The filtrate was concentrated under reduced pressure, and the resulting residue was purified by thin-layer chromatography with elution system A to obtain the title compound 13 (7 mg, yield 30%) as a white solid.

MS m/z (ESI): 525.5 [M+1]

$^1$H NMR (400 MHz, DMSO-$d_6$) δ 11.44 (brs, 1H), 8.00 (brs, 1H), 7.37 (s, 1H), 6.51 (s, 1H), 6.10 (s, 1H), 4.28 (d, 2H), 3.85 (brs, 2H), 3.82 (s, 3H), 3.52 (s, 2H), 3.21 (t, 2H), 3.02-3.06 (m, 2H), 2.92-2.96 (m, 1H), 2.77-2.83 (m, 2H), 2.19 (s, 6H), 2.17 (s, 3H), 1.63-1.67 (m, 2H), 1.46-1.53 (m, 2H), 1.06 (t, 3H), 0.82 (t, 3H).

Example 14

2-Cyclopentyl-N-((4,6-dimethyl-2-oxo-1,2-dihydropyridin-3-yl)methyl)-5-ethyl-6-(ethyl(tetrahydro-2H-pyran-4-yl)amino)benzofuran-4-carboxamide 14

14

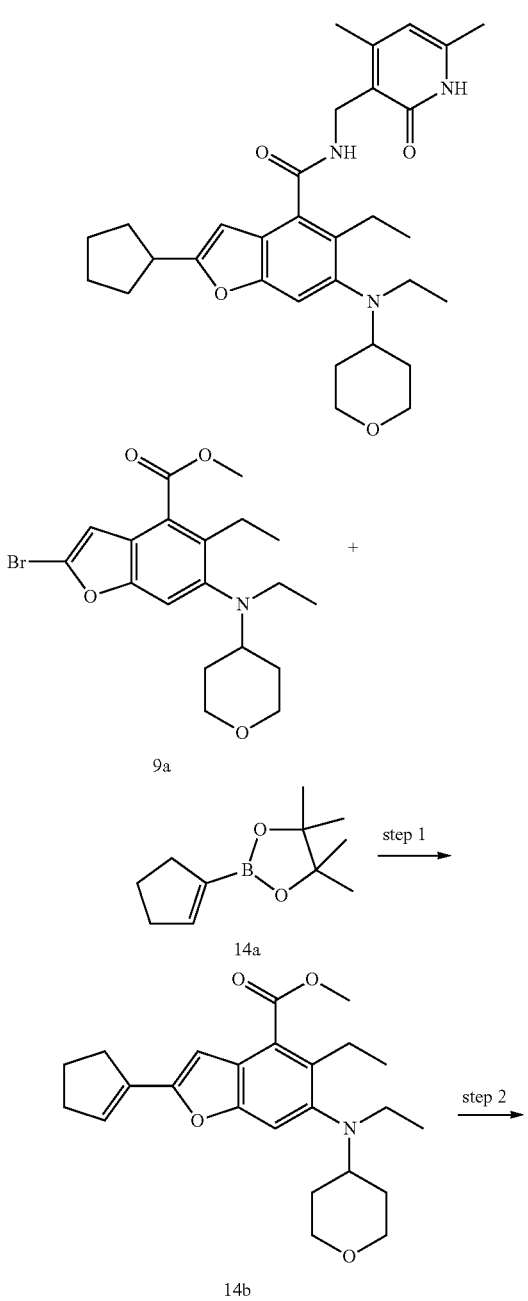

-continued

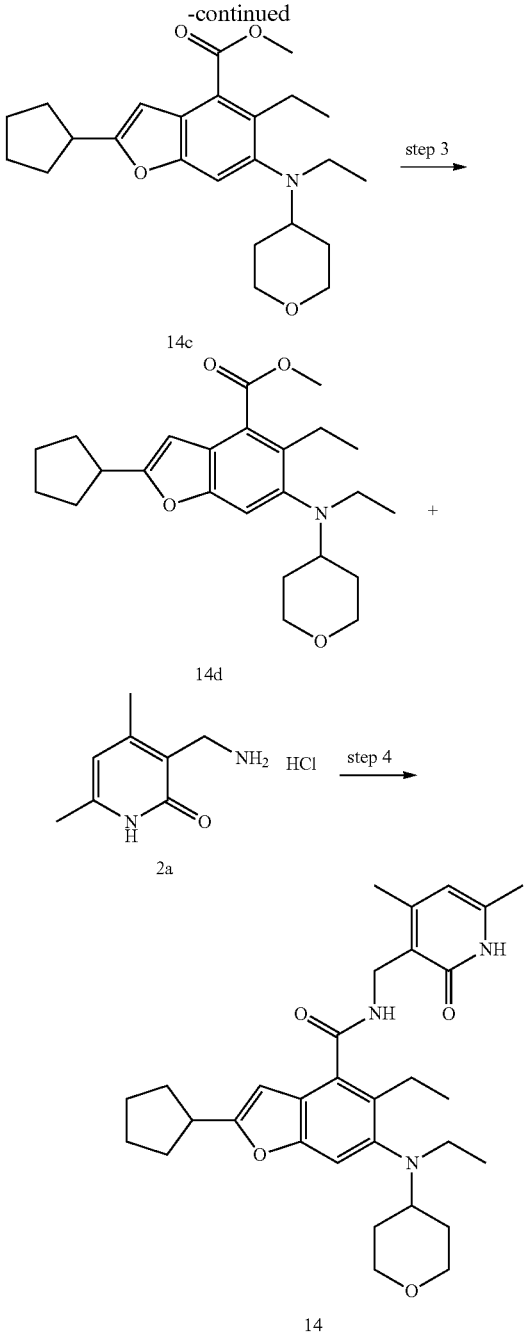

Step 1

Methyl 2-(cyclopent-1-en-1-yl)-5-ethyl-6-(ethyl(tetrahydro-2H-pyran-4-yl)amino)benzofuran-4-carboxylate 14b Compound 9a (70 mg, 0.17 mmol), 2-(cyclopent-1-en-1-yl)-4,4,5,5-tetramethyl-1,3,2-dioxaborolane 14a (40 mg, 0.20 mmol), tris(dibenzylideneacetone)dipalladium (16 mg, 0.017 mmol), 2-dicyclohexylphosphino-2',4',6'-triisopropylbiphenyl (16 mg, 0.034 mmol) and sodium carbonate (52 mg, 0.51 mmol) were dissolved in 5 m of toluene. The mixture was stirred for 12 hours at 100° C. under an argon atmosphere. After the reaction was completed, the mixture was filtered through celite. The filtrate was concentrated under reduced pressure, and the resulting residue was purified by thin-layer chromatography with elution system A to obtain the title compound 14b (50 mg, yield 75%) as a yellow oil.

Step 2

Methyl 2-cyclopentyl-5-ethyl-6-(ethyl(tetrahydro-2H-pyran-4-yl)amino)benzofuran-4-carboxylate 14c Compound 14b (75 mg, 0.19 mmol) was dissolved in 5 mL of methanol, then 20 mg of 10% Pd/C was added. The reaction system was purged three times with hydrogen and stirred for 1 hour. After the reaction was completed, the mixture was filtered through celite. The filtrate was concentrated under reduced pressure, and the resulting residue was purified by thin-layer chromatography with elution system A to obtain the title compound 14c (55 mg, yield 73%) as a colorless oil.

Step 3

2-Cyclopentyl-5-ethyl-6-(ethyl(tetrahydro-2H-pyran-4-yl)amino)benzofuran-4-carboxylic acid 14d Compound 14c (55 mg, 0.14 mmol) was dissolved in 5 mL of a mixture of methanol and tetrahydrofuran (V:V=3:2), then 2 mL of 2N sodium hydroxide solution was added. The mixture was stirred for 12 hours at 60° C. After the reaction was completed, the mixture was concentrated under reduced pressure to remove organic solvents, neutralized with 12M hydrochloric acid to adjust the pH to 3, and extracted with ethyl acetate (10 mL×3). The organic phases were combined, washed with saturated sodium chloride solution (10 mL), dried over anhydrous sodium sulfate, and filtered. The filtrate was concentrated under reduced pressure to obtain the crude title compound 14d (45 mg, yield 85%)) as a colorless oil.

Step 4

2-Cyclopentyl-N-((4,6-dimethyl-2-oxo-1,2-dihydropyridin-3-yl)methyl)-5-ethyl-6-(ethyl(tetrahydro-2H-pyran-4-yl)amino)benzofuran-4-carboxamide 14

Compound 14d (15 mg, 0.065 mmol) was dissolved in 4 mL of N,N-dimethylformamide, then 1-ethyl-3-(3-dimethylaminopropyl)carbodiimide (20 mg, 0.097 mmol), 1-hydroxybenzotriazole (15 mg, 0.097 mmol) and N,N-diisopropylethylamine (50 mg, 0.33 mmol) were added to the reaction solution. The mixture was stirred 1 hour, then compound 2a (18 mg, 0.097 mmol) was added. The mixture was stirred for 12 hours. After the reaction was completed, 20 mL of water was added, and the reaction solution was extracted with a mixture of dichloromethane and methanol (V:V=8:1) (10 mL×3). The organic phases were combined, washed successively with water and saturated sodium chloride solution, dried over anhydrous sodium sulfate, and filtered. The filtrate was concentrated under reduced pressure, and the resulting residue was purified by thin-layer chromatography with elution system A to obtain the title compound 14 (18 mg, yield 53%) as a white solid.

MS m/z (ESI): 520.5 [M+1]

$^1$H NMR (400 MHz, DMSO-$d_6$) δ 11.49 (brs, 1H), 8.09 (s, 1H), 7.35 (s, 1H), 6.30 (s, 1H), 5.87 (s, 1H), 4.31 (d, 2H), 3.82 (brd, 2H), 3.16-3.23 (m, 3H), 3.03 (q, 2H), 2.90-2.96

(m, 1H), 2.79 (q, 2H), 2.24 (s, 3H), 2.11 (s, 3H), 2.00 (brd, 2H), 1.67 (brs, 8H), 1.43-1.53 (m, 2H), 1.01 (t, 3H), 0.81 (t, 3H).
Example 15
N-((4,6-Dimethyl-2-oxo-1,2-dihydropyridin-3-yl)methyl)-6-(ethyl(tetrahydro-2H-pyran-4-yl)amino)-5-methyl-2-(1-methylpiperidin-4-yl)benzofuran-4-carboxamide
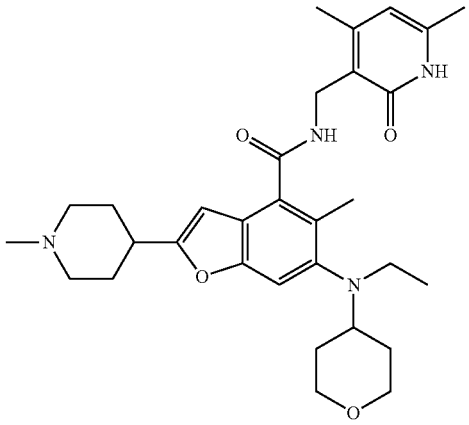
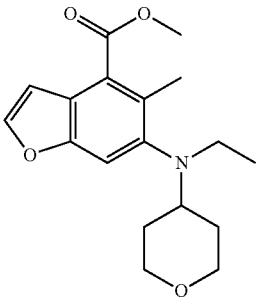
4g
step 1
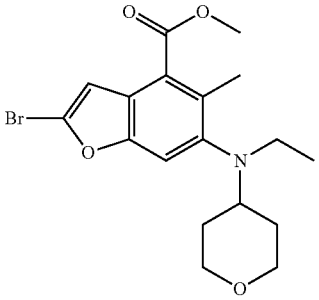
15a
step 2
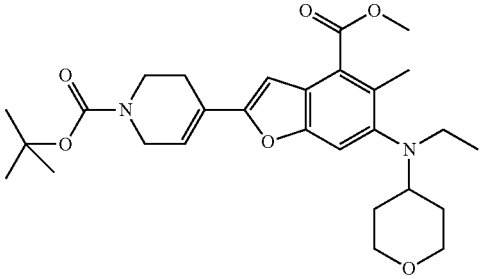
15b
step 3
-continued
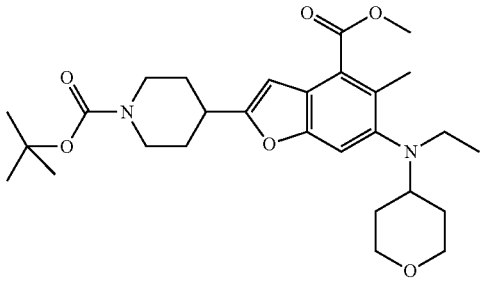
15c
step 4
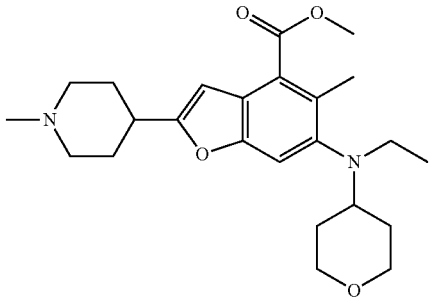
15d
step 5
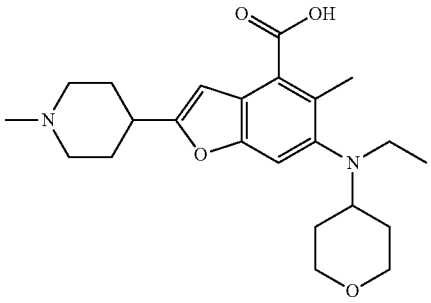
15e
+
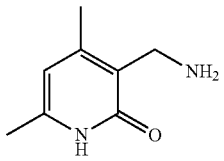
2a
HCl
step 6
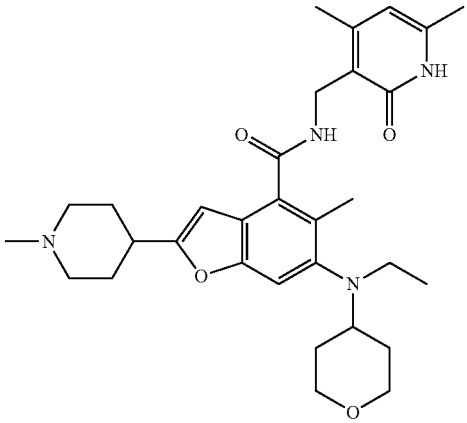
15

Step 1

Methyl 2-bromo-6-(ethyl(tetrahydro-2H-pyran-4-yl) amino)-5-methylbenzofuran-4-carboxylate 15a Compound 4g (330 mg, 1.04 mmol) was dissolved in 6 mL of tetrahydrofuran, then 0.63 mL of 2M lithium diisopropylamide was added dropwise at −70° C. under an argon atmosphere. At −70° C., the mixture was stirred for 1 hour, then 20 mL of a pre-prepared solution of 1,2-dibromotetrachloroethane (170 mg, 0.53 mmol) in tetrahydrofuran was added. The mixture was slowly warmed up and stirred for 1 hour. After the reaction was completed, 5 mL of saturated ammonium chloride solution was added to quench the reaction, and the mixture was extracted with ethyl acetate (10 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system B to obtain the title compound 15a (145 mg, yield 35%) as a yellow oil.

Step 2 tert-Butyl 4-(6-(ethyl(tetrahydro-2H-pyran-4-yl) amino)-4-(methoxycarbonyl)-5-methylbenzofuran-2-yl)-5,6-dihydropyridine-1 (2H)-carboxylate 15b Compound 15a (90 mg, 0.23 mmol), tert-butyl 4-(4,4,5,5-tetramethyl-1,3,2-dioxaborolan-2-yl)-5,6-dihydropyridine-1(2H)-carboxylate (105 mg, 0.34 mmol), tris(dibenzylideneacetone)dipalladium (21 mg, 0.023 mmol), 2-dicyclohexylphosphino-2',4',6'-triisopropylbiphenyl (22 mg, 0.045 mmol) and sodium carbonate (72 mg, 0.68 mmol) were dissolved in 5 mL of a mixture of 1,4-dioxane and water (V:V=4:1). The mixture was stirred for 12 hours at 90° C. under an argon atmosphere. After the reaction was completed, the mixture was filtered through a pad of celite, and two phases were separated. The organic phase was washed successively with water and saturated sodium chloride solution, dried over anhydrous sodium sulfate, and filtered. The filtrate was concentrated under reduced pressure, and the resulting residue was purified by thin-layer chromatography with elution system B to obtain the title compound 15b (100 mg, yield 88%) as a yellow solid.

Step 3 tert-Butyl 4-(6-(ethyl(tetrahydro-2H-pyran-4-yl) amino)-4-(methoxycarbonyl)-5-methylbenzofuran-2-yl)piperidine-1-carboxylate 15c Compound 15b (100 mg, 0.2 mmol) was dissolved in 6 mL of ethanol, and 30 mg of 10% Pd/C was added. The reaction system was purged three times with hydrogen and stirred for 0.5 hour. The reaction solution was filtered, the filtrate was concentrated under reduced pressure, and the resulting residue was purified by thin-layer chromatography with elution system B to obtain the title compound 15c (80 mg, yield 80%) as a yellow oil.

Step 4

Methyl 6-(ethyl(tetrahydro-2H-pyran-4-yl)amino)-5-methyl-2-(1-methylpiperidin-4-yl)benzofuran-4-carboxylate 15d Compound 15c (80 mg, 0.16 mmol) was dissolved in 10 mL of dichloromethane, then 1 mL of trifluoroacetic acid was added. After stirring for 1 hour, the mixture was concentrated under reduced pressure. Then, 5 mL of methanol and 5 mL of formaldehyde were added, and the mixture was stirred for 1 hour, then sodium triacetoxyborohydride (100 mg, 0.48 mmol) were added. After stirring for 3 hours, the reaction solution was concentrated under reduced pressure, neutralized with saturated sodium bicarbonate solution, and extracted with a mixture of dichloromethane and methanol (V:V=8:1). The organic phases were combined, washed with saturated sodium chloride solution, and dried over anhydrous sodium sulfate. The resulting residue was purified by thin-layer chromatography with elution system A to obtain the title compound 15d (60 mg, yield 90%) as a yellow oil.

Step 5

6-(Ethyl(tetrahydro-2H-pyran-4-yl)amino)-5-methyl-2-(1-methylpiperidin-4-yl)benzofuran-4-carboxylic acid Compound 15d (30 mg, 0.072 mmol) was dissolved in 5 mL of methanol and 2 mL of tetrahydrofuran, then 2 mL of 4M sodium hydroxide solution were added. The mixture was stirred for 12 hours at 60° C. 12 M hydrochloric acid was added to adjust the pH of the reaction solution to 4, and the mixture was concentrated under reduced pressure. The residue was dissolved in 10 mL of methanol, and filtered. The filtrate was concentrated under reduced pressure to obtain the crude title compound 15e (30 mg) as a white solid, which was directly used in the next step without further purification.

Step 6

N-((4,6-Dimethyl-2-oxo-1,2-dihydropyridin-3-yl) methyl)-6-(ethyl(tetrahydro-2H-pyran-4-yl)amino)-5-methyl-2-(1-methylpiperidin-4-yl)benzofuran-4-carboxamide 15

The crude 15e (25 mg, 0.06 mmol) was dissolved in 3 mL of N,N-dimethylformamide, then 1-ethyl-3-(3-dimethylaminopropyl)carbodiimide (18 mg, 0.094 mmol), 1-hydroxybenzotriazole (15 mg, 0.094 mmol) and N,N-diisopropylethylamine (40 mg, 0.31 mmol) were added. The mixture was stirred 1 hour, then compound 2a (18 mg, 0.094 mmol) was added. The mixture was stirred for 12 hours. After the reaction was completed, 20 mL of water were added, and the reaction solution was extracted with a mixture of dichloromethane and methanol. The organic phases were combined, washed successively with water and saturated sodium chloride solution, dried over anhydrous sodium sulfate, and filtered. The filtrate was concentrated under reduced pressure, and the resulting residue was purified by thin-layer chromatography with elution system A to obtain the title compound 15 (24 mg, yield 73%) as a white solid.

MS m/z (ESI): 535.5 [M+1]

$^1$H NMR (400 MHz, DMSO-$d_6$) δ 11.50 (brs, 1H), 8.10 (s, 1H), 7.34 (s, 1H), 6.29 (s, 1H), 5.87 (s, 1H), 4.31 (d, 2H), 3.81 (brd, 2H), 3.22 (t, 2H), 3.03 (q, 2H), 2.91-2.94 (m, 1H), 2.80 (brd, 2H), 2.67 (brs, 1H), 2.23 (s, 3H), 2.22 (s, 3H), 2.18 (s, 3H), 2.11 (s, 3H), 1.92-2.02 (m, 4H), 1.61-1.64 (m, 4H), 1.45-1.48 (m, 2H), 0.78 (t, 3H).

Example 16

N-((4,6-Dimethyl-2-oxo-1,2-dihydropyridin-3-yl)methyl)-6-(ethyl(tetrahydro-2H-pyran-4-yl)amino)-5-methyl-2-(1-methyl-1,2,3,6-tetrahydropyridin-4-yl)benzofuran-4-carboxamide 16

16

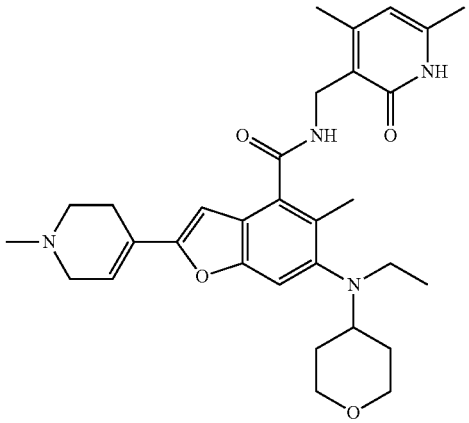

In accordance with the synthetic route of Example 12, the starting material 5a was replaced with compound 15b, and compound 1o was replaced with compound 2a, accordingly, the title compound 16 (18 mg, yield 62%) as a white solid was prepared.

MS m/z (ESI): 533.5 [M+1]

$^1$H NMR (400 MHz, DMSO-$d_6$) δ 11.51 (brs, 1H), 8.17 (t, 1H), 7.35 (s, 1H), 6.58 (s, 1H), 6.35 (s, 1H), 5.87 (s, 1H), 4.31 (d, 2H), 3.81 (brd, 2H), 3.19-3.25 (m, 3H), 3.02-3.07 (m, 3H), 2.90-2.97 (m, 1H), 2.43 (brs, 2H), 2.23 (s, 3H), 2.22 (s, 3H), 2.11 (s, 3H), 1.62-1.64 (m, 2H), 1.44-1.51 (m, 2H), 1.17 (t, 2H), 0.79 (t, 3H).

Example 17

5-Ethyl-6-(ethyl(tetrahydro-2H-pyran-4-yl)amino)-N-((4-methoxy-6-methyl-2-oxo-1,2-dihydropyridin-3-yl)methyl)-2-(1-methylpiperidin-4-yl)benzofuran-4-carboxamide 17

17

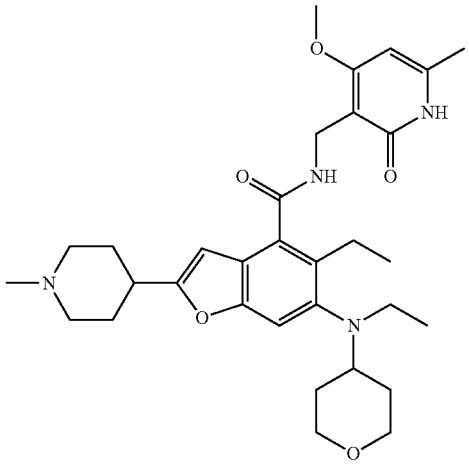

In accordance with the synthetic route of Example 12, the starting material 5a was replaced with compound 9c, accordingly, the title compound 17 (17 mg, yield 50%) as a white solid was prepared.

MS m/z (ESI): 565.2 [M+1]

$^1$H NMR (400 MHz, DMSO-$d_6$) δ 11.43 (brs, 1H), 7.94 (brs, 1H), 7.35 (s, 1H), 6.39 (brs, 1H), 6.10 (s, 1H), 4.27 (d, 2H), 3.83 (brs, 2H), 3.81 (s, 3H), 3.20 (t, 2H), 3.02 (q, 2H), 2.90-2.95 (m, 2H), 2.79 (q, 2H), 2.44 (brs, 4H), 2.18 (s, 3H), 2.07 (brs, 2H), 1.81 (brs, 2H), 1.62-1.64 (m, 2H), 1.43-1.52 (m, 2H), 1.03 (t, 3H), 0.80 (t, 3H).

Example 18

6-(Ethyl(tetrahydro-2H-pyran-4-yl)amino)-N-((4-methoxy-6-methyl-2-oxo-1,2-dihydro pyridin-3-yl)methyl)-5-methylbenzofuran-4-carboxamide 18

18

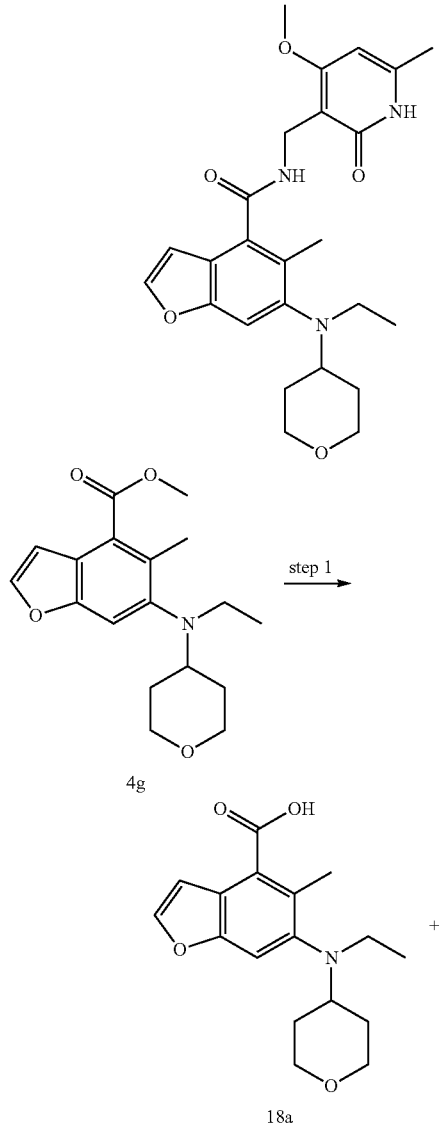

-continued

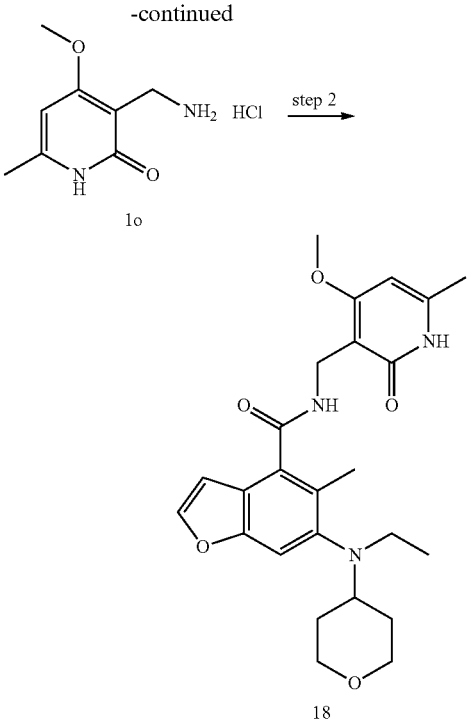

Step 1

6-(Ethyl(tetrahydro-2H-pyran-4-yl)amino)-5-methyl-benzofuran-4-carboxylic acid 18a Compound 4g (45 mg, 0.142 mmol) was dissolved in 4 m/of a mixture of methanol and water (V:V=1:1), then sodium hydroxide (60 mg, 1.58 mmol) was added. The mixture was stirred for 12 hours at 70° C. After the reaction was completed, the reaction solution was concentrated under reduced pressure to remove methanol. Then, 10% hydrochloric acid was added to adjust the pH to 3, and the mixture was extracted with ethyl acetate (10 mL×3). The organic phases were combined, washed with saturated sodium chloride solution (20 mL×1), and dried over anhydrous sodium sulfate. The filtrate was concentrated under reduced pressure, and the resulting residue was purified by thin-layer chromatography with elution system B to obtain the title compound 18a (40 mg, yield 93%) as a white solid.

Step 2

6-(Ethyl(tetrahydro-2H-pyran-4-yl)amino)-N-((4-methoxy-6-methyl-2-oxo-1,2-dihydro pyridin-3-yl) methyl)-5-methylbenzofuran-4-carboxamide 18

Compound 18a (15 mg, 0.049 mmol) was dissolved in 3 mL of N,N-dimethylformamide, then N,N-diisopropylethylamine (18.9 mg, 0.147 mmol) and 2-(7-azabenzotriazol-1-yl)-N,N,N',N'-tetramethyluronium hexafluorophosphate (27.9 mg, 0.0735 mmol) were added. The reaction system was stirred for 1 hour at 0° C. Compound 1o (12 mg, 0.0558 mmol) was added under a nitrogen atmosphere. The mixture was stirred for 12 hours at room temperature. After the reaction was completed, 30 mL of water was added, the mixture was extracted with ethyl acetate (10 mL×3). The organic phases were combined, washed with saturated sodium chloride solution (20 mL×1), dried over anhydrous sodium sulfate, and filtered. The filtrate was concentrated under reduced pressure, and the resulting residue was purified by thin-layer chromatography with elution system A to obtain the title compound 18 (4.4 mg, yield 20%) as a white solid.

MS m/z (ESI): 454.2 [M+1]

$^1$H NMR (400 MHz, $CDCl_3$) δ 10.90 (s, 1H), 7.43 (s, 1H), 7.27 (s, 1H), 6.76 (s, 1H), 6.61 (s, 1H), 5.85 (s, 1H), 4.52 (brs, 2H), 3.90-3.93 (brd, 2H), 3.82 (s, 3H), 3.28 (t, 2H), 3.02-3.07 (m, 2H), 2.91-2.95 (m, 1H), 2.29 (s, 3H), 1.83 (s, 3H), 1.56-1.68 (m, 4H), 0.83 (t, 3H).

Example 19

6-(Ethyl(tetrahydro-2H-pyran-4-yl)amino)-N-((4-methoxy-6-methyl-2-oxo-1,2-dihydro pyridin-3-yl) methyl)-2,5-dimethylbenzofuran-4-carboxamide 19

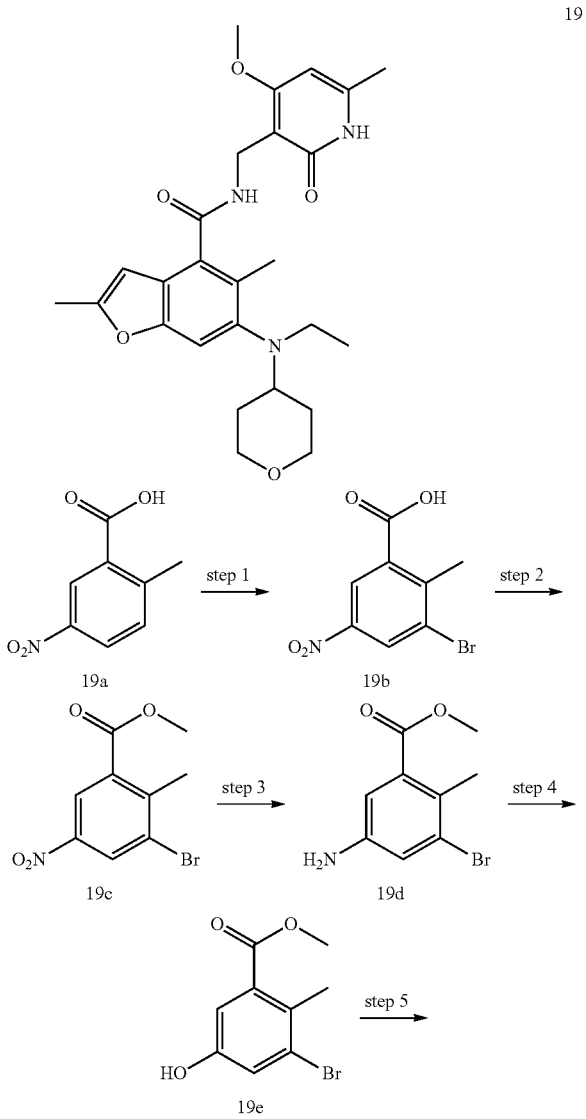

-continued

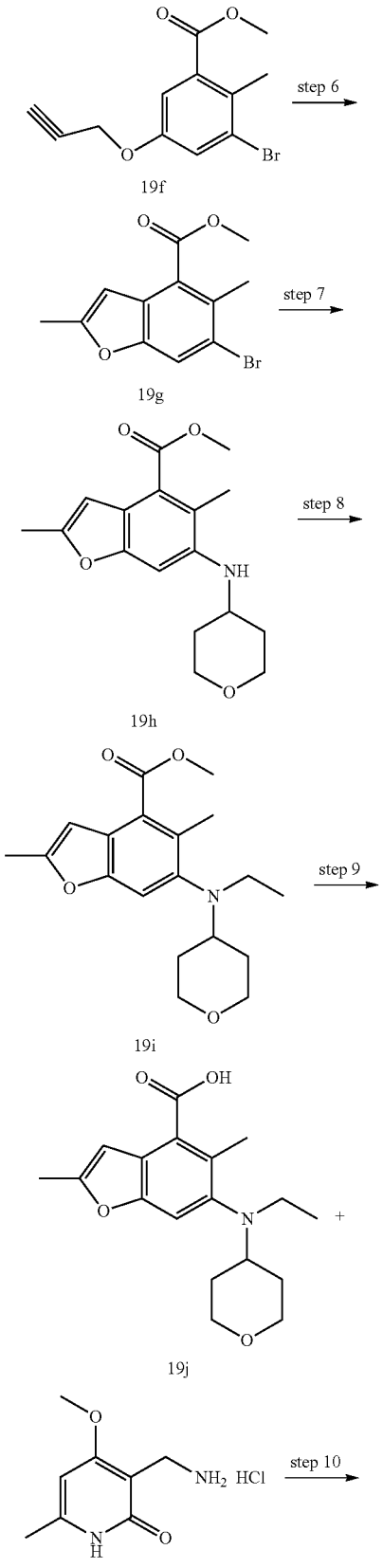

-continued

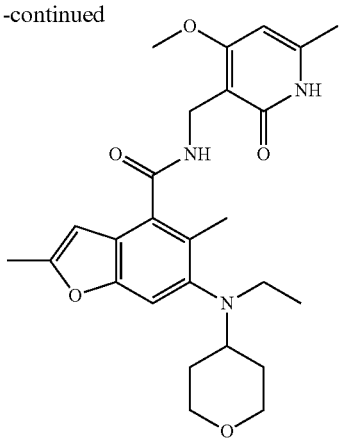

Step 1

3-Bromo-2-methyl-5-nitrobenzoic Acid 19b

2-Methyl-5-nitrobenzoic acid (30 g, 0.166 mol, Bide) was dissolved in 70 mL of concentrated sulfuric acid, then N-bromosuccinimide (35.4 g, 0.199 mol) was added in batches. The reaction system was stirred for 3 hours at 60° C. After the reaction was completed, the reaction solution of the title compound 19b was obtained, which was used directly in the next step without further treatment.

Step 2

Methyl 3-bromo-2-methyl-5-nitrobenzoate 19c

The above reaction solution of compound 19b was added with 100 mL of methanol and continuously stirred for 6 hours. After the reaction was completed, the reaction solution was poured into 1 L of water, and extracted with ethyl acetate (100 mL×3). The organic phases were combined, washed successively with water (100 mL) and saturated sodium chloride solution (200 mL), dried over anhydrous sodium sulfate, and filtered. The filtrate was concentrated under reduced pressure to obtain the crude title compound 19c (53 g) as a white solid, which was directly used in the next step without further purification.

Step 3

Methyl 5-amino-3-bromo-2-methylbenzoate 19d

The crude 19c (52 g, 0.189 mol) was dissolved in 200 mL of ethanol, then iron powder (31.7 g, 0.569 mol) was added, and 16 mL of 4 N hydrochloric acid were slowly added dropwise. The mixture was heated to 75° C. and stirred for 4 hours. After the reaction was completed, 200 mL of water were added, and the mixture was extracted with ethyl acetate (100 mL×3). The organic phases were combined, washed with saturated sodium chloride solution (200 mL), dried over anhydrous sodium sulfate, and filtered. The filtrate was concentrated under reduced pressure, and the resulting residue was purified by silica gel column chromatography with elution system B to obtain the title compound 19d (27 g, yield 59%) as a yellow solid.

Step 4

Methyl 3-bromo-5-hydroxy-2-methylbenzoate 19e

Compound 19d (5 g, 0.02 mol) was dissolved in 50 mL of 10% sulfuric acid, then 10 mL of a pre-prepared solution of sodium nitrite (1.55 g, 0.023 mol) were added at 0° C. The mixture was stirred for 1 hour, then 50 mL of 50% sulfuric acid were added. The mixture was heated to 100° C. and stirred for 1 hour. After the reaction was completed, the reaction solution was extracted with ethyl acetate (50 mL×3). The organic phases were combined, washed with saturated sodium chloride solution (100 mL), dried over anhydrous sodium sulfate, and filtered. The filtrate was concentrated under reduced pressure, and the resulting residue was purified by silica gel column chromatography with elution system B to obtain the title compound 19e (1.4 g, yield 29%) as a yellow solid.

Step 5

Methyl 3-bromo-2-methyl-5-(prop-2-yn-1-yloxy) benzoate 19f

Compound 19e (0.5 g, 2.04 mmol) was dissolved in 20 mL of acetone, then 3-bromopropyne (0.73 g, 6.12 mmol) and potassium carbonate (0.85 g, 6.12 mmol) were added. The reaction system was stirred at 80° C. for 12 hours. After the reaction was completed, the reaction solution was concentrated under reduced pressure, then 20 mL of water were added, and the mixture was extracted with ethyl acetate (10 mL×3). The organic phases were combined, washed with saturated sodium chloride solution (20 mL), dried over anhydrous sodium sulfate, and filtered. The filtrate was concentrated under reduced pressure, and the resulting residue was purified by silica gel column chromatography with elution system B to obtain the title compound 19f (0.5 g, yield 86.7%) as a yellow liquid.

Step 6

Methyl 6-bromo-2,5-dimethylbenzofuran-4-carboxylate 19g

Compound 19f (0.5 g, 1.76 mmol) and cesium fluoride (0.79 g, 5.28 mmol) were added to 5 mL of N,N-diethylaniline. The mixture was stirred for 2 hours at 200° C. in a microwave. After the reaction was completed, 20 mL of water was added, and the mixture was extracted with ethyl acetate (20 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system B to obtain the title compound 19g (0.2 g, yield 40%) as a yellow liquid.

Step 7

Methyl 2,5-dimethyl-6-((tetrahydro-2H-pyran-4-yl) amino)benzofuran-4-carboxylate 19h Compound 19h (0.2 g, 0.70 mmol), tetrahydro-2H-pyran-4-amine (14 mg, 0.14 mmol), tris(dibenzylideneacetone) dipalladium (64 mg, 0.07 mmol), (±)-2,2'-bis(diphenylphosphino)-1,1'-binaphthalene (87.15 mg, 0.14 mmol) and cesium carbonate (455 mg, 1.4 mmol) were dissolved in 5 mL of toluene. The mixture was stirred for 12 hours at 110° C. under a nitrogen atmosphere. After the reaction was completed, 10 mL of water were added, and the mixture was extracted with ethyl acetate (10 mL×3). The organic phases were combined, dried over anhydrous sodium sulfate, and filtered. The filtrate was concentrated under reduced pressure, and the resulting residue was purified by thin-layer chromatography with elution system B to obtain the title compound 19h (140 g, yield 67%) as a yellow solid.

Step 8

Methyl 6-(ethyl(tetrahydro-2H-pyran-4-yl)amino)-2, 5-dimethylbenzofuran-4-carboxylate 19i Compound 19h (90.0 g, 0.297 mmol), acetaldehyde (39.2 mg, 0.89 mmol) and acetic acid (89.1 mg, 1.48 mmol) were dissolved in 8 mL of methanol. The mixture was stirred for 1 hour at 0° C. and another 4 hours at room temperature under a nitrogen atmosphere, then sodium cyanoborohydride (55.9 mg, 0.891 mmol) was added. The mixture was stirred for 12 hours. After the reaction was completed, the reaction solution was concentrated under reduced pressure, 20 mL of water were added, and the mixture was extracted with ethyl acetate (10 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system B to obtain the title compound 19i (60 mg, yield 61%) as a colorless liquid.

Step 9

6-(Ethyl(tetrahydro-2H-pyran-4-yl)amino)-2,5-dimethylbenzofuran-4-carboxylic acid 19j Compound 19i (60 mg, 0.18 mmol) and potassium hydroxide (50.6 mg, 0.90 mmol) were added to 4 mL of a mixture of methanol and water (V:V=1:1). The mixture was stirred for 16 hours at 75° C. After the reaction was completed, the mixture was cooled, and 2N hydrochloric acid was added to adjust the pH of the reaction solution to 3-4. The mixture was extracted with a mixture of dichloromethane and methanol (V:V=10:1) (10 mL×3). The organic phases were combined, washed with saturated sodium chloride solution (20 mL), dried over anhydrous sodium sulfate, and filtered. The filtrate was concentrated under reduced pressure to obtain the crude title compound 19j (30 mg) as a yellow solid, which was used directly in the next step without further purification.

Step 10

6-(Ethyl(tetrahydro-2H-pyran-4-yl)amino)-N-((4-methoxy-6-methyl-2-oxo-1,2-dihydro pyridin-3-yl) methyl)-2,5-dimethylbenzofuran-4-carboxamide 19

The crude 19j (15 mg, 0.047 mmol) was dissolved in 2 mL of N,N-dimethylformamide, then N,N-diisopropylethylamine (18.3 mg, 0.14 mmol) and 2-(7-azabenzotriazol-1-yl)-N,N,N',N'-tetramethyluronium hexafluorophosphate (47.7 mg, 0.125 mmol) were added. The mixture was stirred 1 hour at 0° C., then compound 1o (11.58 mg, 0.057 mmol) was added. The mixture was stirred for 12 hours at room temperature. After the reaction was completed, 50 mL of water were added, then the mixture was extracted with a mixture of dichloromethane and methanol (V:V=10:1) (10 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system A to obtain the title compound 19 (20 mg, yield 91%) as a white solid.

MS m/z (ESI): 468.2 [M+1]

$^1$H NMR (400 MHz, $CDCl_3$) δ 11.57 (s, 1H), 7.19 (s, 1H), 6.38 (s, 1H), 5.93 (s, 1H), 5.36 (s, 1H), 4.64 (d, 2H), 3.95 (brs, 2H), 3.91 (s, 3H), 3.28-3.33 (m, 2H), 3.03-3.05 (m, 2H), 2.92-2.96 (m, 1H), 2.37 (s, 3H), 2.34 (s, 3H), 2.19 (s, 3H), 1.69 (brs, 2H), 1.25 (brs, 2H), 0.85 (t, 3H).

Example 20

6-(Ethyl(tetrahydro-2H-pyran-4-yl)amino)-N-((4-methoxy-6-methyl-2-oxo-1,2-dihydro pyridin-3-yl) methyl)-3,5-dimethylbenzofuran-4-carboxamide 20

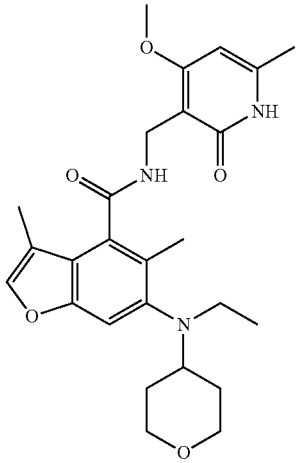

In accordance with the synthetic route of Example 19, the starting material 3-bromopropyne used in step 5 was replaced with 1-bromopropan-2-one, accordingly, the title compound 20 (17 mg, yield 11%) as a white solid was prepared.

MS m/z (ESI): 468.3 [M+1]

$^1$H NMR (400 MHz, $CDCl_3$) δ 11.22 (s, 1H), 7.27 (s, 1H), 7.21 (s, 1H), 6.94 (s, 1H), 5.94 (s, 1H), 4.61-4.62 (brd, 2H), 3.92-3.95 (brd, 2H), 3.89 (s, 3H), 3.29 (dt, 2H), 3.16-3.20 (m, 3H), 2.29 (s, 3H), 2.22 (s, 3H), 2.11 (s, 3H), 1.65 (brs, 2H), 1.31 (brs, 2H), 0.86 (t, 3H).

Example 21

6-(Ethyl(tetrahydro-2H-pyran-4-yl)amino)-N-((4-methoxy-6-methyl-2-oxo-1,2-dihydro pyridin-3-yl) methyl)-5-(trifluoromethyl)benzofuran-4-carboxamide

21

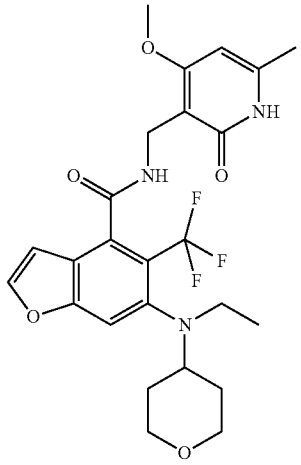

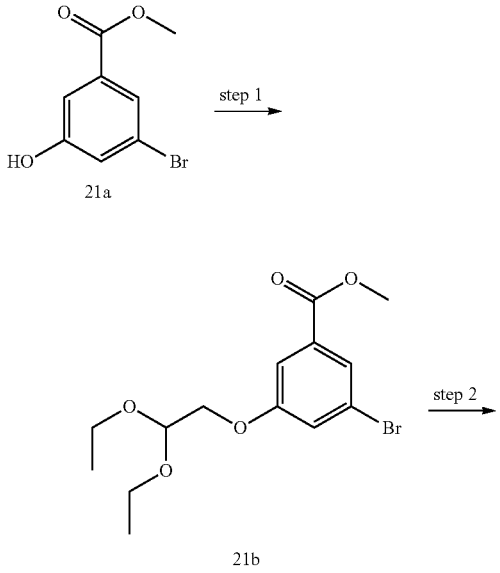

-continued

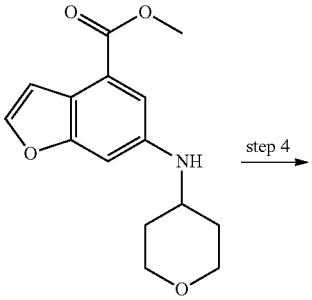

21d

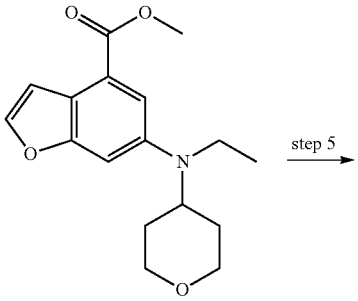

21e

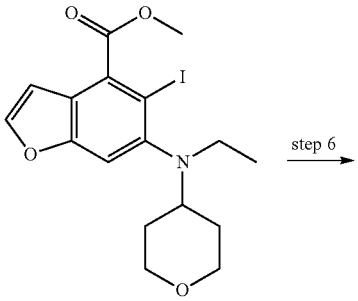

21f

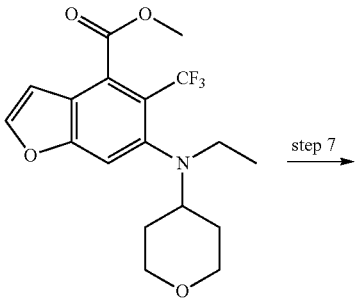

21g

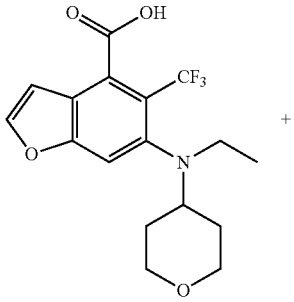

21h

-continued

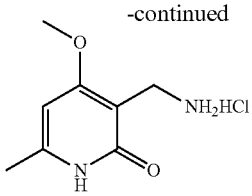

1o

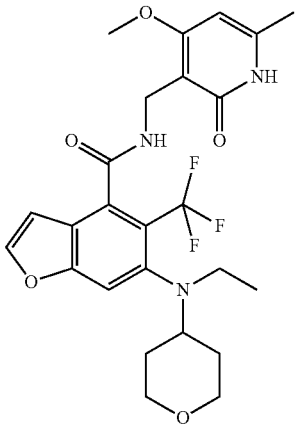

21

Step 1

Methyl 3-bromo-5-(2,2-diethoxyethoxy)benzoate 21b

Methyl 3-bromo-5-hydroxybenzoate 21a (1.9 g, 8.23 mmol, prepared by a method disclosed in "Journal of Medicinal Chemistry, 2013, 56(8), 3217-3227") was dissolved in 60 mL of N,N-dimethylformamide, then 2-bromo-1,1-diethoxyethane (3.23 g, 16.4 mmol) and cesium carbonate (5.35 g, 16.4 mmol) were added. The reaction system was stirred for 4 hours at 95° C. After the reaction was completed, the reaction solution was poured into ice water, extracted with ethyl acetate (50 mL×3), dried over anhydrous sodium sulfate, and filtered. The filtrate was concentrated under reduced pressure to obtain the crude title compound 21b (3.5 g) as a yellow oil, which was used directly in the next step without further purification.

Step 2

Methyl 6-bromobenzofuran-4-carboxylate 21c

Polyphosphoric acid (5.46 g, 16.4 mmol) was added to 20 mL of toluene. The mixture was heated to 115° C., then 40 mL of a pre-prepared solution of 21b (3.5 g, 10 mmol) in toluene were added with stirring. The mixture was stirred for 5 hours. After the reaction was completed, the mixture was poured into ice water, neutralized with saturated sodium bicarbonate solution, extracted with ethyl acetate (20 mL×3), dried over anhydrous sodium sulfate, and filtered. The filtrate was concentrated under reduced pressure, and the resulting residue was purified by silica gel column chromatography with elution system B to obtain the title compound 21c (1.08 g, yield 52%) as a yellow solid.

Step 3

Methyl 6-((tetrahydro-2H-pyran-4-yl)amino)benzofuran-4-carboxylate 21d

Compound 21c (1.08 g, 4.25 mmol), tetrahydro-2H-pyran-4-amine (0.644 g, 6.38 mmol), tris(dibenzylideneacetone)dipalladium (393 mg, 0.43 mmol), (±)-2, 2'-bis-bis (diphenylphosphino)-1,1'-binaphthalene (267 mg, 0.43 mmol) and cesium carbonate (2.6 g, 8.5 mmol) were dissolved in 60 mL of toluene. The mixture was stirred for 36 hours under a nitrogen atmosphere. After the reaction was completed, the reaction solution was poured into ice water, extracted with ethyl acetate (30 mL×3), dried over anhydrous sodium sulfate, and filtered. The filtrate was concentrated under reduced pressure, and the resulting residue was purified by silica gel column chromatography with elution system B to obtain the title compound 21d (200 mg, yield 17%) as a yellow solid.

Step 4

Methyl 6-(ethyl(tetrahydro-2H-pyran-4-yl)amino) benzofuran-4-carboxylate 21e

Compound 21d (200 mg, 0.727 mmol), acetaldehyde (160 mg, 3.64 mmol) and 0.2 mL of acetic acid were dissolved in 4 mL of methanol. After stirring for 24 hours, the mixture was cooled down to below 0° C. Sodium cyanoborohydride (227 mg, 3.6 mmol) was added, and the mixture was naturally warmed up to room temperature. The reaction was monitored by TLC until most of the starting materials disappeared. After the reaction was completed, the reaction solution was cooled down to 0° C., and 20 mL of saturated sodium bicarbonate solution were added to quench the reaction. The mixture was extracted with ethyl acetate (10 mL×3), dried over anhydrous sodium sulfate, and filtered. The filtrate was concentrated under reduced pressure, and the resulting residue was purified by silica gel column chromatography with elution system B to obtain the title compound 21e (140 mg, yield 64%) as a yellow-green solid.

Step 5

Methyl 6-(ethyl(tetrahydro-2H-pyran-4-yl)amino)-5-iodobenzofuran-4-carboxylate 21f Compound 21e (13 mg, 0.043 mmol) was dissolved in 2 mL of N,N-dimethylformamide, then 5 drops of trifluoroacetic acid were added, and N-iodosuccinimide (12 mg, 0.052 mL) was added at 0° C. The mixture was naturally warmed up to room temperature. The reaction was monitored by TLC until most of the starting materials disappeared. After the reaction was completed, the reaction solution was cooled down to 0° C., neutralized by saturated sodium carbonate solution, and extracted with ethyl acetate. The organic phases were combined, dried over anhydrous sodium sulfate, and filtered. The filtrate was concentrated under reduced pressure, and the resulting residue was purified by thin-layer chromatography with elution system B to obtain the title compound 21f (16 mg, yield 86%) as a yellow oil.

Step 6

Methyl 6-(ethyl(tetrahydro-2H-pyran-4-yl)amino)-5-(trifluoromethyl)benzofuran-4-carboxylate 21g Compound 21f (16 mg, 0.0373 mmol), cuprous iodide (36 mg, 0.187 mmol) and methyl fluorosulfonyl difluoroacetate (140 mg, 0.75 mmol) were dissolved in 2 mL of N,N-dimethylformamide. The mixture was stirred for 12 hours at 80° C. under a nitrogen atmosphere. After the reaction was completed, the mixture was concentrated under reduced pressure. The resulting residue was purified by thin-layer chromatography with elution system B to obtain the title compound 21g (10 mg, yield 72%) as a yellow-green solid.

Step 7

6-(Ethyl(tetrahydro-2H-pyran-4-yl)amino)-5-(trifluoromethyl)benzofuran-4-carboxylic acid 21h Compound 21g (10 mg, 0.027 mmol) was dissolved in 4 mL of a mixture of methanol and tetrahydrofuran (V:V=1:1), then 0.27 mL of 2N sodium hydroxide solution was added. The mixture was stirred for 4 hours at 60° C. After the reaction was completed, the mixture was concentration under reduced pressure to remove most of the solvent. Then, 2 mL of tetrahydrofuran were added to the residue at 0° C., and 1N hydrochloric acid was added to adjust the pH to 3-4. The mixture was concentrated under reduced pressure to obtain the crude title compound 21h (9 mg) as a yellow solid, which was directly used in the next step without further purification.

Step 8

6-(Ethyl(tetrahydro-2H-pyran-4-yl)amino)-N-((4-methoxy-6-methyl-2-oxo-1,2-dihydro pyridin-3-yl) methyl)-5-(trifluoromethyl)benzofuran-4-carboxamide 21

The crude 21h (9 mg, 0.025 mmol) was dissolved in 3 mL of N,N-dimethylformamide, then 2-(7-azabenzotriazol-1-yl)-N,N,N',N'-tetramethyluronium hexafluorophosphate (14 mg, 0.041 mmol) and N,N-diisopropylethylamine (17 mg, 0.135 mmol) were added. The mixture was stirred for 20 minutes, then compound 1o (8.3 mg, 0.041 mmol) was added to the the reaction solution. The mixture was stirred for 5 hours. After the reaction was completed, 20 mL of saturated sodium chloride solution were added, and the mixture was extracted with ethyl acetate (10 mL×3). The organic phases were combined, dried over anhydrous sodium sulfate, and filtered. The filtrate was concentrated under reduced pressure, and the resulting residue was purified by thin-layer chromatography with elution system A to obtain the title compound 21 (10 mg, yield 78%) as a white solid.

MS (ESI) m/z: 508.3 [M+1]

$^1$H NMR (400 MHz, $CDCl_3$) δ 7.98 (brs, 1H), 7.53 (m, 1H), 7.32 (m, 1H), 6.92 (s, 1H), 5.96 (s, 1H), 4.65 (d, 2H), 4.09-4.05 (m, 2H), 3.92 (s, 3H), 3.89-3.85 (m, 1H), 3.55-3.50 (m, 2H), 3.37 (q, 2H), 2.27 (s, 3H), 1.85-1.79 (m, 4H), 1.20 (t, 3H).

Example 22
5-Chloro-6-(ethyl(tetrahydro-2H-pyran-4-yl)amino)-N-((4-methoxy-6-methyl-2-oxo-1,2-dihydropyridin-3-yl)methyl)benzofuran-4-carboxamide
22
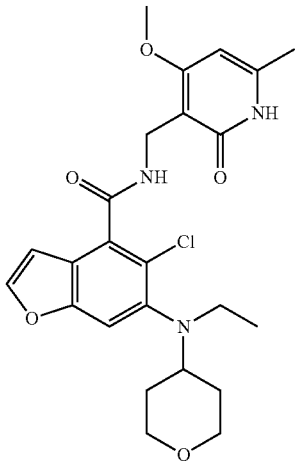
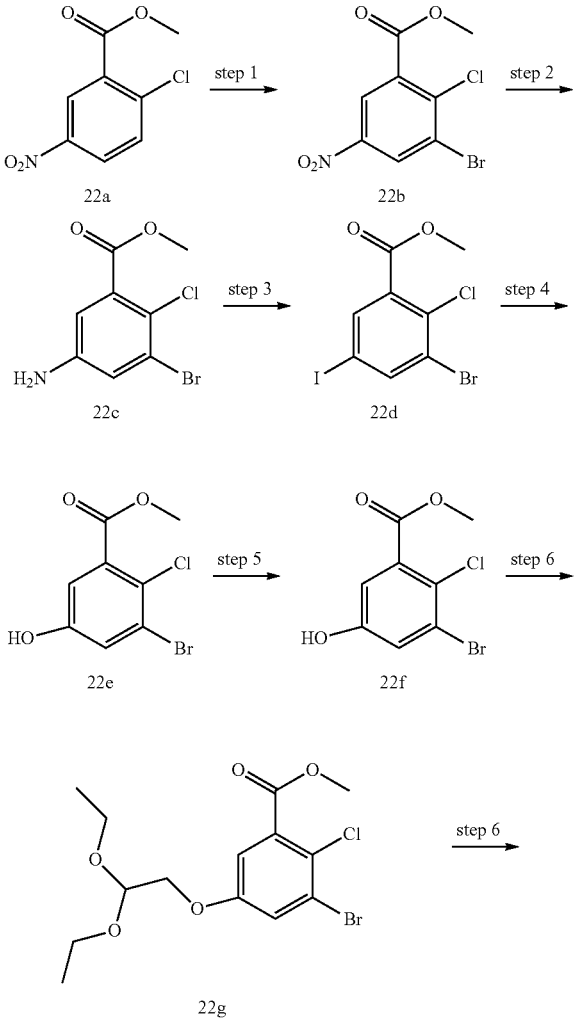
22a 22b 22c 22d 22e 22f 22g
-continued
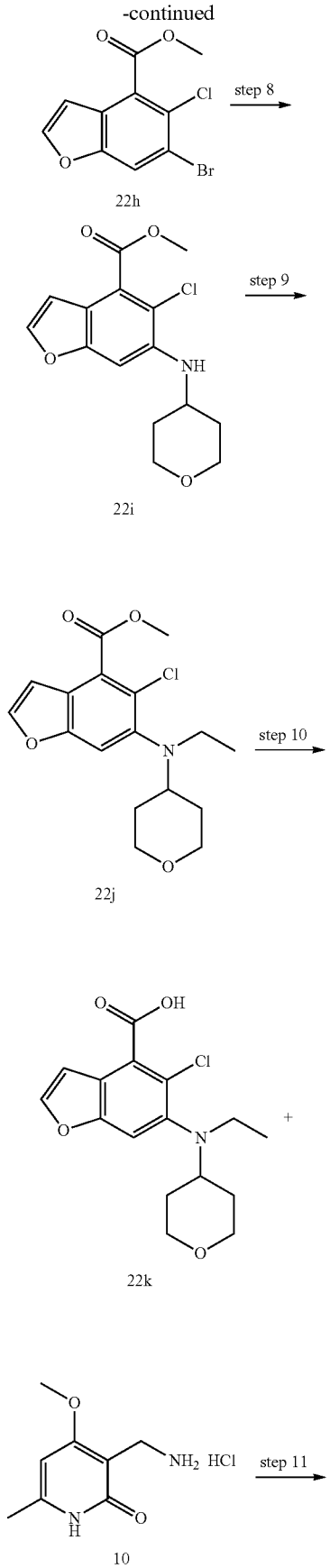
22h 22i 22j 22k 10

-continued

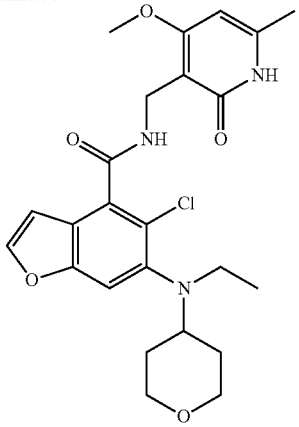

22

Step 1

Methyl 3-bromo-2-chloro-5-nitrobenzoate 22b

Methyl 2-chloro-5-nitrobenzoate (6.0 g, 27.8 mmol) was dissolved in 30 mL of concentrated sulfuric acid, then N-bromosuccinimide (5.2 g, 29.2 mmol) was added to the above reaction solution. The reaction system was stirred for 1 hour at 60° C. After the reaction was completed, the reaction system was poured into 300 mL of ice water and extracted with ethyl acetate (50 mL×3). The organic phases were combined, washed with saturated sodium bicarbonate solution (100 mL) and saturated sodium chloride solution (100 mL), dried over anhydrous sodium sulfate, and filtered. The filtrate was concentrated under reduced pressure to obtain the crude title compound 22b (7.58 g) as a light green solid, which was used directly in the next reaction without purification.

Step 2

Methyl 5-amino-3-bromo-2-chlorobenzoate 22c

The crude 22b (7.5 g, 25 mmol) was dissolved in 55 mL of a mixture of ethanol and water (V:V=8:3), and ammonium chloride (11.2 g, 203 mmol) was added. The reaction system was heated to 70° C., added with iron powder (7.1 g, 127 mmol), and stirred for 2 hours. After the reaction was completed, the mixture was filtered through a pad of celite. The filtrate was concentrated under reduced pressure, neutralized with saturated sodium bicarbonate, and extracted with ethyl acetate (50 mL×3). The organic phases were combined, washed with saturated sodium chloride solution (100 mL), dried over anhydrous sodium sulfate, and filtered. The filtrate was concentrated under reduced pressure to obtain the crude title compound 22c (5.0 g) as a yellow solid, which was used directly in the next step without further purification.

Step 3

Methyl 3-bromo-2-chloro-5-iodobenzoate 22d

The crude 22c (7.0 g, 26.5 mmol) was dissolved in 50 mL of 40% sulfuric acid and 10 mL of N,N-dimethylformamide. The mixture was cooled down to 0° C., and 5 mL of a pre-prepared solution of sodium nitrite (2.0 g, 29.1 mmol) was added dropwise. The mixture was stirred for 1 hour, then 50 mL of a pre-prepared solution of potassium iodide (22 g, 132 mmol) was added to the above reaction solution. The mixture was heated to 70° C. and stirred for 30 minutes. After the reaction was completed, the mixture was extracted with ethyl acetate (50 mL×3). The organic phases were combined, washed with water (100 mL) and saturated sodium chloride solution (100 mL), dried over anhydrous sodium sulfate, and filtered. The filtrate was concentrated under reduced pressure, and the resulting residue was purified by silica gel column chromatography with eluent system B to obtain the title compound 22d (8.0 g, yield 80%) as a light yellow solid.

Step 4

3-Bromo-2-chloro-5-hydroxybenzoic acid 22e

Compound 22d (7.0 g, 18.7 mmol) was dissolved in 10 mL of tetrahydrofuran, then 70 mL of 4N sodium hydroxide solution was added. The mixture was stirred for 2 hours at 60° C., then concentrated under reduced pressure to remove organic solvents, and cuprous oxide (7.7 g, 53.5 mmol) was added. The mixture was stirred for 1 hour at 120° C. in a microwave. After the reaction was completed, the mixture was filtered. The filtrate was neutralized with 12M hydrochloric acid, and extracted with ethyl acetate (100 mL×3). The organic phases were combined, washed with saturated sodium chloride solution (100 mL), dried over anhydrous sodium sulfate, and filtered. The filtrate was concentrated under reduced pressure to obtain the crude title compound 22e (6.0 g) as a brown oil, which was directly used in the next step without further purification.

Step 5

Methyl 3-bromo-2-chloro-5-hydroxybenzoate 22f

The crude 22e (6.0 g, 24 mmol) was dissolved in 30 mL of methanol, then 2 mL of concentrated sulfuric acid were added dropwise to the reaction solution. The reaction system was stirred for 12 hours at 60° C. After the reaction was completed, the mixture was concentrated under reduced pressure, and dissolved in 50 mL of ethyl acetate. Then, 100 mL of water were added, and the mixture was extracted with ethyl acetate (50 mL×3). The organic phases were combined, washed successively with water (100 mL) and saturated sodium chloride solution (100 mL), dried over anhydrous sodium sulfate, and filtered. The filtrate was concentrated under reduced pressure, and the resulting residue was purified by silica gel column chromatography with eluent system B to obtain the title compound 22f (3.3 g, yield 52%) as a white solid.

Step 6

Methyl 3-bromo-2-chloro-5-(2,2-diethoxyethoxy)benzoate 22g

Compound 22f (3.3 g, 12.5 mmol) was dissolved in 30 mL of N,N-dimethylformamide, then 2-bromo-1,1-diethoxyethane (2.96 g, 15 mmol) and potassium carbonate (3.4 g, 25 mmol) were added. The mixture was stirred for 3 hours at 120° C. After the reaction was completed, 150 mL of water were added, and the mixture was extracted with ethyl acetate (50 mL×3). The organic phases were combined, washed successively with water (100 mL) and saturated sodium chloride solution (100 mL), dried over anhydrous sodium sulfate, and filtered. The filtrate was concentrated under reduced pressure, and the resulting residue was purified by silica gel column chromatography with eluent system B to obtain the title compound 22 g (3.5 g, yield 74%) as a colorless oil.

Step 7

Methyl 6-bromo-5-chlorobenzofuran-4-carboxylate 22h

Polyphosphoric acid (1.0 g) was added to 15 mL of toluene. The mixture was heated to 100° C., and 10 mL of a pre-prepared solution of compound 22g (780 mg, 2.1 mmol) in toluene was added with stirring. The mixture was stirred for 4 hours. After the reaction was completed, the supernatant was separated, and the residue was added with water and extracted with ethyl acetate (20 mL×3). Ethyl acetate phase and the supernatant were combined, washed successively with saturated sodium bicarbonate solution (30 mL) and saturated sodium chloride solution (100 mL), dried over anhydrous sodium sulfate, and filtered. The filtrate was concentrated under reduced pressure, and the resulting residue was purified by thin-layer chromatography with elution system B to obtain the title compound 22h (150 g, yield 25%) as a light yellow solid.

Step 8

Methyl 5-chloro-6-((tetrahydro-2H-pyran-4-yl) amino)benzofuran-4-carboxylate 22i Compound 22h (120 mg, 0.41 mmol), tetrahydro-2H-pyran-4-amine (60 mg, 0.6 mmol), tris(dibenzylideneacetone)dipalladium (38 g, 0.04 mmol), (±)-2,2'-bis(diphenylphosphino)-1,1'-binaphthalene (26 mg, 0.04 mmol) and cesium carbonate (405 mg, 1.24 mmol) were dissolved in 2 mL of toluene. The reaction system was stirred for 16 hours at 80° C. under an argon atmosphere. After the reaction was completed, the mixture was filtered through a pad of celite. The filtrate was concentrated under reduced pressure, and the resulting residue was purified by thin-layer chromatography with elution system B to obtain the title compound 22i (125 mg, yield 87%) as a yellow solid.

Step 9

Methyl 5-chloro-6-(ethyl(tetrahydro-2H-pyran-4-yl) amino)benzofuran-4-carboxylate 22j Compound 22i (50 mg, 0.16 mmol), acetaldehyde (36 mg, 0.81 mmol) and acetic acid (49 mg, 0.81 mmol) were added to 5 mL of 1,2-dichloroethane. The mixture was stirred for 2 hours, then sodium triacetoxyborohydride (102 mg, 0.48 mmol) was added. The mixture was stirred for 12 hours. After the reaction was completed, the reaction solution was concentrated under reduced pressure, neutralized with saturated sodium bicarbonate solution, and extracted with ethyl acetate (10 mL×3). The organic phases were combined, washed successively with water (50 mL) and saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 22j (26 mg, yield 50%) as a yellow solid.

Step 10

5-Chloro-6-(ethyl(tetrahydro-2H-pyran-4-yl)amino) benzofuran-4-carboxylic acid 22k Compound 22j (51 mg, 0.16 mmol) was dissolved in 3 mL of a mixture of tetrahydrofuran and methanol (V:V=1:2), then 3 mL of 2N sodium hydroxide solution were added. The mixture was stirred for 1 hour at 60° C. After the reaction was completed, the mixture was concentrated under reduced pressure to remove organic solvents, 12 M hydrochloric acid was added to adjust the pH of the reaction solution to 5, and the mixture was extracted with ethyl acetate (10 mL×3). The organic phases were combined, washed with saturated sodium chloride solution (50 mL), dried over anhydrous sodium sulfate, and filtered. The filtrate was concentrated under reduced pressure to obtain the crude title compound 22k (42 mg) as a red-brown oil, which was used directly in the next step without further purification.

Step 11

5-Chloro-6-(ethyl(tetrahydro-2H-pyran-4-yl)amino)-N-((4-methoxy-6-methyl-2-oxo-1,2-dihydropyridin-3-yl)methyl)benzofuran-4-carboxamide 22

The crude 22k (8 mg, 0.025 mmol) was dissolved in 1 mL of N,N-dimethylformamide, then 2-(7-azabenzotriazol-1-yl)-N,N,N',N'-tetramethyluronium hexafluorophosphate (14 mg, 0.037 mmol), N,N-diisopropylethylamine (16 mg, 0.12 mmol) and compound 1o (7 mg, 0.032 mmol) were added to the above solution. The mixture was stirred for 12 hours. After the reaction was completed, 10 mL of water were added, and the reaction solution was extracted with a mixture of dichloromethane and methanol (V:V=8:1) (10 mL×3). The organic phases were combined, washed with water (50 mL) and saturated sodium chloride (50 mL), dried over anhydrous sodium sulfate, and filtered. The filtrate was concentrated under reduced pressure, and the resulting residue was purified by thin-layer chromatography with elution system A to obtain the title compound 22 (8 mg, yield 70%) as a white solid.

MS (ESI) m/z: 474.3 [M+1]

$^1$H NMR (400 MHz, DMSO-$d_6$) δ 11.46 (brs, 1H), 8.17 (s, 1H), 7.97 (s, 1H), 7.56 (s, 1H), 6.78 (s, 1H), 6.10 (s, 1H), 4.27 (d, 2H), 3.85 (brs, 2H), 3.82 (s, 3H), 3.23 (t, 2H), 3.11-3.15 (m, 3H), 2.18 (s, 3H), 1.66-1.69 (m, 2H), 1.50-1.57 (m, 2H), 0.83 (t, 3H).

Example 23

N-((4-Methoxy-6-methyl-2-oxo-1,2-dihydropyridin-3-yl)methyl)-5-methyl-6-(methyl(tetrahydro-2H-pyran-4-yl)amino)benzofuran-4-carboxamide

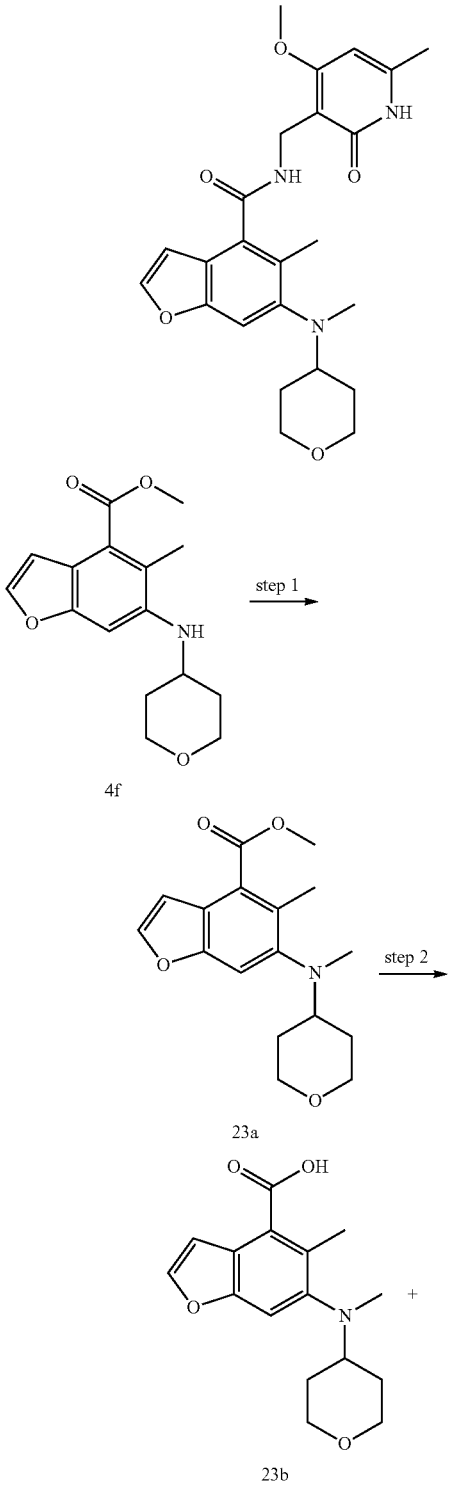

-continued

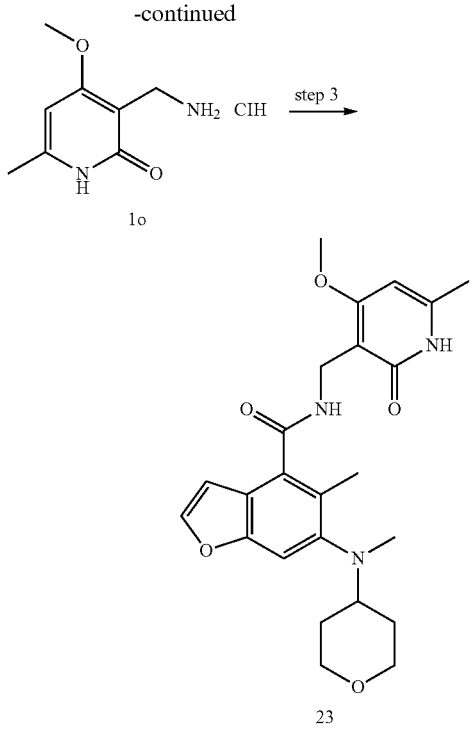

Step 1

Methyl 5-methyl-6-(methyl(tetrahydro-2H-pyran-4-yl)amino)benzofuran-4-carboxylate 23a Compound 4f (60 mg, 0.208 mmol) was dissolved in 5 mL of methanol, then formaldehyde (18.7 mg, 0.623 mmol) and acetic acid (62.4 mg, 1.04 mmol) were added. The mixture was stirred for 1 hour at 0° C., then warmed up to room temperature. The mixture was stirred 12 hours, then sodium cyanoborohydride (39.2 mg, 0.624 mmol) was added to the above solution. The reaction was stirred for 6 hours. After the reaction was completed, the reaction solution was concentrated under reduced pressure, then 20 mL of water were added, and extracted with ethyl acetate (10 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 23a (50 mg, yield 75%) as a colorless liquid.

Step 2

5-Methyl-6-(methyl(tetrahydro-2H-pyran-4-yl)amino)benzofuran-4-carboxylic acid 23b Compound 23a (50 mg, 0.165 mmol) was dissolved in 2 mL mixture of methanol and water (V:V=1:1), then sodium hydroxide (33 mg, 0.825 mmol) was added. The reaction system was stirred for 16 hours at 75° C. After the reaction was completed, the mixture was cooled down to room temperature. 2N hydrochloric acid was added to adjust the pH of the reaction solution to 3-4, and the mixture was extracted with ethyl acetate (10 mL×3). The organic phases were combined, washed with saturated sodium chloride solution (30 mL), dried over anhydrous sodium sulfate, and filtered. The resulting residue was purified by thin-layer chromatography with elution system B to obtain the title compound 23b (20 mg, yield 48%) as a colorless liquid.

Step 3

N-((4-Methoxy-6-methyl-2-oxo-1,2-dihydropyridin-3-yl)methyl)-5-methyl-6-(methyl(tetrahydro-2H-pyran-4-yl)amino)benzofuran-4-carboxamide 23

23b (15 mg, 0.052 mmol) was dissolved in 2 mL of N,N-dimethylformamide, then 2-(7-azabenzotriazol-1-yl)-N,N,N',N'-tetramethyluronium hexafluorophosphate (47.7 mg, 0.125 mmol) and N,N-diisopropylethylamine (18.3 mg, 0.14 mmol) were added. The mixture was stirred 1 hour at 0° C., then compound 1o (11.58 mg, 0.057 mmol) was added. The mixture was stirred for 12 hours. After the reaction was completed, 50 mL of water were added, and the reaction solution was extracted with a mixture of dichloromethane and methanol (V:V=10:1) (10 mL×3). The organic phases were combined, washed with saturated sodium chloride solution (30 mL), dried over anhydrous sodium sulfate, and filtered. The filtrate was concentrated under reduced pressure, and the resulting residue was purified by thin-layer chromatography with elution system A to obtain the title compound 23 (21 mg, yield 91%) as a white solid.

MS (ESI) m/z: 440.3 [M+1]

$^1$H NMR (400 MHz, $CDCl_3$) δ 12.30 (brs, 1H), 7.48 (d, 1H), 7.18 (brs, 1H), 6.74 (s, 1H), 5.94 (s, 1H), 4.64 (d, 2H), 3.95-3.98 (m, 2H), 3.91 (s, 3H), 3.30-3.36 (m, 2H), 2.96-3.01 (m, 1H), 2.65 (s, 3H), 2.39 (s, 3H), 2.19 (s, 3H), 1.69-1.73 (m, 2H), 1.45 (brs, 2H).

Example 24

6-(((1r,4r)-4-(Dimethylamino)cyclohexyl)(ethyl)amino)-N-((4-methoxy-6-methyl-2-oxo-1,2-dihydropyridin-3-yl)methyl)-5-methylbenzofuran-4-carboxamide

24

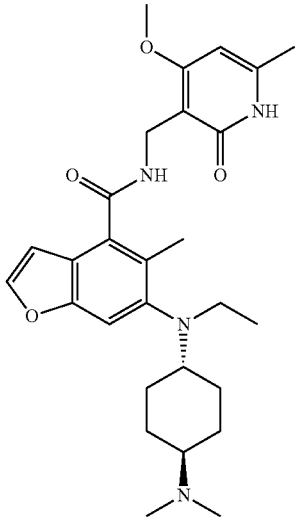

-continued

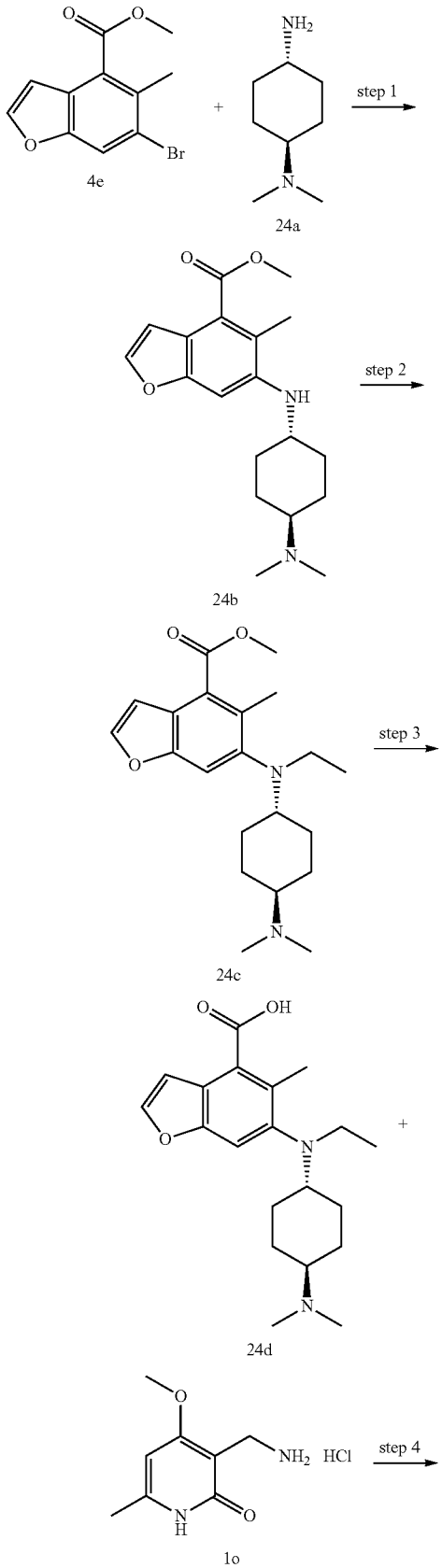

-continued

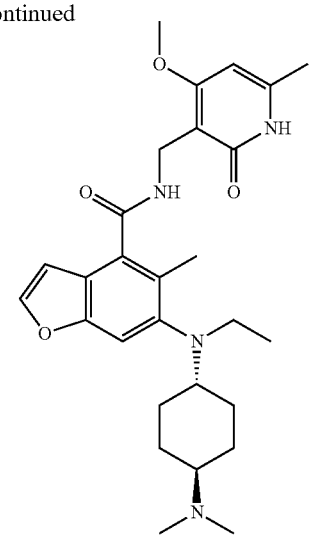

24

Step 1

Methyl 6-(((1 r,4r)-4-(dimethylamino)cyclohexyl) amino)-5-methylbenzofuran-4-carboxylate 24b Compound 4e (200 mg, 0.75 mmol), (1r, 4r)-N1,N1-dimethylcyclohexane-1,4-diamine 24a (260 mg, 1.49 mmol, prepared by a method disclosed in "Bioorganic & Medicinal Chemistry Letters, 2011, 21(15), 4622-4628"), tris(dibenzylideneacetone)dipalladium (137 mg, 0.15 mmol), (±)-2, 2'-bis(diphenylphosphino)-1,1'-binaphthalene (140 mg, 0.22 mmol) and cesium carbonate (731.25 mg, 2.25 mmol) were dissolved in 20 mL of toluene. The reaction system was stirred under reflux for 12 hours under a nitrogen atmosphere. After the reaction was completed, 100 mL of water were added to the reaction system, and the mixture was extracted with a mixture of dichloromethane and methanol (V:V=10:1) (20 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system A to obtain the title compound 24b (15 mg, yield 6.1%) as a yellow solid.

Step 2

Methyl 6-(((1r,4r)-4-(dimethylamino)cyclohexyl) (ethyl)amino)-5-methylbenzofuran-4-carboxylate 24c Compound 24b (15 mg, 0.045 mmol), acetaldehyde (6.3 mg, 0.136 mmol) and acetic acid (13.3 mg, 0.22 mmol) were added to 3 mL of ethanol. The mixture was stirred for 1 hour at 0° C., then slowly warmed up to room temperature and stirred for 12 hours. Sodium cyanoborohydride (8.5 mg, 0.135 mmol) was added, and the mixture was stirred for 10 hours. After the reaction was completed, the reaction system was added with 20 mL of water and extracted with a mixture of dichloromethane and methanol (V:V=10:1) (10 mL×3). The organic phases were combined, washed with saturated sodium chloride (30 mL), dried over anhydrous sodium sulfate, and filtered. The filtrate was concentrated under reduced pressure to obtain the crude title compound 24c (20 mg) as a yellow solid, which was used directly in the next step without further purification.

Step 3

6-(((r,4r)-4-(Dimethylamino)cyclohexyl)(ethyl) amino)-5-methylbenzofuran-4-carboxylic acid 24d The crude 24c (20 mg, 0.056 mmol) was dissolved in 4 mL of a mixture of methanol and water (V:V=1:1), then potassium hydroxide (18.7 mg, 0.335 mmol) was added. The mixture was stirred for 12 hours at 80° C. After the reaction was completed, 2N hydrochloric acid was added to adjust the pH of the reaction solution to 3-4. After the mixture was concentrated under reduced pressure, the crude product was dissolved in 8 mL of a mixture of methylene chloride and tetrahydrofuran (V:V=1:1), and filtered. The filtrate was concentrated under reduced pressure to obtain the crude title compound 24d (25 mg) as a brown solid, which was directly used in the next step without further purification.

Step 4

6-(((1 r,4r)-4-(Dimethylamino)cyclohexyl)(ethyl) amino)-N-((4-methoxy-6-methyl-2-oxo-1,2-dihydro-pyridin-3-yl)methyl)-5-methylbenzofuran-4-carbox-amide 24

The crude 24d (25 mg, 0.073 mmol) was dissolved in 2 mL of N,N-dimethylformamide, then 2-(7-azabenzotriazol-1-yl)-N,N,N',N'-tetramethyluronium hexafluorophosphate (41.8 mg, 0.110 mmol) and N,N-diisopropylethylamine (28 mg, 0.219 mmol) were added. The reaction was stirred for 1 hour at 0° C. Compound 1o (11.58 mg, 0.057 mmol) was added, and the mixture was stirred for 12 hours. After the reaction was completed, 2 mL of water were added to quench the reaction, and the mixture was filtered. The filtrate was concentrated under reduced pressure, and the resulting residue was purified by thin-layer chromatography with elution system A to obtain the title compound 24 (4.9 mg, yield 14%) as a white solid.

MS (ESI) m/z: 495.4 [M+1]

$^1$H NMR (400 MHz, $CDCl_3$) δ 11.62 (brs, 1H), 7.49 (s, 1H), 7.20 (brs, 1H), 6.77 (s, 1H), 5.93 (s, 1H), 5.35 (brs, 1H), 4.66 (d, 2H), 3.91 (s, 3H), 3.07 (q, 2H), 2.65-2.71 (m, 1H), 2.39 (s, 3H), 2.21 (s, 6H), 2.15 (s, 3H), 2.02 (brs, 1H), 1.85-1.93 (m, 4H), 1.32-1.43 (m, 4H), 0.86 (t, 3H).

Example 25
6-(Ethyl(1-(methylsulfonyl)piperidin-4-yl)amino)-N-((4-methoxy-6-methyl-2-oxo-1,2-dihydropyridin-3-yl)methyl)-5-methylbenzofuran-4-carboxamide
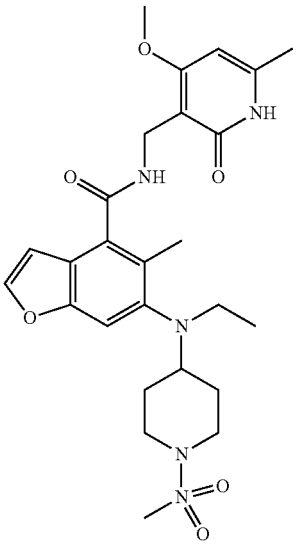
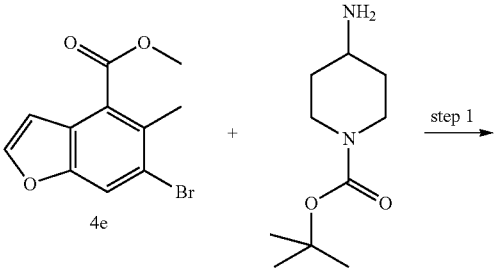
4e
25a
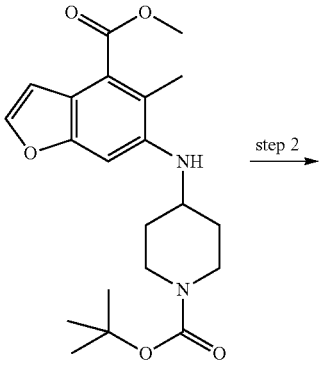
25b
-continued
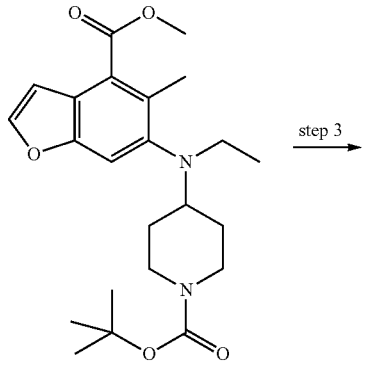
25c
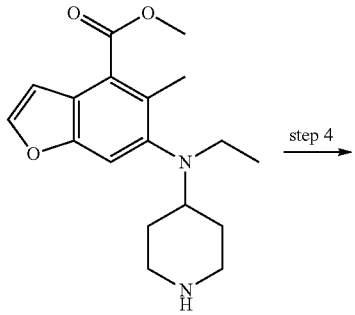
25d
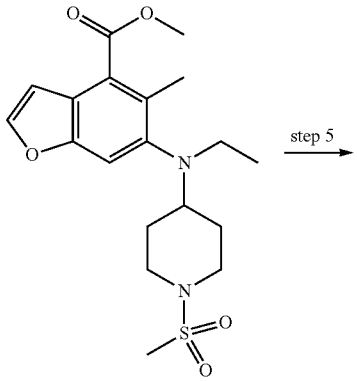
25e
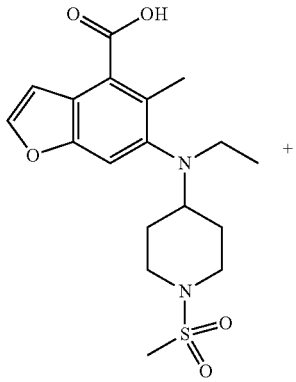
25f -continued

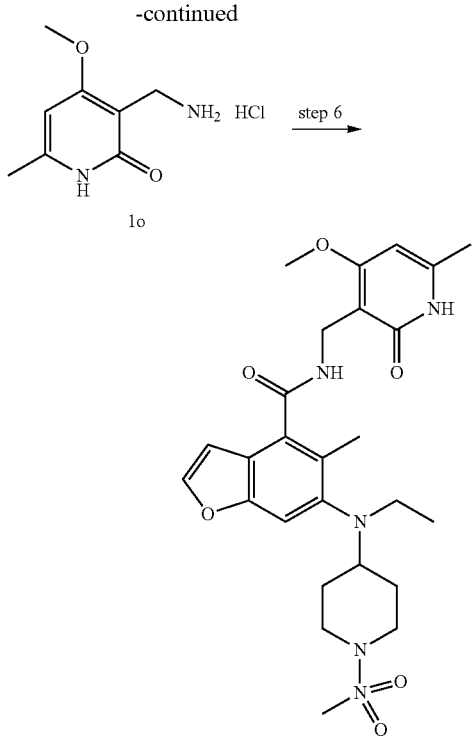

25

Step 1 tert-Butyl 4-((4-(methoxycarbonyl)-5-methylbenzofuran-6-yl)amino)piperidine-1-carboxylate 25b Compound 4e (810 mg, 3.02 mmol), tert-butyl 4-aminopiperidine-1-carboxylate 25a (1200 mg, 6.04 mmol, prepared by a method disclosed in "Bioorganic & Medicinal Chemistry Letters, 2011, 21(3), 983-988"), tris(dibenzylideneacetone)dipalladium (553 mg, 0.604 mmol), (±)-2, 2'-bis (diphenylphosphino)-1,1'-binaphthalene (564 mg, 6.04 mmol) and cesium carbonate (1.96 g, 6.04 mmol) were dissolved in 10 mL of toluene. The mixture was stirred for 72 hours at 110° C. After the reaction was completed, the mixture was filtered through celite. Then, 60 mL of ethyl acetate was added, and the mixture was washed with saturated sodium chloride (100 mL), dried over anhydrous sodium sulfate, and filtered. The filtrate was concentrated under reduced pressure, and the resulting residue was purified by silica gel column chromatography with elution system B to obtain the title compound 25b (1 g, yield 83%) as a yellow liquid.

Step 2 tert-Butyl 4-(ethyl(4-(methoxycarbonyl)-5-methylbenzofuran-6-yl)amino)piperidine-1-carboxylate 25c Compound 25b (1 g, 2.58 mmol) was dissolved in 10 mL of methanol, then acetaldehyde (360 mg, 7.73 mmol) and acetic acid (774 mg, 12.9 mmol) were added. The mixture was stirred at 0° C. for 1 hour, then warmed up to room temperature and stirred for 12 hours. Sodium cyanoborohydride (486 mg, 7.74 mmol) was added, and the mixture was stirred for 10 hours. After the reaction was completed, 50 mL of water were added to the reaction solution, and the mixture was extracted with ethyl acetate (20 mL×3). The organic phases were combined, washed with saturated sodium chloride solution (100 mL), dried over anhydrous sodium sulfate, and filtered. The filtrate was concentrated under reduced pressure, and the resulting residue was purified by silica gel column chromatography with elution system B to obtain the title compound 25c (573.8 mg, yield 62.8%) as a yellow liquid.

Step 3

Methyl 6-(ethyl(piperidin-4-yl)amino)-5-methylbenzofuran-4-carboxylate 25d

Compound 25c (184 mg, 0.58 mmol) was added to 12 mL of dichloromethane, then 3 mL of trifluoroacetic acid were added. The mixture was stirred for 2 hours. After the reaction was completed, the mixture was neutralized with saturated sodium bicarbonate solution, and extracted with ethyl acetate (20 mL×3). The organic phases were combined, dried over anhydrous sodium sulfate, and filtered. The filtrate was concentrated under reduced pressure to obtain the crude title compound 25d (156) as a brown liquid, which was directly used in the next step without further purification.

Step 4

Methyl 6-(ethyl(1-(methylsulfonyl)piperidin-4-yl)amino)-5-methylbenzofuran-4-carboxylate 25e The crude 25d (52 mg, 0.16 mmol) was added to 10 mL dichloromethane, triethylamine (64.6 mg, 0.64 mmol) was added, then methanesulfonyl chloride (37.8 mg, 0.33 mmol) was added at 0° C. The mixture was slowly warmed up to room temperature, and stirred for 12 hours. After the reaction was completed, 50 mL of water were added to the reaction solution, and the mixture was extracted with ethyl acetate (20 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system B to obtain the title compound 25e (20 mg, yield 33%) as a colorless liquid.

Step 5

6-(Ethyl(1-(methylsulfonyl)piperidin-4-yl)amino)-5-methylbenzofuran-4-carboxylic Acid 25f Compound 25e (20 mg, 0.05 mmol) was dissolved in 1 mL of methanol and 1 mL of water, then potassium hydroxide (14.2 mg, 0.25 mmol) was added. The mixture was stirred for 12 hours at 70° C. After the reaction was completed, 2N hydrochloric acid was added to adjust the pH of the reaction solution to 3-4, and the mixture was extracted with a mixture of dichloromethane and tetrahydrofuran (V:V=1:1) (10 mL×3). The organic phases were combined, washed with saturated sodium chloride solution (20 mL), dried over anhydrous sodium sulfate, and filtered. The filtrate was concentrated under reduced pressure to obtain the crude title compound 25f (16 mg) as a colorless liquid, which was directly used in the next step without further purification.

Step 6

6-(Ethyl(1-(methylsulfonyl)piperidin-4-yl)amino)-N-((4-methoxy-6-methyl-2-oxo-1,2-dihydropyridin-3-yl)methyl)-5-methylbenzofuran-4-carboxamide 25

The crude 25f (8 mg, 0.21 mmol) was dissolved in 2 mL of N,N-dimethylformamide, then 2-(7-azabenzotriazol-1-yl)-N,N,N',N'-tetramethyluronium hexafluorophosphate (12 mg, 0.0315 mmol) and N,N-diisopropylethylamine (8 mg, 0.063 mmol) were added to the above solution. The mixture was stirred for 1 hour at 0° C. Compound 1o (5.2 mg, 0.025 mmol) was added, and the reaction was stirred for 48 hours at room temperature. After the reaction was completed, 20 mL of water were added, and the mixture was extracted with a mixture of dichloromethane and methanol (V:V=10:1) (10 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system A to obtain the title compound 25 (12.5 mg, yield 11%) as a white solid.

MS (ESI) m/z: 531.2 [M+1]

$^1$H NMR (400 MHz, $CDCl_3$) δ 12.5 (brs, 1H), 7.51 (d, 1H), 7.29 (s, 1H), 7.22 (brs, 1H), 6.77 (s, 1H), 5.96 (s, 1H), 4.65 (d, 2H), 3.92 (s, 3H), 3.72-3.69 (m, 2H), 3.17-3.11 (m, 1H), 3.07 (q, 2H), 2.96-2.89 (m, 2H), 2.74 (s, 3H), 2.67 (t, 2H), 2.39 (s, 3H), 2.19 (s, 3H), 1.90-1.71 (m, 4H), 0.88 (t, 3H).

Example 26

6-((1-Acetylpiperidin-4-yl)(ethyl)amino)-N-((4-methoxy-6-methyl-2-oxo-1,2-dihydropyridin-3-yl)methyl)-5-methylbenzofuran-4-carboxamide 26

26

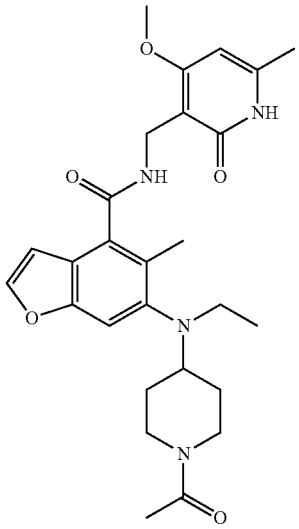

In accordance with the synthetic route of Example 25, the starting material methanesulfonyl chloride used in step 4 was replaced with acetic anhydride, accordingly, the title compound 26 (10.1 mg, yield 50%) as a white solid was prepared.

MS (ESI) m/z: 495.3 [M+1]

$^1$H NMR (400 MHz, $CD_3OD$) δ 7.76 (brs, 1H), 7.45 (brs, 1H), 6.80 (brs, 1H), 6.30 (s, 1H), 4.53 (s, 2H), 3.96 (s, 3H), 3.91 (brs, 2H), 3.36-3.30 (m, 2H), 3.23 (q, 2H), 3.11-3.05 (m, 3H), 2.41 (brs, 3H), 2.33 (s, 3H), 2.07 (s, 3H), 1.85 (brs, 2H), 1.60 (brs, 2H), 0.90 (t, 3H).

Example 27

5-Ethyl-6-(ethyl(tetrahydro-2H-pyran-4-yl)amino)-2-fluoro-N-((4-methoxy-6-methyl-2-oxo-1,2-dihydropyridin-3-yl)methyl)benzofuran-4-carboxamide

27

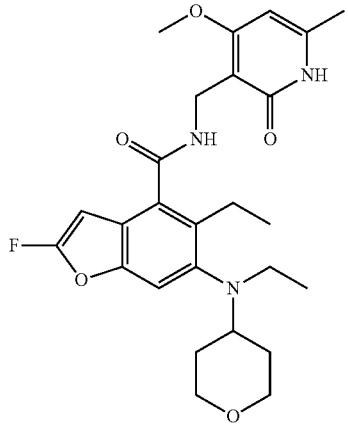

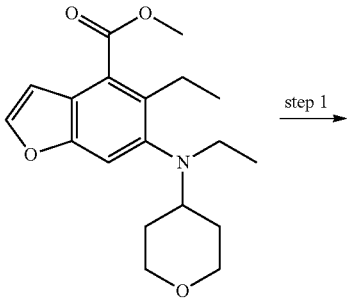

1i

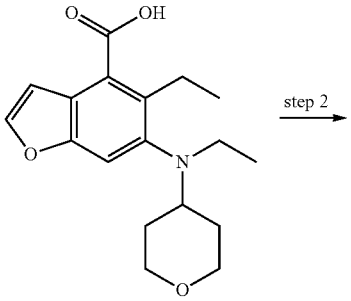

27a

-continued

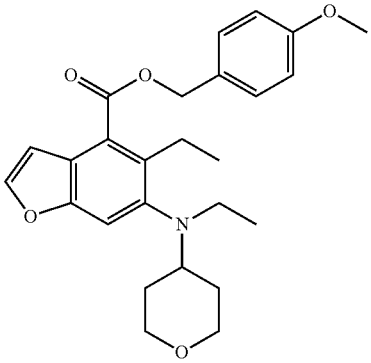

27b step 3

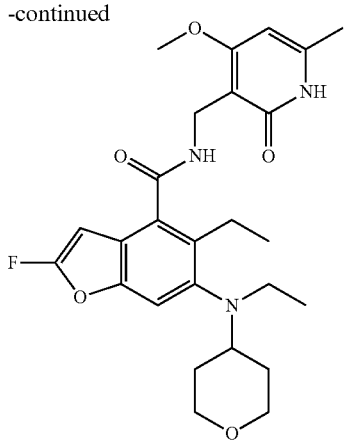

27

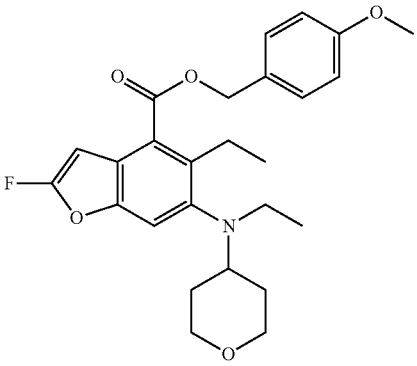

27c step 4

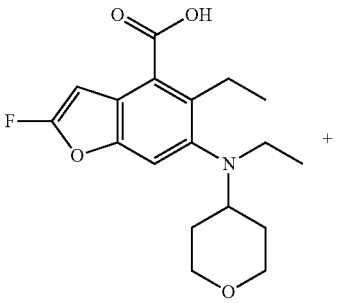

27d

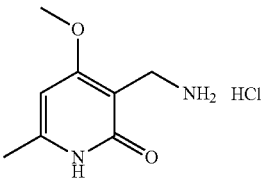

1o step 5

Step 1

5-Ethyl-6-(ethyl(tetrahydro-2H-pyran-4-yl)amino) benzofuran-4-carboxylic Acid 27a Compound 1i (260 mg, 0.79 mmol) was dissolved in 15 mL of a mixture of methanol and tetrahydrofuran (V:V=2:1), then 5 mL of 4 N sodium hydroxide solution were added. The mixture was stirred for 12 hours at 60° C. After the reaction was completed, 12 M hydrochloric acid was added to adjust the pH of the reaction solution to 4, and the mixture was extracted with ethyl acetate (20 mL×3). The organic phases were combined, washed with saturated sodium chloride solution (50 mL), dried over anhydrous sodium sulfate, and filtered. The filtrate was concentrated under reduced pressure to obtain the crude title compound 27a (220 mg) as a white solid, which was directly used in the next step within further purification.

Step 2

4-Methoxybenzyl 5-ethyl-6-(ethyl(tetrahydro-2H-pyran-4-yl)amino)benzofuran-4-carboxylate 27b The crude 27a (170 mg, 0.54 mmol) was dissolved in 15 mL of acetone, then 1-(chloromethyl)-4-methoxybenzene (168 mg, 1.07 mol, Accela) and potassium carbonate (148 mg, 1.07 mmol) were added to the above solution. The mixture was stirred for 48 hours. After the reaction was completed, the mixture was concentrated under reduced pressure, and 30 mL of water and 20 mL of ethyl acetate were successively added. Two phases were separated, and the aqueous phase was extracted with ethyl acetate (20 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 27b (230 mg, yield 99%) as a colorless oil.

Step 3

4-Methoxybenzyl 5-ethyl-6-(ethyl(tetrahydro-2H-pyran-4-yl)amino)-2-fluorobenzofuran-4-carboxylate 27c Compound 27b (230 mg, 0.53 mmol) was added to 8 mL of tetrahydrofuran. The mixture was cooled down to −70°

C., 0.79 mL of 2.0 M lithium diisopropylamide was added, and the mixture was stirred for 1 hour at −70° C. N-fluorodibenzenesulfonamide (182 mg, 0.58 mmol, Bepharm) was added, and the mixture was stirred for 1 hour at −70° C. After the reaction was completed, the mixture was slowly warmed up to room temperature, then 20 mL of saturated ammonium chloride solution was added to quench the reaction. The mixture was extracted with ethyl acetate (10 mL×3). The organic phases were combined, washed with saturated sodium chloride solution (20 mL), dried over sodium sulfate, and filtered. The filtrate was concentrated under reduced pressure, and the resulting residue was purified by thin-layer chromatography with elution system B to obtain the title compound 27c (17 mg, yield 7%) as a yellow oil.

Step 4

5-Ethyl-6-(ethyl(tetrahydro-2H-pyran-4-yl)amino)-2-fluorobenzofuran-4-carboxylic acid 27d Compound 27c (17 mg, 0.037 mmol) was dissolved in 3 mL of dichloromethane, then 0.5 mL of trifluoroacetic acid was added. The reaction was stirred for 1 hour at room temperature. After the reaction was completed, the mixture was concentrated under reduced pressure to to obtain the crude title compound 27d (20 mg) as a yellow oil, which was directly used in the next step without further purification.

Step 5

5-Ethyl-6-(ethyl(tetrahydro-2H-pyran-4-yl)amino)-2-fluoro-N-((4-methoxy-6-methyl-2-oxo-1,2-dihydropyridin-3-yl)methyl)benzofuran-4-carboxamide 27

The crude 27d (20 mg, 0.06 mmol) was dissolved in 3 mL of N,N-dimethylformamide, then 2-(7-azabenzotriazol-1-yl)-N,N,N',N'-tetramethyluronium hexafluorophosphate (32.6 mg, 0.85 mmol) and N,N-diisopropylethylamine (39 mg, 0.30 mmol) were added to the above solution. The mixture was stirred for 1 hour. Then, compound 1o (18 mg, 0.00 mmol) was added, and the mixture was stirred for 12 hours. After the reaction was completed, 20 mL of water were added, and the mixture was extracted with a mixture of dichloromethane and methanol (V:V=8:1). The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound 27 (12 mg, yield 41%) as a white solid.

MS (ESI) m/z: 486.4 [M+1]

$^1$H NMR (400 MHz, DMSO-$d_6$) δ 11.48 (brs, 1H), 8.06 (t, 1H), 7.43 (s, 1H), 1.55 (d, 1H), 6.10 (s, 1H), 4.25 (d, 2H), 3.83 (brd, 2H), 3.81 (s, 3H), 3.21 (t, 2H), 3.03 (q, 2H), 3.90-3.96 (m, 1H), 2.82 (q, 2H), 2.18 (s, 3H), 1.63-1.67 (brd, 2H), 1.45-1.53 (m, 2H), 1.05 (t, 3H), 0.81 (t, 3H).

Example 28

2-Cyclopropyl-6-((cyclopropylmethyl)(tetrahydro-2H-pyran-4-yl)amino)-5-ethyl-N-((4-methoxy-6-methyl-2-oxo-1,2-dihydropyridin-3-yl)methyl)benzofuran-4-carboxamide

28

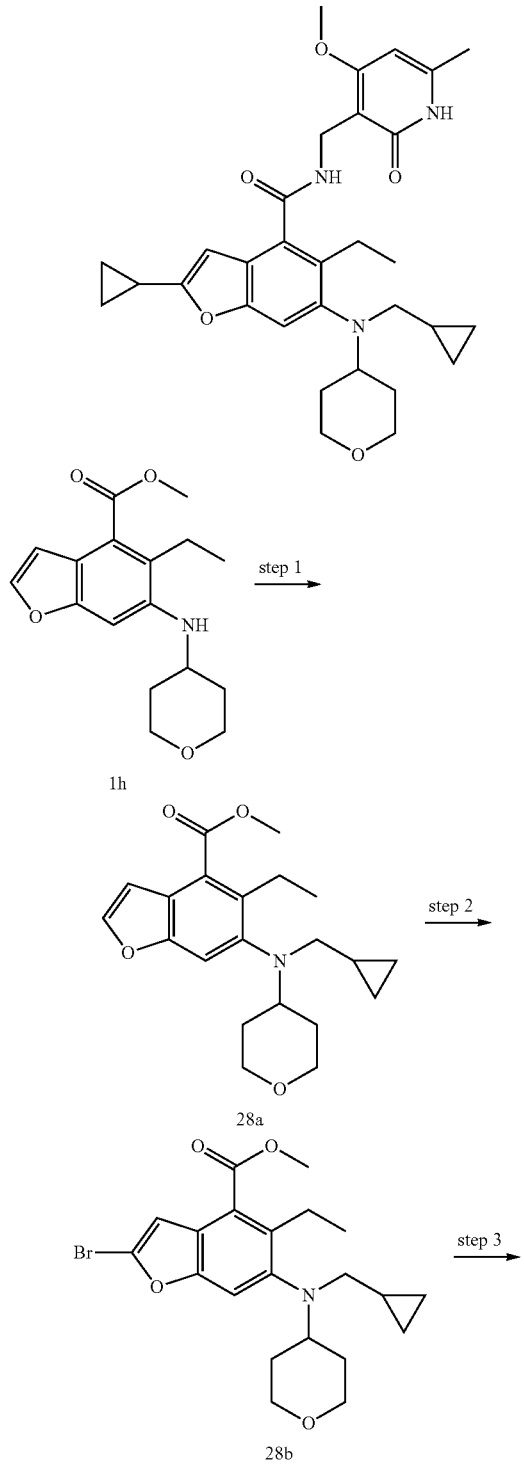

-continued

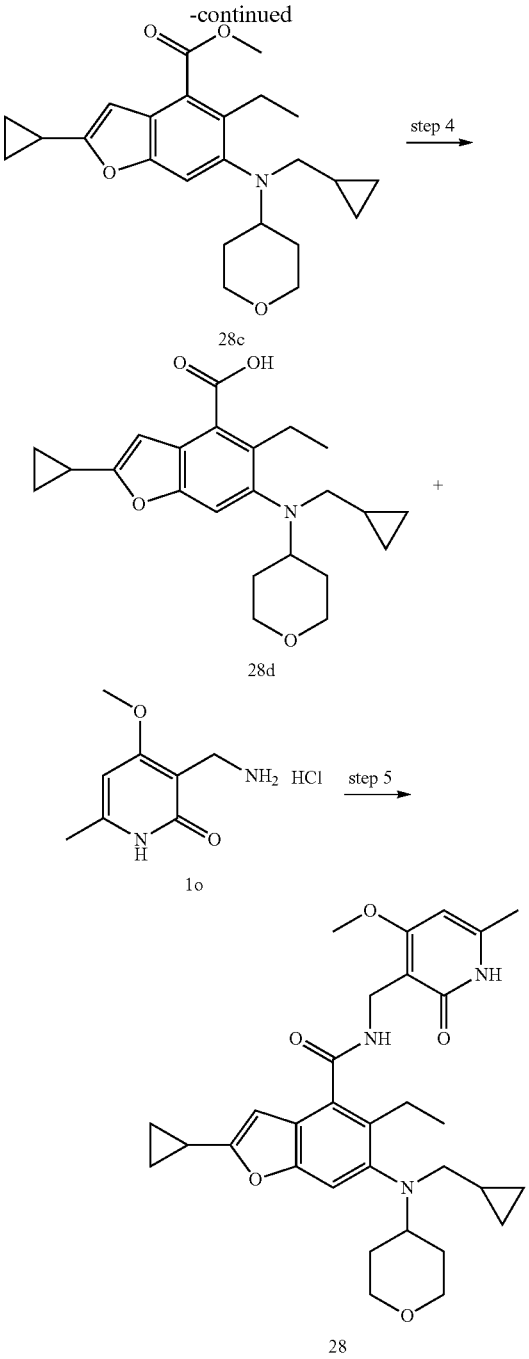

Step 1

Methyl 6-((cyclopropylmethyl)(tetrahydro-2H-pyran-4-yl)amino)-5-ethylbenzofuran-4-carboxylate 28a Compound 1h (950 mg, 3.03 mmol) was dissolved in 50 mL of 1,2-dichloroethane, then cyclopropanecarbaldehyde (1.1 g, 15.7 mmol) and acetic acid (940 mg, 15.7 mmol) were added to the above solution. The mixture was stirred for 12 hours, then sodium triacetoxyborohydride (1.97 g, 9.4 mmol) was added. The mixture was stirred for 3 hours. After the reaction was completed, the reaction solution was concentrated under reduced pressure, neutralized with saturated sodium bicarbonate solution, and extracted with ethyl acetate (20 mL×3). The organic phases were combined, washed successively with water (50 mL) and saturated sodium chloride solution (50 mL), dried over anhydrous sodium sulfate, and filtered. The filtrate was concentrated under reduced pressure, and the resulting residue was purified by silica gel chromatography with elution system B to obtain the title compound 28a (850 mg, yield 76%) as a light yellow oil.

Step 2

Methyl 2-bromo-6-((cyclopropylmethyl)(tetrahydro-2H-pyran-4-yl)amino)-5-ethylbenzofuran-4-carboxylate 28b Compound 28a (400 mg, 1.1 mmol) was dissolved in 15 mL of tetrahydrofuran. The mixture was cooled down to −70° C., then 1.65 mL of 2.0 M lithium diisopropylamide was added to the above solution. The mixture was stirred for 1 hour at −70° C. before 15 mL of a pre-prepared solution of 1,2-dibromo-1,1,2,2-tetrachloroethane (429 mg, 1.3 mmol) in tetrahydrofuran were added dropwise to the reaction solution. The reaction was stirred for 1 hour at −70° C. After the reaction was completed, 50 mL of saturated ammonium chloride solution were added to quench the reaction, and the mixture was extracted with ethyl acetate (20 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 28b (150 mg, yield 31%) as a light yellow oil.

Step 3

Methyl 2-cyclopropyl-6-((cyclopropylmethyl)(tetrahydro-2H-pyran-4-yl)amino)-5-ethylbenzofuran-4-carboxylate 28c Compound 28b (50 mg, 0.11 mmol) was dissolved in 5 mL of toluene, then cyclopropylboronic acid (20 mg, 0.23 mmol), palladium acetate (5 mg, 0.2 mmol), tricyclohexylphosphine (10 mg, 0.03 mmol) and potassium phosphate trihydrate (91 mg, 0.34 mmol) were added to the above solution. The reaction was stirred for 12 hours at 100° C. under an argon atmosphere. After the reaction was completed, the mixture was filtered through celite. The filtrate was concentrated under reduced pressure, and the resulting residue was purified by thin-layer chromatography with elution system B to obtain the title compound 28c (33 mg, yield 73%) as a colorless oil.

Step 4

2-Cyclopropyl-6-((cyclopropylmethyl)(tetrahydro-2H-pyran-4-yl)amino)-5-ethylbenzofuran-4-carboxylic acid 28d Compound 28c (33 mg, 0.08 mmol) was added to 5 mL of tetrahydrofuran and 15 mL of methanol, then 5 mL of 4 M sodium hydroxide solution were added. The reaction system was stirred for 12 hours at 60° C. After the reaction was completed, the mixture was concentrated to remove organic solvents. A small amount of water was added, 12 M hydrochloric acid was added to adjusted the pH to 3, and the mixture was extracted with ethyl acetate (10 mL×3). The organic phases were combined, washed with saturated sodium chloride solution (50 mL), dried over anhydrous sodium sulfate, and filtered. The filtrate was concentrated under reduced pressure to obtain the crude title compound 28d (25 mg) as a white solid, which was directly used in the next step without further purification.

Step 5

2-Cyclopropyl-6-((cyclopropylmethyl)(tetrahydro-2H-pyran-4-yl)amino)-5-ethyl-N-((4-methoxy-6-methyl-2-oxo-1,2-dihydropyridin-3-yl)methyl)benzofuran-4-carboxamide 28

The crude 28d (25 mg, 0.065 mmol) was dissolved in 3 mL of N,N-dimethylformamide, then 2-(7-azabenzotriazol-1-yl)-N,N,N',N'-tetramethyluronium hexafluorophosphate (47 mg, 0.098 mmol) and N,N-diisopropylethylamine (42 mg, 0.33 mmol) were added to the above solution. The mixture was stirred for 1 hour. Compound 1o (20 mg, 0.098 mmol) was added, and the mixture was stirred for 12 hours. After the reaction was completed, 20 mL of water were added to the reaction solution, and the mixture was extracted with a mixture of dichloromethane and methanol (V:V=8:1). The organic phases were combined, washed successively with water and saturated sodium chloride solution, dried over anhydrous sodium sulfate, and filtered. The filtrate was concentrated under reduced pressure, and the resulting residue was purified by thin-layer chromatography with elution system A to obtain the title compound 28 (12 mg, yield 34%) as a light yellow solid.

MS (ESI) m/z: 534.5 [M+1]

$^1$H NMR (400 MHz, DMSO-$d_6$) δ 11.48 (brs, 1H), 7.91 (s, 1H), 7.38 (s, 1H), 6.36 (s, 1H), 6.12 (s, 1H), 4.27 (brs, 2H), 3.83 (s, 3H), 3.79 (brs, 2H), 3.28 (brs, 2H), 3.17-3.23 (m, 2H), 2.96-3.00 (m, 1H), 2.83-2.86 (m, 2H), 2.19 (s, 3H), 2.06 (brs, 1H), 1.38-1.46 (m, 2H), 1.24 (brs, 2H), 1.06 (t, 3H), 0.98 (brs, 2H), 0.83 (brs, 2H), 0.64 (brs, 1H), 0.28 (brs, 2H), 0.03 (brs, 2H).

Example 29

6-(Ethyl(tetrahydro-2H-pyran-4-yl)amino)-N-((4-methoxy-6-methyl-2-oxo-1,2-dihydro pyridin-3-yl)methyl)-5-methyl-2-(trifluoromethyl)benzofuran-4-carboxamide

29

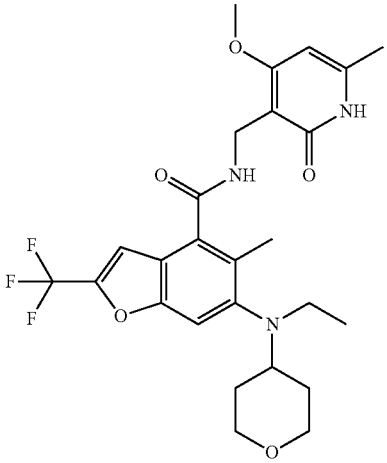

-continued

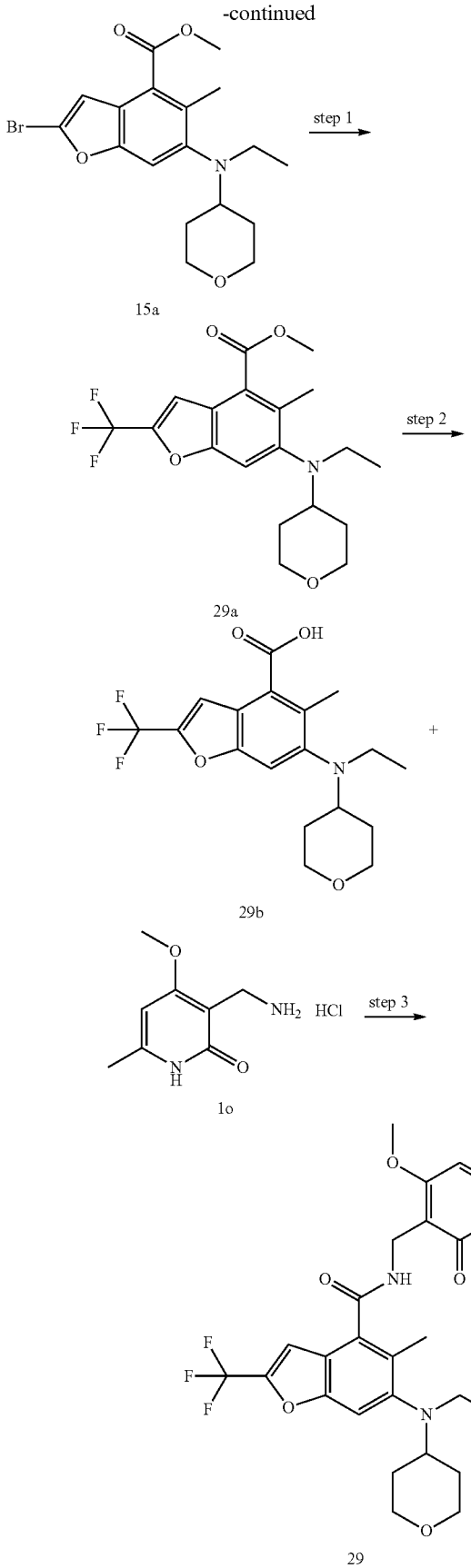

Step 1

Methyl 6-(ethyl(tetrahydro-2H-pyran-4-yl)amino)-5-methyl-2-(trifluoromethyl)benzofuran-4-carboxylate 29a Compound 15a (50 mg, 0.126 mmol) was dissolved in 8 mL of N,N-dimethylformamide, then methyl fluorosulfonyl difluoroacetate (500 mg, 2.52 mmol) and cuprous iodide (120 mg, 0.63 mmol) were added to the above solution. The reaction was stirred for 24 hours at 120° C. under a nitrogen atmosphere. After the reaction was completed, 50 mL of water were added to the reaction solution, and the mixture was extracted with ethyl acetate (10 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 29a (10 mg, yield 20.8%) as a yellow liquid.

Step 2

6-(Ethyl(tetrahydro-2H-pyran-4-yl)amino)-5-methyl-2-(trifluoromethyl)benzofuran-4-carboxylic acid 29b Compound 29a (10 mg, 0.026 mmol) was added to 2 mL of a mixture of water and methanol (V:V=1:1), then sodium hydroxide (5.16 mg, 0.129 mmol) was added. The reaction system was stirred for 16 hours at 70° C. After the reaction was completed, the reaction solution was cooled down to 5° C., 2 N hydrochloric acid was added to adjusted the pH to 3-4, and the mixture was concentrated under reduced pressure to obtain the crude title compound 29b (10 mg) as a white solid, which was directly used in the next step without further purification.

Step 3

6-(Ethyl(tetrahydro-2H-pyran-4-yl)amino)-N-((4-methoxy-6-methyl-2-oxo-1,2-dihydro pyridin-3-yl) methyl)-5-methyl-2-(trifluoromethyl)benzofuran-4-carboxamide 29

The crude 29b (10 mg, 0.027 mmol) was dissolved in 3 mL of N,N-dimethylformamide, then 2-(7-azabenzotriazol-1-yl)-N,N,N',N'-tetramethyluronium hexafluorophosphate (15.4 mg, 0.041 mmol) and N,N-diisopropylethylamine (10.5 mg, 0.081 mmol) were added. The reaction system was cooled down to 0° C. and stirred for 1 hour. Compound 1o (6.6 mg, 0.032 mmol) was added, and the mixture was stirred for 12 hours at room temperature. After the reaction was completed, 40 mL of water was added, and the mixture was extracted with a mixture of dichloromethane and methanol (V:V=8:1) (10 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system A to obtain the title compound 29 (1.6 mg, yield 11.4%) as a white solid.

MS (ESI) m/z: 522.3 [M+1]

$^1$H NMR (400 MHz, $CDCl_3$) δ 7.52 (s, 1H), 7.33 (s, 1H), 7.19 (brs, 1H), 5.98 (s, 1H), 4.66 (s, 2H), 4.00-3.95 (m, 2H), 3.95 (s, 3H), 3.36-3.30 (m, 2H), 3.12 (q, 2H), 3.04-2.99 (m, 1H), 2.41 (s, 3H), 2.28 (s, 3H), 1.72 (brs, 4H), 0.89 (t, 3H).

Example 30

2-Cyano-6-(ethyl(tetrahydro-2H-pyran-4-yl)amino)-N-((4-methoxy-6-methyl-2-oxo-1,2-dihydropyridin-3-yl)methyl)-5-methylbenzofuran-4-carboxamide

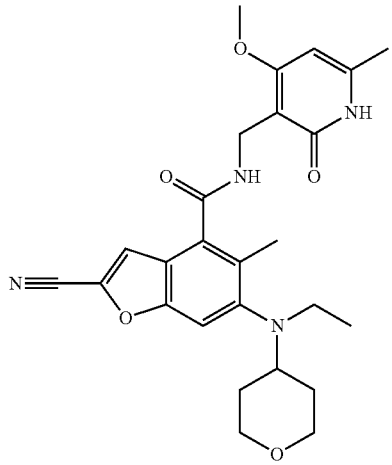

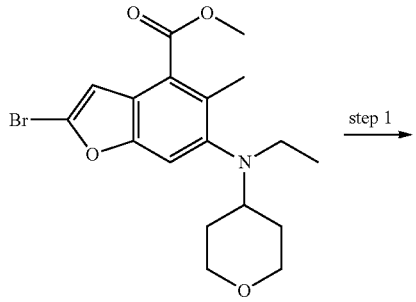

15a

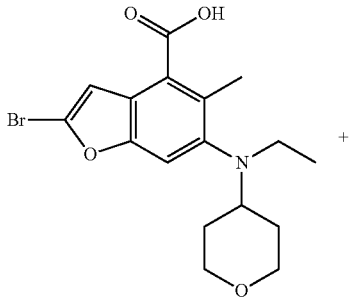

30a

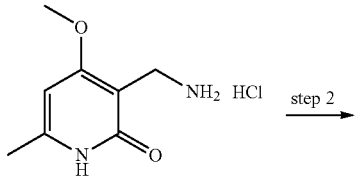

1o

-continued

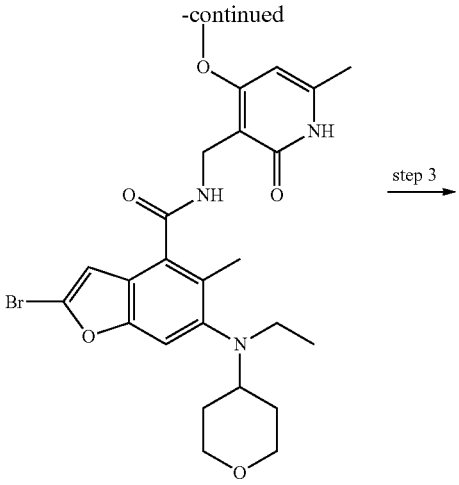

30b

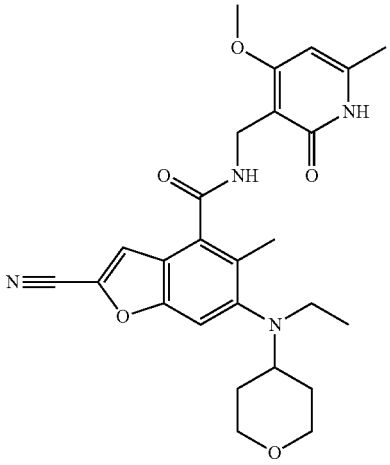

30

Step 1

2-Bromo-6-(ethyl(tetrahydro-2H-pyran-4-yl)amino)-5-methylbenzofuran-4-carboxylic Acid Compound 15a (30 mg, 0.076 mmol) was added to 2 mL of a mixture of water and methanol (V:V=1:1), then sodium hydroxide (15.1 mg, 0.378 mmol) was added. The reaction system was stirred for 12 hours at 70° C. After the reaction was completed, the reaction solution was cooled down to 5° C., 2 N hydrochloric acid was added to adjust the pH to 3-4, and the mixture was concentrated under reduced pressure to obtain the crude title compound 30a (30 mg) as a white solid, which was used directly in the next step without further purification.

Step 2

2-Bromo-6-(ethyl(tetrahydro-2H-pyran-4-yl)amino)-N-((4-methoxy-6-methyl-2-oxo-1,2-dihydropyridin-3-yl)methyl)-5-methylbenzofuran-4-carboxamide 30b The crude 30a (30 mg, 0.078 mmol) was dissolved in 5 mL of N,N-dimethylformamide, then 2-(7-azabenzotriazol-1-yl)-N,N,N',N'-tetramethyluronium hexafluorophosphate (44.5 mg, 0.117 mmol) and N,N-diisopropylethylamine (30.2 mg, 0.234 mmol) were added to the above solution. The reaction system was cooled down to 0° C. and stirred for 1 hour. Compound 1o (6.6 mg, 0.032 mmol) was added, and the mixture was stirred for 12 hours. After the reaction was completed, 50 mL of water were added, and the mixture was extracted with a mixture of dichloromethane and methanol (V:V=8:1) (10 mL×3). The organic phases were combined, washed with saturated sodium chloride solution (20 mL), dried over anhydrous sodium sulfate, and filtered. The filtrate was concentrated under reduced pressure to obtain the crude title compound 30b (50 mg) as a yellow liquid, which was used directly in the next step without further purification.

Step 3

2-Cyano-6-(ethyl(tetrahydro-2H-pyran-4-yl)amino)-N-((4-methoxy-6-methyl-2-oxo-1,2-dihydropyridin-3-yl)methyl)-5-methylbenzofuran-4-carboxamide 30

The crude 30b (40 mg, 0.075 mmol) was dissolved in 5 mL of N,N-dimethylacetamide, then cuprous cyanide (13.6 mg, 0.15 mmol) and cuprous iodide (14.3 mg, 0.075 mmol) were added to the above solution. The reaction system was stirred for 1 hour at 170° C. After the reaction was completed, the mixture was filtered, and the filtrate was washed with a mixture of dichloromethane and methanol (V:V=10:1) (10 mL). The organic phases were combined, concentrated under reduced pressure, and the resulting residue was purified by thin-layer chromatography with elution system A to obtain the title compound 30 (4.7 mg, yield 12.5%) as a white solid.

MS (ESI) m/z: 479.4 [M+1]

$^1$H NMR (400 MHz, $CDCl_3$) δ 11.5 (brs, 1H), 7.55 (s, 1H), 7.26 (s, 1H), 7.16 (brs, 1H), 5.97 (s, 1H), 4.66 (s, 2H), 3.98-3.96 (m, 2H), 3.93 (s, 3H), 3.35-3.30 (m, 2H), 3.11 (q, 2H), 3.04-2.99 (m, 1H), 2.41 (s, 3H), 2.27 (s, 3H), 1.75-1.66 (m, 4H), 0.89 (t, 3H).

Example 31

6-((4,4-Difluorocyclohexyl)(ethyl)amino)-5-ethyl-N-((4-methoxy-6-methyl-2-oxo-1,2-dihydropyridin-3-yl)methyl)benzofuran-4-carboxamide 31

31

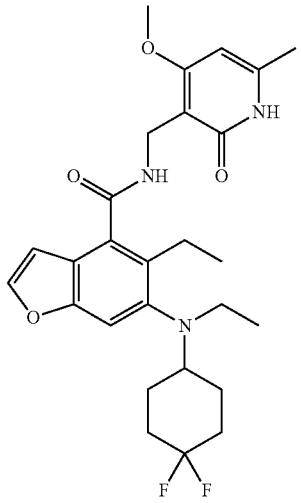

In accordance with the synthetic route of Example 24, the starting material 4e was replaced with compound 1g, and compound 24a was replaced with 4,4-difluorocyclohexylamine, accordingly, the title compound 31 (10 mg, yield 77%) as a white solid was prepared.

MS (ESI) m/z: 502.4 [M+1]

$^1$H NMR (400 MHz, DMSO-$d_6$) δ 11.47 (brs, 1H), 8.02 (t, 1H), 7.88 (d, 1H), 7.46 (s, 1H), 6.75 (d, 1H), 6.11 (s, 1H), 4.29 (d, 2H), 3.82 (s, 3H), 3.05 (brs, 2H), 2.97 (m, 1H), 2.82 (q, 2H), 2.18 (s, 3H), 1.98 (brs, 2H), 1.81 (brs, 2H), 1.73 (m, 2H), 1.58 (q, 2H), 1.08 (t, 3H), 0.83 (t, 3H).

Example 32

6-((3,3-Difluorocyclobutyl)(ethyl)amino)-5-ethyl-N-((4-methoxy-6-methyl-2-oxo-1,2-di hydropyridin-3-yl)methyl)benzofuran-4-carboxamide 32

32

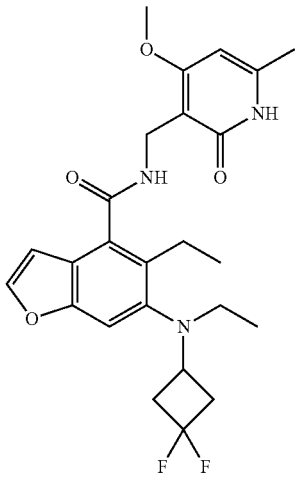

In accordance with the synthetic route of Example 24, the starting material 4e was replaced with compound 1g, and compound 24a was replaced with 3,3-difluorocyclobutanamine, accordingly, the title compound 32 (15 mg, yield 83%) as a white solid was prepared.

MS (ESI) m/z: 474.4 [M+1]

$^1$H NMR (400 MHz, DMSO-d6) δ 11.45 (brs, 1H), 8.04 (t, 1H), 7.88 (d, 1H), 7.41 (s, 1H), 6.75 (d, 1H), 6.10 (s, 1H), 4.28 (d, 2H), 3.81 (s, 3H), 3.79 (brs, 1H), 2.93 (q, 2H), 2.81 (q, 2H), 2.70 (brs, 2H), 2.25 (brs, 2H), 2.18 (s, 3H), 1.07 (t, 3H), 0.86 (t, 3H).

Example 33

6-((1,1-Dioxidotetrahydro-2H-thiopyran-4-yl)(ethyl)amino)-5-ethyl-N-((4-methoxy-6-m ethyl-2-oxo-1,2-dihydropyridin-3-yl)methyl)benzofuran-4-carboxamide 33

33

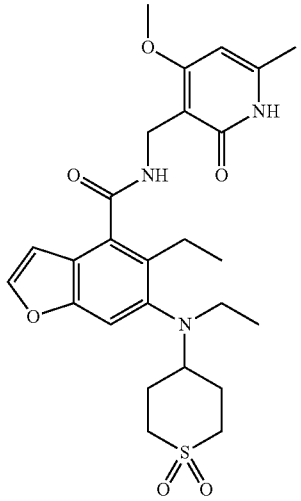

In accordance with the synthetic route of Example 24, the starting material 4e was replaced with compound 1g, and compound 24a was replaced with 4-aminotetrahydro-2H-thiopyran 1,1-dioxide, accordingly, the title compound 33 (9 mg, yield 64%) as a white solid was prepared.

MS (ESI) m/z: 516.3 [M+1]

$^1$H NMR (400 MHz, DMSO-$d_6$) δ 11.46 (brs, 1H), 8.02 (t, 1H), 7.88 (d, 1H), 7.47 (s, 1H), 6.75 (d, 1H), 6.10 (s, 1H), 4.29 (d, 2H), 3.81 (s, 3H), 2.98-3.07 (m, 5H), 3.01 (q, 2H), 2.80 (q, 2H), 2.18 (s, 3H), 2.07 (brs, 4H), 1.09 (t, 3H), 0.83 (t, 3H).

Example 34

6-((Cyclopropylmethyl)(1-(2,2,2-trifluoroethyl)piperidin-4-yl)amino)-5-ethyl-N-((4-methoxy-6-methyl-2-oxo-1,2-dihydropyridin-3-yl)methyl)benzofuran-4-carboxamide 34

34

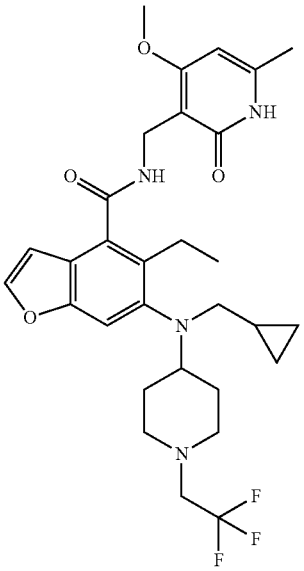

In accordance with the synthetic route of Example 25, the starting material 4e was replaced with compound 1g, the starting material acetaldehyde used in step 2 was replaced with cyclopropanecarboxaldehyde, the starting material methanesulfonyl chloride used in step 4 was replaced with trichloromethyl (2,2,2-trifluoroethyl) sulfate, accordingly, the title compound 34 (14 mg, yield 65%) as a white solid was prepared.

MS (ESI) m/z: 575.5 [M+1]

$^1$H NMR (400 MHz, DMSO-$d_6$) δ 8.01 (brs, 1H), 7.87 (s, 1H), 7.50 (s, 1H), 6.75 (s, 1H), 6.11 (s, 1H), 4.29 (d, 2H), 3.83 (s, 3H), 3.10 (q, 2H), 2.83-2.91 (m, 4H), 2.76 (brs, 1H), 2.26 (t, 2H), 2.19 (3H), 1.70 (brs, 2H), 1.49 (q, 2H), 1.24 (brs, 2H), 1.10 (t, 3H), 0.65 (brs, 1H), 0.28 (d, 2H), 0.003 (d, 2H).

Biological Assay

The present invention will be further described with reference to the following test examples, but the examples should not be considered as limiting the scope of the invention.

Test Example 1. Assay for Determining the Activity of the Example Compounds of the Present Invention on EZH2 Enzyme (A677G Mutant or Y641F Mutant)

The activity of EZH2 enzyme (with A677G mutant or Y641F mutant) was tested by the following method.

The method was used to determine the inhibitory effect of the compounds of the present invention on the activity of EZH2-A677G mutant or EZH2-Y641F mutant.

1. Experimental Materials and Instruments (1). EZH2-A677G (BPS Bioscience)

(2). EZH2-Y641F (BPS Bioscience)

(3). Histone H3 biotin labeling (AnaSpec)

(4). S-adenosyl methionine (abbreviated as SAM, Sigma)

(5). Histone H3K27 Me3 monoclonal antibody (Cisbio)

(6). Streptavidin-XL665 (Cisbio)

(7). HTRF detection buffer (Cisbio)

(8). Multi-functional microplate reader (Tecan)

2. Experimental Procedure

EZH2-A677G (or EZH2-Y641F) mutant was diluted to a concentration of 15 ng/μl by using a kinase buffer (5× buffer: 5 mg/ml BSA, 150 mM Tris-Cl, 100 mM $MgCl_2$) and added to a 384-well microtiter plate at 2 μl/well. Histone H3 biotin labeling and S-adenosyl methionine were respectively diluted to 50 nM and 50 μM with a kinase buffer, then added to a 384-well plate at 4 μl/well. The test compound was diluted with a kinase buffer (it was diluted from the highest concentration 30 μM in 10 fold concentration gradient to 7 concentration points), then added to the 384-well microtiter plate at 4 μl/well. The plate was incubated at room temperature for 2 hours. Histone H3K27 Me3 monoclonal antibody and Streptavidin-XL665 were diluted to 30 nM and 500 nM by HTRF detection buffer, then added to the 384-well microplate at 10 l/well and incubated for 1 hour. A well without an EZH2 enzyme and a compound was used as a negative control, and a well with an EZH2 enzyme but without a compound was used as a positive control. The fluorescent values were read on a multi-functional microplate reader at a emission wavelength of 620 nM and 665 nM. The compound logarithm concentration vs the inhibition percentage relative to the positive control well was plotted using GraphPad Prism, then the IC50 values were calculated.

The activity of the compounds of the present invention on enzyme EZH2-A677G was tested by the assay described above, and the $IC_{50}$ values are showed in Table 1.

TABLE 1

$IC_{50}$ of the compounds of the present invention for inhibiting the activity of enzyme EZH2-A677G

| Example No. | $IC_{50}$ (nM) |
|---|---|
| 1 | 6.4 |
| 2 | 5.7 |
| 3 | 38 |
| 4 | 14 |
| 5 | 1.2 |
| 6 | 7.8 |
| 7 | 3.5 |
| 8 | 6.2 |
| 9 | 5.7 |
| 10 | 1.7 |
| 11 | 5.6 |
| 12 | 10 |
| 13 | 2.9 |
| 14 | 9.6 |
| 15 | 16 |
| 16 | 31 |
| 17 | 9.9 |
| 18 | 4.0 |
| 19 | 2.9 |
| 20 | 5.9 |
| 22 | 6.5 |
| 23 | 4.8 |
| 25 | 0.9 |
| 26 | 2.9 |
| 27 | 3.5 |
| 28 | 6.8 |
| 29 | 2.7 |
| 30 | 0.8 |
| 31 | 2.7 |
| 32 | 4.0 |
| 33 | 2.7 |
| 34 | 14 |

Conclusion: The compounds of the present invention have a significant inhibitory effect on the activity of enzyme EZH2-A677G The activity of the compounds of the present invention on enzyme EZH2-Y641F was tested by the assay described above, and the $IC_{50}$ values are showed in Table 2.

TABLE 2

$IC_{50}$ of the compounds of the present invention for inhibiting the activity of enzyme EZH2-Y641F

| Example No. | $IC_{50}$ (nM) |
|---|---|
| 2 | 4.0 |
| 9 | 4.0 |
| 18 | 2.3 |
| 19 | 2.8 |
| 20 | 5.6 |
| 23 | 0.3 |
| 24 | 3.4 |
| 25 | 3.2 |
| 26 | 2.8 |
| 31 | 4.5 |
| 33 | 0.8 |

Test Example 2. Assay for Determining In Vitro Anti-Tumor Cell Growth Activity of the Example Compounds of the Present Invention This method was used to determinate the inhibitory effect of the compounds of the present invention on the growth activity of tumor cells (Pfeiffer or WSU-DLCL2) in vitro. Pfeiffer cells carry A677G mutant, and WSU-DLCL2 cells carry Y641F mutant.

1. Experimental Materials and Instruments (1). RPMI-1640, Inactivated Fetal Bovine Serum, Penicillin, Streptomycin (Life technology)

(2). Pfeiffer and WSU-DLCL2 cell line (ATCC)

(3). 96-well cell culture plate (Fisher Scientific)

(4). Cell incubator (Fisher Scientific)

(5). CellTiter-Gloluminescent cell vitality detection (Promega)

(6). Microplate reader (Tecan)

2. Experimental Procedure

The lymphoma suspension cell line (Pfeiffer or WSU-DLCL2) was cultured in a RPMI-1640 medium containing 10% inactivated Fetal Bovine Serum, 100 U/mL penicillin, and 100 μg/mL streptomycin, and incubated in an incubator with 5% carbon dioxide at 37° C. under a saturated humidity condition, and passaged every 3-4 days.

A cell sudpension was prepared with a fresh cell medium, added to a 96-well cell culture plate at 8000 cells/well (Pfeiffer) or 2000 cells/well (WSU-DLCL2), and incubated in 5% carbon dioxide at 37° C. incubator overnight. On the day of the experiment, the EZH2 test compounds (final concentration: 20000, 2000, 200, 20, 2, 0.2 nM) were added into the experimental wells for 3 parallel wells per group. A control well with the medium alone but without cells was set up to obtain the background luminescent value. The cell culture plate was incubated in an incubator with 5% carbon dioxide at 37° C. for 5 days.

After the compounds were applied to the cells for 5 days, the cell culture plate was placed at room temperature for 30 minutes, then a CellTiter-Glo reagent equal to the volume of cell culture medium was added to each well. The contents were mixed on a shaker for 10 minutes, and the fluorescent signal values were recorded. The cell growth inhibition rate was calculated, and the formula was: cell growth inhibiton rate=[(negative control control−experimental group)/(negative control group−background luminescent value)]×100%. The $IC_{50}$ values (half inhibition rate $IC_{50}$, i.e., a drug concentration that is required for 50% cell growth inhibition rate) were calculated by software from the cell growth inhibiton rate and the corresponding concentration.

The in vitro anti-tumor cell (Pfeiffer or WSU-DLCL2) growth activity of the compounds of the present invention was tested by the assay described above, and the $IC_{50}$ values are showed in Table 3 and 4.

TABLE 3

$IC_{50}$ of the compounds of the present invention for inhibiting the growth activity of tumor cells (Pfeiffer) in vitro

| Example No. | $IC_{50}$(nM) |
|---|---|
| 1 | 2 |
| 2 | 13 |
| 3 | 4 |
| 4 | 19 |
| 5 | 19 |
| 6 | 3 |
| 7 | 11 |
| 8 | 12 |
| 9 | 7 |
| 10 | 5 |
| 11 | 22 |
| 12 | 22 |
| 13 | 9 |
| 15 | 13 |
| 16 | 18 |

TABLE 3-continued $IC_{50}$ of the compounds of the present invention for inhibiting the growth activity of tumor cells (Pfeiffer) in vitro

| Example No. | $IC_{50}$(nM) |
|---|---|
| 17 | 9 |
| 18 | 20 |
| 19 | 14 |
| 23 | 68 |
| 24 | 19 |
| 25 | 15 |
| 27 | 4 |
| 28 | 78 |
| 29 | 17 |
| 30 | 17 |
| 31 | 69 |
| 32 | 18 |
| 33 | 22 |

Conclusion: The compounds of the present invention have a significant inhibitory effect on the growth of lymphoma cell (Pfeiffer) in vitro.

TABLE 4

$IC_{50}$ of the compounds of the present invention for inhibiting the growth activity of tumor cells (WSU-DLCL2) in vitro.

| Example No. | $IC_{50}$(nM) |
|---|---|
| 2 | 39 |
| 9 | 55 |
| 18 | 113 |
| 19 | 232 |
| 24 | 45 |
| 25 | 160 |
| 32 | 190 |

Conclusion: The compounds of the present invention have a significant inhibitory effect on the growth activity of lymphoma cells (WSU-DLCL2) in vitro.

Pharmacokinetics Assay

Test Example 3. Pharmacokinetics Assay of the Compounds of Examples 1, 2, 3 and 9 of the Present Invention 1. Abstract SD rats were used as test animals. The drug concentration in plasma at different time points was determined by LC/MS/MS after intragastrical administration of the compounds of Examples 1, 2, 3 and 9 to the rats. The pharmacokinetic behavior of the compounds of the present invention was studied and evaluated in rats.

2. Protocol 2.1 Test Compounds

Compounds of Examples 1, 2, 3 and 9

2.2 Test Animals 16 healthy adult Sprague-Dawley (SD) rats, half male and half female, were purchased from SINO-BRITSH SIPPR/BK LAB. ANIMAL LTD., CO, with Certificate No.: SCXK (Shanghai) 2008-0016.

2.3 Preparation of the Test Compounds

The appropriate amount of each compound was weighed, and added with 0.5% CMC-Na (containing 1% Tween 80) to prepare a 1.0 mg/mL suspension by grinding.

2.4 Administration

After an overnight fast, 16 SD rats were divided into 4 groups equally, half male and half female, and administered intragastrically the test compounds at an administration volume of 5 mL/kg.

3. Process

Blood (0.2 mL) was taken from the orbital sinus before administration and at 0.5, 1.0, 2.0, 4.0, 6.0, 8.0, 11.0, and 24.0 hours after administration. The samples were stored in heparinized tubes, and centrifuged for 10 minutes at 3,500 rpm to separate the blood plasma. The plasma samples were stored at −20° C.

The plasma concentration of the test compounds in rat plasma after intragastric administration was determined by LC-MS/MS.

4. Results of Pharmacokinetic Parameters

Pharmacokinetic parameters of the compounds of Examples 1, 2, 3 and 9 of the present invention are shown below:

| | Pharmacokinetics Parameters (5 mg/kg) | | | | | |
|---|---|---|---|---|---|---|
| Example No. | Plasma Conc. Cmax (ng/mL) | Area Under Curve AUC (ng/mL * hour) | Half-Life $t_{1/2}$ (hour) | Mean Residence Time MRT (hour) | Clearance CL/F (ml/minute/kg) | Apparent Distribution Volume Vz/F (ml/kg) |
| 1 | 88.9 ± 77.1 | 246 ± 127 | 0.80 ± 0.13 | 2.37 ± 0.18 | 390 ± 201 | 28127 ± 18370 |
| 2 | 105 ± 44.5 | 378 ± 4 2 | 2.20 ± 0.68 | 3.18 ± 0.30 | 222 ± 23.0 | 41367 ± 7914 |
| 3 | 91.5 ± 5.6 | 487 ± 12 | 2.73 ± 0.53 | 4.65 ± 0.184 | 171 ± 4.4 | 40480 ± 7967 |
| 9 | 79.1 ± 50.7 | 274 ± 180 | 0.719 ± 0.15 | 3.48 ± 0.107 | 562 ± 592 | 35102 ± 37075 |

Conclusion: The compounds of the present invention are well absorbed and have a remarkable pharmacological absorption effect.

What is claimed is:

1. A compound of formula (I):

(I)

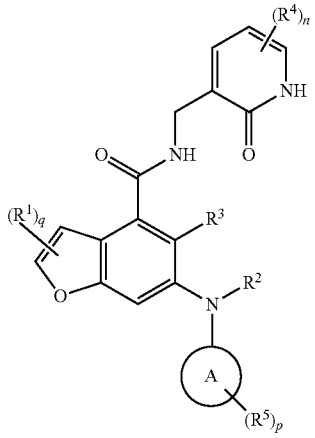

or a tautomer, mesomer, racemate, enantiomer, diastereomer, or mixture thereof, or a pharmaceutically acceptable salt thereof, wherein:

ring A is selected from the group consisting of heterocyclyl and cycloalkyl;

each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, —$OR^6$, [—C(O)$R^6$] —*C(O)R*$^6$, [—C(O)$OR^6$] —*C(O)OR*$^6$, —S(O)$_m R^6$, —S(O)$_m NR^7R^8$ and —$(CH_2)_x R^a$, wherein the alkyl, haloalkyl, heterocyclyl, aryl and heteroaryl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, and heteroaryl;

$R^2$ is hydrogen or alkyl, wherein the alkyl is optionally substituted by one or more groups selected from the group consisting of halogen, hydroxy, cyano, cycloalkyl and heterocyclyl;

$R^3$ is selected from the group consisting of hydrogen, alkyl, halogen, cyano, alkoxy and haloalkyl;

each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$OR^6$, —C(O)$R^6$, —C(O)$OR^6$, —S(O)$_m R^6$, —S(O)$_m NR^7R^8$ and —$NR^7R^8$;

each $R^5$ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, —$OR^6$, —C(O)$R^6$, —C(O)$OR^6$, —S(O)$_m R^6$, —S(O)$_m NR^7R^8$ and —$NR^7R^8$;

$R^6$ is selected from the group consisting of hydrogen, alkyl, haloalkyl, alkoxy, hydroxyalkyl, hydroxy, amino, cycloalkyl, heterocyclyl, aryl and heteroaryl;

$R^7$ and $R^8$ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

m is 0, 1 or 2;

n is 0, 1, 2 or 3;

p is 0, 1, 2, 3, 4 or 5;

q is 0, 1 or 2; and x is 0, 1, 2 or 3.

2. The compound according to claim 1, wherein n is 2.

3. The compound according to claim 1, wherein p and q are each 0, 1 or 2.

4. The compound according to claim 1, wherein each $R^1$ is identical or different and each is independently selected from the group consisting of hydrogen, halogen, alkyl, haloalkyl, cyano, cycloalkyl, heterocyclyl and —$(CH_2)_xR^a$, wherein the alkyl and heterocyclyl are each independently and optionally substituted by one or more groups selected from the group consisting of alkyl, hydroxyalkyl and halogen; and $R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of hydroxyalkyl, alkyl and halogen; and $R^7$, $R^8$ and x are as defined in claim 1.

5. The compound according to claim 1, wherein each $R^1$ is identical or different and each is independently selected from the group consisting of hydrogen, alkyl, haloalkyl, cyano and —$(CH_2)_xR^a$, wherein x is 0, and $R^a$ is halogen or cycloalkyl.

6. The compound according to claim 1, wherein $R^2$ is alkyl optionally substituted by cycloalkyl.

7. The compound according to claim 1, wherein $R^3$ is selected from the group consisting of alkyl, halogen and haloalkyl.

8. The compound according to claim 1, wherein each $R^4$ is identical or different and each is independently selected from the group consisting of hydrogen, alkyl and alkoxy.

9. The compound according to claim 1, wherein each $R^5$ is identical or different and each is independently selected from the group consisting of hydrogen, halogen, oxo, haloalkyl, —$C(O)R^6$, —$S(O)_mR^6$ and —$NR^7R^8$.

10. The compound according to claim 1, which is a compound of formula (II):

(II)

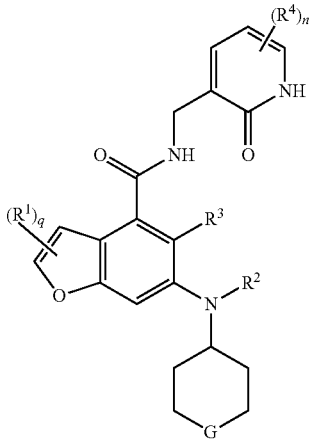

or a tautomer, mesomer, racemate, enantiomer, diastereomer, or mixture thereof, or a pharmaceutically acceptable salt thereof, wherein:

G is selected from the group consisting of $CR^bR^c$, C═O, $NR^d$, $S(O)_m$ and oxygen;

$R^b$ and $R^c$ are each independently selected from the group consisting of hydrogen, alkyl, alkoxy, halogen, amino, hydroxy, cycloalkyl, heterocyclyl, aryl, heteroaryl, —$OR^6$, —$C(O)R^6$, —$C(O)OR^6$, —$S(O)_m$ $R^6$ and —$NR^7R^8$;

$R^d$ is selected from the group consisting of hydrogen, alkyl, cycloalkyl, haloalkyl, heterocyclyl, aryl, heteroaryl, —$C(O)R^6$, —$C(O)OR^6$ and —$S(O)_mR^6$; and $R^1$ to $R^4$, $R^6$ to $R^8$, n, m and q are as defined in claim 1.

11. The compound according to claim 1, which is a compound of formula (III):

(III)

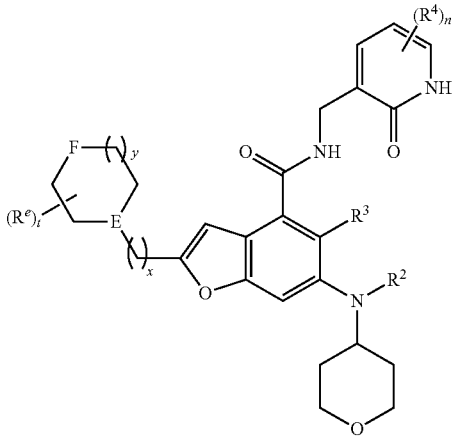

or a tautomer, mesomer, racemate, enantiomer, diastereomer, or mixture thereof, or a pharmaceutically acceptable salt thereof, wherein:

E is CH or nitrogen;

F is selected from the group consisting of $CR^bR^c$, $NR^d$ and oxygen;

$R^b$ and $R^c$ are each independently selected from the group consisting of hydrogen, alkyl, alkoxy, halogen, amino, nitro, hydroxy, cyano, cycloalkyl, heterocyclyl, aryl and heteroaryl;

$R^d$ is selected from the group consisting of hydrogen, alkyl, cycloalkyl, haloalkyl, hydroxyalkyl, heterocyclyl, aryl and heteroaryl;

each $R^e$ is identical or different and each is independently selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl;

t is 0, 1, 2, 3, 4 or 5;

x is 0, 1, 2 or 3;

y is 0, 1, 2 or 3; and $R^2$ to $R^4$, and n are as defined in claim 1.

12. The compound according to claim 11, which is a compound of formula (IV):

(IV)

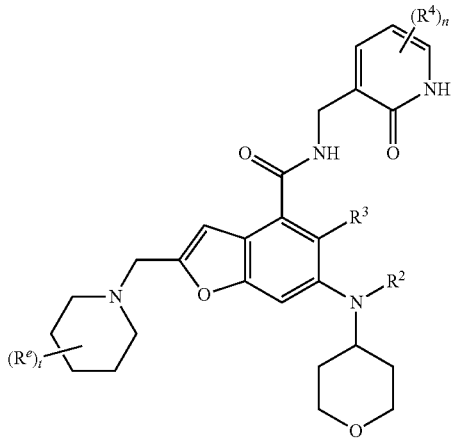

or a tautomer, mesomer, racemate, enantiomer, diastereomer, or mixture thereof, or a pharmaceutically acceptable salt thereof, wherein:

each $R^e$ is identical or different and each is independently selected from the group consisting of hydrogen, alkyl and halogen;

t is 0, 1, 2, 3, 4 or 5; and $R^2$ to $R^4$ and n are as defined in claim 11.

13. The compound according to claim 1, which is a compound of formula (V):

(V)

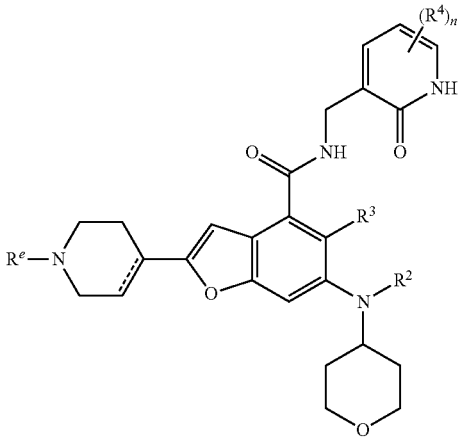

or a tautomer, mesomer, racemate, enantiomer, diastereomer, or mixture thereof, or a pharmaceutically acceptable salt thereof, wherein:

$R^e$ is selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl;

$R^2$ to $R^4$ and n are as defined in claim 1, and the dotted line represents a single bond or a double bond.

14. A compound selected from the group consisting of:

1

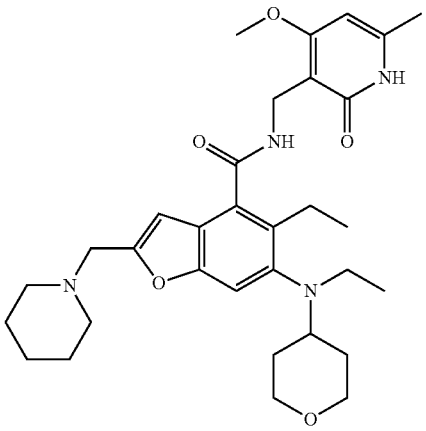

2

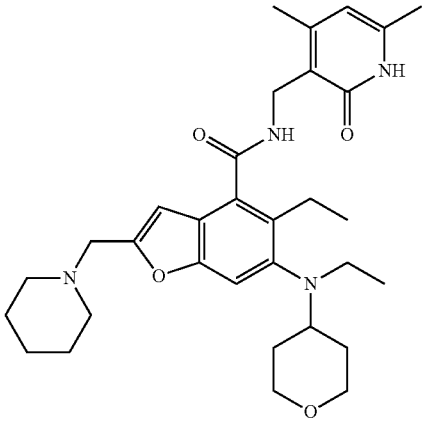

3

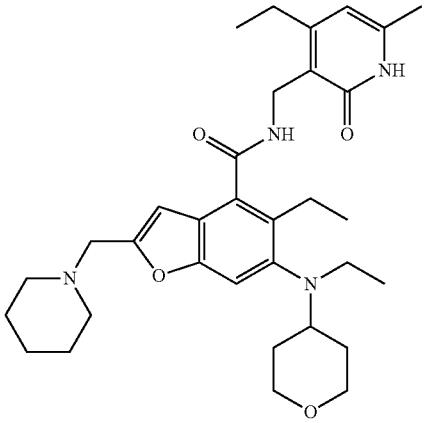

-continued
4
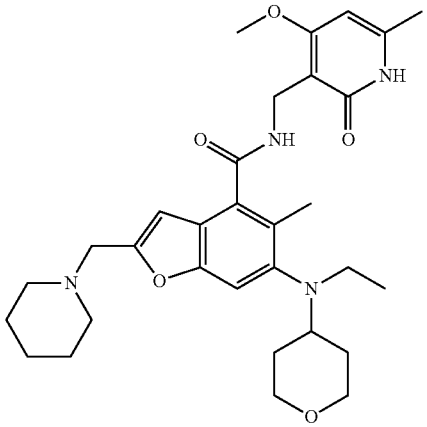
5
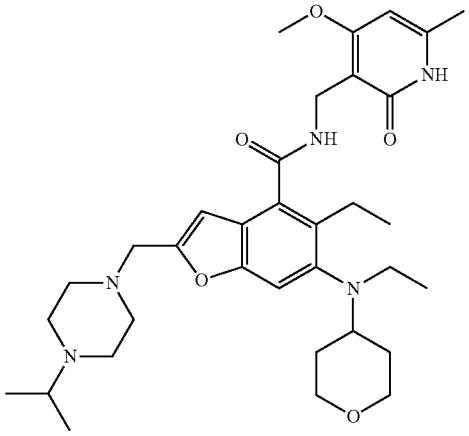
6
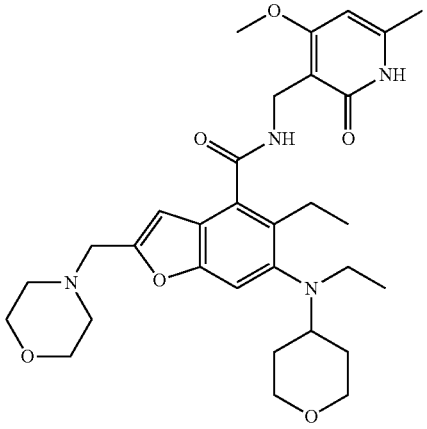
-continued
7
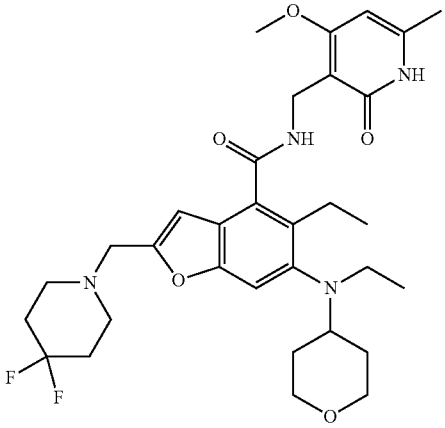
8
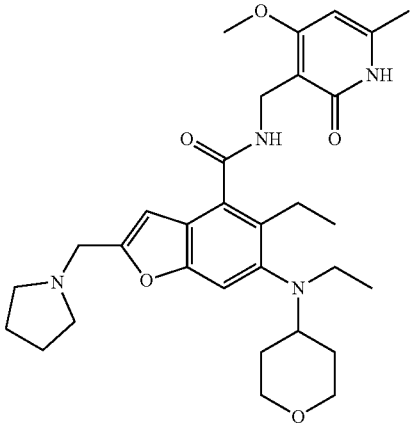
9
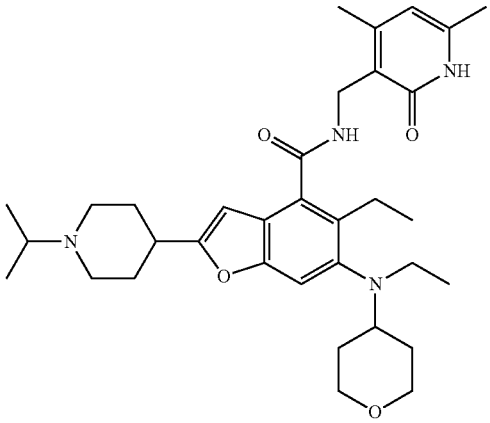

-continued
10
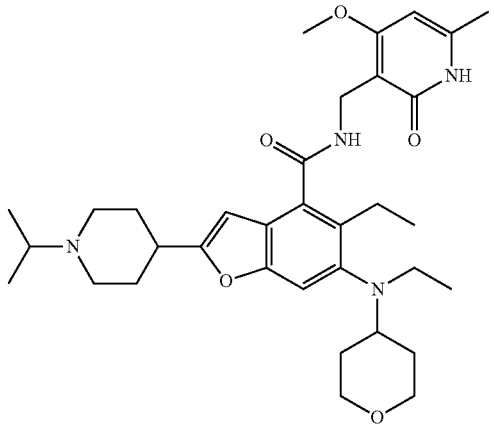
11
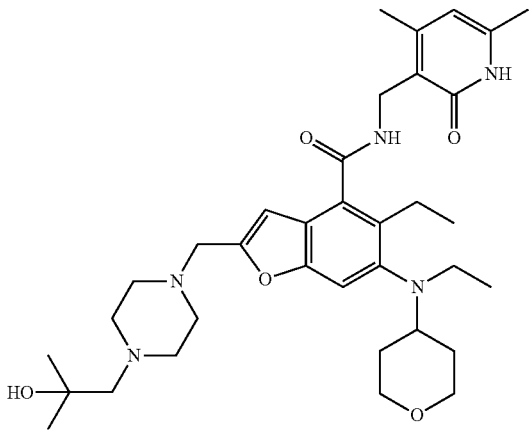
12
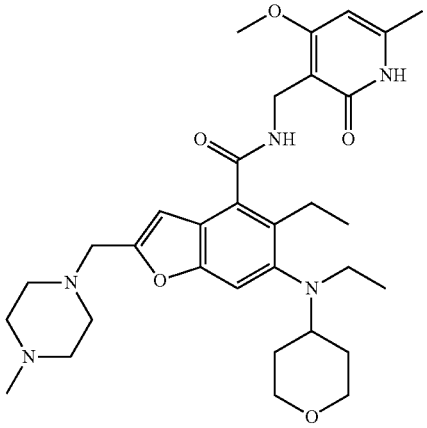
-continued
13
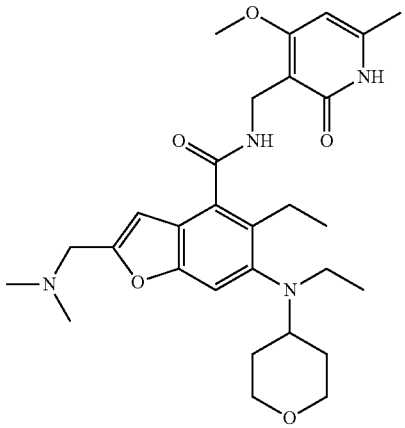
14
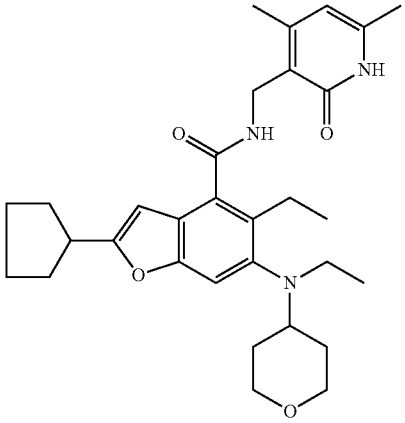
15
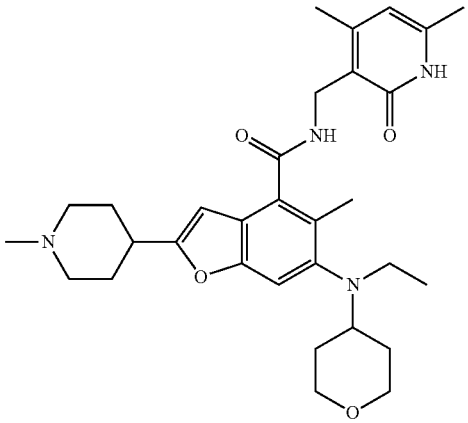

-continued
16
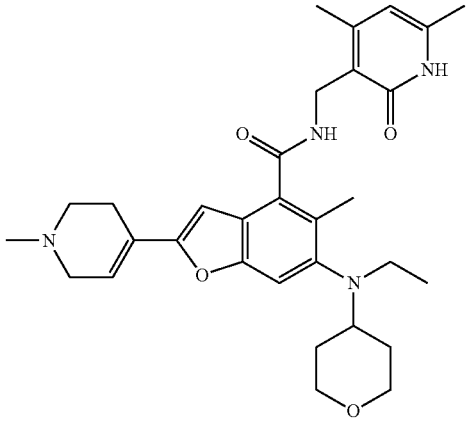
17
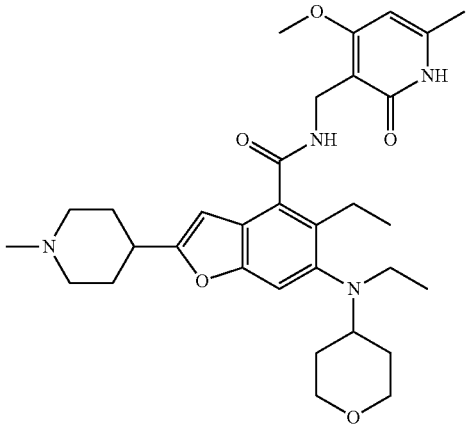
18
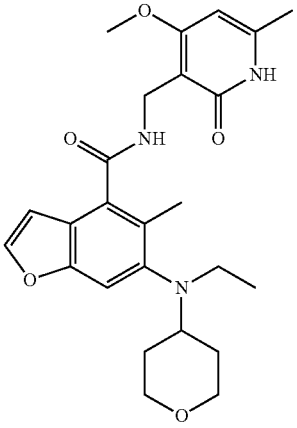
-continued
19
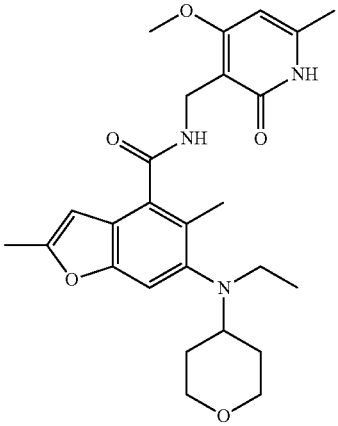
20
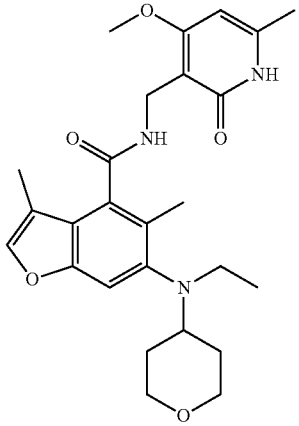
21
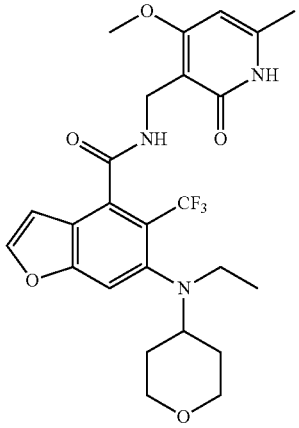

-continued
22
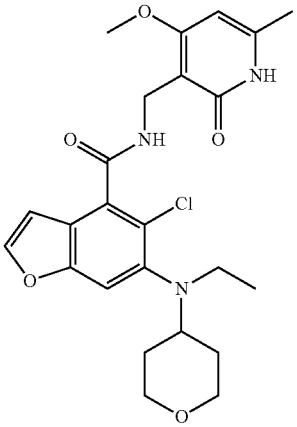
23
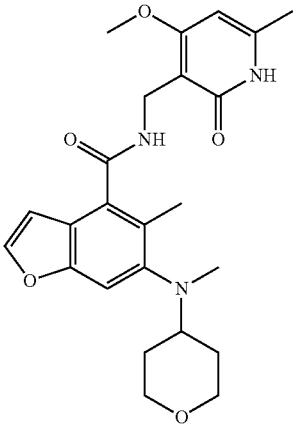
24
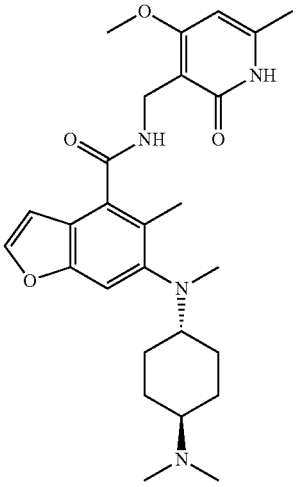
-continued
25
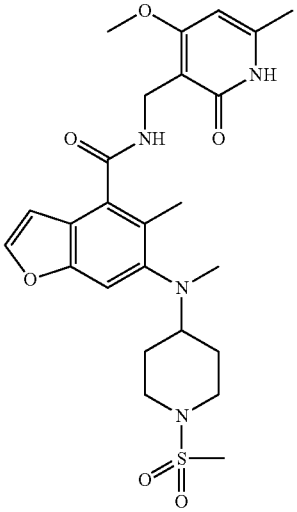
26
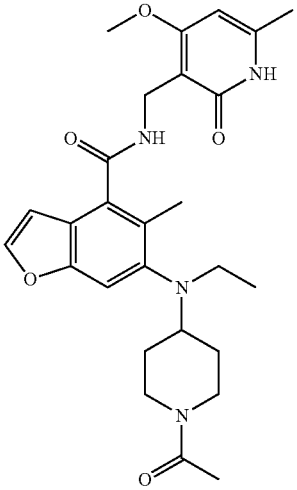
27
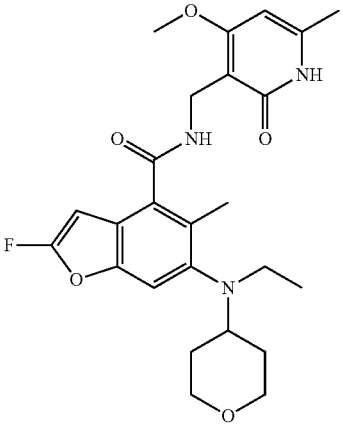

-continued
28
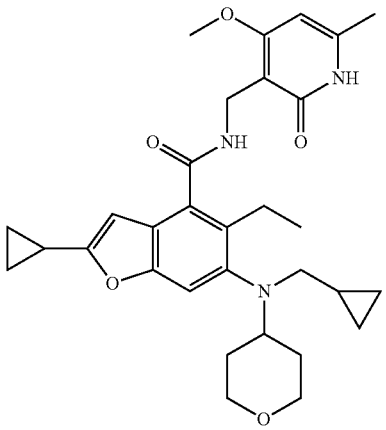
29
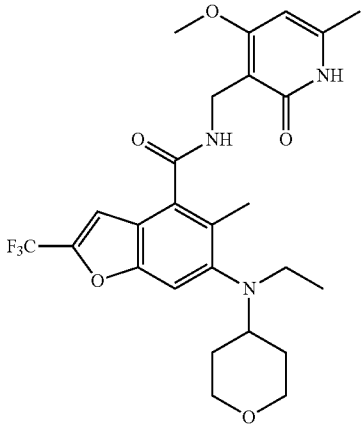
30
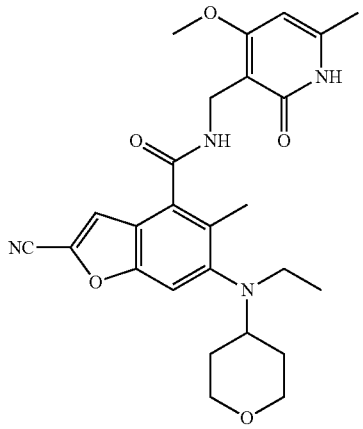
-continued
31
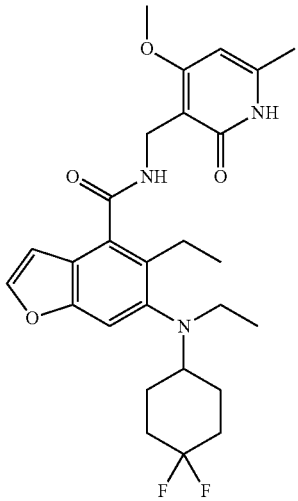
32
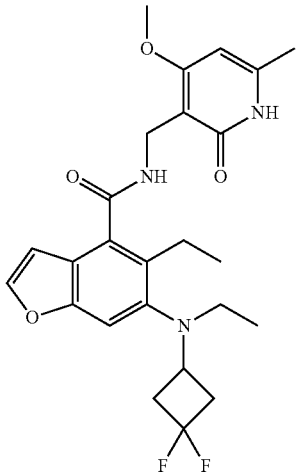
33
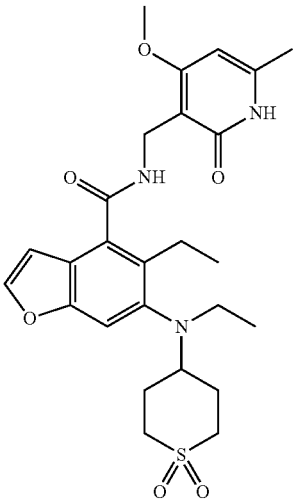
and

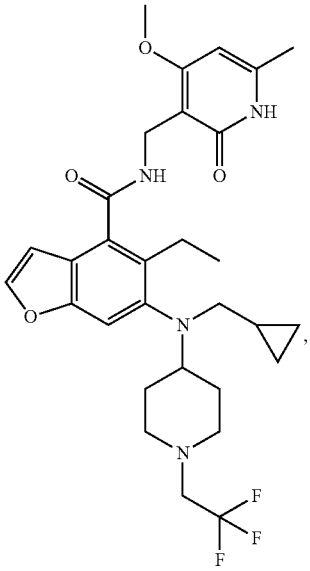

or a tautomer, mesomer, racemate, enantiomer, diastereomer, or mixture thereof, or a pharmaceutically acceptable salt thereof.

15. The compound according to claim 14, wherein the compound is

2

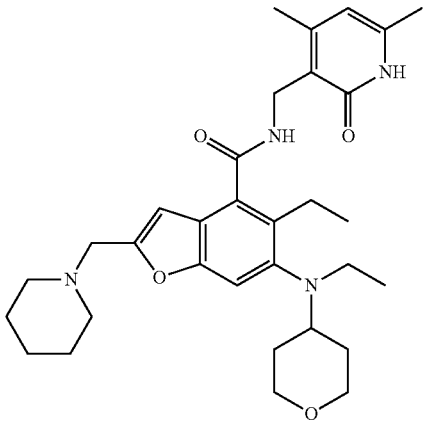

or a pharmaceutically acceptable salt thereof.

16. The compound according to claim 14, wherein the compound is

9

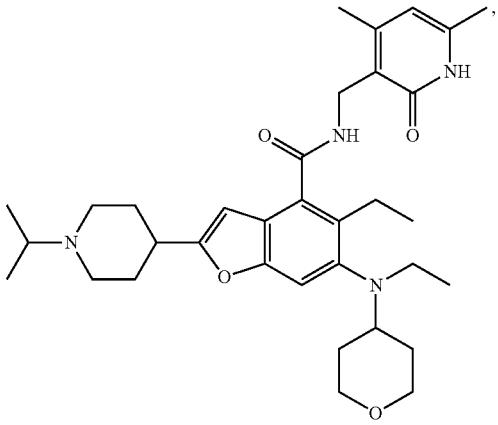

or a pharmaceutically acceptable salt thereof.

17. The compound according to claim 14, wherein the compound is

24

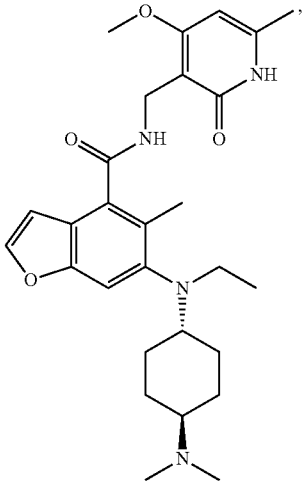

or a pharmaceutically acceptable salt thereof.

18. A pharmaceutical composition comprising a therapeutically effective amount of [the compound according to claim 1,] *a compound of formula* (*I*):

(I)

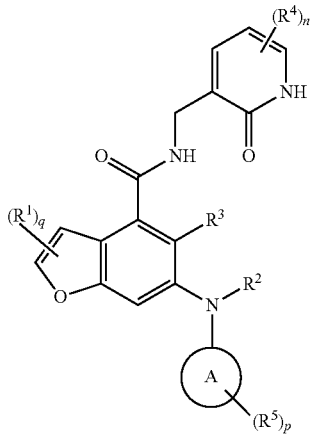

*or a tautomer, mesomer, racemate, enantiomer, diastereomer, or mixture thereof, or a pharmaceutically acceptable salt thereof,*

*wherein:*

*ring A is selected from the group consisting of heterocyclyl and cycloalkyl;*

*each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, —$OR^6$, —$C(O)R^6$, —$C(O)OR^6$, —$S(O)_mNR^7R^8$ and —$(CH_2)_xR^a$, wherein the alkyl, haloalkyl, heterocyclyl, aryl and heteroaryl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;*

*$R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, and heteroaryl;*

*$R^2$ is hydrogen or alkyl, wherein the alkyl is optionally substituted by one or more groups selected from the group consisting of halogen, hydroxy, cyano, cycloalkyl and heterocyclyl;*

*$R^3$ is selected from the group consisting of hydrogen, alkyl, halogen, cyano, alkoxy and haloalkyl; each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$; each $R^5$ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;*

*$R^6$ is selected from the group consisting of hydrogen, alkyl, haloalkyl, alkoxy, hydroxyalkyl, hydroxy, amino, cycloalkyl, heterocyclyl, aryl and heteroaryl;*

*$R^7$ and $R^8$ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;*

*m is 0, 1, 2;*

*n is 0, 1, 2 or 3;*

*p is 0, 1, 2, 3, 4 or 5;*

*q is 0, 1, or 2; and*

*x is 0, 1, 2, or 3;* and one or more pharmaceutically acceptable carriers, diluents or excipients.

19. A method for inhibiting EZH2 in a patient in need thereof, comprising administering to the patient [the] a pharmaceutical composition [according to claim 18] *comprising a compound of formula (I):*

(I)

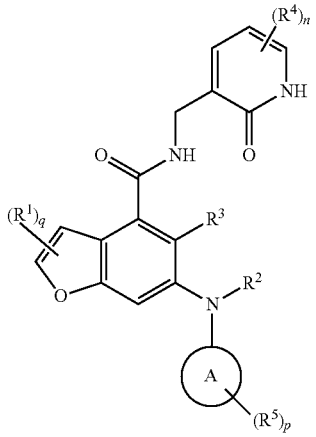

*or a tautomer, mesomer, racemate, enantiomer, diastereomer, or mixture thereof, or a pharmaceutically acceptable salt thereof,*

*wherein:*

*ring A is selected from the group consisting of heterocyclyl and cycloalkyl;*

*each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$(CH_2)_xR^a$, wherein the alkyl, haloalkyl, heterocyclyl, aryl and heteroaryl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;*

*$R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, and heteroaryl;*

$R^2$ is hydrogen or alkyl, wherein the alkyl is optionally substituted by one or more groups selected from the group consisting of halogen, hydroxy, cyano, cycloalkyl and heterocyclyl;

$R^3$ is selected from the group consisting of hydrogen, alkyl, halogen, cyano, alkoxy and haloalkyl; each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;

each $R^5$ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;

$R^6$ is selected from the group consisting of hydrogen, alkyl, haloalkyl, alkoxy, hydroxyalkyl, hydroxy, amino, cycloalkyl, heterocyclyl, aryl and heteroaryl;

$R^7$ and $R^8$ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

m is 0, 1 or 2;

n is 0, 1, 2 or 3;

p is 0, 1, 2, 3, 4 or 5;

q is 0, 1 or 2; and x is 0, 1, 2 or 3;

and one or more pharmaceutically acceptable carriers, diluents or excipients.

20. A method for treating a tumor or cancer, comprising administering to a patient in need thereof [the] *a* pharmaceutical composition [according to claim 18] comprising a compound of formula (I):*

(I)

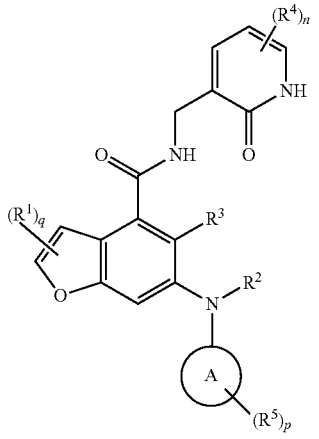

*or a tautomer, mesomer, racemate, enantiomer, diastereomer, or mixture thereof, or a pharmaceutically acceptable salt thereof,*

*wherein:* ring A is selected from the group consisting of heterocyclyl and cycloalkyl;

each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$(CH_2)_xR^a$, wherein the alkyl, haloalkyl, heterocyclyl, aryl and heteroaryl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, and heteroaryl;

$R^2$ is hydrogen or alkyl, wherein the alkyl is optionally substituted by one or more groups selected from the group consisting of halogen, hydroxy, cyano, cycloalkyl and heterocyclyl;

$R^3$ is selected from the group consisting of hydrogen, alkyl, halogen, cyano, alkoxy and haloalkyl; each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;

each $R^5$ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;

$R^6$ is selected from the group consisting of hydrogen, alkyl, haloalkyl, alkoxy, hydroxyalkyl, hydroxy, amino, cycloalkyl, heterocyclyl, aryl and heteroaryl;

$R^7$ and $R^8$ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

m is 0, 1 or 2;

n is 0, 1, 2 or 3;

p is 0, 1, 2, 3, 4 or 5;

q is 0, 1 or 2; and x is 0, 1, 2 or 3;

and one or more pharmaceutically acceptable carriers, diluents or excipients.

21. The method according to claim 20, wherein the tumor and cancer are selected from the group consisting of lymphoma, leukemia, breast cancer, lung cancer, prostate cancer, ovarian cancer, liver cancer, melanoma, rhabdomyosarcoma, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck cancer, and myeloma.

22. The method according to claim 21, wherein the leukemia is chronic myeloid leukemia, acute myeloid leukemia, or mixed lineage leukemia; and the lymphoma is non-Hodgkin's lymphoma, diffuse large B-cell lymphoma, or follicular lymphoma.

23. A process for preparing the compound of formula (I) according to claim 1, comprising:

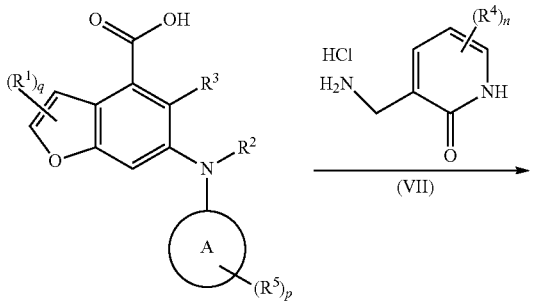

(VI)

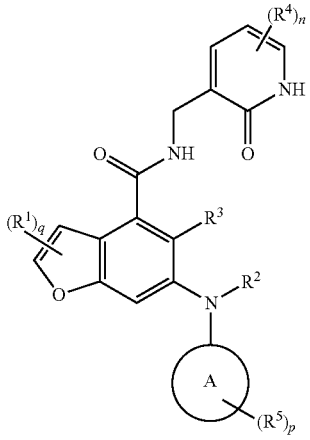

(I)

condensing a compound of formula (VI) with a compound of formula (VII) at room temperature to obtain the compound of formula (I);

wherein:

$R^1$ to $R^5$, ring A, p, q and n are as defined in claim 1.

*24. The method according to claim 22, wherein the lymphoma is non-Hodgkin's lymphoma, diffuse large B-cell lymphoma, or follicular lymphoma.*

*25. The method according to claim 24, wherein the lymphoma is non-Hodgkin's lymphoma.*

*26. The method according to claim 24, wherein the lymphoma is diffuse large B-cell lymphoma.*

*27. The method according to claim 24, wherein the lymphoma is follicular lymphoma.*

*28. The method according to claim 24, wherein the lymphoma is associated with one or more of an EZH2 mutation, amplification, or overexpression.*

*29. The method of claim 24, wherein the lymphoma is associated with an EZH2 mutation.*

*30. The method of claim 29, wherein the mutation is a gain-of-function mutation.*

*31. The method of claim 29, wherein the EZH2 mutation is a single amino acid mutation.*

*32. The method of claim 31, wherein the EZH2 mutation occurs at amino acid position 641 or 677.*

*33. The method of claim 32, wherein the EZH2 mutation is an A677G or Y641F mutation.*

*34. The method of claim 24, wherein the lymphoma exhibits enhanced trimethylation of histone H3K27.*

*35. The method according to claim 21, wherein the tumor or cancer is an ovarian tumor or an ovarian cancer.*

*36. The method according to claim 35, wherein the ovarian tumor or ovarian cancer is associated with one or more of an EZH2 mutation, amplification, or overexpression.*

*37. The method of claim 36, wherein the ovarian tumor or ovarian cancer is associated with an EZH2 mutation.*

*38. The method of claim 37, wherein the mutation is a gain-of-function mutation.*

*39. The method of claim 37, wherein the EZH2 mutation is a single amino acid mutation.*

*40. The method of claim 39, wherein the EZH2 mutation occurs at amino acid position 641 or 677.*

*41. The method of claim 40, wherein the EZH2 mutation is an A677G or Y641F mutation.*

*42. The method of claim 35, wherein the ovarian tumor or ovarian cancer exhibits enhanced trimethylation of histone H3K27.*

*43. The pharmaceutical composition of claim 18, wherein the compound is*

2

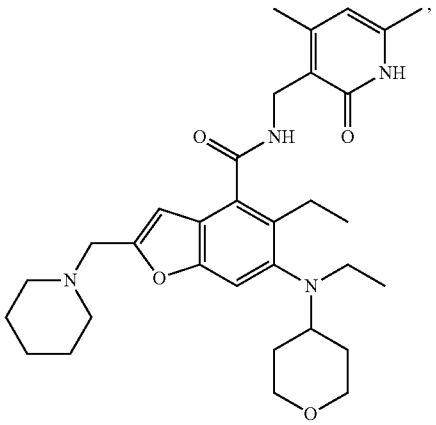

*or a tautomer, mesomer, racemate, enantiomer, diastereomer, or mixture thereof, or a pharmaceutically acceptable salt thereof.*

*44. The method according to claim 19, wherein the compound is*

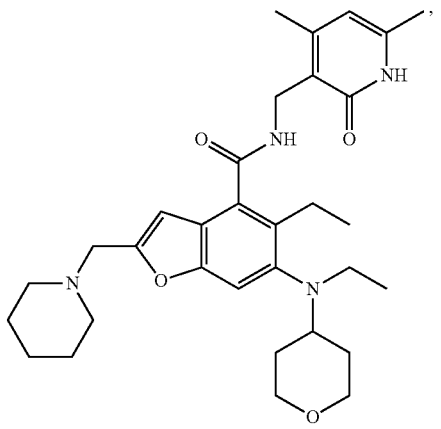

*or a tautomer, mesomer, racemate, enantiomer, diastereomer, or mixture thereof, or a pharmaceutically acceptable salt thereof.*

*45. The method according to claim 20, wherein the compound is*

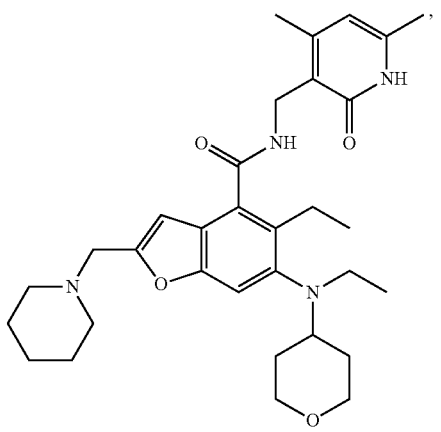

*or a tautomer, mesomer, racemate, enantiomer, diastereomer, or mixture thereof, or a pharmaceutically acceptable salt thereof.*

*46. The method according to claim 45, wherein the tumor and cancer are selected from the group consisting of lymphoma, leukemia, breast cancer, lung cancer, prostate cancer, ovarian cancer, liver cancer, melanoma, rhabdomyosarcoma, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck cancer, and myeloma.*

*47. The method according to claim 46, wherein the leukemia is chronic myeloid leukemia, acute myeloid leukemia, or mixed lineage leukemia.*

*48. The method according to claim 46, wherein the lymphoma is non-Hodgkin's lymphoma, diffuse large B-cell lymphoma, or follicular lymphoma.*

*49. The method according to claim 48, wherein the lymphoma is non-Hodgkin's lymphoma.*

*50. The method according to claim 48, wherein the lymphoma is diffuse large B-cell lymphoma.*

*51. The method according to claim 48, wherein the lymphoma is follicular lymphoma.*

*52. The method according to claim 48, wherein the lymphoma is associated with one or more of an EZH2 mutation, amplification, or overexpression.*

*53. The method of claim 52 wherein the lymphoma is associated with an EZH2 mutation.*

*54. The method of claim 53, wherein the mutation is a gain-of-function mutation.*

*55. The method of claim 53, wherein the EZH2 mutation is a single amino acid mutation.*

*56. The method of claim 55, wherein the EZH2 mutation occurs at amino acid position 641 or 677.*

*57. The method of claim 56, wherein the EZH2 mutation is an A677G or Y641F mutation.*

*58. The method of claim 48, wherein the lymphoma exhibits enhanced trimethylation of histone H3K27.*

*59. The method according to claim 46, wherein the tumor or cancer is an ovarian tumor or an ovarian cancer.*

*60. The method according to claim 59, wherein the ovarian tumor or ovarian cancer is associated with one or more of an EZH2 mutation, amplification, or overexpression.*

*61. The method of claim 60, wherein the ovarian tumor or ovarian cancer is associated with an EZH2 mutation.*

*62. The method of claim 61, wherein the mutation is a gain-of-function mutation.*

*63. The method of claim 61, wherein the EZH2 mutation is a single amino acid mutation.*

*64. The method of claim 63, wherein the EZH2 mutation occurs at amino acid position 641 or 677.*

*65. The method of claim 64, wherein the EZH2 mutation is an A677G or Y641F mutation.*

*66. The method of claim 59, wherein the ovarian tumor or ovarian cancer exhibits enhanced trimethylation of histone H3K27.*

*67. The pharmaceutical composition according to claim 18, wherein the compound is a compound of formula (IV):*

(IV)

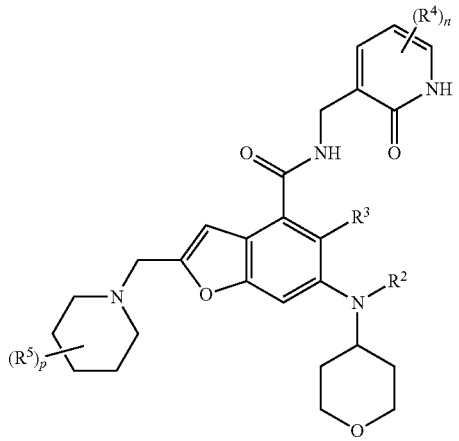

*or a tautomer, mesomer, racemate, enantiomer, diastereomer, or mixture thereof, or a pharmaceutically acceptable salt thereof,*

*wherein:*

*each $R^e$ is identical or different and each is independently selected from the group consisting of hydrogen, alkyl and halogen;*

*t is 0, 1, 2, 3, 4 or 5; and*

*$R^2$ is hydrogen or alkyl, wherein the alkyl is optionally substituted by one or more groups selected from the group consisting of halogen, hydroxy, cyano, cycloalkyl and heterocyclyl;*

*$R^3$ is selected from the group consisting of hydrogen, alkyl, halogen, cyano, alkoxy and haloalkyl; each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$; and n is 0, 1, 2 or 3.*

*68. The method according to claim 19, wherein the compound is a compound of formula (IV):*

(IV)

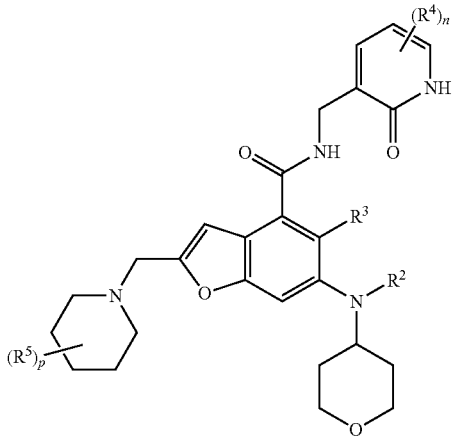

*or a tautomer, mesomer, racemate, enantiomer, diastereomer, or mixture thereof, or a pharmaceutically acceptable salt thereof,*

*wherein:*

*each $R^e$ is identical or different and each is independently selected from the group consisting of hydrogen, alkyl and halogen;*

*t is 0, 1, 2, 3, 4 or 5; and*

*$R^2$ is hydrogen or alkyl, wherein the alkyl is optionally substituted by one or more groups selected from the group consisting of halogen, hydroxy, cyano, cycloalkyl and heterocyclyl;*

*$R^3$ is selected from the group consisting of hydrogen, alkyl, halogen, cyano, alkoxy and haloalkyl; each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$; and n is 0, 1, 2 or 3.*

*69. The method according to claim 20, wherein the compound is a compound of formula (IV):*

(IV)

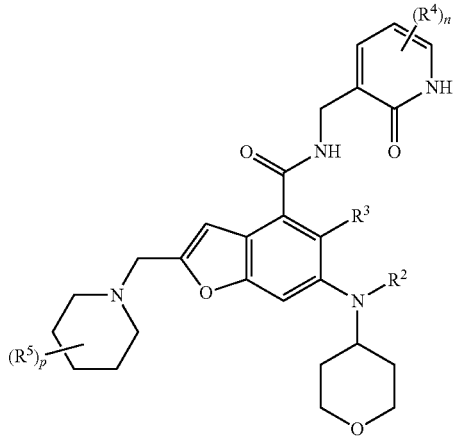

*or a tautomer, mesomer, racemate, enantiomer, diastereomer, or mixture thereof, or a pharmaceutically acceptable salt thereof,*

*wherein:*

*each $R^e$ is identical or different and each is independently selected from the group consisting of hydrogen, alkyl and halogen;*

*t is 0,1, 2, 3, 4 or 5; and*

*$R^2$ is hydrogen or alkyl, wherein the alkyl is optionally substituted by one or more groups selected from the group consisting of halogen, hydroxy, cyano, cycloalkyl and heterocyclyl;*

*$R^3$ is selected from the group consisting of hydrogen, alkyl, halogen, cyano, alkoxy and haloalkyl; each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$; and n is 0, 1, 2 or 3.*

*70. The method according to claim 59, wherein the tumor and cancer are selected from the group consisting of lymphoma, leukemia, breast cancer, lung cancer, prostate cancer, ovarian cancer, liver cancer, melanoma, rhabdomyosarcoma, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck cancer, and myeloma.*

*71. The method according to claim 70, wherein the leukemia is chronic myeloid leukemia, acute myeloid leukemia, or mixed lineage leukemia.*

*72. The method according to claim 70, wherein the lymphoma is non-Hodgkin's lymphoma, diffuse large B-cell lymphoma, or follicular lymphoma.*

*73. The method according to claim 72, wherein the lymphoma is non-Hodgkin's lymphoma.*

*74. The method according to claim 72, wherein the lymphoma is diffuse large B-cell lymphoma.*

*75. The method according to claim 72, wherein the lymphoma is follicular lymphoma.*

*76. The method according to claim 72, wherein the lymphoma is associated with one or more of an EZH2 mutation, amplification, or overexpression.*

*77. The method of claim 76, wherein the lymphoma is associated with an EZH2 mutation.*

*78. The method of claim 77, wherein the mutation is a gain-of-function mutation.*

*79. The method of claim 77, wherein the EZH2 mutation is a single amino acid mutation.*

*80. The method of claim 79, wherein the EZH2 mutation occurs at amino acid position 641 or 677.*

*81. The method of claim 80, wherein the EZH2 mutation is an A677G or Y641F mutation.*

*82. The method of claim 72, wherein the lymphoma exhibits enhanced trimethylation of histone H3K27.*

*83. The method according to claim 70, wherein the tumor or cancer is an ovarian tumor or an ovarian cancer.*

*84. The method according to claim 83, wherein the ovarian tumor or ovarian cancer is associated with one or more of an EZH2 mutation, amplification, or overexpression.*

*85. The method of claim 84, wherein the ovarian tumor or ovarian cancer is associated with an EZH2 mutation.*

*86. The method of claim 85, wherein the mutation is a gain-of-function mutation.*

*87. The method of claim 85, wherein the EZH2 mutation is a single amino acid mutation.*

*88. The method of claim 87, wherein the EZH2 mutation occurs at amino acid position 641 or 677.*

*89. The method of claim 88, wherein the EZH2 mutation is an A677G or Y641F mutation.*

*90. The method of claim 83, wherein the ovarian tumor or ovarian cancer exhibits enhanced trimethylation of histone H3K27.*

* * * * *